(12) United States Patent
McClain et al.

(10) Patent No.: US 9,486,431 B2
(45) Date of Patent: Nov. 8, 2016

(54) DRUG DELIVERY MEDICAL DEVICE

(75) Inventors: James B. McClain, Raleigh, NC (US); Douglas Taylor, Franklinton, NC (US); John Neet, Lawrence, KS (US)

(73) Assignee: Micell Technologies, Inc., Durham, NC (US)

( * ) Notice: Subject to any disclaimer, the term of this patent is extended or adjusted under 35 U.S.C. 154(b) by 615 days.

(21) Appl. No.: 12/504,597

(22) Filed: Jul. 16, 2009

(65) Prior Publication Data

US 2010/0015200 A1      Jan. 21, 2010

Related U.S. Application Data

(60) Provisional application No. 61/081,691, filed on Jul. 17, 2008, provisional application No. 61/212,964, filed on Apr. 17, 2009, provisional application No. 61/162,558, filed on Mar. 23, 2009.

(51) Int. Cl.

| | |
|---|---|
| A61K 31/20 | (2006.01) |
| A61K 31/7088 | (2006.01) |
| A61K 31/7105 | (2006.01) |
| A61K 31/715 | (2006.01) |
| A61L 27/34 | (2006.01) |
| A61L 27/54 | (2006.01) |
| A61L 29/08 | (2006.01) |
| A61L 29/16 | (2006.01) |
| A61L 31/10 | (2006.01) |
| A61L 31/16 | (2006.01) |
| A61F 2/30 | (2006.01) |
| A61K 9/00 | (2006.01) |
| A61K 38/00 | (2006.01) |
| A61M 25/10 | (2013.01) |

(52) U.S. Cl.
CPC .......... *A61K 31/20* (2013.01); *A61K 31/7088* (2013.01); *A61K 31/715* (2013.01); *A61K 31/7105* (2013.01); *A61L 27/34* (2013.01); *A61L 27/54* (2013.01); *A61L 29/085* (2013.01); *A61L 29/16* (2013.01); *A61L 31/10* (2013.01); *A61L 31/16* (2013.01); *A61F 2002/30535* (2013.01); *A61F 2250/0058* (2013.01); *A61K 9/0024* (2013.01); *A61K 9/0034* (2013.01); *A61K 38/00* (2013.01); *A61L 2300/608* (2013.01); *A61L 2300/63* (2013.01); *A61L 2420/08* (2013.01); *A61M 2025/105* (2013.01)

(58) Field of Classification Search
None
See application file for complete search history.

(56) References Cited

U.S. PATENT DOCUMENTS

| | | |
|---|---|---|
| 3,087,660 A | 4/1963 | Endicott |
| 3,087,860 A | 4/1963 | Endicott. |
| 3,123,077 A | 3/1964 | Alcamo |
| 3,457,280 A | 7/1969 | Schmitt et al. |
| 3,597,449 A | 8/1971 | Deprospero et al. |
| 3,737,337 A | 6/1973 | Schnoring et al. |
| 3,773,919 A | 11/1973 | Boswell et al. |
| 3,929,992 A | 12/1975 | Sehgal et al. |
| 4,000,137 A | 12/1976 | Dvonch et al. |
| 4,188,373 A | 2/1980 | Krezanoski |
| 4,285,987 A | 8/1981 | Ayer et al. |
| 4,326,532 A | 4/1982 | Hammar |
| 4,336,381 A | 6/1982 | Nagata et al. |
| 4,389,330 A | 6/1983 | Tice et al. |
| 4,474,572 A | 10/1984 | McNaughton et al. |
| 4,474,751 A | 10/1984 | Haslam et al. |
| 4,478,822 A | 10/1984 | Haslam et al. |
| 4,530,840 A | 7/1985 | Tice et al. |
| 4,582,731 A | 4/1986 | Smith |
| 4,606,347 A | 8/1986 | Fogarty et al. |
| 4,617,751 A | 10/1986 | Johansson |
| 4,655,771 A | 4/1987 | Wallsten |
| 4,675,189 A | 6/1987 | Kent et al. |
| 4,733,665 A | 3/1988 | Palmaz |
| 4,734,227 A | 3/1988 | Smith |
| 4,734,451 A | 3/1988 | Smith |
| 4,758,435 A | 7/1988 | Schaaf |

(Continued)

FOREIGN PATENT DOCUMENTS

| | | |
|---|---|---|
| CA | 2237466 A1 | 11/1998 |
| CA | 2589761 | 12/2004 |

(Continued)

OTHER PUBLICATIONS

Latella et al., "Nanoindentation hardness. Young's modulus, and creep behavior of organic-inorganic silica-based sol-gel thin films on copper," J Mater Res 23(9): 2357-2365 (2008).

(Continued)

*Primary Examiner* — Carlos Azpuru
*Assistant Examiner* — Casey Hagopian
(74) *Attorney, Agent, or Firm* — Lerner, David, Littenberg, Krumholz & Mentlik, LLP

(57) ABSTRACT

Provided is a coated implantable medical device, comprising: a substrate; and a coating disposed on said substrate, wherein said coating comprises at least one polymer and at least one pharmaceutical agent in a therapeutically desirable morphology and/or at least one active biological agent and optionally, one or more pharmaceutical carrying agents; wherein substantially all of pharmaceutical agent and/or active biological agent remains within said coating and on said substrate until the implantable device is deployed at an intervention site inside the body of a subject and wherein upon deployment of said medical device in the body of said subject a portion of said pharmaceutical agent and/or active biological agent is delivered at said intervention site along with at least a portion of said polymer and/or a at least a portion of said pharmaceutical carrying agents.

19 Claims, No Drawings

(56) References Cited

U.S. PATENT DOCUMENTS

| | | |
|---|---|---|
| 4,762,593 A | 8/1988 | Youngner |
| 4,931,037 A | 6/1990 | Wetterman |
| 4,950,239 A | 8/1990 | Gahara |
| 4,985,625 A | 1/1991 | Hurst |
| 5,000,519 A | 3/1991 | Moore |
| 5,090,419 A | 2/1992 | Palestrant |
| 5,096,848 A | 3/1992 | Kawamura |
| 5,102,417 A | 4/1992 | Palmaz |
| 5,104,404 A | 4/1992 | Wolff |
| 5,106,650 A | 4/1992 | Hoy et al. |
| 5,125,570 A | 6/1992 | Jones |
| 5,158,986 A | 10/1992 | Cha et al. |
| 5,185,776 A | 2/1993 | Townsend |
| 5,195,969 A | 3/1993 | Wang et al. |
| 5,243,023 A | 9/1993 | Dezern |
| 5,270,086 A | 12/1993 | Hamlin |
| 5,288,711 A | 2/1994 | Mitchell et al. |
| 5,320,634 A | 6/1994 | Vigil et al. |
| 5,324,049 A | 6/1994 | Mistrater et al. |
| 5,340,614 A | 8/1994 | Perman et al. |
| 5,342,621 A | 8/1994 | Eury |
| 5,350,361 A | 9/1994 | Tsukashima et al. |
| 5,350,627 A | 9/1994 | Nemphos et al. |
| 5,356,433 A | 10/1994 | Rowland et al. |
| 5,360,403 A | 11/1994 | Mische |
| 5,362,718 A | 11/1994 | Skotnicki et al. |
| 5,366,504 A | 11/1994 | Andersen et al. |
| 5,368,045 A | 11/1994 | Clement et al. |
| 5,372,676 A | 12/1994 | Lowe |
| 5,385,776 A | 1/1995 | Maxfield et al. |
| 5,387,313 A | 2/1995 | Thoms |
| 5,403,347 A | 4/1995 | Roby et al. |
| 5,470,603 A | 11/1995 | Staniforth et al. |
| 5,494,620 A | 2/1996 | Liu et al. |
| 5,500,180 A | 3/1996 | Anderson et al. |
| 5,545,208 A | 8/1996 | Wolff et al. |
| 5,556,383 A | 9/1996 | Wang et al. |
| 5,562,922 A | 10/1996 | Lambert |
| 5,569,463 A | 10/1996 | Helmus et al. |
| 5,570,537 A | 11/1996 | Black et al. |
| 5,578,709 A | 11/1996 | Woiszwillo |
| 5,599,576 A | 2/1997 | Opolski |
| 5,607,442 A | 3/1997 | Fischell et al. |
| 5,609,629 A | 3/1997 | Fearnot et al. |
| 5,626,611 A | 5/1997 | Liu et al. |
| 5,626,862 A | 5/1997 | Brem et al. |
| 5,632,772 A | 5/1997 | Alcime et al. |
| 5,669,932 A | 9/1997 | Fischell et al. |
| 5,674,192 A | 10/1997 | Sahatjian et al. |
| 5,674,242 A | 10/1997 | Phan et al. |
| 5,725,570 A | 3/1998 | Heath |
| 5,733,303 A | 3/1998 | Israel et al. |
| 5,800,511 A | 9/1998 | Mayer |
| 5,807,404 A | 9/1998 | Richter |
| 5,811,032 A | 9/1998 | Kawai et al. |
| 5,824,049 A | 10/1998 | Ragheb et al. |
| 5,837,313 A | 11/1998 | Ding et al. |
| 5,843,120 A | 12/1998 | Israel et al. |
| 5,871,436 A | 2/1999 | Eury |
| 5,873,904 A | 2/1999 | Ragheb et al. |
| 5,876,426 A | 3/1999 | Kume et al. |
| 5,913,895 A | 6/1999 | Burpee et al. |
| 5,924,631 A | 7/1999 | Rodrigues et al. |
| 5,948,020 A | 9/1999 | Yoon et al. |
| 5,957,975 A | 9/1999 | Lafont et al. |
| 5,981,568 A | 11/1999 | Kunz et al. |
| 5,981,719 A | 11/1999 | Woiszwillo et al. |
| 6,013,855 A | 1/2000 | McPherson et al. |
| 6,036,978 A | 3/2000 | Gombotz et al. |
| 6,039,721 A | 3/2000 | Johnson et al. |
| 6,068,656 A | 5/2000 | Von Oepen |
| 6,071,308 A | 6/2000 | Ballou et al. |
| 6,077,880 A | 6/2000 | Castillo et al. |
| 6,090,925 A | 7/2000 | Woiszwillo et al. |
| 6,129,755 A | 10/2000 | Mathis et al. |
| 6,143,037 A | 11/2000 | Goldsten et al. |
| 6,143,314 A | 11/2000 | Chandrashekar et al. |
| 6,146,356 A | 11/2000 | Wang et al. |
| 6,146,404 A | 11/2000 | Kim et al. |
| 6,153,252 A | 11/2000 | Hossainy et al. |
| 6,171,327 B1 | 1/2001 | Daniel et al. |
| 6,190,699 B1 | 2/2001 | Luzzi et al. |
| 6,193,744 B1 | 2/2001 | Ehr et al. |
| 6,206,914 B1 | 3/2001 | Soykan et al. |
| 6,217,608 B1 | 4/2001 | Penn et al. |
| 6,231,599 B1 | 5/2001 | Ley |
| 6,231,600 B1 | 5/2001 | Zhong et al. |
| 6,245,104 B1 | 6/2001 | Alt |
| 6,248,127 B1 | 6/2001 | Shah et al. |
| 6,248,129 B1 | 6/2001 | Froix |
| 6,251,980 B1 | 6/2001 | Lan et al. |
| 6,268,053 B1 | 7/2001 | Woiszwillo et al. |
| 6,273,913 B1 | 8/2001 | Wright et al. |
| 6,284,758 B1 | 9/2001 | Egi et al. |
| 6,299,635 B1 | 10/2001 | Frantzen |
| 6,309,669 B1 | 10/2001 | Setterstrom et al. |
| 6,319,541 B1 | 11/2001 | Pletcher et al. |
| 6,325,821 B1 | 12/2001 | Gaschino et al. |
| 6,336,934 B1 | 1/2002 | Gilson et al. |
| 6,342,062 B1 | 1/2002 | Suon et al. |
| 6,355,691 B1 | 3/2002 | Goodman |
| 6,358,556 B1 | 3/2002 | Ding et al. |
| 6,361,819 B1 | 3/2002 | Tedeschi et al. |
| 6,362,718 B1 | 3/2002 | Patrick et al. |
| 6,364,903 B2 | 4/2002 | Tseng et al. |
| 6,368,658 B1 | 4/2002 | Schwarz et al. |
| 6,372,246 B1 | 4/2002 | Wei et al. |
| 6,387,121 B1 | 5/2002 | Alt |
| 6,409,716 B1 * | 6/2002 | Sahatjian et al. ............ 604/509 |
| 6,414,050 B1 | 7/2002 | Howdle et al. |
| 6,416,779 B1 | 7/2002 | D'Augustine et al. |
| 6,448,315 B1 | 9/2002 | Lidgren et al. |
| 6,458,387 B1 | 10/2002 | Scott et al. |
| 6,461,380 B1 | 10/2002 | Cox |
| 6,461,644 B1 | 10/2002 | Jackson et al. |
| 6,488,703 B1 | 12/2002 | Kveen et al. |
| 6,495,163 B1 | 12/2002 | Jordan |
| 6,497,729 B1 | 12/2002 | Moussy et al. |
| 6,506,213 B1 | 1/2003 | Mandel et al. |
| 6,517,860 B1 | 2/2003 | Roser et al. |
| 6,521,258 B1 | 2/2003 | Mandel et al. |
| 6,524,698 B1 | 2/2003 | Schmoock |
| 6,530,951 B1 | 3/2003 | Bates et al. |
| 6,537,310 B1 | 3/2003 | Palmaz et al. |
| 6,541,033 B1 | 4/2003 | Shah |
| 6,572,813 B1 | 6/2003 | Zhang et al. |
| 6,602,281 B1 | 8/2003 | Klein |
| 6,610,013 B1 | 8/2003 | Fenster et al. |
| 6,627,246 B2 | 9/2003 | Mehta et al. |
| 6,649,627 B1 | 11/2003 | Cecchi et al. |
| 6,660,176 B2 | 12/2003 | Tepper et al. |
| 6,669,785 B2 | 12/2003 | DeYoung et al. |
| 6,669,980 B2 | 12/2003 | Hansen et al. |
| 6,670,407 B2 | 12/2003 | Howdle et al. |
| 6,682,757 B1 | 1/2004 | Wright |
| 6,706,283 B1 | 3/2004 | Appel et al. |
| 6,710,059 B1 | 3/2004 | Labrie et al. |
| 6,720,003 B2 | 4/2004 | Cheng et al. |
| 6,726,712 B1 | 4/2004 | Raeder-Devens et al. |
| 6,736,996 B1 | 5/2004 | Carbonell et al. |
| 6,743,505 B2 | 6/2004 | Antall et al. |
| 6,749,902 B2 | 6/2004 | Yonker et al. |
| 6,755,871 B2 | 6/2004 | Damaso et al. |
| 6,756,084 B2 | 6/2004 | Fulton et al. |
| 6,767,558 B2 | 7/2004 | Wang et al. |
| 6,780,475 B2 | 8/2004 | Fulton et al. |
| 6,794,902 B2 | 9/2004 | Becker et al. |
| 6,800,663 B2 | 10/2004 | Asgarzadeh et al. |
| 6,815,218 B1 | 11/2004 | Jacobsen et al. |
| 6,821,549 B2 | 11/2004 | Jayaraman |
| 6,837,611 B2 | 1/2005 | Kuo et al. |
| 6,838,089 B1 | 1/2005 | Carlsson et al. |
| 6,838,528 B2 | 1/2005 | Zhou |
| 6,858,598 B1 | 2/2005 | McKearn et al. |

(56) References Cited

U.S. PATENT DOCUMENTS

| | | |
|---|---|---|
| 6,860,123 B1 | 3/2005 | Uhlin |
| 6,868,123 B2 | 3/2005 | Bellas et al. |
| 6,884,377 B1 | 4/2005 | Burnham et al. |
| 6,884,823 B1 | 4/2005 | Pierick et al. |
| 6,897,205 B2 | 5/2005 | Beckert et al. |
| 6,905,555 B2 | 6/2005 | DeYoung et al. |
| 6,908,624 B2 | 6/2005 | Hossainy et al. |
| 6,916,800 B2 | 7/2005 | McKearn et al. |
| 6,923,979 B2 | 8/2005 | Fotland et al. |
| 6,936,270 B2 | 8/2005 | Watson et al. |
| 6,939,569 B1 | 9/2005 | Green et al. |
| 6,973,718 B2 | 12/2005 | Sheppard et al. |
| 7,056,591 B1 | 6/2006 | Pacetti et al. |
| 7,094,256 B1 | 8/2006 | Shah et al. |
| 7,148,201 B2 | 12/2006 | Stern et al. |
| 7,152,452 B2 | 12/2006 | Kokish |
| 7,160,592 B2 | 1/2007 | Rypacek et al. |
| 7,163,715 B1 | 1/2007 | Kramer |
| 7,169,404 B2 | 1/2007 | Hossainy et al. |
| 7,171,255 B2 | 1/2007 | Holupka et al. |
| 7,201,750 B1 | 4/2007 | Eggers et al. |
| 7,201,940 B1 | 4/2007 | Kramer |
| 7,229,837 B2 | 6/2007 | Chen |
| 7,278,174 B2 | 10/2007 | Villalobos |
| 7,279,174 B2 | 10/2007 | Pacetti et al. |
| 7,282,020 B2 | 10/2007 | Kaplan |
| 7,308,748 B2 | 12/2007 | Kokish |
| 7,323,454 B2 | 1/2008 | De Nijs et al. |
| 7,326,734 B2 | 2/2008 | Zi et al. |
| 7,329,383 B2 | 2/2008 | Stinson |
| 7,378,105 B2 | 5/2008 | Burke et al. |
| 7,419,696 B2 | 9/2008 | Berg et al. |
| 7,429,378 B2 | 9/2008 | Serhan et al. |
| 7,444,162 B2 | 10/2008 | Hassan |
| 7,455,658 B2 | 11/2008 | Wang |
| 7,455,688 B2 | 11/2008 | Furst et al. |
| 7,456,151 B2 | 11/2008 | Li et al. |
| 7,462,593 B2 | 12/2008 | Cuttitta et al. |
| 7,485,113 B2 | 2/2009 | Varner et al. |
| 7,498,042 B2 | 3/2009 | Igaki et al. |
| 7,524,865 B2 | 4/2009 | D'Amato et al. |
| 7,537,610 B2 | 5/2009 | Reiss |
| 7,537,785 B2 | 5/2009 | Loscalzo et al. |
| 7,553,827 B2 | 6/2009 | Attawia et al. |
| 7,713,538 B2 | 5/2010 | Lewis et al. |
| 7,727,275 B2 | 6/2010 | Betts et al. |
| 7,745,566 B2 | 6/2010 | Chattopadhyay et al. |
| 7,763,277 B1 | 7/2010 | Canham et al. |
| 7,771,468 B2 | 8/2010 | Whitbourne et al. |
| 7,837,726 B2 | 11/2010 | Von Oepen et al. |
| 7,842,312 B2 | 11/2010 | Burgermeister et al. |
| 7,919,108 B2 | 4/2011 | Reyes et al. |
| 7,955,383 B2 | 6/2011 | Krivoruchko et al. |
| 7,967,855 B2 | 6/2011 | Furst et al. |
| 7,972,661 B2 | 7/2011 | Pui et al. |
| 8,070,796 B2 | 12/2011 | Furst et al. |
| 8,298,565 B2 | 10/2012 | Taylor et al. |
| 8,377,356 B2 | 2/2013 | Huang |
| 8,535,372 B1 | 9/2013 | Fox et al. |
| 8,709,071 B1 | 4/2014 | Huang et al. |
| 8,753,659 B2 | 6/2014 | Lewis et al. |
| 8,753,709 B2 | 6/2014 | Hossainy et al. |
| 8,758,429 B2 | 6/2014 | Taylor et al. |
| 8,795,762 B2 | 8/2014 | Fulton et al. |
| 8,834,913 B2 | 9/2014 | Shaw et al. |
| 8,852,625 B2 | 10/2014 | DeYoung et al. |
| 8,900,651 B2 | 12/2014 | McClain et al. |
| 2001/0026804 A1 | 10/2001 | Boutignon |
| 2001/0034336 A1 | 10/2001 | Shah et al. |
| 2001/0044629 A1 | 11/2001 | Stinson |
| 2001/0049551 A1 | 12/2001 | Tseng et al. |
| 2002/0007209 A1 | 1/2002 | Scheerder et al. |
| 2002/0051485 A1 | 5/2002 | Bottomley |
| 2002/0051845 A1 | 5/2002 | Mehta et al. |
| 2002/0082680 A1 | 6/2002 | Shanley et al. |
| 2002/0091433 A1 | 7/2002 | Ding et al. |
| 2002/0099332 A1 | 7/2002 | Slepian et al. |
| 2002/0125860 A1 | 9/2002 | Schworm et al. |
| 2002/0133072 A1 | 9/2002 | Wang et al. |
| 2002/0144757 A1 | 10/2002 | Craig et al. |
| 2003/0001830 A1 | 1/2003 | Wampler et al. |
| 2003/0031699 A1 | 2/2003 | Van Antwerp |
| 2003/0077200 A1 | 4/2003 | Craig et al. |
| 2003/0088307 A1 | 5/2003 | Shulze et al. |
| 2003/0125800 A1 | 7/2003 | Shulze et al. |
| 2003/0143315 A1 | 7/2003 | Pui et al. |
| 2003/0170305 A1 | 9/2003 | O'Neil et al. |
| 2003/0180376 A1 | 9/2003 | Dalal et al. |
| 2003/0185964 A1 | 10/2003 | Weber et al. |
| 2003/0204238 A1 | 10/2003 | Tedeschi |
| 2003/0222017 A1 | 12/2003 | Fulton et al. |
| 2003/0222018 A1 | 12/2003 | Yonker et al. |
| 2003/0232014 A1 | 12/2003 | Burke et al. |
| 2004/0013792 A1 | 1/2004 | Epstein et al. |
| 2004/0018228 A1 | 1/2004 | Fischell et al. |
| 2004/0022400 A1 | 2/2004 | Magrath |
| 2004/0022853 A1 | 2/2004 | Ashton et al. |
| 2004/0044397 A1 | 3/2004 | Stinson |
| 2004/0059290 A1 | 3/2004 | Palasis et al. |
| 2004/0102758 A1 | 5/2004 | Davila et al. |
| 2004/0106982 A1 | 6/2004 | Jalisi |
| 2004/0122205 A1 | 6/2004 | Nathan |
| 2004/0126542 A1 | 7/2004 | Fujiwara et al. |
| 2004/0143317 A1 | 7/2004 | Stinson et al. |
| 2004/0144317 A1 | 7/2004 | Chuman et al. |
| 2004/0147904 A1 | 7/2004 | Hung et al. |
| 2004/0157789 A1 | 8/2004 | Geall |
| 2004/0170685 A1 | 9/2004 | Carpenter et al. |
| 2004/0193177 A1 | 9/2004 | Houghton et al. |
| 2004/0193262 A1 | 9/2004 | Shadduck |
| 2004/0220660 A1 | 11/2004 | Shanley et al. |
| 2004/0224001 A1 | 11/2004 | Pacetti et al. |
| 2004/0236416 A1 | 11/2004 | Falotico |
| 2004/0260000 A1 | 12/2004 | Chaiko |
| 2005/0003074 A1 | 1/2005 | Brown et al. |
| 2005/0004661 A1* | 1/2005 | Lewis et al. ............ 623/1.42 |
| 2005/0010275 A1 | 1/2005 | Sahatjian et al. |
| 2005/0015046 A1 | 1/2005 | Weber et al. |
| 2005/0019747 A1 | 1/2005 | Anderson et al. |
| 2005/0033414 A1 | 2/2005 | Zhang et al. |
| 2005/0038498 A1 | 2/2005 | Dubrow et al. |
| 2005/0048121 A1 | 3/2005 | East et al. |
| 2005/0049694 A1 | 3/2005 | Neary |
| 2005/0060028 A1 | 3/2005 | Horres et al. |
| 2005/0069630 A1 | 3/2005 | Fox et al. |
| 2005/0070989 A1 | 3/2005 | Lye et al. |
| 2005/0070990 A1 | 3/2005 | Stinson |
| 2005/0074479 A1 | 4/2005 | Weber et al. |
| 2005/0075714 A1 | 4/2005 | Cheng et al. |
| 2005/0079199 A1 | 4/2005 | Heruth et al. |
| 2005/0079274 A1 | 4/2005 | Palasis et al. |
| 2005/0084533 A1 | 4/2005 | Howdle et al. |
| 2005/0131513 A1 | 6/2005 | Myers |
| 2005/0147734 A1 | 7/2005 | Seppala et al. |
| 2005/0166841 A1 | 8/2005 | Robida |
| 2005/0175772 A1 | 8/2005 | Worsham et al. |
| 2005/0177223 A1 | 8/2005 | Palmaz |
| 2005/0191491 A1 | 9/2005 | Wang et al. |
| 2005/0196424 A1 | 9/2005 | Chappa |
| 2005/0208102 A1 | 9/2005 | Schultz |
| 2005/0209244 A1 | 9/2005 | Prescott et al. |
| 2005/0216075 A1 | 9/2005 | Wang et al. |
| 2005/0238829 A1 | 10/2005 | Motherwell et al. |
| 2005/0255327 A1 | 11/2005 | Chaney |
| 2005/0260186 A1 | 11/2005 | Bookbinder et al. |
| 2005/0268573 A1 | 12/2005 | Yan |
| 2005/0288481 A1 | 12/2005 | DesNoyer et al. |
| 2005/0288629 A1 | 12/2005 | Kunis |
| 2006/0001011 A1 | 1/2006 | Wilson et al. |
| 2006/0002974 A1 | 1/2006 | Pacetti et al. |
| 2006/0020325 A1 | 1/2006 | Burgermeister et al. |
| 2006/0030652 A1 | 2/2006 | Adams et al. |
| 2006/0045901 A1 | 3/2006 | Weber et al. |
| 2006/0073329 A1 | 4/2006 | Boyce et al. |

(56) References Cited

U.S. PATENT DOCUMENTS

| | | |
|---|---|---|
| 2006/0089705 A1 | 4/2006 | Ding et al. |
| 2006/0093771 A1 | 5/2006 | Rypacek et al. |
| 2006/0094744 A1 | 5/2006 | Maryanoff et al. |
| 2006/0106455 A1 | 5/2006 | Furst et al. |
| 2006/0116755 A1 | 6/2006 | Stinson |
| 2006/0121080 A1 | 6/2006 | Lye et al. |
| 2006/0121089 A1 | 6/2006 | Michal et al. |
| 2006/0134168 A1 | 6/2006 | Chappa et al. |
| 2006/0134211 A1 | 6/2006 | Lien et al. |
| 2006/0136041 A1 | 6/2006 | Schmid et al. |
| 2006/0147698 A1 | 7/2006 | Carroll et al. |
| 2006/0153729 A1 | 7/2006 | Stinson |
| 2006/0160455 A1 | 7/2006 | Sugyo et al. |
| 2006/0188547 A1 | 8/2006 | Bezwada |
| 2006/0193886 A1 | 8/2006 | Owens et al. |
| 2006/0193890 A1 | 8/2006 | Owens et al. |
| 2006/0198868 A1 | 9/2006 | DeWitt et al. |
| 2006/0210638 A1 | 9/2006 | Liversidge et al. |
| 2006/0216324 A1 | 9/2006 | Stucke et al. |
| 2006/0222756 A1 | 10/2006 | Davila et al. |
| 2006/0228415 A1 | 10/2006 | Oberegger et al. |
| 2006/0228453 A1 | 10/2006 | Cromack et al. |
| 2006/0276877 A1 | 12/2006 | Owens et al. |
| 2006/0287611 A1 | 12/2006 | Fleming |
| 2007/0009564 A1 | 1/2007 | McClain et al. |
| 2007/0009664 A1 | 1/2007 | Fallais et al. |
| 2007/0026042 A1 | 2/2007 | Narayanan |
| 2007/0032864 A1 | 2/2007 | Furst et al. |
| 2007/0038227 A1 | 2/2007 | Massicotte et al. |
| 2007/0038289 A1 | 2/2007 | Nishide et al. |
| 2007/0059350 A1 | 3/2007 | Kennedy et al. |
| 2007/0065478 A1 | 3/2007 | Hossainy |
| 2007/0110888 A1 | 5/2007 | Radhakrishnan et al. |
| 2007/0123973 A1 | 5/2007 | Roth et al. |
| 2007/0123977 A1 | 5/2007 | Cottone et al. |
| 2007/0128274 A1 | 6/2007 | Zhu et al. |
| 2007/0148251 A1 | 6/2007 | Hossainy et al. |
| 2007/0154513 A1 | 7/2007 | Atanasoska et al. |
| 2007/0154554 A1 | 7/2007 | Burgermeister et al. |
| 2007/0196242 A1 | 8/2007 | Boozer et al. |
| 2007/0196423 A1 | 8/2007 | Ruane et al. |
| 2007/0198081 A1 | 8/2007 | Castro et al. |
| 2007/0200268 A1 | 8/2007 | Dave |
| 2007/0203569 A1 | 8/2007 | Burgermeister et al. |
| 2007/0225795 A1 | 9/2007 | Granada et al. |
| 2007/0259017 A1 | 11/2007 | Francis |
| 2007/0280992 A1 | 12/2007 | Margaron et al. |
| 2008/0030066 A1 | 2/2008 | Mercier et al. |
| 2008/0051866 A1 | 2/2008 | Chen et al. |
| 2008/0065192 A1 | 3/2008 | Berglund |
| 2008/0071347 A1 | 3/2008 | Cambronne |
| 2008/0071358 A1 | 3/2008 | Weber et al. |
| 2008/0071359 A1 | 3/2008 | Thornton et al. |
| 2008/0075753 A1 | 3/2008 | Chappa |
| 2008/0077232 A1 | 3/2008 | Nishide |
| 2008/0085880 A1 | 4/2008 | Viswanath et al. |
| 2008/0095919 A1 | 4/2008 | McClain et al. |
| 2008/0097575 A1* | 4/2008 | Cottone ............ 623/1.13 |
| 2008/0097591 A1 | 4/2008 | Savage et al. |
| 2008/0098178 A1 | 4/2008 | Veazey et al. |
| 2008/0107702 A1 | 5/2008 | Jennissen |
| 2008/0118543 A1 | 5/2008 | Pacetti et al. |
| 2008/0124372 A1 | 5/2008 | Hossainy et al. |
| 2008/0138375 A1 | 6/2008 | Yan et al. |
| 2008/0206304 A1 | 8/2008 | Lindquist et al. |
| 2008/0213464 A1 | 9/2008 | O'Connor |
| 2008/0233267 A1 | 9/2008 | Berglund |
| 2008/0255510 A1 | 10/2008 | Wang |
| 2008/0269449 A1 | 10/2008 | Chattopadhyay et al. |
| 2008/0292776 A1 | 11/2008 | Dias et al. |
| 2008/0300669 A1 | 12/2008 | Hossainy |
| 2008/0300689 A1 | 12/2008 | Mc Kinnon et al. |
| 2009/0043379 A1 | 2/2009 | Prescott |
| 2009/0062909 A1 | 3/2009 | Taylor et al. |
| 2009/0068266 A1 | 3/2009 | Raheja et al. |
| 2009/0076446 A1 | 3/2009 | Dubuclet et al. |
| 2009/0082855 A1 | 3/2009 | Borges et al. |
| 2009/0098178 A1 | 4/2009 | Hofmann et al. |
| 2009/0105687 A1 | 4/2009 | Deckman et al. |
| 2009/0105809 A1 | 4/2009 | Lee et al. |
| 2009/0110711 A1 | 4/2009 | Trollsas et al. |
| 2009/0111787 A1 | 4/2009 | Lim et al. |
| 2009/0123515 A1 | 5/2009 | Taylor et al. |
| 2009/0186069 A1 | 7/2009 | DeYoung et al. |
| 2009/0202609 A1 | 8/2009 | Keough et al. |
| 2009/0216317 A1 | 8/2009 | Cromack et al. |
| 2009/0227949 A1 | 9/2009 | Freyman et al. |
| 2009/0231578 A1 | 9/2009 | Ling et al. |
| 2009/0263460 A1 | 10/2009 | McDonald |
| 2009/0285974 A1 | 11/2009 | Kerrigan |
| 2009/0292351 A1 | 11/2009 | McClain et al. |
| 2009/0297578 A1 | 12/2009 | Trollsas et al. |
| 2010/0000328 A1 | 1/2010 | Mahmoud |
| 2010/0006358 A1 | 1/2010 | Ishikawa |
| 2010/0015200 A1 | 1/2010 | McClain et al. |
| 2010/0030261 A1 | 2/2010 | McClain et al. |
| 2010/0042206 A1 | 2/2010 | Yadav et al. |
| 2010/0055145 A1 | 3/2010 | Betts et al. |
| 2010/0055294 A1 | 3/2010 | Wang et al. |
| 2010/0063570 A1 | 3/2010 | Pacetti et al. |
| 2010/0063580 A1 | 3/2010 | McClain et al. |
| 2010/0074934 A1 | 3/2010 | Hunter |
| 2010/0131044 A1 | 5/2010 | Patel |
| 2010/0155496 A1 | 6/2010 | Stark et al. |
| 2010/0166869 A1 | 7/2010 | Desai et al. |
| 2010/0196482 A1 | 8/2010 | Radovic-Moreno et al. |
| 2010/0198330 A1 | 8/2010 | Hossainy et al. |
| 2010/0198331 A1 | 8/2010 | Rapoza et al. |
| 2010/0211164 A1 | 8/2010 | McClain et al. |
| 2010/0228348 A1 | 9/2010 | McClain et al. |
| 2010/0233332 A1 | 9/2010 | Xing et al. |
| 2010/0239635 A1 | 9/2010 | McClain et al. |
| 2010/0241220 A1 | 9/2010 | McClain et al. |
| 2010/0256746 A1 | 10/2010 | Taylor et al. |
| 2010/0256748 A1 | 10/2010 | Taylor et al. |
| 2010/0272775 A1 | 10/2010 | Cleek et al. |
| 2010/0272778 A1 | 10/2010 | McClain et al. |
| 2010/0298928 A1 | 11/2010 | McClain et al. |
| 2010/0305689 A1 | 12/2010 | Venkatraman et al. |
| 2011/0009953 A1 | 1/2011 | Luk et al. |
| 2011/0034422 A1 | 2/2011 | Kannan et al. |
| 2011/0159069 A1 | 6/2011 | Shaw et al. |
| 2011/0160751 A1 | 6/2011 | Granja Filho |
| 2011/0172763 A1 | 7/2011 | Ndondo-Lay |
| 2011/0190864 A1 | 8/2011 | McClain et al. |
| 2011/0223212 A1 | 9/2011 | Taton et al. |
| 2011/0238161 A1 | 9/2011 | Fulton et al. |
| 2011/0257732 A1 | 10/2011 | McClain et al. |
| 2011/0264190 A1 | 10/2011 | McClain et al. |
| 2011/0301697 A1 | 12/2011 | Hoffmann et al. |
| 2012/0064124 A1 | 3/2012 | McClain et al. |
| 2012/0064143 A1 | 3/2012 | Sharp et al. |
| 2012/0065723 A1 | 3/2012 | Drasler et al. |
| 2012/0101566 A1 | 4/2012 | Mews et al. |
| 2012/0150275 A1 | 6/2012 | Shaw-Klein |
| 2012/0160408 A1 | 6/2012 | Clerc et al. |
| 2012/0172787 A1 | 7/2012 | McClain et al. |
| 2012/0177742 A1 | 7/2012 | McClain et al. |
| 2012/0271396 A1 | 10/2012 | Zheng et al. |
| 2012/0280432 A1 | 11/2012 | Chen et al. |
| 2012/0323311 A1 | 12/2012 | McClain et al. |
| 2013/0006351 A1 | 1/2013 | Taylor et al. |
| 2013/0035754 A1 | 2/2013 | Shulze et al. |
| 2013/0087270 A1 | 4/2013 | Hossainy et al. |
| 2013/0172853 A1 | 7/2013 | McClain et al. |
| 2014/0343667 A1 | 11/2014 | McClain |
| 2014/0350522 A1 | 11/2014 | McClain |
| 2014/0371717 A1 | 12/2014 | McClain |

(56) References Cited

U.S. PATENT DOCUMENTS

| | | |
|---|---|---|
| 2015/0024116 A1 | 1/2015 | Matson et al. |
| 2015/0025620 A1 | 1/2015 | Taylor et al. |

FOREIGN PATENT DOCUMENTS

| | | |
|---|---|---|
| CA | 2615452 | 1/2007 |
| CA | 2650590 A1 | 11/2007 |
| CA | 2679712 | 7/2008 |
| CA | 2684482 A1 | 10/2008 |
| CA | 2721832 A1 | 12/2009 |
| CN | 2423899 Y | 3/2001 |
| CN | 1465410 | 1/2004 |
| CN | 1575860 A | 2/2005 |
| CN | 1649551 | 8/2005 |
| CN | 1684641 A | 10/2005 |
| DE | 4336209 A1 | 3/1995 |
| DE | 29702671 U1 | 4/1997 |
| DE | 29716476 U1 | 12/1997 |
| DE | 19633901 A1 | 2/1998 |
| DE | 29716467 U1 | 2/1998 |
| DE | 19740506 A1 | 3/1998 |
| DE | 19754870 A1 | 8/1998 |
| DE | 19822157 A1 | 11/1999 |
| DE | 69611186 T2 | 5/2001 |
| EP | 0335341 | 10/1989 |
| EP | 0604022 | 6/1994 |
| EP | 800801 A1 | 10/1997 |
| EP | 0876806 A1 | 11/1998 |
| EP | 0982041 | 3/2000 |
| EP | 1195822 A2 | 4/2002 |
| EP | 1325758 A2 | 6/2002 |
| EP | 1327422 A1 | 7/2003 |
| EP | 1454677 | 9/2004 |
| EP | 1502655 A2 | 2/2005 |
| EP | 1909973 A2 | 4/2008 |
| EP | 2197070 A1 | 6/2010 |
| EP | 2293357 A1 | 3/2011 |
| EP | 2293366 A1 | 3/2011 |
| FR | 2758253 A1 | 7/1998 |
| JP | 1994-098902 | 4/1994 |
| JP | H06218063 A | 8/1994 |
| JP | H08206223 A | 8/1996 |
| JP | H09-056807 | 3/1997 |
| JP | H1029524 A | 2/1998 |
| JP | H10151207 A | 6/1998 |
| JP | H10314313 A | 12/1998 |
| JP | H1157018 A | 3/1999 |
| JP | 2000316981 A | 11/2001 |
| JP | 2001521503 A | 11/2001 |
| JP | 2003533493 | 11/2001 |
| JP | 2003-205037 | 7/2003 |
| JP | 2003-533286 | 11/2003 |
| JP | 2003533492 | 11/2003 |
| JP | 2004512059 A | 4/2004 |
| JP | 2004/173770 | 6/2004 |
| JP | 2004-518458 | 6/2004 |
| JP | 2004-529674 | 9/2004 |
| JP | 2004528060 A | 9/2004 |
| JP | 2005-505318 | 2/2005 |
| JP | 2005519080 A | 6/2005 |
| JP | 2005-523119 | 8/2005 |
| JP | 2005-523332 | 8/2005 |
| JP | 2005-296690 | 10/2005 |
| JP | 2006506191 A | 2/2006 |
| JP | 2006512175 A | 4/2006 |
| JP | 2007502281 A | 2/2007 |
| JP | 2009-501566 | 1/2009 |
| JP | 2010052503 A | 3/2010 |
| KR | 1020040034064 | 4/2004 |
| WO | 9409010 A1 | 4/1994 |
| WO | WO-95/06487 | 3/1995 |
| WO | 9616691 A1 | 6/1996 |
| WO | WO-96/20698 | 7/1996 |
| WO | WO-96/32907 | 10/1996 |
| WO | 9641807 A1 | 12/1996 |
| WO | WO-97/45502 | 12/1997 |
| WO | 9802441 A2 | 1/1998 |
| WO | WO-99/08729 A1 | 2/1999 |
| WO | 9915530 A1 | 4/1999 |
| WO | 9916388 A1 | 4/1999 |
| WO | 9917680 A1 | 4/1999 |
| WO | 0006051 A1 | 2/2000 |
| WO | 0025702 A1 | 5/2000 |
| WO | WO-00/32238 A1 | 6/2000 |
| WO | 0114387 A1 | 3/2001 |
| WO | WO-01/54662 | 8/2001 |
| WO | 0187345 A1 | 11/2001 |
| WO | WO-01/87368 | 11/2001 |
| WO | WO-01-87371 | 11/2001 |
| WO | WO-01/87372 | 11/2001 |
| WO | WO-02/40702 | 5/2002 |
| WO | WO 02/43799 | 6/2002 |
| WO | 02055122 A1 | 7/2002 |
| WO | WO-02/074194 A2 | 9/2002 |
| WO | WO-02/090085 | 11/2002 |
| WO | WO-02/100456 | 12/2002 |
| WO | WO-03/039553 | 5/2003 |
| WO | WO-03-082368 A | 10/2003 |
| WO | 03090684 A2 | 11/2003 |
| WO | WO-03/101624 A1 | 12/2003 |
| WO | WO-2004/009145 | 1/2004 |
| WO | 2004028406 A1 | 4/2004 |
| WO | WO-2004/028589 | 4/2004 |
| WO | WO-2004/043506 | 5/2004 |
| WO | WO-2004/045450 | 6/2004 |
| WO | WO-2004/098574 | 11/2004 |
| WO | WO-2005-042623 A1 | 5/2005 |
| WO | WO-2005/063319 | 7/2005 |
| WO | WO-2005/069889 | 8/2005 |
| WO | WO-2005-117942 A2 | 12/2005 |
| WO | WO-2006/014534 | 2/2006 |
| WO | WO-2006/052575 | 5/2006 |
| WO | 2006063430 A1 | 6/2006 |
| WO | WO-2006/065685 | 6/2006 |
| WO | WO-2006-083796 A2 | 8/2006 |
| WO | WO-2006-099276 A2 | 9/2006 |
| WO | 2007017707 A2 | 1/2007 |
| WO | 2007017708 A3 | 1/2007 |
| WO | WO-2007-002238 | 1/2007 |
| WO | WO-2007-011707 A2 | 1/2007 |
| WO | WO-2007-011707 A3 | 1/2007 |
| WO | WO-2007-011708 A2 | 1/2007 |
| WO | WO-2007-011708 A3 | 1/2007 |
| WO | WO-2007-127363 A2 | 1/2007 |
| WO | WO 2007011707 A2 * | 1/2007 |
| WO | WO-2007/092179 | 8/2007 |
| WO | WO 2007/143609 | 12/2007 |
| WO | WO-2008/042909 | 4/2008 |
| WO | WO-2008-046641 A2 | 4/2008 |
| WO | WO-2008-046642 A1 | 4/2008 |
| WO | WO-2008/052000 | 5/2008 |
| WO | WO-2008/070996 | 6/2008 |
| WO | WO 2008/086369 | 7/2008 |
| WO | WO-2008-131131 A1 | 10/2008 |
| WO | WO-2008/0148013 | 12/2008 |
| WO | 2009039553 A1 | 4/2009 |
| WO | WO-2009/051614 | 4/2009 |
| WO | WO 2009/051780 | 4/2009 |
| WO | WO-2009/146209 | 12/2009 |
| WO | WO 2010/009335 | 1/2010 |
| WO | WO-2010/075590 | 7/2010 |
| WO | WO-2010-111196 A2 | 9/2010 |
| WO | WO-2010-111196 A3 | 9/2010 |
| WO | WO-2010-111232 A3 | 9/2010 |
| WO | WO-2010-111232 A9 | 9/2010 |
| WO | WO-2010-111238 A2 | 9/2010 |
| WO | WO-2010-111238 A3 | 9/2010 |
| WO | WO-2010-120552 A2 | 10/2010 |
| WO | WO-2010-120552 A3 | 10/2010 |
| WO | WO-2010-121187 A2 | 10/2010 |
| WO | WO-2010-121187 A3 | 10/2010 |
| WO | WO-2010/136604 A1 | 12/2010 |
| WO | WO-2011-009096 A1 | 1/2011 |
| WO | WO-2011/097103 | 8/2011 |

(56) References Cited

FOREIGN PATENT DOCUMENTS

| | | |
|---|---|---|
| WO | WO-2011/119762 | 9/2011 |
| WO | WO-2011/133655 | 10/2011 |
| WO | WO-20111130448 | 10/2011 |
| WO | WO-2012/009684 | 1/2012 |
| WO | WO-2012/034079 | 3/2012 |
| WO | WO-2012/082502 | 6/2012 |
| WO | WO-2012/092504 | 7/2012 |
| WO | WO-2012/142319 | 10/2012 |
| WO | WO-2012/166819 | 12/2012 |
| WO | WO-2013/012689 | 1/2013 |
| WO | WO-2013/025535 | 2/2013 |
| WO | WO-2013/059509 | 4/2013 |
| WO | WO-2013/173657 | 11/2013 |
| WO | WO-2013/177211 | 11/2013 |
| WO | WO-2014/063111 | 4/2014 |
| WO | WO-2014/165264 | 10/2014 |
| WO | WO-2014/186532 | 11/2014 |

OTHER PUBLICATIONS

Schmidt et al., "Trackability, Crossability, and Pushability of Coronary Stent Systems—An Experimental Approach," Biomed Techn 47 (2002), Erg. 1, S. 124-126.
Schmidt et al., "In vitro measurement of quality parameters of stent-catheter systems," Biomed Techn 50(S1):1505-1506 (2005).
PCT/US10/42355 Search Report mailed Sep. 2, 2010.
PCT/US10/28253 Search Report and Written Opinion mailed Dec. 6, 2010.
PCT/US10/28265 Search Report and Written Opinion mailed Dec. 13, 2010.
PCT/US10/31470 Search Report and Written Opinion mailed Jan. 28, 2011.
PCT/US10/29494 Search Report and Written Opinion mailed Feb. 7, 2011.
PCT/US11/22623 Search Report and Written Opinion mailed Mar. 28, 2011.
U.S. Appl. No. 11/995,685 Office Action Mailed Aug. 20, 2010.
U.S. Appl. No. 11/995,685 Office Action Mailed Nov. 24, 2009.
U.S. Appl. No. 11/158,724 Office Action Mailed Sep. 17, 2009.
PCT/US09/50883 Search Report dated Nov. 17, 2009.
PCT/US10/42355 Search Report and Written Opinion dated Sep. 2, 2010.
Serruys, Patrick et al., Comparison of Coronary-Artery Bypass Surgery and Stenting for the Treatment of Multivessel Disease, N. Engl. J. Med., 2001, vol. 344, No. 15, pp. 1117-1124.
PCT/US2011/032371, International Search Report dated Jul. 7, 2011.
Domingo, C. et al., "Precipication of ultrafine organic crystals from the rapid expansion of supercritical solutions over a capillary and a frit nozzle," J. Supercritical Fluids 10:39-55 (1997).
Mario et al., "Drug-Eluting Bioabsorbable Magnesium Stent," J. Inverventional Cardiology 16(6):391=395 (2004).
McAlpine, J.B. et al., "Revised NMR Assignments for Rapamycine," J. Antibiotics 44:688-690 (1991).
Ong and Serruys, "Technology Insight: an overview of research in drug-eluting stents," Nat. Clin. Parct. Cardiovas. Med. 2(12):647-658 (2005).
PCT/US06/24221 Search Report mailed Jan. 29, 2007.
PCT/US06/27321 Search Report mailed Oct. 16, 2007.
PCT/US06/27322 Search Report mailed Apr. 25, 2007.
PCT/US07/10227 Search Report mailed Aug. 8, 2008.
PCT/US07/80213 Search Report dated Apr. 16, 2008.
PCT/US07/82275 Search Report dated Apr. 18, 2008.
PCT/US08/11852 Search Report dated Dec. 19, 2008.
PCT/US08/50536 Search Report dated Jun. 2, 2008.
PCT/US08/60671 Search Report dated Sep. 5, 2008.
PCT/US08/64732 Search Report dated Sep. 4, 2008.
PCT/US09/41045 Search Report dated Aug. 11, 2009.

Akoh et al., "One-Stage Synthesis of Raffinose Fatty Acid Polyesters." Journal Food Science (1987) 52:1570.
Albert et al., "Antibiotics for preventing recurrent urinary tract infection in non-pregnant women," Cochrane Database System Rev. 3, CD001209 (2004).
Au et al., "Methods to improve efficacy of intravesical mitomycin C: Results of a randomized phase III trial," Journal of the National Cancer Institute, 93(8), 597-604 (2001).
AU2007243268 Exam Report dated Aug. 31, 2011.
AU2009251504 Exam Report dated Dec. 8, 2011.
AU2009270849 Exam Report dated Feb. 14, 2012.
Balss et al., "Quantitative spatial distribution of sirolumus and polymers in drug-eluting stents using confocal Raman microscopy," J. of Biomedical Materials Research Part A, 258-270 (2007).
Belu et al., "Three-Dimensional Compositional Analysis of Drug Eluting Stent Coatings Using Cluster Secondary Ioan Mass Spectroscopy," Anal. Chem. 80:624-632 (2008).
Belu, et al., "Chemical imaging of drug eluting coatings: Combining surface analysis and confocal Rama microscopy" J. Controlled Release 126: 111-121 (2008).
Boneff, "Topical Treatment of Chronic Prostatitis and Premature Ejaculation," International Urology and Nephrology 4(2):183-186 (1971).
Bookbinder et al., "A recombinant human enzyme for enhanced interstitial transport of therapeutics," Journal of Controlled Release 114:230-241 (2006).
Borchert et al., "Prevention and treatement of urinary tract infection with probiotics: Review and research perspective," Indian Journal Urol. 24(2):139-144 (2008).
Brunstein et al., "Histamine, a vasoactive agent with vascular disrupting potential improves tumour response by enhancing local drug delivery," British Journal of Cancer 95:1663-1669 (2006).
Bugay et al., "Raman Analysis of Pharmaceuticals," in "Applications of Vibrational Spectroscopy in Pharmaceutical Research and Development," Ed. Pivonka, D.E., Chalmers, J.M., Griffiths, P.R. (2007) Wiley and Sons.
CA 2615452 Office Action dated Dec. 19, 2012.
CA 2684482 Office Action Jul. 11, 2012.
CA 2684482 Office Action dated Nov. 10, 2011.
CA 2688314 Office Action dated Jun. 6, 2012.
CA 2730995 Office Action dated Sep. 26, 2012.
Cadieux et al., "Use of triclosan-eluting ureteral stents in patients with long-term stents," J. Endourol (Epub) (Jun. 19, 2009).
Channon et al., "Nitric Oxide Synthase in Atherosclerosis and Vascular Injury: Insights from Experimental Gene Therapy," Arteriosclerosis, Thrombosis and Vascular Biology, 20(8):1873-1881 (2000).
Chen et al. Immobilization of heparin on a silicone surface through a heterobifunctional PEG spacer. Biomaterials. Dec. 2005;26(35):7418-24.
Clair and Burks, "Thermoplastic/Melt-Processable Polyimides," NASA Conf. Pub. #2334 (1984), pp. 337-355.
CN 2006800258093 Office Action dated May 30, 2012.
CN 200880007308.1 Office Action dated Nov. 23, 2011.
CN 200880007308.1 Office Action dated Oct. 18, 2012.
CN 200880020515 Office Action dated Oct. 9, 2012.
CN 200880100102.3 Office Action dated Jun. 1, 2012.
CN 200980122691 Office Action dated Oct. 10, 2012.
CN 200780047425.6 Office action dated Aug. 3, 2012.
CRC Handbook of chemistry and physics. 71st ed. David R. Lide, Editor-in-Chief. Boca Raton, FL, CRC Press; 1990; 6-140.
Cyrus et al., "Intramural delivery of rapamycin with alphavbeta3-targeted paramagnetic nanoparticles inhibits stenosis after balloon injury," Arterioscler Thromb Vase Biol 2008;28:820-826.
Derwent-Acc-No. 2004-108578 Abstracting 2004003077; Jan. 8, 2004; 3 pages.
DiStasi et al., "Percutaneous sequential bacillus Calmette-Guerin and mitomycin C for panurothelial carcinomatosis," Can. J. Urol. 12(6):2895-2898 (2005).
Domb and Langer, "Polyanhydrides. I. Preparation of High Molecular Weight Polyanhydrides. " J. Polym Sci. 25:3373-3386 (1987).
Dzik-Jurasz, "Molecular imaging in vivo: an introduction," The British Journal of Radiology, 76:S98-S109 (2003).

(56) References Cited

OTHER PUBLICATIONS

EA 200901254/28 Office Action dated Jul. 18, 2012.
Electrostatic Process, Wiley Encyclopedia of Electrical and Electronics Engineering, John Wiley & Sons, Inc. 1999; 7:15-39.
Eltze et al., "Imidazoquinolinon, imidazopyridine, and isoquinolindione derivatives as novel and potent inhibitors of the poly (ADP-ribose) polymerase (PARP): a comparison with standard PARP inhibitors," Mol. Pharmacal 74(6):1587-1598 (2008).
EP06773731.2 Search Report dated Oct. 2, 2012.
EP06787258.0 Search Report dated Feb. 6, 2012.
EP07756094.4 Search Report dated Aug. 31, 2012.
EP08733210.2 Search Report dated Oct. 23, 2012.
EP08756215.3 Search Report dated Oct. 5, 2011.
Ettmayer et al. Lessons learned from marketed and investigational prodrugs. J Med Chem. May 6, 2004;47(10):2393-404.
Fibbi et al., "Chronic inflammation in the pathogenesis of benign prostatic hyperplasia," Int J Androl. Jun. 1, 2010;33(3):475-88.
Fleischmann et al., "High Expression of Gastrin-Releasing Peptide Receptors in the Vascular bed of Urinary Tract Cancers: Promising Candidates for Vascular Targeting Applications." Jun. 2009, Endocr. Relat. Cancer 16(2):623-33.
Froehlich et al., "Conscious sedation for gastroscopy: patient tolerance and cardiorespiratory parameters," Gastroenterology 108(3):697-704 (1995).
Fujiwara et al., "Insulin-like growth factor 1 treatment via hydrogels rescues cochlear hair cells from ischemic injury," Oct. 29, 2008, NeuroReport 19(16):1585-1588.
Fulton et al. Thin Fluoropolymer films and nanoparticle coatings from the rapid expansion of supercritical carbon dioxide solutions with electrostatic collection, Polymer Communication. 2003; 2627-3632.
Green et al., "Simple conjugated polymer nanoparticles as biological labels," Proc Roy Soc A. published online Jun. 24, 2009 doi:10.1098/rspa.2009.0181.
Griebenow et al., "On Protein Denaturation in Aqueous-Organic Mixtures but not in Pure Organic Solvents," J. Am Chem Soc., vol. 118. No. 47, 11695-11700 (1996).
Hamilos et al., "Differential effects of Drug-Eluting Stents on Local Endothelium-Dependent Coronary Vasomotion." JACC vol. 51, No. 22, 2008, Endothelium and DES Jun. 3, 2008:2123-9.
Hartmann et al., "Tubo-ovarian abscess in virginal adolescents: exposure of the underlying etiology," J. Pediatr Adolesc Gynecol, 22(3):313-16 (2009).
Hasegawa et al., "Nylong 6/Na-montmorillonite nanocomposites prepared by compounding Nylon 6 with Na-montmorillonite slurry," Polymer 44 (2003) 2933-2937.
Hinds, WC. Aerosol Technology, Properties, Behavior and Measurement of Airborne Particles, Department of Environmental Health Sciences, Harvard University School of Public Health, Boston, Massachusetts. 1982; 283-314.
Hladik et al., "Can a topical microbicide prevent rectal HIV transmission?" PLoS Med. 5(8):e167 (2008).
Iconomidou et al., "Secondary Structure of Chorion Proteins of the Teleosatan Fish Dentex dentex by ATR FR-IR and FT-Raman Spectroscopy," J. of Structural Biology, 132, 112-122 (2000).
Jackson et al., "Characterization of perivascular poly(lactic-co-glycolic acid) films containing paclitaxel" *Int. J. of Pharmaceutics*, 283:97-109 (2004), incorporated in its entirety herein by reference.
Jensen et al., Neointimal hyperplasia after sirollmus-eluting and paclitaxel-eluting stend implantation in diabetic patients: the randomized diabetes and drug eluting stent (DiabeDES) intravascular ultrasound trial. European heart journal (29), pp. 2733-2741. Oct. 2, 2008. Retrieved from the Internet. Retrieved on [Jul. 17, 2012]. URL:<http://eurheartj.oxfordjournals.org/content/29/22/2733.full.pdf> entire document.
Jewell, et aL, "Release of Plasmid DNA from Intravascular Stents Coated with Ultrathin Multilayered Polyelectrolyte Films" *Biomacromolecules*. 7: 2483-2491 (2006).
Johns, H.E, J.R.Cunningham, Thomas, Charles C., Publisher, "The Physics of Radiology, " 1983, Springfield, IL, pp. 133-143.

Joner et al. "Site-specific targeting of nanoparticle prednisolone reduces in-stent restenosis in a rabbit model of established atheroma," Arterioscler Thromb Vase Biol. 2008;28:1960-1966.
Mei et al., "Local Delivery of Modified Paclitaxel-Loaded Poly(ε-caprolactone)/Pluronic F68 Nanoparticles for Long-Term Inhibition of Hyperplasia," Journal of Pharmaceutical Sciences, vol. 98, No. 6, Jun. 2009.
Jovanovic et al. "Stabilization of Proteins in Dry Powder Formulations Using Supercritical Fluid Technology," Pharm. Res. 2004; 21(11).
JP 2008-521633 Office Action dated Oct. 12, 2012.
JP2008-521633 Office Action dated Dec. 28, 2011.
JP-2009-534823 Office Action dated Sep. 20, 2012.
JP-2009-534823 Office Action dated Feb. 21, 2012.
JP-2010-504253 Office Action dated Dec. 12, 2011.
JP-2010-504253 Office Action dated Dec. 7, 2012.
JP-2011-518920 Office action dated Dec. 17, 2012.
Kazemi et al., "The effect of betamethasone gel in reducing sore throat, cough, and hoarseness after laryngo-tracheal intubation," Middle East J. Anesthesiol, 19(1):197-204 (2007).
Kehinde et al., "Bacteriology of urinary tract infection associated with indwelling J ureteral stents," J. Endourol. 18(9):891-896 (2004).
Kelly et al., "Double-balloon trapping technique for embolization of a large wide-necked superior cerebellar artery aneurysm: case report," Neurosurgery 63(4 Suppl 2):291-292 (2008).
Khan et al., "Cyclic Acetals of 4,1',6'-Trichloro-4,1',6',-Trideoxy-Trideoxy-galacto-Sucrose and their Conversion into Methyl Ether Derivatives." Carb. Res. (1990) 198:275-283.
Khan et al., "Chemistry and the new uses of Sucrose: How Important?" Pur and Appl. Chem (1984) 56:833-844.
Khan et al., "Enzymic Regioselective Hydrolysis of Peracetylated Reducing Disaccharides, Specifically at the Anomeric Centre: Intermediates for the Synthesis of Oligosaccharides." Tetrahedron Letters (1933) 34:7767.
Khayankarn et al., "Adhesion and Permeability of Polyimide-Clay Nanocomposite Films for Protective Coatings," Journal of Applied Polymer Science, vol. 89, 2875-2881 (2003).
Kurt et al., "Tandem oral, rectal and nasal administrations of Ankaferd Blood Stopper to control profuse bleeding leading to hemodynamic instability," Am J. Emerg. Med. 27(5):631, el-2 (2009).
Labhasetwar et al., "Arterial uptake of biodegradable nanoparticles: effect of surface modifications," Journal of Pharmaceutical Sciences, vol. 87, No. 10, Oct. 1998; 1229-1234.
Lamm et al., "Bladder Cancer: Current Optimal Intravesical Treatment: Pharmacologic Treatment," Urologic Nursing 25(5):323-6, 331-2 (Oct. 26, 2005).
Lawrence et al., "Rectal tacrolimus in the treatment of resistant ulcerative proctitis," Aliment. Pharmacal Ther. 28(10):1214-20 (2008).
Lehmann et al, "Drug treatment of nonviral sexually transmitted diseases: specific issues in adolescents," Pediatr Drugs 3(7):481-494 (2001.
Mahoney et al., "Three-Dimensional Compositional Analysis of Drug Eluting Stent Coatings Using Cluster Secondary Ion mass Spectrometry," Anal. Chem. , 80, 624-632 (2008).
Mehik et al., "Alfuzosin treatment for chronic prostatitis/chronic pelvic pain syndrome: a prospecitve, randomized, double-blind, placebo-controlled, pilot study," Urology 62(3):425-429 (2003).
Melonakos et al., Treatment of low-grade bulbar transitional cell carcinoma with urethral instillation of mitomycin C, Oct. 28, 2008, Adv. Urol., 173694 Epub.
Merrett et al., "Interaction of corneal cells with transforming growth factor beta2-modified poly dimethyl siloxane surfaces," Journal of Biomedical Materials Research, Part A, vol. 67A, No. 3, pp. 981-993 (2003).
Middleton and Tipton, Synthetic biodegradable polymers as orthopedic devises. Biomaterials 2000; 21:2335-46.
Minchin, "Nanomedicine: sizing up targets with nanoparticles," Nature Nanotechnology, vol. 33, Jan. 2008, 12-13.

(56) References Cited

OTHER PUBLICATIONS

Minoque et al., "Laryngotracheal topicalization with lidocaine before intubation decreases the incidence of coughing on emergence from general anesthesia," Anesth. Analg. 99(4):1253-1257 (2004).
Mishima et al. "Microencapsulation of Proteins by Rapid Expansion of Supercritical Solution with a Nonsolvent," AIChE J. 2000;46(4):857-65.
Mocco et al., "Pharos neurovascular intracranail stent: Elective use for a symptomatic stenosis refractory to medical therapy," Catheter Cardiovasc. Interv. (epub) (Mar. 2009).
Mollen et al., "Prevalence of tubo-ovarian abcess in adolescents diagnosed with pelvice inflammatory disease in a pediatric emergency department," Pediatr. Emerg. Care, 22(9): 621-625 (2006).
Moroni et al., "Post-ischemic brain damage:targeting PARP-1 within the ischemic neurovaschular units as a realistic avenue to stroke treatment," FEBS J. 276(1):36-45 (2009).
Muhlen et al., "Magnetic Resonance Imaging Contrast Agent Targeted Toward Activated Platelets Allows in Vivo Detection of Thrombosis and Monitoring of Thrombolysis Circulation," 118:258-267 (2008).
Murphy et al., "Chronic prostatitis: management strategies," Drugs 69(1): 71-84 (2009_.
NZ 600814 Examination Report dated Jun. 29, 2012.
O'Neil et al., "Extracellular matrix binding mixed micelles for drug delivery applications," Journal of Controlled Release 137 (2009) 146-151.
O'Donnell et al., "Salvage intravesical therapy with interferon-alpha 2b plus low dose bacillus Calmette-Guerin alone perviously failed," Journ. Urology, 166(4):1300-1304 (2001).
Olbert et al., "In vitro and in vivo effects of CpG-Oligodeoxynucleotides (CpG-ODN) on murine transitional cell carcinoma and on the native murine urinary bladder wall," Anticancer Res. 29(6):2067-2076 (2009).
O'Donnell et al., "Salvage intravesical therapy with interferon-alpha 2b plus low dose bacillus Calmette-Guerin alone perviously failed," Bourn. Urology, 166(4):1300-1304 (2001).
PCT/US12/50408 International Search Report mailed Oct. 19, 2012.
PCT/US2012/040040 International Search Report mailed Sep. 7, 2012.
Perry et al., Chemical Engineer's Handbook, 5th Edition, McGraw-Hill, New York, 1973; 20-106.
Torchlin, "Micellar Nanocarriers: Pharmaecutial Perspectives," Pharmaceutical Research, vol. 24, No. 1, Jan. 2007.
Plas et al., "Tubers and tumors: rapamycin therapy for benign and malignant tumors", Curr Opin Cell Bio 21: 230-236, (2009).
Poling et al., The Properties of Gases and Liquids. McGraw-Hill. 2001; 9:1-9.97.
Pontari, "Chronic prostatitis/chronic pelvic pain syndrome in elderly men: toward better understanding and treatment," Drugs Aging 20(15):1111-1115 (2003).
Pontari, "Inflammation and anti-inflammatory therapy in chronic prostatits," Urology 60(6Suppl):29-33 (2002).
Raganath et al., "Hydrogel matrix entrapping PLGA-paclitaxel microspheres: drug delivery with near zero-order release and implantability advantages for malignant brain tumour," Pharm Res (Epub) Jun. 20, 2009).
Ranade et al., "Physical characterization of controlled release of paclitaxel from the TAXUS Express2 drug-eluting stent," J. Biomed Mater. Res. 71(4):625-634 (2004).
Reddy et al., "Inhibition of apoptosis through localized delivery of rapamycin-loaded nanoparticles prevented neointimal hyperplasia and reendothelialized injured artery," Circ Cardiovasc Intery 2008;1;209-216.
Ristikankare et al., "Sedation, topical pharnygeal anesthesia and cardiorespiratory safety during gastroscopy," J. Clin Gastorenterol. 40(1):899-905 (2006).
Salo et al., "Biofilm formation by *Escherichia coli* isolated from patients with urinary tract infections," Clin Nephrol. 71(5):501-507 (2009).
Saxena et al., "Haemodialysis catheter-related bloodstream infections: current treatment options and strategies for prevention," Swiss Med Wkly 135:127-138 (2005).
Schetsky, L. McDonald, "Shape Memory Alloys", Encyclopedia of Chemical Technology (3d Ed), John Wiley & Sons 1982, vol. 20 pp. 726-736.
Scheuffler et al., "Crystal Structure of Human Bone Morphogenetic Protein-2 at 2.7 Angstrom resolution," Journal of Molecular Biology, vol. 287, Issue 1, Mar. 1999, retrieved online at http://www.sciencedirect.com/science/article/pii/S002283699925901.
Sen et al., "Topical heparin: A promising agent for the prevention of tracheal stenosis in airway surgery," J. Surg. Res (Epub ahead of print) Feb. 21, 2009.
SG201007602-4 Written Opinion dated May 25, 2012.
Simpson et al., "Hyaluronan and hyaluronidase in genitourinary tumors." Front Biosci. 13:5664-5680.
Smith et al., "Mitomycin C and the endoscopic treatment of laryngotracheal stenosis: are two applications better than one?" Laryngoscope 119(2):272-283 (2009).
Sumathi et al., "Controlled comparison between betamethasone gel and lidocaine jelly applied over tracheal tube to reduce postoperative sore throat, cough, and hoarseness of voice," Br. J. Anaesth. 100(2):215-218 (2008.
Testa, B. Prodrug research: futile or fertile? Biochem Pharmacol. Dec. 1, 2004;68(11):2097-106.
Merriam-Webster Online Dictionary, obtained onlie at: http://www.merriam-webster.com/dictionary/derivative, downloaded 07 Jul. 5, 2008.
U.S. Appl. No. 11/158,724 Office Action Mailed Sep. 26, 2012.
U.S. Appl. No. 11/877,591 Office Action Mailed Feb. 29, 2012.
U.S. Appl. No. 11/877,591 Office Action Mailed Sep. 21, 2012.
U.S. Appl. No. 11/995,687 Office Action Mailed Apr. 6, 2012.
U.S. Appl. No. 12,298,459 Office Action Mailed Aug. 10, 2011.
U.S. Appl. No. 12/298,459 Office Action mailed Apr. 6, 2012.
U.S. Appl. No. 12/443,959 Office Action Mailed Dec. 13, 2012.
U.S. Appl. No. 12/443,959 Office Action mailed Feb. 15, 2012.
U.S. Appl. No. 12/522,379 Office Action Mailed Dec. 26, 2012.
U.S. Appl. No. 12/595,848 Office Action Mailed Jan. 13, 2012.
U.S. Appl. No. 12/601,101 Office Action Mailed Dec. 27, 2012.
U.S. Appl. No. 12/601,101 Office Action Mailed Mar. 27, 2012.
U.S. Appl. No. 12/648,106 Final Office Action Mailed Sep. 25, 2012.
U.S. Appl. No. 12/648,106 Office Action Mailed Jan. 30, 2012.
U.S. Serial No, 12/729,156 Final Office Action Mailed Oct. 16, 2012.
U.S. Appl. No. 12/729,156 Office Action Mailed Feb. 1, 2012.
U.S. Appl. No. 12/729,580 Office Action Mailed Apr. 10, 2012.
U.S. Appl. No. 12/729,603 Office Action Mailed Mar. 27, 2012.
U.S. Appl. No. 12/751,902 Office Action Mailed Jul. 13, 2012.
Unger et al., "Poly(ethylene carbonate): A thermoelastic and biodegradable biomaterial for drug eluting stent coatings?" Journal fo Controlled Release, vol. 117, Issue 3, 312-321 (2007).
Verma et al., "Effect of surface properties on nanoparticle-cell interactions," *Small 2010*, 6, No. 1, 12-21.
Wagenlehner et al., "A pollen extract (Cernilton) in patients with inflammatory chronic prostatitis/chronic pelvic pain syndrome: a multicentre, randomized, prospective, double-blind, placebo-controlled phase 3 study," Eur Urol 9 (Epub) (Jun. 3, 2009).
Wang et al. Controlled release of sirolimus from a multilayered PLGA stent matrix. Biomaterials 2000; 27:5588-95.
Wang et al., "Treatment with melagatran alone or in combination with thrombolytic therapy reduced ischemic brain injury," Exp. Neural 213(1):171-175 (2008).
Warner et al., "Mitomycin C and airway surgery: how well does it work?" Ontolaryngol Head Neck Surg. 138(6):700-709 (2008).
Wermuth, CG Similarity in drugs: reflections on analogue design. Drug Discov Today. Apr. 2006;11(7-8):348-54.
Witjes et al., "Intravesical pharmacotherapy for non-muscle-invasive bladder cancer: a critical analysis of currently available drugs, treatment schedules, and long-term results," Eur. Urol. 53(1):45-52.
Xu et all, "Biodegradation of poly(l-lactide-co-glycolide tube stents in bile" *Polymer Degradation and Stability*. 93:811-817 (2008).

(56) References Cited

OTHER PUBLICATIONS

Xue et al., "Spray-as-you-go airway topical anesthesia in patients with a difficult airway: a randomized, double-blind comparison of 2% and 4% lidocaine," Anesth. Analg. 108(2): 536-543 (2009).
Yepes et al., "Tissue-type plasminogen activator in the ischemic brain: more than a thrombolytic," Trends Neurosci. 32(1):48-55 (2009).
Yousof et al., "Reveratrol exerts its neuroprotective effect by modulating mitochondrial dysfunction and associated cell death during cerebral ischemia," Brain Res. 1250:242-253 (2009).
Zhou et al. Synthesis and Characterization of Biodegradable Low Molecular Weight Aliphatic Polyesters and Their Use in Protein-Delivery Systems. J Appl Polym Sci 2004; 91:1848-56.
PCT/US2007/82775 International Preliminary Report on Patentability dated Apr. 28,2009.
PCT/US09/69603 International Search Report mailed Nov. 5, 2010.
PCT/US10/42355 International Preliminary Report on Patentability dated Jan. 17, 2012.
PCT/US10/28195 International Preliminary Report on Patentability dated Oct. 6, 2011.
Abreu Filho et al., "Influence of metal alloy and the profile of coronary stents in patients with multivessel coronary disease," CLINICS 2011;66(6):985-989.
AU2006270221 Exam Report dated Apr. 6, 2010.
AU2007243268 Exam Report dated May 15, 2013.
AU2011232760 Exam Report dated Apr. 10, 2013.
AU2011256902 Exam Report dated Jun. 13, 2013.
AU2012203203 Exam Report dated Apr. 12, 2013.
AU2012203577 Exam Report dated Jun. 7, 2013.
CA 2757276 Office Action dated Feb. 15, 2013.
CA 2757276 Office Action dated Feb. 5, 2014.
CA 2794704 Office action dated Feb. 7, 2014.
CA 2613280 Office Action dated Oct. 2, 2012.
CA 2615452 Office Action dated Oct. 8, 2013.
CA 2650590 Office action dated Jul. 23, 2013.
CA 2613280 Office action dated Dec. 10, 2013.
CA 2667228 Office action dated Jan. 22, 2014.
CA 2679712 Office action dated Feb. 24, 2014.
CA 2667228 office action dated May 7, 2013.
CA 2730995 Office action dated May 29, 2013.
CA 2730995 Office Action dated Feb. 20, 2014.
CA 2756307 Office action dated Feb. 18, 2013.
CA 2756307 Office action dated Mar. 24,2014.
CA 2756386 Office action dated Mar. 15, 2013.
CA 2756388 Office Action dated Apr. 11, 2013.
CA 2756388 Office Action dated Apr. 14, 2014.
CA 2759015 Office action dated Apr. 8, 2013.
CA 2756386 Office action dated Oct. 24, 2013.
CA 2805631 Office Action dated Jan. 17, 2014.
CA 2823355 Office action dated Apr. 14, 2014.
ChŁopek et al. "The influence of carbon fibres on the resorption time and mechanical properties of the lactide—glycolide co-polymer." J. Biomater. Sci. Polymer Edn, vol. 18, No. 11, pp. 1355-1368 (2007).
CN 200780047425.6 Office action dated Feb. 28, 2013.
CN 200880007308.1 Office Action dated Jul. 3, 2013.
CN 200880007308.1 Office Action dated Jan. 2, 2014.
CN 200880020515 Office Action dated Jul. 22, 2013.
CN 200880020515 Office Action dated Apr. 15, 2014.
CN 200880100102.3 Office Action dated Apr. 11, 2013.
CN 200880100102.3 Office Action dated Dec. 11, 2013.
CN 200980136432.2 Office action dated Jan. 14, 2013.
CN 200980136432.2 Office action dated Nov. 4, 2013.
CN 201080024973.9 Office action dated Dec. 20, 2013.
Cohen, et al. "Sintering Technique for the Preparation of Polymer Matrices for the Controlled Release of Macromolecules." Journal of Pharmaceutical Sciences, vol. 73, No. 8, 1984, p. 1034-1037.
Colombo et al. "Selection of Coronary Stents," Journal of the American College of Cardiology, vol. 40, No. 6, 2002, p. 1021-1033.
Domingo, C. et al., "Precipitation of ultrafine organic crystals from the rapid expansion of supercritical solutions over a capillary and a frit nozzle," J. Supercritical Fluids 10:39-55 (1997).
EA 200901254 Office Action dated Jul. 29, 2013.
EA 201001497 Office Action dated Feb. 11, 2013.
EA 201001497 Office Action dated Jul. 29, 2013.
EP06787258.0 Office Action dated Mar. 15, 2013.
EP07756094.4 Office Action dated Jan. 21, 2014.
EP07756094.4 Office action dated May 29, 2013.
EP08705772.5 Office Action dated Oct. 30, 2013.
EP08733210.2 Office action dated Jul. 16, 2013.
EP08756215.3 Search Report dated Jan. 28, 2013.
EP09755571.8 Office Action dated Dec. 13, 2013.
EP09755571.8 Search Report dated Apr. 9, 2013.
EP09798764.8 Search Report dated Sep. 30, 2013.
EP09805981.9 Office Action dated Feb. 13, 2013.
EP10756676.2 Search Report dated Jan. 31, 2014.
EP10756696.0 Search Report dated Oct. 10, 2013.
EP10764884.2 Search Report dated Oct. 28, 2013.
EP10765295.0 Search Report dated Oct. 17, 2013.
EP11769546.0 Search Report dated Sep. 19, 2013.
EP10800642.0 Search Report dated Mar. 19, 2014.
EP11772624.0 Search Report dated Jun. 5, 2014.
ID-W00201003529 Office action dated Apr. 28, 2014.
IL-208648 Official Notification dated Feb. 9, 2012.
IL-201550 Official Notification dated Dec. 8, 2013.
IN-368/DELNP/2008 Exam Report dated Oct. 17, 2011.
IN-6884DEFNP2009 Office Action dated Oct. 31, 2013.
JP-2009-534823 Office Action dated Apr. 23, 2013.
JP-2009-545647 Office Action dated Jun. 5, 2012.
JP-2009-545647 Office Action dated May 14, 2013.
JP-2009-545647 Office Action dated Apr. 22, 2014.
JP-2010-510441 Office action dated May 7, 2013.
JP-2011-505248 Office action dated Jun. 4, 2013.
JP-2011-518920 Office action dated Oct. 23, 2013.
JP-2012-503677 Office action dated Nov. 1, 2013.
JP-2012-151964 Office Action dated Dec. 10, 2013.
JP-2013-024508 Office Action dated Apr. 24, 2014.
Koh et al., A novel nanostructured poly(lactic-co-glycolic-acid)—multi-walled carbon nanotube composite for blood-contacting applications: Thrombogenicity studies, Acta Biomaterialia 5 (2009): 3411-3422.
KR10-2008-7003756 Office Action dated Sep. 23, 2013.
KR10-2008-7003756 Office Action dated Oct. 30, 2012.
KR10-2013-7031237 Office action dated Mar. 17, 2014.
Lee et al., "Novel therapy for hearing loss: delivery of insulin-like growth factor 1 to the cochlea using gelatin hydrogel," Otol. Neurotol. 28(7):976-81 (2007).
Matsumoto, D, et al. Neointimal Coverage of Sirolimus-Eluting Stents at 6-month Follow-up: Evaluated by Optical Coherence Tomography, European Heart Journal, Nov. 29, 2006; 28:961-967.
MX/a/2010/01148 Office action dated Feb. 11, 2014.
NZ 588549 Examination Report dated Mar. 28, 2011.
PCT/US06/24221 International Preliminary Report on Patentability dated Dec. 24, 2007.
PCT/US06/27321 International Preliminary Report on Patentability dated Jan. 16, 2008.
PCT/US06/27322 International Preliminary Report on Patentability dated Jan. 16, 2008.
PCT/US07/10227 International Preliminary Report on Patentability dated Oct. 28, 2008.
PCT/US07/80213 International Preliminary Report on Patentability dated Apr. 7, 2009.
PCT/US07/82775 International Preliminary Report on Patentability dated Apr. 28, 2009.
PCT/US08/11852 International Preliminary Report on Patentability dated Apr. 20, 2010.
PCT/US08/50536 International Preliminary Report on Patentability dated Jul. 14, 2009.
PCT/US08/50536 International Search Report mailed Jun. 2, 2008.

(56) References Cited

OTHER PUBLICATIONS

PCT/US08/60671 International Preliminary Report on Patentability dated Oct. 20, 2009.
PCT/US08/64732 International Preliminary Report on Patentability dated Dec. 1, 2009.
PCT/US09/41045 International Preliminary Report on Patentability dated Oct. 19, 2010.
PCT/US09/50883 International Preliminary Report on Patentability dated Jan. 18, 2011.
PCT/US09/69603 International Preliminary Report on Patentability dated Jun. 29, 2011.
PCT/US10/28195 International Preliminary Report on Patentability dated Sep. 27, 2011.
PCT/US10/28195 Search Report and Written Opinion mailed Jan. 21, 2011.
PCT/US10/28253 International Preliminary Report on Patentability dated Sep. 27, 2011.
PCT/US10/28265 International Report on Patentability dated Sep. 27, 2011.
PCT/US10/28265 Search Report and Written Opinion mailed Dec. 3, 2010.
PCT/US10/29494 International Preliminary Report on Patentability dated Oct. 4, 2011.
PCT/US10/31470 International Preliminary Report on Patentability dated Oct. 18, 2011.
PCT/US11/032371 International Report on Patentability dated Oct. 16, 2012.
PCT/US11/051092 International Preliminary Report on Patentability dated Mar. 21, 2013.
PCT/US11/051092 International Search Report dated Mar. 27, 2012.
PCT/US11/051092 Written Opinion dated Mar. 27, 2012.
PCT/US11/22623 International Preliminary Report on Patentability dated Aug. 7, 2012.
PCT/US11/29667 International Search Report and Written Opinion mailed Jun. 1, 2011.
PCT/US11/67921 International Preliminary Report on Patentability dated Jul. 11, 2013.
PCT/US11/67921 Search Report and Written Opinion mailed Jun. 22, 2012.
PCT/US12/33367 International Preliminary Report on Patentability dated Oct. 15, 2013.
PCT/US12/33367 International Search Report mailed Aug. 1, 2012.
PCT/US13/41466 International Search Report and Written Opinion dated Oct. 17, 2013.
PCT/US13/42093 International Search Report and Written Opinion dated Oct. 24, 2013.
PCT/US2011/033225 International Search Report and Written Opinion dated Jul. 7, 2011.
PCT/US2012/60896 International Search Report and Written Opinion dated Dec. 28, 2012.
PCT/US2013/065777 International Search Report and Written Opinion dated Jan. 29, 2014.
Putkisto, K. et al. "Polymer Coating of Paper Using Dry Surface Treatment—Coating Structure and Performance", ePlace newsletter, Apr. 12, 2004, vol. 1, No. 8, pp. 1-20.
Sahajanand Medical Technologies (Supralimus Core; Jul. 6, 2008).
Schmidt et al., "A Comparison of the Mechanical Performance Characteristics of Seven Drug-Eluting Stent Systems," Catheterization and Cardiovascular Interventions 73:350-360 (2009).
Schmidt et al., "New aspects of in vitro testing of arterial stents based on the new European standard," EN 14299, [online] (2009), [retrieved on Mar. 10, 2001] http://www.lib0ev.de/pl/pdf/EN14299.pdf (2009).
Schreiber, S.L. et al., "Atomic Structure of the Rapamycin Human Immunophilin FKBP-12 Complex," J. Am. Chem. Soc. 113:7433-7435 (1991).
SG201007602-4 Examination Report dated Feb. 13, 2013.

Shekunov et al. "Crystallization Processes in Pharmaceutical Technology and Drug Delivery Design." Journal of Crystal Growth 211 (2000), pp. 122-136.
Szabadits et al., "Flexibility and trackability of laser cut coronary stent systems," Acta of Bioengineering and Biomechanics 11(3):11-18 (2009).
Thalmann et al., "Long-term experience with bacillus Calmette-Guerin therapy of upper urinary tract transitional cell carcinoma in patients not eligible for surgery," J Urol. 168(4 Pt 1):1381-1385 (2002).
U.S. Appl. No. 11/158,724 Office action Mailed Dec. 31, 2013.
U.S. Appl. No. 11/158,724 Office action Mailed May 23, 2013.
U.S. Appl. No. 11/158,724 Office Action Mailed Sep. 8, 2008.
U.S. Appl. No. 11/158,724 Office Action Mailed Jun. 25, 2014.
U.S. Appl. No. 11/877,591 Final Action dated Nov. 4, 2013.
U.S. Appl. No. 11/877,591 Office Action Mailed Jul. 1, 2013.
U.S. Appl. No. 11/877,591 Office Action Mailed May 7, 2014.
U.S. Appl. No. 11/995,687 Office Action Mailed Sep. 28, 2011.
U.S. Appl. No. 12/298,459 Office Action Mailed Aug. 10, 2011.
U.S. Appl. No. 12/298,459 Office Action Mailed May 31, 2013.
U.S. Appl. No. 12/426,198 Office Action Mailed Feb. 6, 2012.
U.S. Appl. No. 12/426,198 Office Action mailed Feb. 7, 2014.
U.S. Appl. No. 12/426,198 Office Action Mailed Mar. 23, 2011.
U.S. Appl. No. 12/522,379 Office Action Mailed Apr. 8, 2014.
U.S. Appl. No. 12/522,379 Final Office Action Mailed Aug. 28, 2013.
U.S. Appl. No. 12/595,848 Office Action Mailed Oct. 22, 2013.
U.S. Appl. No. 12/601,101 Office Action mailed Feb. 13, 2014.
U.S. Appl. No. 12/601,101 Office action Mailed May 22, 2013.
U.S. Appl. No. 12/648,106 Office Action Mailed Sep. 18, 2013.
U.S. Appl. No. 12/729,156 Office Action Mailed Feb. 13, 2014.
U.S. Appl. No. 12/729,156 Office action Mailed May 8, 2013.
U.S. Appl. No. 12/729,580 Final Action dated Nov. 14, 2013.
U.S. Appl. No. 12/729,580 Office Action Mailed Jan. 22, 2013.
U.S. Appl. No. 12/729,603 Final Office Action Mailed Oct. 10, 2012.
U.S. Appl. No. 12/729,603 Office Action Mailed Jun. 25, 2014.
U.S. Appl. No. 12/738,411 Final Office action Mailed Apr. 11, 2013.
U.S. Appl. No. 12/738,411 Office action Mailed Aug. 21, 2013.
U.S. Appl. No. 12/738,411 Office Action mailed Feb. 6, 2014.
U.S. Appl. No. 12/738,411 Office Action mailed May 30, 2014.
U.S. Appl. No. 12/748,134 Office Action Mailed Jul. 18, 2013.
U.S. Appl. No. 12/751,902 Office Action Mailed Dec. 19, 2013.
U.S. Appl. No. 12/762,007 Final Office action Mailed Oct. 22, 2013.
U.S. Appl. No. 12/762,007 Final Office action Mailed Apr. 30, 2014.
U.S. Appl. No. 13/014,632 Office action Mailed Jan. 10, 2014.
U.S. Appl. No. 13/014,632 Office action Mailed May 8, 2013.
U.S. Appl. No. 13/086,335 Office action Mailed May 22, 2013.
U.S. Appl. No. 13/086,335 Office action Mailed Apr. 4, 2014.
U.S. Appl. No. 13/229,473 Office Action Mailed Jun. 17, 2013.
U.S. Appl. No. 13/340,472 Office action Mailed Apr. 26, 2013.
U.S. Appl. No. 13/340,472 Office action Mailed Jan. 15, 2014.
U.S. Appl. No. 13/384,216 Final Action dated Nov. 6, 2013.
U.S. Appl. No. 13/384,216 Office action Mailed Apr. 24, 2013.
U.S. Appl. No. 13/605,904 Office Action Mailed Jun. 28, 2013.
U.S. Appl. No. 13/605,904 Office Action Mailed Nov. 27, 2012.
U.S. Appl. No. 13/445,723 Office action mailed Mar. 14, 2014.
U.S. Appl. No. 13/090,525 Office action mailed Apr. 11, 2014.
U.S. Appl. No. 11/995,685 Office Action Mailed Jun. 18, 2014.
Wu et al., "Study on the preparation and characterization of biodegradable polylactide/multi-walled carbon nanotubes nanocomposites." Polymer 48 (2007) 4449-4458.
Zilberman et al., Drug-Eluting bioresorbable stents for various applications, Annu Rev Biomed Eng., 2006;8:158-180.
AU2011256902 Office Action dated Jun. 10, 2014.
AU2011256902 Exam Report dated Nov. 11, 2014.
CA 2756386 Office Action dated May 16, 2014.
CA 2759015 Office Action dated Jul. 21, 2014.
CA 2650590 Office action dated Sep. 18, 2014.
CA 2679712 Office Action dated Nov. 20, 2014.
CA 2730995 Office Action dated Nov. 20, 2014.
CN 200880020515 Office action dated Oct. 21, 2014.
CN 200980136432.2 Office action dated Jul. 3, 2014.

(56) References Cited

OTHER PUBLICATIONS

CN 200980136432.2 Office action dated Dec. 24, 2014.
CN 201080024973.9 Office action dated Aug. 7, 2014.
EP09798764.8 Office action dated Jun. 30, 2014.
EP118077601.7 Search Report dated Sep. 17, 2014.
EP12771847.6 Search Report dated Oct. 15, 2014.
IN-311/DELNP/2011 Office Action dated Nov. 20, 2014.
JP 2008-521633 Office Action dated Oct. 3, 2014.
JP-2013-190903 Office Action dated Sep. 2, 2014.
PCT/US2013/042093 IPRP dated Dec. 4, 2014.
PCT/US2014/025017 International Search Report and Written Opinion dated Jul. 7, 2014.
PCT/US2014/038117 International Search Report and Written Opinion dated Oct. 7, 2014.
U.S. Appl. No. 12/426,198 Office Action Mailed Nov. 3, 2014.
U.S. Appl. No. 12/522,379 Office Action mailed Jan. 8, 2015.
U.S. Appl. No. 12/595,848 Office Action Mailed Jun. 3, 2014.
U.S. Appl. No. 12/729,580 Office Action Mailed Sep. 10, 2014.
U.S. Appl. No. 13/086,335 Office Action Mailed Dec. 23, 2014.
U.S. Appl. No. 13/384,216 Office Action mailed Jan. 13, 2015.
U.S. Appl. No. 13/809,324 Restriction Requirement mailed Jan. 13, 2015.
U.S. Appl. No. 14/262,163 Office Action Mailed Dec. 5, 2014.
Han, et al., "Studies of a Novel Human Thrombomodulin Immobilized Substrate: Surface Characterization and Anticoagulation Activity Evaluation." J. Biomater. Sci. Polymer Edn, 2001, 12 (10), 1075-1089.
PCT/US07/82775 International Preliminary Report on Patentablity dated May 5, 2009.
PCT/US11/44263 International Preliminary Report on Patentability dated Jan. 22, 2013.
PCT/US11/44263 International Search Report and Written Opinion dated Feb. 9, 2012.
PCT/US11/51092 International Preliminary Report on Patentability dated Mar. 12, 2013.
PCT/US12/40040 International Search Report mailed Sep. 7, 2012.
PCT/US12/46545 International Search Report mailed Nov. 20, 2012.
PCT/US12/50408 International Search Report and Written Opinion mailed Oct. 16, 2012.
PCT/US13/42093 International Preliminary Report on Patentability dated Nov. 25, 2014.
Analytical Ultracentrifugation of Polymers and Nanoparticles, W. Machtle and L. Borger, (Springer) 2006, p. 41.
Chalmers, et al. (2007) Wiley and Sons.
European International Search Report of PCT/EP01/05736 dated Oct. 24, 2001.
Finn et al. Differential Response of Delayed Healing . . . Circulation vol. 112 (2005) 270-8.
Greco et al. (Journal of Thermal Analysis and Calorimetry, vol. 72 (2003) 1167-1174.).
Handschumacher, R.E. et al., Purine and Pyrimidine Antimetabolites, Chemotherapeutic Agents, pp. 712-732, Ch. XV1-2, 3rd Edition, Edited by J. Holland, et al., Lea and Febigol, publishers.
Higuchi, Rate of Release of Medicaments from Ointment Bases Containing Drugs in Suspension, Journal of Pharmaceutical Sciences, vol. 50, No. 10, p. 874, Oct. 1961.
Ji, et al., "96-Wellliquid-liquid extraction liquid chromatographytandem mass spectrometry method for the quantitative determination of ABT -578 in human blood samples" Journal of Chromatography B. 805:67-75 (2004).
Ju et al., J. Pharm. Sci. vol. 84, No. 12, 1455-1463.
Levit, et al., "Supercritical C02 Assisted Electrospinning" J. Of Supercritical Fluids, 329-333, vol. 31, Issue 3, (Nov. 2004).
Lewis, D. H., "Controlled Release of Bioactive Agents from Lactides/Glycolide Polymers" in Biodegradable Polymers as Drug Delivery Systems, Chasin, M. And Langer, R., eds., Marcel Decker (1990).
Luzzi, L.A., J. Phann. Psy. 59:1367 (1970).
Park et al., Pharm. Res. (1987) 4(6):457-464.
PCT/EP01/05736 International Preliminary Examination Report dated Jan. 14, 2002.
PCT/EP2000/004658 International Search Report from dated Sep. 15, 2000.
PCT/US06/27321 Written Opinion dated Oct. 16, 2007.
PCT/US11/33225 International Search Report and Written Opinion dated Jul. 7, 2011.
PCT/US12/50408 International Search Report mailed Oct. 16, 2012.
PCT/US13/41466 International Preliminary Report on Patentability dated Nov. 18, 2014.
Wang et al. "Synthesis, characterization, biodegradation, and drug delivery application of biodegradable lactic/glycolic acid polymers: I. Synthesis and characterization" J. Biomater. Sci. Polymer Edn. 11(3):301-318 (2000).

* cited by examiner

DRUG DELIVERY MEDICAL DEVICE

CROSS-REFERENCE

This application claims the benefit of U.S. Provisional Application No. 61/081,691, filed Jul. 17, 2008; and U.S. Provisional Application No. 61/212,964, filed Apr. 17, 2009, and U.S. Provisional Application No. 61/162,558, filed Mar. 23, 2009, which applications are incorporated herein by reference in their entirety.

BACKGROUND OF THE INVENTION

There is a need for medical device technology that can rapidly, efficiently, reproducibly and safely transfer a Drug Delivery Formulation from the surface of a percutaneous medical device (a coating) onto/into a specific site in the body.

SUMMARY OF THE INVENTION

Provided herein is a medical device comprising a substrate and a coating on at least a portion of the substrate, wherein the coating comprises a plurality of layers, wherein at least one layer comprises a pharmaceutical agent that is crystalline, and wherein the device is adapted to free at least a portion of the coating from the substrate upon stimulation of the coating.

Provided herein is a medical device comprising a substrate and a coating on at least a portion of the substrate, wherein the coating comprises a plurality of layers, wherein at least one layer comprises a pharmaceutical agent that is crystalline, and wherein the device is adapted to dissociate at least a portion of the coating from the substrate upon stimulation of the coating.

Provided herein is a medical device comprising a substrate and a coating on at least a portion of said substrate, wherein the coating comprises a plurality of layers, wherein at least one layer comprises a pharmaceutical agent that is crystalline, and wherein the device is adapted to transfer at least a portion of the coating from the substrate to an intervention site upon stimulation of the coating.

Provided herein is a medical device comprising a substrate and a coating on at least a portion of said substrate, wherein said coating is at least partially continuous, has at least one portion conformal to the substrate, and comprises a pharmaceutical agent that is crystalline, and wherein the device is adapted to free at least a portion of the coating from the substrate upon stimulation of the coating.

Provided herein is a medical device comprising: a substrate and a coating on at least a portion of said substrate, wherein said coating is at least partially continuous, has at least one portion conformal to the substrate, and comprises a pharmaceutical agent that is crystalline, and wherein the device is adapted to dissociate at least a portion of the coating from the substrate upon stimulation of the coating.

Provided herein is a medical device comprising a substrate and a coating on at least a portion of said substrate, wherein said coating is at least partially continuous, has at least one portion conformal to the substrate, and comprises a pharmaceutical agent that is crystalline, and wherein the device is adapted to transfer at least a portion of the coating from the substrate to an intervention site upon stimulation of the coating.

Provided herein is a medical device comprising a substrate and a coating on at least a portion of said substrate, wherein said coating comprises an active agent, and wherein the device is adapted to free greater than 35% of the coating from the substrate upon a single stimulation of the coating.

Provided herein is a medical device comprising a substrate and a coating on at least a portion of said substrate, wherein said coating comprises an active agent, and wherein the device is adapted to dissociate greater than 35% of the coating from the substrate upon a single stimulation of the coating.

Provided herein is a medical device comprising a substrate and a coating on at least a portion of said substrate, wherein said coating comprises an active agent, and wherein the device is adapted to transfer greater than 35% of the coating from the substrate to an intervention site upon a single stimulation of the coating.

Provided herein is a medical device comprising a substrate and a coating on at least a portion of said substrate, wherein said coating comprises an active agent, wherein the coating is patterned, and wherein at least a portion of the coating is adapted to free from the substrate upon stimulation of the coating.

Provided herein is a medical device comprising a substrate and a coating on at least a portion of said substrate, wherein said coating comprises an active agent, wherein the coating is patterned, and wherein at least a portion of the coating is adapted to dissociate from the substrate upon stimulation of the coating.

Provided herein is a medical device comprising a substrate and a coating on at least a portion of said substrate, wherein said coating comprises an active agent, wherein the coating is patterned, and wherein at least a portion of the coating is adapted to transfer from the substrate to an intervention site upon stimulation of the coating.

In some embodiments, the therapeutically desirable morphology comprises a crystalline form of the pharmaceutical agent that is not a microcapsule.

In some embodiments, the single stimulation lasts at most 20 seconds. In some embodiments, the device is adapted to free substantially all of the coating upon the single stimulation of the coating. In some embodiments, the single stimulation lasts at most 20 seconds. In some embodiments, substantially all of the coating frees from the substrate instantaneously upon stimulation of the coating.

In some embodiments, the patterned coating comprises at least two different shapes.

Provided herein is a medical device comprising: a substrate; and a coating on at least a portion of said substrate, wherein said coating comprises an active agent, and wherein at least a portion of the coating is adapted to transfer from the substrate to an intervention site. In some embodiments, the portion of the coating is adapted to transfer from the substrate to the intervention site upon stimulation of the coating.

Provided herein is a medical device comprising: a substrate; and a coating on at least a portion of said substrate, wherein said coating comprises an active agent, and wherein at least a portion of the active agent is adapted to transfer from the substrate to an intervention site. In some embodiments, the portion of the active agent is adapted to transfer from the substrate to the intervention site upon stimulation of the coating.

Provided herein is a medical device comprising: a substrate; and a coating on at least a portion of said substrate, wherein said coating comprises an active agent, and wherein the device is adapted to transfer at least a portion of the coating from the substrate to an intervention site. In some embodiments, the device is adapted to transfer the portion of the coating (coating portion) from the substrate to the intervention site upon stimulation of the coating.

Provided herein is a medical device comprising: a substrate; and a coating on at least a portion of said substrate, wherein said coating comprises an active agent, and wherein the device is adapted to transfer at least a portion of the active agent from the substrate to an intervention site. In some embodiments, the device is adapted to transfer the portion of the active agent from the substrate to the intervention site upon stimulation of the coating.

Provided herein is a medical device comprising: a substrate; and a coating on at least a portion of said substrate, wherein said coating comprises an active agent, wherein the device is adapted to free at least a portion of the coating from the substrate at an intervention site. In some embodiments, the device is adapted to free the portion of the coating from the substrate at the intervention site upon stimulation of the coating.

Provided herein is a medical device comprising: a substrate; and a coating on at least a portion of said substrate, wherein said coating comprises an active agent, wherein the device is adapted to dissociate at least a portion of the coating from the substrate at an intervention site. In some embodiments, the device is adapted to dissociate the portion of the coating from the substrate at the intervention site upon stimulation of the coating.

Provided herein is a medical device comprising: a substrate; and a coating on at least a portion of said substrate, wherein said coating comprises an active agent, wherein the device is adapted to dissociate at least a portion of the coating from the substrate and to deliver said portion of the coating to an intervention site. In some embodiments, the device is adapted to deliver the portion of the coating to the intervention site upon stimulation of the coating.

In some embodiments of the methods and/or devices provided herein, the substrate comprises a balloon. In some embodiments, the portion of the balloon having coating thereon comprises an outer surface of the balloon. In some embodiments, the outer surface is a surface of the balloon exposed to a coating prior to balloon folding. In some embodiments, the outer surface is a surface of the balloon exposed to a coating following balloon folding. In some embodiments, the outer surface is a surface of the balloon exposed to a coating following balloon crimping. In some embodiments, the coating comprises a material that undergoes plastic deformation at pressures provided by inflation of the balloon. In some embodiments, the coating comprises a material that undergoes plastic deformation at a pressure that is less than the rated burst pressure of the balloon.

In some embodiments of the methods and/or devices provided herein, the coating comprises a material that undergoes plastic deformation at a pressure that is less than the nominal inflation pressure of the balloon. In some embodiments, the coating comprises a material that undergoes plastic deformation with at least 8 ATM of pressure. In some embodiments, the coating comprises a material that undergoes plastic deformation with at least 6 ATM of pressure. In some embodiments, the coating comprises a material that undergoes plastic deformation with at least 4 ATM of pressure. In some embodiments, the coating comprises a material that undergoes plastic deformation with at least 2 ATM of pressure.

In some embodiments of the methods and/or devices provided herein, the balloon is a compliant balloon. In some embodiments, the balloon is a semi-compliant balloon. In some embodiments, the balloon is a non-compliant balloon. In some embodiments, the balloon conforms to a shape of the intervention site.

In some embodiments of the methods and/or devices provided herein, the balloon comprises a cylindrical portion. In some embodiments, the balloon comprises a substantially spherical portion. In some embodiments, the balloon comprises a complex shape. In some embodiments, the complex shape comprises at least one of a double noded shape, a triple noded shape, a waisted shape, an hourglass shape, and a ribbed shape.

In some embodiments of the methods and/or devices provided herein, the substrate comprises a cutting balloon. In some embodiments, the cutting balloon comprises at least one tacking element adapted to tack the coating to the intervention site. In some embodiments, the tacking element is adapted to secure the coating to the cutting balloon until inflation of the cutting balloon. In some embodiments, the tacking element comprises a wire. In some embodiments, the wire is shaped in the form of an outward pointing wedge. In some embodiments, the tacking element does not cut tissue at the intervention site.

In some embodiments of the methods and/or devices provided herein, the substrate comprises a biomedical implant. In some embodiments, the substrate comprises a surgical tool.

In some embodiments of the methods and/or devices provided herein, the substrate comprises at least one of a stent, a joint, a screw, a rod, a pin, a plate, a staple, a shunt, a clamp, a clip, a suture, a suture anchor, an electrode, a catheter, a lead, a graft, a dressing, a pacemaker, a pacemaker housing, a cardioverter, a cardioverter housing, a defibrillator, a defibrillator housing, a prostheses, an ear drainage tube, an ophthalmic implant, an orthopedic device, a vertebral disk, a bone substitute, an anastomotic device, a perivascular wrap, a colostomy bag attachment device, a hemostatic barrier, a vascular implant, a vascular support, a tissue adhesive, a tissue sealant, a tissue scaffold, and an intraluminal device.

In some embodiments of the methods and/or devices provided herein, the substrate comprises at least a portion of a tool for delivering to the intervention site a biomedical implant, wherein the substrate is the biomedical implant or wherein the substrate is a portion of the device that is not the biomedical implant. In some embodiments, the substrate comprises at least a portion of a tool for performing a medical procedure. In some embodiments, the tool comprises at least one of: a knife, a scalpel, a guidewire, a guiding catheter, a introduction catheter, a distracter, a needle, a syringe, a biopsy device, an articulator, a Galotti articulator, a bone chisel, a bone crusher, a cottle cartilage crusher, a bone cutter, a bone distractor, an Ilizarov apparatus, an intramedullary kinetic bone distractor, a bone drill, a bone extender, a bone file, a bone lever, a bone mallet, a bone rasp, a bone saw, a bone skid, a bone splint, a bone button, a caliper, a cannula, a catheter, a cautery, a clamp, a coagulator, a curette, a depressor, a dilator, a dissecting knife, a distractor, a dermatome, forceps, dissecting forceps, tissue forceps, sponge forceps, bone forceps, Carmalt forceps, Cushing forceps, Dandy forceps, DeBakey forceps, Doyen intestinal forceps, epilation forceps, Halstead forceps, Kelly forceps, Kocher forceps, mosquito forceps, a hemostat, a hook, a nerve hook, an obstetrical hook, a skin hook, a hypodermic needle, a lancet, a luxator, a lythotome, a lythotript, a mallet, a partsch mallet, a mouth prop, a mouth gag, a mammotome, a needle holder, an occluder, an osteotome, an Epker osteotome, a periosteal elevator, a Joseph elevator, a Molt periosteal elevator, an Obweg periosteal elevator, a septum elevator, a Tessier periosteal elevator, a probe, a retractor, a Senn retractor, a Gelpi retractor, a Weitlaner retractor, a USA-Army/Navy retractor, an O'Connor-O'Sullivan retractor, a Deaver retractor, a Bookwalter retractor, a Sweetheart retractor, a Joseph skin hook, a Lahey retractor, a Blair (Rollet) retractor, a rigid rake retractor, a flexible rake retractor, a Ragnell retractor, a Linde-Ragnell retractor, a Davis retractor, a Volkman retractor, a Mathieu retractor, a Jackson tracheal hook, a Crile retractor, a Meyerding finger retractor, a Little retractor, a Love Nerve retractor, a Green retractor, a Goelet retractor, a Cushing vein retractor, a Langenbeck retractor, a Richardson retractor, a Richardson-Eastmann retractor, a Kelly retractor, a Parker retractor, a Parker-Mott retractor, a Roux retractor, a Mayo-Collins retractor, a Ribbon retractor, an Alm retractor, a self retaining retractor, a Weitlaner retractor, a Beckman-Weitlaner retractor, a Beckman-Eaton retractor, a Beckman retractor, an Adson retractor, a rib spreader, a rongeur, a scalpel, an ultrasonic scalpel, a laser scalpel, scissors, iris scissors, Kiene scissors, Metzenbaum scissors, Mayo scissors, Tenotomy scissors, a spatula, a speculum, a mouth speculum, a rectal speculum, Sim's vaginal speculum, Cusco's vaginal speculum, a sternal saw, a suction tube, a surgical elevator, a surgical hook, a surgical knife, surgical mesh, a surgical needle, a surgical snare, a surgical sponge, a surgical spoon, a surgical stapler, a suture, a syringe, a tongue depressor, a tonsillotome, a tooth extractor, a towel clamp, towel forceps, Backhaus towel forceps, Lorna towel forceps, a tracheotome, a tissue expander, a subcutaneus inflatable balloon expander, a trephine, a trocar, tweezers, and a venous cliping.

In some embodiments of the methods and/or devices provided herein, the coating is freed, dissociated, and/or transferred from the substrate using a mechanical stimulation. In some embodiments, the coating is freed from the substrate using a mechanical stimulation. In some embodiments, the coating is dissociated from the substrate using a mechanical stimulation. In some embodiments, the coating is transferred from the substrate using a mechanical stimulation. In some embodiments, the coating is transferred to the intervention site using a mechanical stimulation. In some embodiments, the coating is delivered to the intervention site using a mechanical stimulation. In some embodiments, the mechanical stimulation is adapted to augment the freeing, dissociation and/or transference of the coating from the substrate. In some embodiments, the mechanical stimulation is adapted to initiate the freeing, dissociation and/or transference of the coating from the substrate. In some embodiments, the mechanical stimulation is adapted to cause the freeing, dissociation and/or transference of the coating from the substrate. In some embodiments, the mechanical stimulation comprises at least one of a compressive force, a shear force, a tensile force, a force exerted on the coating from a substrate side of the coating, a force exerted on the coating by the substrate, a force exerted on the coating from an external element, a translation, a rotation, a vibration, and a combination thereof. In some embodiments, the external element is a part of the subject. In some embodiments, the external element is not part of the device. In some embodiments, the external element comprises a liquid. In some embodiments, the liquid is forced between the coating and the substrate. In some embodiments, the liquid comprises saline. In some embodiments, the liquid comprises water. In some embodiments, the mechanical stimulation comprises a geometric configuration of the substrate that maximizes a shear force on the coating. In some embodiments, the mechanical stimulation comprises a geometric configuration of the substrate that increases a shear force on the coating. In some embodiments, the mechanical stimulation comprises a geometric configuration of the substrate that enhances a shear force on the coating.

In some embodiments of the methods and/or devices provided herein, the coating is freed, dissociated, and/or transferred from the substrate using a chemical stimulation. In some embodiments, the coating is freed from the substrate using a chemical stimulation. In some embodiments, the coating is dissociated from the substrate using a chemical stimulation. In some embodiments, the coating is transferred from the substrate using a chemical stimulation. In some embodiments, the coating is transferred to the intervention site using a chemical stimulation. In some embodiments, the coating is delivered to the intervention site using a chemical stimulation. In some embodiments, the chemical stimulation comprises at least one of bulk degradation, interaction with a bodily fluid, interaction with a bodily tissue, a chemical interaction with a non-bodily fluid, a chemical interaction with a chemical, an acid-base reaction, an enzymatic reaction, hydrolysis, and combinations thereof. In some embodiments, the chemical stimulation comprises bulk degradation of the coating. In some embodiments, the chemical stimulation comprises interaction of the coating or a portion thereof with a bodily fluid. In some embodiments, the chemical stimulation comprises interaction of the coating or a portion thereof with a bodily tissue. In some embodiments, the chemical stimulation comprises a chemical interaction of the coating or a portion thereof with a non-bodily fluid. In some embodiments, the chemical stimulation comprises a chemical interaction of the coating or a portion thereof with a chemical. In some embodiments, the chemical stimulation comprises an acid-base reaction. In some embodiments, the chemical stimulation comprises an enzymatic reaction. In some embodiments, the chemical stimulation comprises hydrolysis.

In some embodiments of the methods and/or devices provided herein, the chemical stimulation is adapted to augment the freeing, dissociation and/or transference of the coating from the substrate. In some embodiments, the chemical stimulation is adapted to initiate the freeing, dissociation and/or transference of the coating from the substrate. In some embodiments, the chemical stimulation is adapted to cause the freeing, dissociation and/or transference of the coating from the substrate. In some embodiments, the coating comprises a material that is adapted to transfer, free, and/or dissociate from the substrate when at the intervention site in response to an in-situ enzymatic reaction resulting in a weak bond between the coating and the substrate.

In some embodiments of the methods and/or devices provided herein, the coating is freed, dissociated, and/or transferred from the substrate using a thermal stimulation. In some embodiments, the coating is freed from the substrate using a thermal stimulation. In some embodiments, the coating is dissociated from the substrate using a thermal stimulation. In some embodiments, the coating is transferred from the substrate using a thermal stimulation. In some embodiments, the coating is transferred to the intervention site using a thermal stimulation. In some embodiments, the coating is delivered to the intervention site using a thermal stimulation. In some embodiments, the thermal stimulation comprises at least one of a hot stimulus and a cold stimulus adapted to augment the freeing, dissociation and/or transference of the coating from the substrate. In some embodiments, the thermal stimulation is adapted to cause the freeing, dissociation and/or transference of the coating from the substrate. In some embodiments, the thermal stimulation comprises at least one of a hot stimulus and a cold stimulus adapted to initiate the freeing, dissociation and/or transference of the coating from the substrate. In some embodiments, the thermal stimulation comprises at least one of a hot stimulus and a cold stimulus adapted to initiate the freeing, dissociation and/or transference of the coating from the substrate.

In some embodiments of the methods and/or devices provided herein, the coating is freed, dissociated, and/or transferred from the device by a electromagnetic stimulation. In some embodiments, the coating is freed from the substrate using a electromagnetic stimulation. In some embodiments, the coating is dissociated from the substrate using a electromagnetic stimulation. In some embodiments, the coating is transferred from the substrate using a electromagnetic stimulation. In some embodiments, the coating is transferred to the intervention site using a electromagnetic stimulation. In some embodiments, the coating is delivered to the intervention site using a electromagnetic stimulation. In some embodiments, the electromagnetic stimulation comprises an electromagnetic wave comprising at least one of a radio wave, a micro wave, a infrared wave, near infrared wave, a visible light wave, an ultraviolet wave, a X-ray wave, and a gamma wave. In some embodiments, the electromagnetic stimulation is adapted to augment the freeing, dissociation and/or transference of the coating from the substrate. In some embodiments, the electromagnetic stimulation is adapted to initiate the freeing, dissociation and/or transference of the coating from the substrate. In some embodiments, the electromagnetic stimulation is adapted to cause the freeing, dissociation and/or transference of the coating from the substrate.

In some embodiments of the methods and/or devices provided herein, the coating is freed, dissociated, and/or transferred from the device by a sonic stimulation. In some embodiments, the coating is freed from the substrate using a sonic stimulation. In some embodiments, the coating is dissociated from the substrate using a sonic stimulation. In some embodiments, the coating is transferred from the substrate using a sonic stimulation. In some embodiments, the coating is transferred to the intervention site using a sonic stimulation. In some embodiments, the coating is delivered to the intervention site using a sonic stimulation. In some embodiments, the sonic stimulation comprises a sound wave, wherein the sound wave is at least one of an ultrasound wave, an acoustic sound wave, and an infrasound wave. In some embodiments, the sonic stimulation is adapted to augment the freeing, dissociation and/or transference of the coating from the substrate. In some embodiments, the sonic stimulation is adapted to initiate the freeing, dissociation and/or transference of the coating from the substrate. In some embodiments, the sonic stimulation is adapted to cause the freeing, dissociation and/or transference of the coating from the substrate.

In some embodiments of the methods and/or devices provided herein, the coating is freed, dissociated, and/or transferred from the device by a combination of at least two of a mechanical stimulation, a chemical stimulation, an electromagnetic stimulation, and a sonic stimulation.

In some embodiments of the methods and/or devices provided herein, the coating is freed, dissociated, and/or transferred from the substrate by extrusion.

In some embodiments of the methods and/or devices provided herein, the device further comprises a release agent. In some embodiments, the release agent is biocompatible. In some embodiments, the release agent is non-biocompatible. In some embodiments, the release agent comprises a powder. In some embodiments, the release agent comprises a lubricant. In some embodiments, the release agent comprises a surface modification of the substrate.

In some embodiments of the methods and/or devices provided herein, the release agent comprises a physical characteristic of the coating. In some embodiments, the physical characteristic of the coating comprises a pattern. In some embodiments, the pattern is a textured surface on the substrate side of the coating, wherein the substrate side of the coating is the part of the coating on the substrate. In some embodiments, the pattern is a textured surface on the intervention site side of the coating, wherein the intervention site side of the coating is the part of the coating that is transferred to, and/or delivered to, and/or deposited at the intervention site.

In some embodiments of the methods and/or devices provided herein, the release agent comprises a viscous fluid. In some embodiments, the viscous fluid comprises oil. In some embodiments, the viscous fluid is a fluid that is viscous relative to water. In some embodiments, the viscous fluid is a fluid that is viscous relative to blood. In some embodiments, the viscous fluid is a fluid that is viscous relative to urine. In some embodiments, the viscous fluid is a fluid that is viscous relative to bile. In some embodiments, the viscous fluid is a fluid that is viscous relative to synovial fluid. In some embodiments, the viscous fluid is a fluid that is viscous relative to saline. In some embodiments, the viscous fluid is a fluid that is viscous relative to a bodily fluid at the intervention site.

In some embodiments of the methods and/or devices provided herein, the release agent comprises a gel.

In some embodiments of the methods and/or devices provided herein, the release agent comprises at least one of the active agent and another active agent. The active agent may be placed on the substrate prior to the coating in order to act as the release agent. The active agent may be a different active agent than the active agent in the coating. The active agent that is the release agent may provide for a second source of drug to be delivered to the intervention site or another location once the coating is released from (or transferred from, or freed from, or dissociated from) the substrate.

In some embodiments of the methods and/or devices provided herein, the release agent comprises a physical characteristic of the substrate. In some embodiments, the physical characteristic of the substrate comprises at least one of a patterned coating surface and a ribbed coating surface. In some embodiments, the patterned coating surface comprises a stent framework. In some embodiments, the ribbed coating surface comprises an undulating substrate surface. In some embodiments, the ribbed coating surface comprises a substrate surface having bumps thereon.

In some embodiments of the methods and/or devices provided herein, the release agent comprises a property that is capable of changing at the intervention site. In some embodiments, the property comprises a physical property. In some embodiments, the property comprises a chemical property. In some embodiments, the release agent is capable of changing a property when in contact with at least one of a biologic tissue and a biologic fluid. In some embodiments, the release agent is capable of changing a property when in contact with an aqueous liquid.

In some embodiments of the methods and/or devices provided herein, the release agent is between the substrate and the coating.

In some embodiments of the methods and/or devices provided herein, substantially all of the coating remains on said substrate until the medical device reaches the intervention site. In some embodiments, at least about 10%, at least about 20%, at least about 30%, greater than 35%, at least about 40%, between about 40% and about 45%, at least about 50%, at least about 75%, at least about 85%, at least about 90%, at least about 95%, and/or at least about 99% of the coating is adapted to transfer from the substrate to the intervention site. In some embodiments, at least about 10% of the coating is adapted to transfer from the substrate to the intervention site. In some embodiments, at least about 20% of the coating is adapted to transfer from the substrate to the intervention site. In some embodiments, at least about 30% of the coating is adapted to transfer from the substrate to the intervention site. In some embodiments, greater than 35% of the coating is adapted to transfer from the substrate to the intervention site. In some embodiments, between about 40% and about 45%, of the coating is adapted to transfer from the substrate to the intervention site. In some embodiments, at least about 50% of the coating is adapted to transfer from the substrate to the intervention site. In some embodiments, at least about 75% of the coating is adapted to transfer from the substrate to the intervention site. In some embodiments, at least about 85% of the coating is adapted to transfer from the substrate to the intervention site. In some embodiments, at least about 90% of the coating is adapted to transfer from the substrate to the intervention site. In some embodiments, at least about 95% of the coating is adapted to transfer from the substrate to the intervention site. In some embodiments, at least about 99% of the coating is adapted to transfer from the substrate to the intervention site. As used herein, "about" when used in reference to a percentage of the coating can mean ranges of 1%-5%, of 5%-10%, of 10%-20%, and/or of 10%-50% (as a percent of the percentage of the coating transferred, or as a variation of the percentage of the coating transferred).

In some embodiments of the methods and/or devices provided herein, the coating portion that is adapted to transfer upon stimulation is on at least one of a distal surface of the substrate, a middle surface of the substrate, a proximal surface of the substrate, and an abluminal surface of the substrate. In some embodiments, the stimulation decreases the contact between the coating and the substrate. In some embodiments, device is adapted to transfer less than about 1%, less than about 5%, less than about 10%. less than about 15%, less than about 25%, about 35% or less, less than about 40%, less than about 50%, less than about 70%, less than about 80%, and/or less than about 90% of the coating absent stimulation of the coating.

In some embodiments of the methods and/or devices provided herein, at least about 10%, at least about 20%, at least about 30%, greater than 35%, at least about 40%, between about 40% and about 45%, at least about 50%, at least about 75%, at least about 85%, at least about 90%, at least about 95%, and/or at least about 99% of the active agent is adapted to transfer from the substrate to the intervention site. In some embodiments, at least about 10% of the active agent is adapted to transfer from the substrate to the intervention site. In some embodiments, at least about 20% of the active agent is adapted to transfer from the substrate to the intervention site. In some embodiments, at least about 30% of the active agent is adapted to transfer from the substrate to the intervention site. In some embodiments, greater than 35% of the active agent is adapted to transfer from the substrate to the intervention site. In some embodiments, between about 40% and about 45%, of the active agent is adapted to transfer from the substrate to the intervention site. In some embodiments, at least about 50% of the active agent is adapted to transfer from the substrate to the intervention site. In some embodiments, at least about 75% of the active agent is adapted to transfer from the substrate to the intervention site. In some embodiments, at least about 85% of the active agent is adapted to transfer from the substrate to the intervention site. In some embodiments, at least about 90% of the active agent is adapted to transfer from the substrate to the intervention site. In some embodiments, at least about 95% of the active agent is adapted to transfer from the substrate to the intervention site. In some embodiments, at least about 99% of the active agent is adapted to transfer from the substrate to the intervention site. As used herein, "about" when used in reference to a percentage of the active agent can mean ranges of 1%-5%, of 5%-10%, of 10%-20%, and/or of 10%-50% (as a percent of the percentage of the active agent transferred, or as a variation of the percentage of the active agent transferred).

In some embodiments of the methods and/or devices provided herein, the active agent portion that is adapted to transfer upon stimulation is on at least one of a distal surface of the substrate, a middle surface of the substrate, a proximal surface of the substrate, and an abluminal surface of the substrate. In some embodiments, the stimulation decreases the contact between the coating and the substrate. In some embodiments, the device is adapted to transfer less than about 1%, less than about 5%, less than about 10%. less than about 15%, less than about 25%, about 35% or less, less than about 40%, less than about 50%, less than about 70%, less than about 80%, and/or less than about 90% of the active agent absent stimulation of the coating.

In some embodiments of the methods and/or devices provided herein, the device is adapted to transfer at least about 10%, at least about 20%, at least about 30%, greater than 35%, at least about 40%, between about 40% and about 45%, at least about 50%, at least about 75%, at least about 85%, at least about 90%, at least about 95%, and/or at least about 99% of the coating from the substrate to the intervention site. In some embodiments, the device is adapted to transfer at least about 10% of the coating from the substrate to the intervention site. In some embodiments, the device is adapted to transfer at least about 20% of the coating from the substrate to the intervention site. In some embodiments, the device is adapted to transfer at least about 30% of the coating from the substrate to the intervention site. In some embodiments, the device is adapted to transfer greater than 35% of the coating from the substrate to the intervention site. In some embodiments, the device is adapted to transfer between about 40% and about 45%, of the coating from the substrate to the intervention site. In some embodiments, the device is adapted to transfer at least about 50% of the coating from the substrate to the intervention site. In some embodiments, the device is adapted to transfer at least about 75% of the coating from the substrate to the intervention site. In some embodiments, the device is adapted to transfer at least about 85% of the coating from the substrate to the intervention site. In some embodiments, the device is adapted to transfer at least about 90% of the coating from the substrate to the intervention site. In some embodiments, the device is adapted to transfer at least about 95% of the coating from the substrate to the intervention site. In some embodiments, the device is adapted to transfer at least about 99% of the coating from the substrate to the intervention site. As used herein, "about" when used in reference to a percentage of the coating can mean ranges of 1%-5%, of 5%-10%, of 10%-20%, and/or of 10%-50% (as a percent of the percentage of the coating transferred, or as a variation of the percentage of the coating transferred).

In some embodiments of the methods and/or devices provided herein, the coating portion that transfers upon stimulation is on at least one of a distal surface of the substrate, a middle surface of the substrate, a proximal surface of the substrate, and an abluminal surface of the substrate. In some embodiments, stimulation decreases the contact between the coating and the substrate. In some embodiments, the device is adapted to transfer less than about 1%, less than about 5%, less than about 10%. less than about 15%, less than about 25%, about 35% or less, less than about 40%, less than about 50%, less than about 70%, less than about 80%, and/or less than about 90% of the coating absent stimulation of the coating.

In some embodiments of the methods and/or devices provided herein, the device is adapted to transfer at least about 10%, at least about 20%, at least about 30%, greater than 35%, at least about 40%, between about 40% and about 45%, at least about 50%, at least about 75%, at least about 85%, at least about 90%, at least about 95%, and/or at least about 99% of the active agent from the substrate to the intervention site. In some embodiments, the device is adapted to transfer at least about 10% of the active agent from the substrate to the intervention site. In some embodiments, the device is adapted to transfer at least about 20% of the active agent from the substrate to the intervention site. In some embodiments, the device is adapted to transfer at least about 30% of the active agent from the substrate to the intervention site. In some embodiments, the device is adapted to transfer greater than 35% of the active agent from the substrate to the intervention site. In some embodiments, the device is adapted to transfer between about 40% and about 45%, of the active agent from the substrate to the intervention site. In some embodiments, the device is adapted to transfer at least about 50% of the active agent from the substrate to the intervention site. In some embodiments, the device is adapted to transfer at least about 75% of the active agent from the substrate to the intervention site. In some embodiments, the device is adapted to transfer at least about 85% of the active agent from the substrate to the intervention site. In some embodiments, the device is adapted to transfer at least about 90% of the active agent from the substrate to the intervention site. In some embodiments, the device is adapted to transfer at least about 95% of the active agent from the substrate to the intervention site. In some embodiments, the device is adapted to transfer at least about 99% of the active agent from the substrate to the intervention site. As used herein, "about" when used in reference to a percentage of the active agent can mean ranges of 1%-5%, of 5%-10%, of 10%-20%, and/or of 10%-50% (as a percent of the percentage of the active agent transferred, or as a variation of the percentage of the active agent transferred).

In some embodiments of the methods and/or devices provided herein, the coating portion that transfers upon stimulation is on at least one of a distal surface of the substrate, a middle surface of the substrate, a proximal surface of the substrate, and an abluminal surface of the substrate. In some embodiments, the stimulation decreases the contact between the coating and the substrate. In some embodiments, the device is adapted to transfer less than about 1%, less than about 5%, less than about 10%. less than about 15%, less than about 25%, about 35% or less, less than about 40%, less than about 50%, less than about 70%, less than about 80%, less than about 90% of the active agent absent stimulation of the coating.

In some embodiments of the methods and/or devices provided herein, the device is adapted to free at least about 10%, at least about 20%, at least about 30%, greater than 35%, at least about 40%, between about 40% and about 45%, at least about 50%, at least about 75%, at least about 85%, at least about 90%, at least about 95%, and/or at least about 99% of the coating from the substrate. In some embodiments, the device is adapted to free at least about 10% of the coating from the substrate to the intervention site. In some embodiments, the device is adapted to free at least about 20% of the coating from the substrate to the intervention site. In some embodiments, the device is adapted to free at least about 30% of the coating from the substrate to the intervention site. In some embodiments, the device is adapted to free greater than 35% of the coating from the substrate. In some embodiments, the device is adapted to free between about 40% and about 45%, of the coating from the substrate. In some embodiments, the device is adapted to free at least about 50% of the coating from the substrate to the intervention site. In some embodiments, the device is adapted to free at least about 75% of the coating from the substrate to the intervention site. In some embodiments, the device is adapted to free at least about 85% of the coating from the substrate to the intervention site. In some embodiments, the device is adapted to free at least about 90% of the coating from the substrate to the intervention site. In some embodiments, the device is adapted to free at least about 95% of the coating from the substrate to the intervention site. In some embodiments, the device is adapted to free at least about 99% of the coating from the substrate to the intervention site. As used herein, "about" when used in reference to a percentage of the coating can mean ranges of 1%-5%, of 5%-10%, of 10%-20%, and/or of 10%-50% (as a percent of the percentage of the coating freed, or as a variation of the percentage of the coating freed).

In some embodiments of the methods and/or devices provided herein, the coating portion that frees upon stimulation is on at least one of a distal surface of the substrate, a middle surface of the substrate, a proximal surface of the substrate, and an abluminal surface of the substrate.

In some embodiments of the methods and/or devices provided herein, the stimulation decreases the contact between the coating and the substrate. In some embodiments, the device is adapted to free less than about 1%, less than about 5%, less than about 10%. less than about 15%, less than about 25%, about 35% or less, less than about 40%, less than about 50%, less than about 70%, less than about 80%, less than about 90% of the coating absent stimulation of the coating.

In some embodiments of the methods and/or devices provided herein, the device is adapted to dissociate at least about 10%, at least about 20%, at least about 30%, greater than 35%, at least about 40%, between about 40% and about 45%, at least about 50%, at least about 75%, at least about 85%, at least about 90%, at least about 95%, and/or at least about 99% of the coating from the substrate. In some embodiments, the device is adapted to dissociate at least about 10% of the coating from the substrate to the intervention site. In some embodiments, the device is adapted to dissociate at least about 20% of the coating from the substrate to the intervention site. In some embodiments, the device is adapted to dissociate at least about 30% of the coating from the substrate to the intervention site. In some embodiments, the device is adapted to dissociate greater than 35% of the coating from the substrate. In some embodiments, the device is adapted to dissociate between about 40% and about 45%, of the coating from the substrate. In some embodiments, the device is adapted to dissociate at least about 50% of the coating from the substrate to the intervention site. In some embodiments, the device is adapted to dissociate at least about 75% of the coating from the substrate to the intervention site. In some embodiments, the device is adapted to dissociate at least about 85% of the coating from the substrate to the intervention site. In some embodiments, the device is adapted to dissociate at least about 90% of the coating from the substrate to the intervention site. In some embodiments, the device is adapted to dissociate at least about 95% of the coating from the substrate to the intervention site. In some embodiments, the device is adapted to dissociate at least about 99% of the coating from the substrate to the intervention site. As used herein, "about" when used in reference to a percentage of the coating can mean ranges of 1%-5%, of 5%-10%, of 10%-20%, and/or of 10%-50% (as a percent of the percentage of the coating dissociated, or as a variation of the percentage of the coating dissociated).

In some embodiments of the methods and/or devices provided herein, the coating portion that dissociates upon stimulation is on at least one of a distal surface of the substrate, a middle surface of the substrate, a proximal surface of the substrate, and an abluminal surface of the substrate. In some embodiments, stimulation decreases the contact between the coating and the substrate. In some embodiments, the device is adapted to dissociate less than about 1%, less than about 5%, less than about 10%. less than about 15%, less than about 25%, about 35% or less, less than about 40%, less than about 50%, less than about 70%, less than about 80%, less than about 90% of the coating absent stimulation of the coating.

In some embodiments of the methods and/or devices provided herein, the device is adapted to deliver at least about 10%, at least about 20%, at least about 30%, greater than 35%, at least about 40%, between about 40% and about 45%, at least about 50%, at least about 75%, at least about 85%, at least about 90%, at least about 95%, and/or at least about 99% of the coating to the intervention site. In some embodiments, the device is adapted to deliver at least about 10% of the coating to the intervention site. In some embodiments, the device is adapted to deliver at least about 20% of the coating to the intervention site. In some embodiments, the device is adapted to deliver at least about 30% of the coating to the intervention site. In some embodiments, the device is adapted to deliver greater than 35% of the coating to the intervention site. In some embodiments, the device is adapted to deliver between about 40% and about 45%, of the coating to the intervention site. In some embodiments, the device is adapted to deliver at least about 50% of the coating to the intervention site. In some embodiments, the device is adapted to deliver at least about 75% of the coating to the intervention site. In some embodiments, the device is adapted to deliver at least about 85% of the coating to the intervention site. In some embodiments, the device is adapted to deliver at least about 90% of the coating to the intervention site. In some embodiments, the device is adapted to deliver at least about 95% of the coating to the intervention site. In some embodiments, the device is adapted to deliver at least about 99% of the coating to the intervention site. As used herein, "about" when used in reference to a percentage of the coating can mean ranges of 1%-5%, of 5%-10%, of 10%-20%, and/or of 10%-50% (as a percent of the percentage of the coating delivered, or as a variation of the percentage of the coating delivered).

In some embodiments of the methods and/or devices provided herein, the coating portion that is delivered upon stimulation is on at least one of a distal surface of the substrate, a middle surface of the substrate, a proximal surface of the substrate, and an abluminal surface of the substrate. In some embodiments, the stimulation decreases the contact between the coating and the substrate. In some embodiments, the device is adapted to deliver less than about 1%, less than about 5%, less than about 10%. less than about 15%, less than about 25%, about 35% or less, less than about 40%, less than about 50%, less than about 70%, less than about 80%, less than about 90% of the coating absent stimulation of the coating.

In some embodiments of the methods and/or devices provided herein, the active agent comprises a pharmaceutical agent.

In some embodiments of the methods and/or devices provided herein, the pharmaceutical agent comprises a macrolide immunosuppressive drug. In some embodiments the macrolide immunosuppressive drug comprises one or more of rapamycin, 40-O-(2-Hydroxyethyl)rapamycin (everolimus), 40-O-Benzyl-rapamycin, 40-O-(4'-Hydroxymethyl)benzyl-rapamycin, 40-O-[4'-(1,2-Dihydroxyethyl)]benzyl-rapamycin, 40-O-Allyl-rapamycin, 40-O-[3'-(2,2-Dimethyl-1,3-dioxolan-4(S)-yl)-prop-2'-en-1'-yl]-rapamycin, (2':E,4'S)-40-O-(4',5'-Dihydroxypent-2'-en-1'-yl)-rapamycin 40-O-(2-Hydroxy)ethoxycar-bonylmethyl-rapamycin, 40-O-(3-Hydroxy)propyl-rapamycin 4O—O-(6-Hydroxy)hexyl-rapamycin 40-O-[2-(2-Hydroxy)ethoxy]ethyl-rapamycin 4O—O-[(3S)-2,2-Dimethyldioxolan-3-yl]methyl-rapamycin, 40-O-[(2S)-2,3-Dihydroxyprop-1-yl]-rapamycin, 4O—O-(2-Acetoxy)ethyl-rapamycin 4O—O-(2-Nicotinoyloxy)ethyl-rapamycin, 4O—O-[2-(N-Morpholino)acetoxy]ethyl-rapamycin 4O—O—(2-N-Imidazolylacetoxy)ethyl-rapamycin, 40-O-[2-(N-Methyl-N'-piperazinyl)acetoxy]ethyl-rapamycin, 39-O-Desmethyl-39,40-O,O-ethylene-rapamycin, (26R)-26-Dihydro-40-O-(2-hydroxy)ethyl-rapamycin, 28-O-Methyl-rapamycin, 4O—O-(2-Aminoethyl)-rapamycin, 4O—O-(2-Acetaminoethyl)-rapamycin 4O—O-(2-Nicotinamidoethyl)-rapamycin, 4O—O-(2-(N-Methyl-imidazo-2'-ylcarbethoxamido)ethyl)-rapamycin, 4O—O-(2-Ethoxycarbonylaminoethyl)-rapamycin, 40-O-(2-Tolylsulfonamidoethyl)-rapamycin, 40-O-[2-(4',5'-Dicarboethoxy-1',2',3'-triazol-1'-yl)-ethyl]-rapamycin, 42-Epi-(tetrazolyl)rapamycin (tacrolimus), and 42-[3-hydroxy-2-(hydroxymethyl)-2-methylpropanoate]rapamycin (temsirolimus).

In some embodiments of the methods and/or devices provided herein, the macrolide immunosuppressive drug is at least 50% crystalline. In some embodiments, the macrolide immunosuppressive drug is at least 75% crystalline. In some embodiments, the macrolide immunosuppressive drug is at least 90% crystalline. In some embodiments of the methods and/or devices provided herein the macrolide immunosuppressive drug is at least 95% crystalline. In some embodiments of the methods and/or devices provided herein the macrolide immunosuppressive drug is at least 97% crystalline. In some embodiments of the methods and/or devices provided herein macrolide immunosuppressive drug is at least 98% crystalline. In some embodiments of the methods and/or devices provided herein the macrolide immunosuppressive drug is at least 99% crystalline.

In some embodiments of the methods and/or devices provided herein wherein the pharmaceutical agent is at least 50% crystalline. In some embodiments of the methods and/or devices provided herein the pharmaceutical agent is at least 75% crystalline. In some embodiments of the methods and/or devices provided herein the pharmaceutical agent is at least 90% crystalline. In some embodiments of the methods and/or devices provided herein the pharmaceutical agent is at least 95% crystalline. In some embodiments of the methods and/or devices provided herein the pharmaceutical agent is at least 97% crystalline. In some embodiments of the methods and/or devices provided herein pharmaceutical agent is at least 98% crystalline. In some embodiments of the methods and/or devices provided herein the pharmaceutical agent is at least 99% crystalline.

In some embodiments of the methods and/or devices provided herein, the pharmaceutical agent is agent is selected form the group consisting of In some embodiments, a pharmaceutical agent is at least one of: Acarbose, acetylsalicylic acid, acyclovir, allopurinol, alprostadil, prostaglandins, amantadine, ambroxol, amlodipine, S-aminosalicylic acid, amitriptyline, atenolol, azathioprine, balsalazide, beclomethasone, betahistine, bezafibrate, diazepam and diazepam derivatives, budesonide, bufexamac, buprenorphine, methadone, calcium salts, potassium salts, magnesium salts, candesartan, carbamazepine, captopril, cetirizine, chenodeoxycholic acid, theophylline and theophylline derivatives, trypsins, cimetidine, clobutinol, clonidine, cotrimoxazole, codeine, caffeine, vitamin D and derivatives of vitamin D, colestyramine, cromoglicic acid, coumarin and coumarin derivatives, cysteine, ciclosporin, cyproterone, cytabarine, dapiprazole, desogestrel, desonide, dihydralazine, diltiazem, ergot alkaloids, dimenhydrinate, dimethyl sulphoxide, dimeticone, domperidone and domperidan derivatives, dopamine, doxazosin, doxylamine, benzodiazepines, diclofenac, desipramine, econazole, ACE inhibitors, enalapril, ephedrine, epinephrine, epoetin and epoetin derivatives, morphinans, calcium antagonists, modafinil, orlistat, peptide antibiotics, phenytoin, riluzoles, risedronate, sildenafil, topiramate, estrogen, progestogen and progestogen derivatives, testosterone derivatives, androgen and androgen derivatives, ethenzamide, etofenamate, etofibrate, fenofibrate, etofylline, famciclovir, famotidine, felodipine, fentanyl, fenticonazole, gyrase inhibitors, fluconazole, fluarizine, fluoxetine, flurbiprofen, ibuprofen, fluvastatin, follitropin, formoterol, fosfomicin, furosemide, fusidic acid, gallopamil, ganciclovir, gemfibrozil, ginkgo, Saint John's wort, glibenclamide, urea derivatives as oral antidiabetics, glucagon, glucosamine and glucosamine derivatives, glutathione, glycerol and glycerol derivatives, hypothalamus hormones, guanethidine, halofantrine, haloperidol, heparin (and derivatives), hyaluronic acid, hydralazine, hydrochlorothiazide (and derivatives), salicylates, hydroxyzine, imipramine, indometacin, indoramine, insulin, iodine and iodine derivatives, isoconazole, isoprenaline, glucitol and glucitol derivatives, itraconazole, ketoprofen, ketotifen, lacidipine, lansoprazole, levodopa, levomethadone, thyroid hormones, lipoic acid (and derivatives), lisinopril, lisuride, lofepramine, loperamide, loratadine, maprotiline, mebendazole, mebeverine, meclozine, mefenamic acid, mefloquine, meloxicam, mepindolol, meprobamate, mesalazine, mesuximide, metamizole, metformin, methylphenidate, metixene, metoprolol, metronidazole, mianserin, miconazole, minoxidil, misoprostol, mizolastine, moexipril, morphine and morphine derivatives, evening primrose, nalbuphine, naloxone, tilidine, naproxen, narcotine, natamycin, neostigmine, nicergoline, nicethamide, nifedipine, niflumic acid, nimodipine, nimorazole, nimustine, nisoldipine, adrenaline and adrenaline derivatives, novamine sulfone, noscapine, nystatin, olanzapine, olsalazine, omeprazole, omoconazole, oxaceprol, oxiconazole, oxymetazoline, pantoprazole, paracetamol (acetaminophen), paroxetine, penciclovir, pentazocine, pentifylline, pentoxifylline, perphenazine, pethidine, plant extracts, phenazone, pheniramine, barbituric acid derivatives, phenylbutazone, pimozide, pindolol, piperazine, piracetam, pirenzepine, piribedil, piroxicam, pramipexole, pravastatin, prazosin, procaine, promazine, propiverine, propranolol, propyphenazone, protionamide, proxyphylline, quetiapine, quinapril, quinaprilat, ramipril, ranitidine, reproterol, reserpine, ribavirin, risperidone, ritonavir, ropinirole, roxatidine, ruscogenin, rutoside (and derivatives), sabadilla, salbutamol, salmeterol, scopolamine, selegiline, sertaconazole, sertindole, sertralion, silicates, simvastatin, sitosterol, sotalol, spaglumic acid, sapiripril, spironolactone, stavudine, streptomycin, sucralfate, sufentanil, sulfasalazine, sulpiride, sultiam, sumatriptan, suxamethonium chloride, tacrine, tacrolimus, taliolol, taurolidine, temazepam, tenoxicam, terazosin, terbinafine, terbutaline, terfenadine, terlipressin, tertatolol, teryzoline, theobromine, butizine, thiamazole, phenothiazines, tiagabine, tiapride, propionic acid derivatives, ticlopidine, timolol, tinidazole, tioconazole, tioguanine, tioxolone, tiropramide, tizanidine, tolazoline, tolbutamide, tolcapone, tolnaftate, tolperisone, topotecan, torasemide, tramadol, tramazoline, trandolapril, tranylcypromine, trapidil, trazodone, triamcinolone derivatives, triamterene, trifluperidol, trifluridine, trimipramine, tripelennamine, triprolidine, trifosfamide, tromantadine, trometamol, tropalpin, troxerutine, tulobuterol, tyramine, tyrothricin, urapidil, valaciclovir, valproic acid, vancomycin, vecuronium chloride, Viagra, venlafaxine, verapamil, vidarabine, vigabatrin, viloazine, vincamine, vinpocetine, viquidil, warfarin, xantinol nicotinate, xipamide, zafirlukast, zalcitabine, zidovudine, zolmitriptan, zolpidem, zoplicone, zotipine, amphotericin B, caspofungin, voriconazole, resveratrol, PARP-1 inhibitors (including imidazoquinolinone, imidazpyridine, and isoquinolindione, tissue plasminogen activator (tPA), melagatran, lanoteplase, reteplase, staphylokinase, streptokinase, tenecteplase, urokinase, abciximab (ReoPro), eptifibatide, tirofiban, prasugrel, clopidogrel, dipyridamole, cilostazol, VEGF, heparan sulfate, chondroitin sulfate, elongated "RGD" peptide binding domain, CD34 antibodies, cerivastatin, etorvastatin, losartan, valartan, erythropoietin, rosiglitazone, pioglitazone, mutant protein Apo A1 Milano, adiponectin, (NOS) gene therapy, glucagon-like peptide 1, atorvastatin, and atrial natriuretic peptide (ANP), lidocaine, tetracaine, dibucaine, hyssop, ginger, turmeric, Arnica montana, helenalin, cannabichromene, rofecoxib, hyaluronidase, and salts, derivatives, isomers, racemates, diastereoisomers, prodrugs, hydrate, ester, or analogs thereof.

In some embodiments of the methods and/or devices provided herein, the pharmaceutical agent comprises hyaluronidase.

In some embodiments of the methods and/or devices provided herein, the pharmaceutical agent comprises cilostazol.

In some embodiments of the methods and/or devices provided herein, the pharmaceutical agent comprises dipyridamole.

In some embodiments of the methods and/or devices provided herein, the pharmaceutical agent comprises an antibiotic agent.

In some embodiments of the methods and/or devices provided herein, the pharmaceutical agent comprises a chemotherapeutic agent.

In some embodiments of the methods and/or devices provided herein, the pharmaceutical agent is in a therapeutically desirable morphology.

In some embodiments of the methods and/or devices provided herein, the active agent comprises a chemotherapeutic agent. In some embodiments of the methods and/or devices provided herein, the pharmaceutical agent comprises a chemotherapeutic agent. In some embodiments, the chemotherapeutic agent comprises at least one of: an angiostatin, DNA topoisomerase, endostatin, genistein, ornithine decarboxylase inhibitors, chlormethine, melphalan, pipobroman, triethylene-melamine, triethylenethiophosphoramine, busulfan, carmustine (BCNU), streptozocin, 6-mercaptopurine, 6-thioguanine, Deoxyco-formycin, IFN-α, 17α-ethinylestradiol, diethylstilbestrol, testosterone, prednisone, fluoxymesterone, dromostanolone propionate, testolactone, megestrolacetate, methylprednisolone, methyltestosterone, prednisolone, triamcinolone, chlorotrianisene, hydroxyprogesterone, estramustine, medroxyprogesteroneacetate, flutamide, zoladex, mitotane, hexamethylmelamine, indolyl-3-glyoxylic acid derivatives, (e.g., indibulin), doxorubicin and idarubicin, plicamycin (mithramycin) and mitomycin, mechlorethamine, cyclophosphamide analogs, trazenes-dacarbazinine (DTIC), pentostatin and 2-chlorodeoxyadenosine, letrozole, camptothecin (and derivatives), navelbine, erlotinib, capecitabine, acivicin, acodazole hydrochloride, acronine, adozelesin, aldesleukin, ambomycin, ametantrone acetate, anthramycin, asperlin, azacitidine, azetepa, azotomycin, batimastat, benzodepa, bisnafide, bisnafide dimesylate, bizelesin, bropirimine, cactinomycin, calusterone, carbetimer, carubicin hydrochloride, carzelesin, cedefingol, celecoxib (COX-2 inhibitor), cirolemycin, crisnatol mesylate, decitabine, dexormaplatin, dezaguanine mesylate, diaziquone, duazomycin, edatrexate, eflomithine, elsamitrucin, enloplatin, enpromate, epipropidine, erbulozole, etanidazole, etoprine, flurocitabine, fosquidone, lometrexol, losoxantrone hydrochloride, masoprocol, maytansine, megestrol acetate, melengestrol acetate, metoprine, meturedepa, mitindomide, mitocarcin, mitocromin, mitogillin, mitomalcin, mitosper, mycophenolic acid, nocodazole, nogalamycin, ormaplatin, oxisuran, pegaspargase, peliomycin, pentamustine, perfosfamide, piposulfan, plomestane, porfimer sodium, porfiromycin, puromycin, pyrazofurin, riboprine, safingol, simtrazene, sparfosate sodium, spiromustine, spiroplatin, streptonigrin, sulofenur, tecogalan sodium, taxotere, tegafur, teloxantrone hydrochloride, temoporfin, thiamiprine, tirapazamine, trestolone acetate, triciribine phosphate, trimetrexate glucuronate, tubulozole hydrochloride, uracil mustard, uredepa, verteporfin, vinepidine sulfate, vinglycinate sulfate, vinleurosine sulfate, vinorelbine tartrate, vinrosidine sulfate, zeniplatin, zinostatin, 20-epi-1,25 dihydroxyvitamin D3, 5-ethynyluracil, acylfulvene, adecypenol, ALL-TK antagonists, ambamustine, amidox, amifostine, aminolevulinic acid, amrubicin, anagrelide, andrographolide, antagonist D, antagonist G, antarelix, anti-dorsalizing morphogenetic protein-1, antiandrogen, antiestrogen, estrogen agonist, apurinic acid, ara-CDP-DL-PTBA, arginine deaminase, asulacrine, atamestane, atrimustine, axinastatin 1, axinastatin 2, axinastatin 3, azasetron, azatoxin, azatyrosine, baccatin III derivatives, balanol, BCR/ABL antagonists, benzochlorins, benzoylstaurosporine, beta lactam derivatives, beta-alethine, betaclamycin B, betulinic acid, bFGF inhibitor, bisaziridinylspermine, bistratene A, breflate, buthionine sulfoximine, calcipotriol, calphostin C, carboxamide-amino-triazole, carboxyamidotriazole, CaRest M3, CARN 700, cartilage derived inhibitor, casein kinase inhibitors (ICOS), castanospermine, cecropin B, cetrorelix, chloroquinoxaline sulfonamide, cicaprost, cisporphyrin, clomifene analogues, clotrimazole, collismycin A, collismycin B, combretastatin A4, combretastatin analogue, conagenin, crambescidin 816, cryptophycin 8, cryptophycin A derivatives, curacin A, cyclopentanthraquinones, cycloplatam, cypemycin, cytolytic factor, cytostatin, dacliximab, dehydrodidemnin B, dexamethasone, dexifosfamide, dexrazoxane, dexverapamil, didemnin B, didox, diethylnorspermine, dihydro-5-azacytidine, dihydrotaxol, 9-, dioxamycin, docosanol, dolasetron, dronabinol, duocarmycin SA, ebselen, ecomustine, edelfosine, edrecolomab, elemene, emitefur, estramustine analogue, filgrastim, flavopiridol, flezelastine, fluasterone, fluorodaunorunicin hydrochloride, forfenimex, gadolinium texaphyrin, galocitabine, gelatinase inhibitors, glutathione inhibitors, hepsulfam, heregulin, hexamethylene bisacetamide, hypericin, ibandronic acid, idramantone, ilomastat, imatinib (e.g., Gleevec), imiquimod, immunostimulant peptides, insulin-like growth factor-1 receptor inhibitor, interferon agonists, interferons, interleukins, iobenguane, iododoxorubicin, ipomeanol, 4-, iroplact, irsogladine, isobengazole, isohomohalicondrin B, itasetron, jasplakinolide, kahalalide F, lamellarin-N triacetate, leinamycin, lenograstim, lentinan sulfate, leptolstatin, leukemia inhibiting factor, leukocyte alpha interferon, leuprolide+estrogen+progesterone, linear polyamine analogue, lipophilic disaccharide peptide, lipophilic platinum compounds, lissoclinamide 7, lobaplatin, lombricine, loxoribine, lurtotecan, lutetium texaphyrin, lysofylline, lytic peptides, maitansine, mannostatin A, marimastat, maspin, matrilysin inhibitors, matrix metalloproteinase inhibitors, meterelin, methioninase, metoclopramide, MIF inhibitor, mifepristone, miltefosine, mirimostim, mitoguazone, mitotoxin fibroblast growth factor-saporin, mofarotene, molgramostim, Erbitux, human chorionic gonadotrophin, monophosphoryl lipid A+myobacterium cell wall sk, mustard anticancer agent, mycaperoxide B, mycobacterial cell wall extract, myriaporone, N-acetyldinaline, N-substituted benzamides, nagrestip, naloxone+pentazocine, napavin, naphterpin, nartograstim, nedaplatin, nemorubicin, neridronic acid, nisamycin, nitric oxide modulators, nitroxide antioxidant, nitrullyn, oblimersen (Genasense), $O^6$-benzylguanine, okicenone, onapristone, ondansetron, oracin, oral cytokine inducer, paclitaxel analogues and derivatives, palauamine, palmitoylrhizoxin, pamidronic acid, panaxytriol, panomifene, parabactin, peldesine, pentosan polysulfate sodium, pentrozole, perflubron, perillyl alcohol, phenazinomycin, phenylacetate, phosphatase inhibitors, picibanil, pilocarpine hydrochloride, placetin A, placetin B, plasminogen activator inhibitor, platinum complex, platinum compounds, platinum-triamine complex, propyl bis-acridone, prostaglandin J2, proteasome inhibitors, protein A-based immune modulator, protein kinase C inhibitors, microalgal, pyrazoloacridine, pyridoxylated hemoglobin polyoxyethylene conjugate, raf antagonists, raltitrexed, ramosetron, ras farnesyl protein transferase inhibitors, ras-GAP inhibitor, retelliptine demethylated, rhenium Re 186 etidronate, ribozymes, RII retinamide, rohitukine, romurtide, roquinimex, rubiginone B1, ruboxyl, saintopin, SarCNU, sarcophytol A, sargramostim, Sdi 1 mimetics, senescence derived inhibitor 1, signal transduction inhibitors, sizofiran, sobuzoxane, sodium borocaptate, solverol, somatomedin binding protein, sonermin, sparfosic acid, spicamycin D, splenopentin, spongistatin 1, squalamine, stipiamide, stromelysin inhibitors, sulfinosine, superactive vasoactive intestinal peptide antagonist, suradista, suramin, swainsonine, tallimustine, tazarotene, tellurapyrylium, telomerase inhibitors, tetrachlorodecaoxide, tetrazomine, thiocoraline, thrombopoietin, thrombopoietin mimetic, thymalfasin, thymopoietin receptor agonist, thymotrinan, thyroid stimulating hormone, tin ethyl etiopurpurin, titanocene bichloride, topsentin, translation inhibitors, tretinoin, triacetyluridine, tropisetron, turosteride, ubenimex, urogenital sinus-derived growth inhibitory factor, variolin B, velaresol, veramine, verdins, vinxaltine, vitaxin, zanoterone, zilascorb, zinostatin stimalamer, acanthifolic acid, aminothiadiazole, anastrozole, bicalutamide, brequinar sodium, capecitabine, carmofur, Ciba-Geigy CGP-30694, cladribine, cyclopentyl cytosine, cytarabine phosphate stearate, cytarabine conjugates, cytarabine ocfosfate, Lilly DATHF, Merrel Dow DDFC, dezaguanine, dideoxycytidine, dideoxyguanosine, didox, Yoshitomi DMDC, doxifluridine, Wellcome EHNA, Merck & Co. EX-015, fazarabine, floxuridine, fludarabine, fludarabine phosphate, N-(2'-furanidyl)-5-fluorouracil, Daiichi Seiyaku FO-152, 5-FU-fibrinogen, isopropyl pyrrolizine, Lilly LY-188011, Lilly LY-264618, methobenzaprim, methotrexate, Wellcome MZPES, norspermidine, nolvadex, NCI NSC-127716, NCI NSC-264880, NCI NSC-39661, NCI NSC-612567, Warner-Lambert PALA, pentostatin, piritrexim, plicamycin, Asahi Chemical PL-AC, stearate, Takeda TAC-788, thioguanine, tiazofurin, Erbamont TIF, trimetrexate, tyrosine kinase inhibitors, tyrosine protein kinase inhibitors, Taiho UFT, uricytin, Shionogi 254-S, aldo-phosphamide analogues, altretamine, anaxirone, Boehringer Mannheim BBR-2207, bestrabucil, budotitane, Wakunaga CA-102, carboplatin, carmustine (BiCNU), Chinoin-139, Chinoin-153, chlorambucil, cisplatin, cyclophosphamide, American Cyanamid CL-286558, Sanofi CY-233, cyplatate, dacarbazine, Degussa D-19-384, Sumimoto DACHP(Myr)2, diphenylspiromustine, diplatinum cytostatic, Chugai DWA-2114R, ITI E09, elmustine, Erbamont FCE-24517, estramustine phosphate sodium, etoposide phosphate, fotemustine, Unimed G-6-M, Chinoin GYKI-17230, hepsul-fam, ifosfamide, iproplatin, lomustine, mafosfamide, mitolactol, mycophenolate, Nippon Kayaku NK-121, NCI NSC-264395, NCI NSC-342215, oxaliplatin, Upjohn PCNU, prednimustine, Proter PTT-119, ranimustine, semustine, SmithKline SK&F-101772, thiotepa, Yakult Honsha SN-22, spiromus-tine, Tanabe Seiyaku TA-077, tauromustine, temozolomide, teroxirone, tetraplatin and trimelamol, Taiho 4181-A, aclarubicin, actinomycin D, actinoplanone, Erbamont ADR-456, aeroplysinin derivative, Ajinomoto AN-201-II, Ajinomoto AN-3, Nippon Soda anisomycins, anthracycline, azino-mycin-A, bisucaberin, Bristol-Myers BL-6859, Bristol-Myers BMY-25067, Bristol-Myers BMY-25551, Bristol-Myers BMY-26605, Bristol-Myers BMY-27557, Bristol-Myers BMY-28438, bleomycin sulfate, bryostatin-1, Taiho C-1027, calichemycin, chromoximycin, dactinomycin, daunorubicin, Kyowa Hakko DC-102, Kyowa Hakko DC-79, Kyowa Hakko DC-88A, Kyowa Hakko DC89-A1, Kyowa Hakko DC92-B, ditrisarubicin B, Shionogi DOB-41, doxorubicin, doxorubicin-fibrinogen, elsamicin-A, epirubicin, erbstatin, esorubicin, esperamicin-A1, esperamicin-A1b, Erbamont FCE-21954, Fujisawa FK-973, fostriecin, Fujisawa FR-900482, glidobactin, gregatin-A, grincamycin, herbimycin, idarubicin, illudins, kazusamycin, kesarirhodins, Kyowa Hakko KM-5539, Kirin Brewery KRN-8602, Kyowa Hakko KT-5432, Kyowa Hakko KT-5594, Kyowa Hakko KT-6149, American Cyanamid LL-D49194, Meiji Seika ME 2303, menogaril, mitomycin, mitomycin analogues, mitoxantrone, SmithKline M-TAG, neoenactin, Nippon Kayaku NK-313, Nippon Kayaku NKT-01, SRI International NSC-357704, oxalysine, oxaunomycin, peplomycin, pilatin, pirarubicin, porothramycin, pyrindamycin A, Tobishi RA-I, rapamycin, rhizoxin, rodorubicin, sibanomicin, siwenmycin, Sumitomo SM-5887, Snow Brand SN-706, Snow Brand SN-07, sorangicin-A, sparsomycin, SS Pharmaceutical SS-21020, SS Pharmaceutical SS-7313B, SS Pharmaceutical SS-9816B, steffimycin B, Taiho 4181-2, talisomycin, Takeda TAN-868A, terpentecin, thrazine, tricrozarin A, Upjohn U-73975, Kyowa Hakko UCN-10028A, Fujisawa WF-3405, Yoshitomi Y-25024, zorubicin, 5-fluorouracil (5-FU), the peroxidate oxidation product of inosine, adenosine, or cytidine with methanol or ethanol, cytosine arabinoside (also referred to as Cytarabin, araC, and Cytosar), 5-Azacytidine, 2-Fluoroadenosine-5'-phosphate (Fludara, also referred to as FaraA), 2-Chlorodeoxyadenosine, Abarelix, Abbott A-84861, Abiraterone acetate, Aminoglutethimide, Asta Medica AN-207, Antide, Chugai AG-041R, Avorelin, aseranox, Sensus B2036-PEG, buserelin, BTG CB-7598, BTG CB-7630, Casodex, cetrolix, clastroban, clodronate disodium, Cosudex, Rotta Research CR-1505, cytadren, crinone, deslorelin, droloxifene, dutasteride, Elimina, Laval University EM-800, Laval University EM-652, epitiostanol, episteride, Mediolanum EP-23904, EntreMed 2-ME, exemestane, fadrozole, finasteride, formestane, Pharmacia & Upjohn FCE-24304, ganirelix, goserelin, Shire gonadorelin agonist, Glaxo Wellcome GW-5638, Hoechst Marion Roussel Hoe-766, NCI hCG, idoxifene, isocordoin, Zeneca ICI-182780, Zeneca ICI-118630, Tulane University J015X, Schering Ag J96, ketanserin, lanreotide, Milkhaus LDI-200, letrozol, leuprolide, leuprorelin, liarozole, lisuride hydrogen maleate, loxiglumide, mepitiostane, Ligand Pharmaceuticals LG-1127, LG-1447, LG-2293, LG-2527, LG-2716, Bone Care International LR-103, Lilly LY-326315, Lilly LY-353381-HCl, Lilly LY-326391, Lilly LY-353381, Lilly LY-357489, miproxifene phosphate, Orion Pharma MPV-2213ad, Tulane University MZ-4-71, nafarelin, nilutamide, Snow Brand NKS01, Azko Nobel ORG-31710, Azko Nobel ORG-31806, orimeten, orimetene, orimetine, ormeloxifene, osaterone, Smithkline Beecham SKB-105657, Tokyo University OSW-1, Peptech PTL-03001, Pharmacia & Upjohn PNU-156765, quinagolide, ramorelix, Raloxifene, statin, sandostatin LAR, Shionogi S-10364, Novartis SMT-487, somavert, somatostatin, tamoxifen, tamoxifen methiodide, teverelix, toremifene, triptorelin, TT-232, vapreotide, vorozole, Yamanouchi YM-116, Yamanouchi YM-511, Yamanouchi YM-55208, Yamanouchi YM-53789, Schering AG ZK-1911703, Schering AG ZK-230211, and Zeneca ZD-182780, alpha-carotene, alpha-difluoromethyl-arginine, acitretin, Biotec AD-5, Kyorin AHC-52, alstonine, amonafide, amphethinile, amsacrine, Angiostat, ankinomycin, antineoplaston A10, antineoplaston A2, antineoplaston A3, antineoplaston A5, antineoplaston AS2-1, Henkel APD, aphidicolin glycinate, asparaginase, Avarol, baccharin, batracylin, benfluron, benzotript, Ipsen-Beaufour BIM-23015, bisantrene, Bristo-Myers BMY-40481, Vestar boron-10, bromofosfamide, Wellcome BW-502, Wellcome BW-773, calcium carbonate, Calcet, Calci-Chew, Calci-Mix, Roxane calcium carbonate tablets, caracemide, carmethizole hydrochloride, Ajinomoto CDAF, chlorsulfaquinoxalone, Chemes CHX-2053, Chemex CHX-100, Warner-Lambert CI-921, Warner-Lambert CI-937, Warner-Lambert CI-941, Warner-Lambert CI-958, clanfenur, claviridenone, ICN compound 1259, ICN compound 4711, Contracan, Cell Pathways CP-461, Yakult Honsha CPT-11, crisnatol, curaderm, cytochalasin B, cytarabine, cytocytin, Merz D-609, DABIS maleate, datelliptinium, DFMO, didemnin-B, dihaematoporphyrin ether, dihydrolenperone dinaline, distamycin, Toyo Pharmar DM-341, Toyo Pharmar DM-75, Daiichi Seiyaku DN-9693, docetaxel, Encore Pharmaceuticals E7869, elliprabin, elliptinium acetate, Tsumura EPMTC, ergotamine, etoposide, etretinate, Eulexin, Cell Pathways Exisulind (sulindac sulphone or CP-246), fenretinide, Florical, Fujisawa FR-57704, gallium nitrate, gemcitabine, genkwadaphnin, Gerimed, Chugai GLA-43, Glaxo GR-63178, grifolan NMF-5N, hexadecylphosphocholine, Green Cross HO-221, homoharringtonine, hydroxyurea, BTG ICRF-187, ilmofosine, irinotecan, isoglutamine, isotretinoin, Otsuka JI-36, Ramot K-477, ketoconazole, Otsuak K-76COONa, Kureha Chemical K-AM, MECT Corp KI-8110, American Cyanamid L-623, leucovorin, levamisole, leukoregulin, lonidamine, Lundbeck LU-23-112, Lilly LY-186641, Materna, NCI (US) MAP, marycin, Merrel Dow MDL-27048, Medco MEDR-340, megestrol, merbarone, merocyanine derivatives, methylanilinoacridine, Molecular Genetics MGI-136, minactivin, mitonafide, mitoquidone, Monocal, mopidamol, motretinide, Zenyaku Kogyo MST-16, Mylanta, N-(retinoyl)amino acids, Nilandron, Nisshin Flour Milling N-021, N-acylated-dehydroalanines, nafazatrom, Taisho NCU-190, Nephro-Calci tablets, nocodazole derivative, Normosang, NCI NSC-145813, NCI NSC-361456, NCI NSC-604782, NCI NSC-95580, octreotide, Ono ONO-112, oquizanocine, Akzo Org-10172, paclitaxel, pancratistatin, pazelliptine, Warner-Lambert PD-111707, Warner-Lambert PD-115934, Warner-Lambert PD-131141, Pierre Fabre PE-1001, ICRT peptide D, piroxantrone, polyhaematoporphyrin, polypreic acid, Efamol porphyrin, probimane, procarbazine, proglumide, Invitron protease nexin I, Tobishi RA-700, razoxane, retinoids, R-flurbiprofen (Encore Pharmaceuticals), Sandostatin, Sapporo Breweries RBS, restrictin-P, retelliptine, retinoic acid, Rhone-Poulenc RP-49532, Rhone-Poulenc RP-56976, Scherring-Plough SC-57050, Scherring-Plough SC-57068, selenium (selenite and selenomethionine), SmithKline SK&F-104864, Sumitomo SM-108, Kuraray SMANCS, SeaPharm SP-10094, spatol, spirocyclopropane derivatives, spirogermanium, Unimed, SS Pharmaceutical SS-554, strypoldinone, Stypoldione, Suntory SUN 0237, Suntory SUN 2071, Sugen SU-101, Sugen SU-5416, Sugen SU-6668, sulindac, sulindac sulfone, superoxide dismutase, Toyama T-506, Toyama T-680, taxol, Teijin TEI-0303, teniposide, thaliblastine, Eastman Kodak TJB-29, tocotrienol, Topostin, Teijin TT-82, Kyowa Hakko UCN-01, Kyowa Hakko UCN-1028, ukrain, Eastman Kodak USB-006, vinblastine, vinblastine sulfate, vincristine, vincristine sulfate, vindesine, vindesine sulfate, vinestramide, vinorelbine, vintriptol, vinzolidine, withanolides, Yamanouchi YM-534, Zileuton, ursodeoxycholic acid, Zanosar.

In some embodiments of the methods and/or devices provided herein, the chemotherapeutic agent comprises Bacillus Calmette-Guerin (BCG).

In some embodiments of the methods and/or devices provided herein, the active agent comprises an antibiotic agent. In some embodiments of the methods and/or devices provided herein, the pharmaceutical agent comprises an antibiotic agent. In some embodiments, the antibiotic agent comprises at least one of: amikacin, amoxicillin, gentamicin, kanamycin, neomycin, netilmicin, paromomycin, tobramycin, geldanamycin, herbimycin, carbacephem (loracarbef), ertapenem, doripenem, imipenem, cefadroxil, cefazolin, cefalotin, cephalexin, cefaclor, cefamandole, cefoxitin, cefprozil, cefuroxime, cefixime, cefdinir, cefditoren, cefoperazone, cefotaxime, cefpodoxime, ceftazidime, ceftibuten, ceftizoxime, ceftriaxone, cefepime, ceftobiprole, clarithromycin, clavulanic acid, clindamycin, teicoplanin, azithromycin, dirithromycin, erythromycin, troleandomycin, telithromycin, aztreonam, ampicillin, azlocillin, bacampicillin, carbenicillin, cloxacillin, dicloxacillin, flucloxacillin, mezlocillin, meticillin, nafcillin, norfloxacin, oxacillin, penicillin G, penicillin V, piperacillin, pvampicillin, pivmecillinam, ticarcillin, bacitracin, colistin, polymyxin B, ciprofloxacin, enoxacin, gatifloxacin, levofloxacin, lomefloxacin, moxifloxacin, ofloxacin, trovafloxacin, grepafloxacin, sparfloxacin, afenide, prontosil, sulfacetamide, sulfamethizole, sulfanilimide, sulfamethoxazole, sulfisoxazole, trimethoprim, trimethoprim-sulfamethoxazole, demeclocycline, doxycycline, oxytetracycline, tetracycline, arsphenamine, chloramphenicol, lincomycin, ethambutol, fosfomycin, furazolidone, isoniazid, linezolid, mupirocin, nitrofurantoin, platensimycin, pyrazinamide, quinupristin/dalfopristin, rifampin, thiamphenicol, rifampicin, minocycline, sultamicillin, sulbactam, sulphonamides, mitomycin, spectinomycin, spiramycin, roxithromycin, and meropenem.

In some embodiments of the methods and/or devices provided herein, the antibiotic agent comprises erythromycin.

In some embodiments of the methods and/or devices provided herein, the active agent comprises an active biological agent. In some embodiments, the active biological agent comprises an active secondary, tertiary or quaternary structure. In some embodiments, the active biological agent comprises at least one of growth factors, cytokines, peptides, proteins, enzymes, glycoproteins, nucleic acids, antisense nucleic acids, fatty acids, antimicrobials, vitamins, hormones, steroids, lipids, polysaccharides, carbohydrates, a hormone, gene therapies, RNA, siRNA, and/or cellular therapies such as stem cells and/or T-cells.

In some embodiments of the methods and/or devices provided herein, the active biological agent comprises siRNA.

In some embodiments of the methods and/or devices provided herein, the coating further comprises a polymer. In some embodiments, the active agent comprises a polymer. In some embodiments, the polymer comprises at least one of polyalkyl methacrylates, polyalkylene-co-vinyl acetates, polyalkylenes, polyurethanes, polyanhydrides, aliphatic polycarbonates, polyhydroxyalkanoates, silicone containing polymers, polyalkyl siloxanes, aliphatic polyesters, polyglycolides, polylactides, polylactide-co-glycolides, poly(e-caprolactone)s, polytetrahalooalkylenes, polystyrenes, poly(phosphasones), copolymers thereof, and combinations thereof.

In some embodiments of the methods and/or devices provided herein, the coating comprises a bioabsorbable polymer. In some embodiments, the active agent comprises a bioabsorbable polymer. In some embodiments, the bioabsorbable polymer comprises at least one of: Polylactides (PLA); PLGA (poly(lactide-co-glycolide)); Polyanhydrides; Polyorthoesters; Poly(N-(2-hydroxypropyl) methacrylamide); DLPLA—poly(dl-lactide); LPLA—poly(1-lactide); PGA-polyglycolide; PDO—poly(dioxanone); PGA-TMC—poly(glycolide-co-trimethylene carbonate); PGA-LPLA—poly(1-lactide-co-glycolide); PGA-DLPLA—poly(dl-lactide-co-glycolide); LPLA-DLPLA—poly(1-lactide-co-dl-lactide); and PDO-PGA-TMC-poly(glycolide-co-trimethylene carbonate-co-dioxanone), and combinations, copolymers, and derivatives thereof. In some embodiments, the bioabsorbable polymer comprises between 1% and 95% glycolic acid content PLGA-based polymer.

In some embodiments of the methods and/or devices provided herein, the polymer comprises at least one of polycarboxylic acids, cellulosic polymers, proteins, polypeptides, polyvinylpyrrolidone, maleic anhydride polymers, polyamides, polyvinyl alcohols, polyethylene oxides, glycosaminoglycans, polysaccharides, polyesters, aliphatic polyesters, polyurethanes, polystyrenes, copolymers, silicones, silicone containing polymers, polyalkyl siloxanes, polyorthoesters, polyanhydrides, copolymers of vinyl monomers, polycarbonates, polyethylenes, polypropytenes, polylactic acids, polylactides, polyglycolic acids, polyglycolides, polylactide-co-glycolides, polycaprolactones, poly(e-caprolactone)s, polyhydroxybutyrate valerates, polyacrylamides, polyethers, polyurethane dispersions, polyacrylates, acrylic latex dispersions, polyacrylic acid, polyalkyl methacrylates, polyalkylene-co-vinyl acetates, polyalkylenes, aliphatic polycarbonates polyhydroxyalkanoates, polytetrahalooalkylenes, poly(phosphasones), polytetrahalooalkylenes, poly(phosphasones), and mixtures, combinations, and copolymers thereof. The polymers of the present invention may be natural or synthetic in origin, including gelatin, chitosan, dextrin, cyclodextrin, Poly(urethanes), Poly(siloxanes) or silicones, Poly(acrylates) such as [rho]oly(methyl methacrylate), poly(butyl methacrylate), and Poly(2-hydroxy ethyl methacrylate), Poly(vinyl alcohol) Poly(olefins) such as poly(ethylene), [rho]oly(isoprene), halogenated polymers such as Poly(tetrafluoroethylene)—and derivatives and copolymers such as those commonly sold as Teflon® products, Poly(vinylidine fluoride), Poly(vinyl acetate), Poly (vinyl pyrrolidone), Poly(acrylic acid), Polyacrylamide, Poly(ethylene-co-vinyl acetate), Poly(ethylene glycol), Poly (propylene glycol), Poly(methacrylic acid); etc. Suitable polymers also include absorbable and/or resorbable polymers including the following, combinations, copolymers and derivatives of the following: Polylactides (PLA), Polyglycolides (PGA), PolyLactide-co-glycolides (PLGA), Polyanhydrides, Polyorthoesters, Poly(N-(2-hydroxypropyl) methacrylamide), Poly(1-aspartamide), including the derivatives DLPLA—poly(dl-lactide); LPLA—poly(1-lactide); PDO—poly(dioxanone); PGA-TMC—poly(glycolide-co-trimethylene carbonate); PGA-LPLA—poly(1-lactide-co-glycolide); PGA-DLPLA—poly(dl-lactide-co-glycolide); LPLA-DLPLA—poly(1-lactide-co-dl-lactide); and PDO-PGA-TMC—poly(glycolide-co-trimethylene carbonate-co-dioxanone), and combinations thereof.

In some embodiments of the methods and/or devices provided herein, the polymer has a dry modulus between 3,000 and 12,000 KPa. In some embodiments, the polymer is capable of becoming soft after implantation. In some embodiments, the polymer is capable of becoming soft after implantation by hydration, degradation or by a combination of hydration and degradation. In some embodiments, the polymer is adapted to transfer, free, and/or dissociate from the substrate when at the intervention site due to hydrolysis of the polymer.

In some embodiments of the methods and/or devices provided herein, the bioabsorbable polymer is capable of resorbtion in at least one of: about 1 day, about 3 days, about 5 days, about 7 days, about 14 days, about 3 weeks, about 4 weeks, about 45 days, about 60 days, about 90 days, about 180 days, about 6 months, about 9 months, about 1 year, about 1 to about 2 days, about 1 to about 5 days, about 1 to about 2 weeks, about 2 to about 4 weeks, about 45 to about 60 days, about 45 to about 90 days, about 30 to about 90 days, about 60 to about 90 days, about 90 to about 180 days, about 60 to about 180 days, about 180 to about 365 days, about 6 months to about 9 months, about 9 months to about 12 months, about 9 months to about 15 months, and about 1 year to about 2 years.

In some embodiments of the methods and/or devices provided herein, at least a portion of the substrate is bioabsorbable. In some embodiments, the substrate comprises at least one of a bioabsorbable polymer and a bioabsorbable metal. In some embodiments, the at least one bioabsorbable polymer or bioabsorbable metal is capable of resorbtion in at least one of: about 1 day, about 3 days, about 5 days, about 7 days, about 14 days, about 3 weeks, about 4 weeks, about 45 days, about 60 days, about 90 days, about 180 days, about 6 months, about 9 months, about 1 year, about 1 to about 2 days, about 1 to about 5 days, about 1 to about 2 weeks, about 2 to about 4 weeks, about 45 to about 60 days, about 45 to about 90 days, about 30 to about 90 days, about 60 to about 90 days, about 90 to about 180 days, about 60 to about 180 days, about 180 to about 365 days, about 6 months to about 9 months, about 9 months to about 12 months, about 9 months to about 15 months, and about 1 year to about 2 years.

In some embodiments of the methods and/or devices provided herein, the coating comprises a hydrogel. In some embodiments, the hydrogel is adapted to degrade by bulk degradation. In some embodiments, the hydrogel is adapted to degrade by surface degradation.

In some embodiments of the methods and/or devices provided herein, the coating comprises laminated layers that allow direct control of the transfer, freeing, and/or dissociation of the coating from the substrate. In some embodiments, the coating comprises laminated layers that allow direct control of the transferring, freeing, depositing, tacking, and/or dissociating of the coating from the substrate, wherein at least one of the layers comprises the active agent. In some embodiments, the coating comprises laminated layers that allow direct control of the transferring, freeing, depositing, tacking, and/or dissociating of the coating from the substrate, wherein at least one of the layers comprises the pharmaceutical agent.

In some embodiments of the methods and/or devices provided herein, the coating further comprises at least one image enhanced polymer. In some embodiments, the image enhanced polymer comprises at least one of: EgadMe in which a galactopyranose ring is synthesized to protect a Gd(III) ion from bulk water; a conjugated polymer MEH-PPV nanoparticle; bismuth trioxide; a near infrared (NIR) fluorochrome; a bioluminescence agent; a SPECT radionuclide; gadolinium diethylenetriamine pentaacetic acid; Echo-Coat, an ultrasound imaging agent (STS-Biopolymers); and barium sulfate. In some embodiments, the coating comprises an imaging agent. In some embodiments, the imaging agent comprises at least one of a barium compound and an iodine compound.

In some embodiments of the methods and/or devices provided herein, the coating comprises a biodegradable material that is adhered and/or cohered to the substrate prior to implantation, wherein the biodegradable material is capable of degrading over time to lose its cohesion and/or adhesion to the substrate. In some embodiments, the pharmaceutical agent and/or the active agent is released from the coating within at least one of about 1 day, about 3 days, about 5 days, about 7 days, about 14 days, about 3 weeks, about 4 weeks, about 45 days, about 60 days, about 90 days, about 180 days, about 6 months, about 9 months, about 1 year, about 1 to about 2 days, about 1 to about 5 days, about 1 to about 2 weeks, about 2 to about 4 weeks, about 45 to about 60 days, about 45 to about 90 days, about 30 to about 90 days, about 60 to about 90 days, about 90 to about 180 days, about 60 to about 180 days, about 180 to about 365 days, about 6 months to about 9 months, about 9 months to about 12 months, about 9 months to about 15 months, and about 1 year to about 2 years.

In some embodiments of the methods and/or devices provided herein, the coating is prepared by a solvent based coating method. In some embodiments, the coating is prepared by a solvent plasma based coating method.

In some embodiments of the methods and/or devices provided herein, the coating comprises a microstructure. In some embodiments, particles of the active agent are sequestered or encapsulated within said microstructure. In some embodiments, the microstructure comprises microchannels, micropores and/or microcavities. In some embodiments, the microstructure is selected to allow sustained release of the active agent. In some embodiments, the microstructure is selected to allow controlled release of the active agent.

In some embodiments of the methods and/or devices provided herein, the coating is formed on said substrate by a process comprising depositing a polymer and/or the active agent by an e-RESS, an e-SEDS, or an e-DPC process. In some embodiments of the methods and/or devices provided herein, wherein the coating is formed on said substrate by a process comprising at least one of: depositing a polymer by an e-RESS, an e-SEDS, or an e-DPC process, and depositing the pharmaceutical agent by an e-RESS, an e-SEDS, or an e-DPC process. In some embodiments of the methods and/or devices provided herein, the coating is formed on said substrate by a process comprising at least one of: depositing a polymer by an e-RESS, an e-SEDS, or an e-DPC process, and depositing the active agent by an e-RESS, an e-SEDS, or an e-DPC process. In some embodiments, the process of forming said coating provides improved adherence of the coating to the substrate prior to deployment of the device at the intervention site and facilitates dissociation of said coating from said substrate at the intervention site. In some embodiments, the coating is formed on said substrate by a process comprising depositing the active agent by an e-RESS, an e-SEDS, or an e-DPC process without electrically charging the substrate. In some embodiments, the coating is formed on said substrate by a process comprising depositing the active agent on the substrate by an e-RESS, an e-SEDS, or an e-DPC process without creating an electrical potential between the substrate and a coating apparatus used to deposit the coating.

In some embodiments of the methods and/or devices provided herein, the intervention site is in or on the body of a subject. In some embodiments, the intervention site is a vascular wall. In some embodiments, the intervention site is a non-vascular lumen wall. In some embodiments, the intervention site is a vascular cavity wall.

In some embodiments of the methods and/or devices provided herein, the intervention site is a wall of a body cavity. In some embodiments, the body cavity is the result of a lumpectomy. In some embodiments, the intervention site is a cannulized site within a subject.

In some embodiments of the methods and/or devices provided herein, the intervention site is a sinus wall. In some embodiments, the intervention site is a sinus cavity wall. In some embodiments, the active agent comprises a corticosteroid.

In some embodiments of the methods and/or devices provided herein, the intervention site is located in the reproductive system of a subject. In some embodiments, the device is adapted to aid in fertility. In some embodiments, the device is adapted to treat a sexually transmitted disease. In some embodiments, the device is adapted to substantially prevent pregnancy. In some embodiments, the active agent comprises a hormone. In some embodiments, the pharmaceutical agent comprises a hormone. In some embodiments, the device is adapted to substantially prevent transmission of a sexually transmitted disease. In some embodiments, the device is adapted to treat an ailment of the reproductive system.

In some embodiments of the methods and/or devices provided herein, the intervention site is located in the urinary system of a subject. In some embodiments, the device is adapted to treat a disease of the urinary system. In some embodiments, the active agent comprises a fluoroquinolone. In some embodiments, the pharmaceutical agent comprises fluoroquinolone.

In some embodiments of the methods and/or devices provided herein, the intervention site is located at a tumor site. In some embodiments, the tumor site is where a tumor is located. In some embodiments, the tumor site is where a tumor was located prior to removal and/or shrinkage of the tumor. In some embodiments, the active agent comprises mitomycin C. In some embodiments, the pharmaceutical agent comprises mitimycin C.

In some embodiments of the methods and/or devices provided herein, the intervention site is located in the ear. In some embodiments, the intervention site is located in the esophagus. In some embodiments, the active agent comprises lidocaine. In some embodiments, the pharmaceutical agent comprises lidocaine.

In some embodiments of the methods and/or devices provided herein, the intervention site is located in the larynx. In some embodiments, the intervention site is a location of an injury. In some embodiments, the active agent comprises CD34 antibodies.

In some embodiments of the methods and/or devices provided herein, the intervention site is an infection site. In some embodiments, the infection site is a site wherein an infection may occur, and wherein the active agent is capable of substantially preventing the infection. In some embodiments, the infection site is a site wherein an infection has occurred, and wherein the active agent is capable of slowing spread of the infection. In some embodiments, the infection site is a site wherein an infection has occurred, and wherein the active agent is capable of treating the infection. In some embodiments, the active agent comprises an anti-infective agent. In some embodiments, the pharmaceutical agent comprises an anti-infective agent. In some embodiments, the anti-infective agent comprises clindamycin.

In some embodiments of the methods and/or devices provided herein, the intervention site is a surgery site. In some embodiments, the intervention site is an ocular site.

In some embodiments of the methods and/or devices provided herein, the coating is capable of promoting healing. In some embodiments, the active agent comprises a growth factor. In some embodiments, the growth factor comprises at least one of: an epidermal growth factor (EGF), a transforming growth factor-alpha (TGF-alpha), a hepatocyte growth factor (HGF), a vacscular endothelial growth factor (VEGF), a platelet derived growth factor (PDGF), a fibroblast growth factor 1 (FGF-1), a fibroblast growth factor 2 (FGF-2), a transforming growth factor-beta (TGF-beta), and a keratinocyte growth factor (KGF). In some embodiments, the active agent comprises a stem cell.

In some embodiments of the methods and/or devices provided herein, the coating is capable of at least one of: retarding healing, delaying healing, and preventing healing. In some embodiments, the coating is capable of at least one of: retarding, delaying, and preventing the inflammatory phase of healing. In some embodiments, the coating is capable of at least one of: retarding, delaying, and preventing the proliferative phase of healing. In some embodiments, the coating is capable of at least one of: retarding, delaying, and preventing the maturation phase of healing. In some embodiments, the coating is capable of at least one of: retarding, delaying, and preventing the remodeling phase of healing. In some embodiments, the active agent comprises an anti-angiogenic agent.

In some embodiments of the methods and/or devices provided herein, the coating is a sheath. In some embodiments, the sheath is plastically deformable. In some embodiments, at least a portion of the sheath is capable of being left at the intervention site upon removal of the substrate from the intervention site. In some embodiments, the substrate is capable of mechanically deforming the sheath at the intervention site.

In some embodiments of the methods and/or devices provided herein, the device comprises a retractable sheath. In some embodiments, the sheath is adapted to expose the coating to the intervention site upon retraction.

In some embodiments of the methods and/or devices provided herein, the coating comprises a bioadhesive. In some embodiments, the active agent comprises a bioadhesive. In some embodiments, the coating closes a vascular puncture. In some embodiments, the coating aids in closing a vascular puncture.

In some embodiments of the methods and/or devices provided herein, the coating substantially prevents adhesion of body tissue. In some embodiments, the coating promotes prevention of adhesion of body tissue. In some embodiments, the coating comprises hyaluronic acid, hyaluronate, salts, acids, conjugates, and/or derivatives thereof. In some embodiments, the active agent comprises hyaluronic acid, hyaluronate, salts, acids, conjugates, and/or derivatives thereof.

In some embodiments of the methods and/or devices provided herein, the coating comprises a plurality of layers deposited on said substrate, wherein at least one of the layers comprises the active agent. In some embodiments, at least one of the layers comprises a polymer. In some embodiments, the polymer is bioabsorbable. In some embodiments, the active agent and the polymer are in the same layer, in separate layers, or form overlapping layers. In some embodiments, the coating comprises a plurality of layers deposited on said substrate, wherein at least one of the layers comprises the pharmaceutical agent. In some embodiments, the pharmaceutical agent and the polymer are in the same layer, in separate layers, or form overlapping layers. In some embodiments, the plurality of layers comprise five layers deposited as follows: a first polymer layer, a first active agent layer, a second polymer layer, a second active agent layer and a third polymer layer. In some embodiments, the plurality of layers comprise five layers deposited as follows: a first polymer layer, a first pharmaceutical agent layer, a second polymer layer, a second pharmaceutical agent layer and a third polymer layer. In some embodiments, the plurality of layers comprise five layers deposited as follows: a first polymer layer, a first active biological agent layer, a second polymer layer, a second active biological agent layer and a third polymer layer.

In some embodiments of the methods and/or devices provided herein, the device provides the coating to the intervention site over an area of delivery greater than the outer surface contact area of the substrate. In some embodiments, the area of delivery is at least 110% greater than the outer surface contact area of the substrate. In some embodiments, the area of delivery is at least 110% to 200% greater than the outer surface contact area of the substrate. In some embodiments, the area of delivery is at least 200% greater than the outer surface contact area of the substrate.

Provided herein is a method comprising providing a medical device, wherein the medical device comprises a substrate and a coating on at least a portion of said substrate, and wherein the coating comprises a plurality of layers, wherein at least one layer comprises a pharmaceutical agent in a therapeutically desirable morphology, and freeing at least a portion of the coating from the substrate upon stimulating the coating with a stimulation.

Provided herein is a method comprising providing a medical device, wherein the medical device comprises a substrate and a coating on at least a portion of said substrate, and wherein the coating comprises a plurality of layers, wherein at least one layer comprises a pharmaceutical agent in a therapeutically desirable morphology, and dissociating at least a portion of the coating from the substrate upon stimulating the coating with a stimulation.

Provided herein is a method comprising providing a medical device, wherein the medical device comprises a substrate and a coating on at least a portion of said substrate, and wherein the coating comprises a plurality of layers, wherein at least one layer comprises a pharmaceutical agent in a therapeutically desirable morphology, and transferring at least a portion of the coating from the substrate to the intervention site upon stimulating the coating with a stimulation.

Provided herein is a method comprising providing a medical device, wherein the medical device comprises a substrate and a coating on at least a portion of said substrate, wherein said coating is at least partially continuous, has at least one portion conformal to the substrate, and comprises a pharmaceutical agent in a therapeutically desirable morphology, and freeing at least a portion of the coating from the substrate upon stimulating the coating with a stimulation.

Provided herein is a method comprising providing a medical device, wherein the medical device comprises a substrate and a coating on at least a portion of said substrate, wherein said coating is at least partially continuous, has at least one portion conformal to the substrate, and comprises a pharmaceutical agent in a therapeutically desirable morphology, and dissociating at least a portion of the coating from the substrate upon stimulating the coating with a stimulation.

Provided herein is a method comprising providing a medical device, wherein the medical device comprises a substrate and a coating on at least a portion of said substrate, wherein said coating is at least partially continuous, has at least one portion conformal to the substrate, and comprises a pharmaceutical agent in a therapeutically desirable morphology, and transferring at least a portion of the coating from the substrate to the intervention site upon stimulating the coating with a stimulation.

In some embodiments, the therapeutically desirable morphology comprises a crystalline form of the pharmaceutical agent that is not a microcapsule.

Provided herein is a method comprising providing a medical device, wherein the medical device comprises a substrate and a coating on at least a portion of said substrate, and wherein said coating comprises an active agent, and freeing greater than 35% of the coating from the substrate upon stimulating the coating with a stimulation.

Provided herein is a method comprising providing a medical device, wherein the medical device comprises a substrate and a coating on at least a portion of said substrate, and wherein said coating comprises an active agent, and dissociating greater than 35% of the coating from the substrate upon stimulating the coating with a stimulation.

Provided herein is a method comprising providing a medical device, wherein the medical device comprises a substrate and a coating on at least a portion of said substrate, and wherein said coating comprises an active agent, and transferring greater than 35% of the coating from the substrate to the intervention site upon stimulating the coating with a stimulation.

In some embodiments, the single stimulation lasts at most 20 seconds. In some embodiments, the device is adapted to free, dissociate, and/or transfer substantially all of the coating upon the single stimulation of the coating. In some embodiments, substantially all of the coating frees, dissociates, and/or transfers from the substrate instantaneously upon stimulating the coating.

Provided herein is a method comprising providing a medical device, wherein the medical device comprises a substrate and a coating on at least a portion of said substrate, wherein said coating comprises an active agent, and wherein the coating is patterned, and freeing at least a portion of the coating from the substrate upon stimulating the coating with a stimulation.

Provided herein is a method comprising providing a medical device, wherein the medical device comprises a substrate and a coating on at least a portion of said substrate, wherein said coating comprises an active agent, and wherein the coating is patterned, and dissociatng at least a portion of the coating from the substrate upon stimulating the coating with a stimulation.

Provided herein is a method comprising providing a medical device, wherein the medical device comprises a substrate and a coating on at least a portion of said substrate, wherein said coating comprises an active agent, and wherein the coating is patterned, and transferring at least a portion of the coating from the substrate to the intervention site upon stimulating the coating with a stimulation.

In some embodiments, the patterned coating comprises at least two different shapes.

Provided herein is a method comprising: providing a medical device, wherein the medical device comprises a substrate and a coating on at least a portion of the substrate, wherein the coating comprises an active agent; and transferring at least a portion of the coating from the substrate to an intervention site. In some embodiments, the transferring the coating portion (i.e. the portion of the coating) from the substrate to the intervention site is upon stimulating the coating with a stimulation.

Provided herein is a method comprising: providing a medical device, wherein the medical device comprises a substrate and a coating on at least a portion of the substrate, wherein the coating comprises an active agent; and transferring at least a portion of the active agent from the substrate to an intervention site. In some embodiments, the transferring the active agent portion (i.e. the portion of the active agent) from the substrate to the intervention site is upon stimulating the coating with a stimulation.

Provided herein is a method comprising: providing a medical device, wherein the medical device comprises a substrate and a coating on at least a portion of the substrate, wherein the coating comprises an active agent; and freeing at least a portion of the coating from the substrate at an intervention site. In some embodiments, the freeing the coating portion (i.e. the portion of the coating) from the substrate is upon stimulating the coating with a stimulation.

Provided herein is a method comprising: providing a medical device, wherein the medical device comprises a substrate and a coating on at least a portion of the substrate, wherein the coating comprises an active agent; and dissociating at least a portion of the coating from the substrate at an intervention site. In some embodiments, the dissociating the coating portion (i.e. the portion of the coating) from the substrate is upon stimulating the coating with a stimulation.

Provided herein is a method comprising: providing a medical device, wherein the medical device comprises a substrate and a coating on at least a portion of the substrate, wherein the coating comprises an active agent; and depositing at least a portion of the coating at an intervention site. In some embodiments, the depositing the coating portion (i.e. the portion of the coating) at the intervention site is upon stimulating the coating with a stimulation.

Provided herein is a method comprising: providing a medical device, wherein the medical device comprises a substrate and a coating on at least a portion of the substrate, wherein the coating comprises an active agent; and tacking at least a portion of the coating to an intervention site. In some embodiments, the tacking the coating portion (i.e. the portion of the coating) to the intervention site is upon stimulating the coating with a stimulation.

In some embodiments of the methods and/or devices provided herein, the transferring, freeing, dissociating, depositing, and/or tacking the coating comprises extruding the coating from the substrate.

In some embodiments of the methods and/or devices provided herein, transferring at least a portion of the coating comprises transferring at least about 10%, at least about 20%, at least about 30%, at least about 50%, at least about 75%, at least about 85%, at least about 90%, at least about 95%, and/or at least about 99% of the coating from the substrate. In some embodiments, stimulating decreases the contact between the coating and the substrate. In some embodiments, transferring transfers less than about 1%, less than about 5%, less than about 10%. less than about 15%, less than about 25%, less than about 50%, less than about 70%, less than about 80%, and/or less than about 90% of the coating absent stimulating at least one of the coating and the substrate.

In some embodiments of the methods and/or devices provided herein, transferring at least a portion of the active agent comprises transferring at least about 10%, at least about 20%, at least about 30%, at least about 50%, at least about 75%, at least about 85%, at least about 90%, at least about 95%, and/or at least about 99% of the active agent from the substrate. In some embodiments, stimulating decreases the contact between the coating and the substrate. In some embodiments, transferring transfers less than about 1%, less than about 5%, less than about 10%. less than about 15%, less than about 25%, less than about 50%, less than about 70%, less than about 80%, and/or less than about 90% of the active agent absent stimulating at least one of the coating and the substrate.

In some embodiments of the methods and/or devices provided herein, freeing at least a portion of the coating comprises freeing at least about 10%, at least about 20%, at least about 30%, at least about 50%, at least about 75%, at least about 85%, at least about 90%, at least about 95%, and/or at least about 99% of the coating from the substrate. In some embodiments, stimulating decreases the contact between the coating and the substrate. In some embodiments, freeing frees less than about 1%, less than about 5%, less than about 10%. less than about 15%, less than about 25%, less than about 50%, less than about 70%, less than about 80%, and/or less than about 90% of the coating absent stimulating at least one of the coating and the substrate.

In some embodiments of the methods and/or devices provided herein, dissociating at least a portion of the coating comprises dissociating at least about 10%, at least about 20%, at least about 30%, at least about 50%, at least about 75%, at least about 85%, at least about 90%, at least about 95%, and/or at least about 99% of the coating from the substrate. In some embodiments, stimulating decreases the contact between the coating and the substrate. In some embodiments, dissociating dissociates less than about 1%, less than about 5%, less than about 10%. less than about 15%, less than about 25%, less than about 50%, less than about 70%, less than about 80%, and/or less than about 90% of the coating absent stimulating at least one of the coating and the substrate.

In some embodiments of the methods and/or devices provided herein, depositing at least a portion of the coating comprises depositing at least about 10%, at least about 20%, at least about 30%, at least about 50%, at least about 75%, at least about 85%, at least about 90%, at least about 95%, and/or at least about 99% of the coating at the intervention site. In some embodiments, stimulating decreases the contact between the coating and the substrate. In some embodiments, depositing deposits less than about 1%, less than about 5%, less than about 10%. less than about 15%, less than about 25%, less than about 50%, less than about 70%, less than about 80%, and/or less than about 90% of the coating absent stimulating at least one of the coating and the substrate.

In some embodiments of the methods and/or devices provided herein, tacking at least a portion of the coating comprises tacking at least about 10%, at least about 20%, at least about 30%, at least about 50%, at least about 75%, at least about 85%, at least about 90%, at least about 95%, and/or at least about 99% of the coating to the intervention site. In some embodiments, stimulating decreases the contact between the coating and the substrate. In some embodiments, tacking tacks less than about 1%, less than about 5%, less than about 10%. less than about 15%, less than about 25%, less than about 50%, less than about 70%, less than about 80%, and/or less than about 90% of the coating absent stimulating at least one of the coating and the substrate.

Provided herein is a method of forming a medical device comprising a substrate and a coating on at least a portion of the substrate, wherein the coating comprises an active agent, the method comprising: providing the substrate; and forming the coating on at least a portion of the substrate by depositing the active agent by on the substrate by at least one of an e-RESS, an e-SEDS, and an e-DPC process, wherein forming the coating results in at least a portion of the coating being adapted to transfer from the substrate to an intervention site upon stimulating the coating with a stimulation.

Provided herein is a method of forming a medical device comprising a substrate and a coating on at least a portion of the substrate, wherein the coating comprises an active agent, the method comprising: providing the substrate; and forming the coating on at least a portion of the substrate by depositing the active agent by on the substrate by at least one of an e-RESS, an e-SEDS, and an e-DPC process without electrically charging the substrate, wherein forming the coating results in at least a portion of the coating being adapted to transfer from the substrate to an intervention site upon stimulating the coating with a stimulation.

Provided herein is a method of forming a medical device comprising a substrate and a coating on at least a portion of the substrate, wherein the coating comprises an active agent, the method comprising: providing the substrate; and forming the coating on at least a portion of the substrate by depositing the active agent by on the substrate by at least one of an e-RESS, an e-SEDS, and an e-DPC process without creating an electrical potential between the substrate and a coating apparatus used in the at least one e-RESS, an e-SEDS, and an e-DPC process, wherein forming the coating results in at least a portion of the coating being adapted to transfer from the substrate to an intervention site upon stimulating the coating with a stimulation.

Provided herein is a method of forming a medical device comprising a substrate and a coating on at least a portion of the substrate, wherein the coating comprises an active agent, the method comprising: providing the substrate; and forming the coating on at least a portion of the substrate by depositing the active agent by on the substrate by at least one of a dipping and/or a spraying process, wherein forming the coating results in at least a portion of the coating being adapted to transfer from the substrate to an intervention site upon stimulating the coating with a stimulation.

Provided herein is a method of forming a medical device comprising a substrate and a coating on at least a portion of the substrate, wherein the coating comprises an active agent, the method comprising providing the substrate; and forming the coating on at least a portion of the substrate by depositing the active agent on ths substrate by a dipping and/or a spraying process, wherein forming the coating results in greater than 35% of the coating being adapted to free from the substrate upon stimulating the coating with a single stimulation.

In some embodiments, the single stimulation lasts at most 20 seconds. In some embodiments, substantially all of the coating is adapted to transfer from the substrate upon stimulating with a single stimulation. In some embodiments, substantially all of the coating frees from the substrate instantaneously upon stimulating the coating.

In some embodiments of the methods and/or devices provided herein, forming the coating results in the coating adhering to the substrate prior to the substrate reaching the intervention site.

Some embodiments of the methods and/or devices provided herein further comprise providing a release agent on said substrate. In some embodiments, providing the release agent step is performed prior to the forming the coating step. In some embodiments, the release agent comprises at least one of: a biocompatible release agent, a non-biocompatible release agent, a powder, a lubricant, a surface modification of the substrate, a viscous fluid, a gel, the active agent, a second active agent, a physical characteristic of the substrate. In some embodiments, the physical characteristic of the substrate comprises at least one of: a patterned coating surface of the substrate, and a ribbed surface of the substrate. In some embodiments, the release agent comprises a property that is capable of changing at the intervention site. In some embodiments, the property comprises a physical property. In some embodiments, the property comprises a chemical property. In some embodiments, the release agent is capable of changing a property when in contact with at least one of a biologic tissue and a biologic fluid. In some embodiments, the release agent is capable of changing a property when in contact with an aqueous liquid. In some embodiments, the coating results in a coating property that facilitates transfer of the coating to the intervention site. In some embodiments, the coating property comprises a physical characteristic of the coating. In some embodiments, the physical characteristic comprises a pattern.

In some embodiments of the methods and/or devices provided herein, forming the coating facilitates transfer of the coating to the intervention site.

In some embodiments of the methods and/or devices provided herein, transferring, freeing, dissociating, depositing, and/or tacking step comprises softening the polymer by hydration, degradation or by a combination of hydration and degradation. In some embodiments, the transferring, freeing, dissociating, depositing, and/or tacking step comprises softening the polymer by hydrolysis of the polymer.

In some embodiments of the methods and/or devices provided herein, providing the medical device comprises forming the coating out of laminated layers that allow direct control of the transferring, freeing, depositing, tacking, and/or dissociating of the coating from the substrate. In some embodiments, the coating comprises laminated layers that allow direct control of the transferring, freeing, depositing, tacking, and/or dissociating of the coating from the substrate, wherein at least one of the layers comprises the active agent. In some embodiments, the coating comprises laminated layers that allow direct control of the transferring, freeing, depositing, tacking, and/or dissociating of the coating from the substrate, wherein at least one of the layers comprises the pharmaceutical agent.

In some embodiments of the methods and/or devices provided herein, the providing step comprises forming the coating by a solvent based coating method. In some embodiments, the providing step comprises forming the coating by a solvent plasma based method.

In some embodiments of the methods and/or devices provided herein, providing the device comprises depositing a plurality of layers on said substrate to form the coating, wherein at least one of the layers comprises the active agent. In some embodiments, at least one of the layers comprises a polymer. In some embodiments, the polymer is bioabsorbable. In some embodiments, the active agent and the polymer are in the same layer, in separate layers, or form overlapping layers. In some embodiments, the plurality of layers comprise five layers deposited as follows: a first polymer layer, a first active agent layer, a second polymer layer, a second active agent layer and a third polymer layer.

In some embodiments of the methods and/or devices provided herein, the device further comprises a stent. In some embodiments, the substrate is not the stent.

INCORPORATION BY REFERENCE

All publications and patent applications mentioned in this specification are herein incorporated by reference to the same extent as if each individual publication or patent application was specifically and individually indicated to be incorporated by reference.

DETAILED DESCRIPTION OF THE INVENTION

The present invention is explained in greater detail below. This description is not intended to be a detailed catalog of all the different ways in which the invention may be implemented, or all the features that may be added to the instant invention. For example, features illustrated with respect to one embodiment may be incorporated into other embodiments, and features illustrated with respect to a particular embodiment may be deleted from that embodiment. In addition, numerous variations and additions to the various embodiments suggested herein will be apparent to those skilled in the art in light of the instant disclosure, which do not depart from the instant invention. Hence, the following specification is intended to illustrate some particular embodiments of the invention, and not to exhaustively specify all permutations, combinations and variations thereof.

DEFINITIONS

As used in the present specification, the following words and phrases are generally intended to have the meanings as set forth below, except to the extent that the context in which they are used indicates otherwise.

"Substrate" as used herein, refers to any surface upon which it is desirable to deposit a coating. Biomedical implants are of particular interest for the present invention; however the present invention is not intended to be restricted to this class of substrates. Those of skill in the art will appreciate alternate substrates that could benefit from the coating process described herein, such as pharmaceutical tablet cores, as part of an assay apparatus or as components in a diagnostic kit (e.g. a test strip). Examples of substrates that can be coated using the methods of the invention include surgery devices or medical devices, e.g., a catheter, a balloon, a cutting balloon, a wire guide, a cannula, tooling, an orthopedic device, a structural implant, stent, stent-graft, graft, vena cava filter, a heart valve, cerebrospinal fluid shunts, pacemaker electrodes, axius coronary shunts, endocardial leads, an artificial heart, and the like.

"Biomedical implant" as used herein refers to any implant for insertion into the body of a human or animal subject, including but not limited to stents (e.g., coronary stents, vascular stents including peripheral stents and graft stents, urinary tract stents, urethral/prostatic stents, rectal stent, oesophageal stent, biliary stent, pancreatic stent), electrodes, catheters, leads, implantable pacemaker, cardioverter or defibrillator housings, joints, screws, rods, ophthalmic implants, femoral pins, bone plates, grafts, anastomotic devices, perivascular wraps, sutures, staples, shunts for hydrocephalus, dialysis grafts, colostomy bag attachment devices, ear drainage tubes, leads for pace makers and implantable cardioverters and defibrillators, vertebral disks, bone pins, suture anchors, hemostatic barriers, clamps, screws, plates, clips, vascular implants, tissue adhesives and sealants, tissue scaffolds, various types of dressings (e.g., wound dressings), bone substitutes, intraluminal devices, vascular supports, etc.

The implants may be formed from any suitable material, including but not limited to polymers (including stable or inert polymers, organic polymers, organic-inorganic copolymers, inorganic polymers, and biodegradable polymers), metals, metal alloys, inorganic materials such as silicon, and composites thereof, including layered structures with a core of one material and one or more coatings of a different material. Substrates made of a conducting material facilitate electrostatic capture. However, the invention contemplates the use of electrostatic capture, as described herein, in conjunction with substrate having low conductivity or which are non-conductive. To enhance electrostatic capture when a non-conductive substrate is employed, the substrate is processed for example while maintaining a strong electrical field in the vicinity of the substrate. In some embodiments, however, no electrostatic capture is employed in applying a coating to the substrate. In some embodiments of the methods and/or devices provided herein, the substrate is not charged in the coating process. In some embodiments of the methods and/or devices provided herein, an electrical potential is not created between the substrate and the coating apparatus.

Subjects into which biomedical implants of the invention may be applied or inserted include both human subjects (including male and female subjects and infant, juvenile, adolescent, adult and geriatric subjects) as well as animal subjects (including but not limited to pig, rabbit, mouse, dog, cat, horse, monkey, etc.) for veterinary purposes and/or medical research.

As used herein, a biological implant may include a medical device that is not permanently implanted. A biological implant in some embodiments may comprise a device which is used in a subject on a transient basis. For non-limiting example, the biomedical implant may be a balloon, which is used transiently to dilate a lumen and thereafter may be deflated and/or removed from the subject during the medical procedure or thereafter. In some embodiments, the biological implant may be temporarily implanted for a limited time, such as during a portion of a medical procedure, or for only a limited time (some time less than permanantly implanted), or may be transiently implanted and/or momentarily placed in the subject. In some embodiments, the biological implant is not implanted at all, rather it is merely inserted into a subject during a medical procedure, and subsequently removed from the subject prior to or at the time the medical procedure is completed. In some embodiments, the biological implant is not permenantly implanted since it completely resorbs into the subject (i.e. is completely resorbed by the subject). In a preferred embodiment the biomedical implant is an expandable balloon that can be expanded within a lumen (naturally occuring or non-naturally occurring) having a coating thereon that is freed (at least in part) from the balloon and left behind in the lumen when the balloon is removed from the lumen.

"Pharmaceutical agent" as used herein refers to any of a variety of drugs or pharmaceutical compounds that can be used as active agents to prevent or treat a disease (meaning any treatment of a disease in a mammal, including preventing the disease, i.e. causing the clinical symptoms of the disease not to develop; inhibiting the disease, i.e. arresting the development of clinical symptoms; and/or relieving the disease, i.e. causing the regression of clinical symptoms). It is possible that the pharmaceutical agents of the invention may also comprise two or more drugs or pharmaceutical compounds. Pharmaceutical agents include but are not limited to antirestenotic agents, antidiabetics, analgesics, antiinflammatory agents, antirheumatics, antihypotensive agents, antihypertensive agents, angiogenesis promoters, angiogenesis inhibitors, psychoactive drugs, tranquillizers, antiemetics, muscle relaxants, glucocorticoids, agents for treating ulcerative colitis or Crohn's disease, antiallergics, antibiotics, antiepileptics, anticoagulants, antimycotics, antifungals, antitussives, arteriosclerosis remedies, diuretics, proteins, peptides, enzymes, enzyme inhibitors, gout remedies, hormones and inhibitors thereof, cardiac glycosides, immunotherapeutic agents and cytokines, laxatives, lipid-lowering agents, migraine remedies, mineral products, otologicals, anti parkinson agents, thyroid therapeutic agents, spasmolytics, platelet aggregation inhibitors, vitamins, cytostatics and metastasis inhibitors, phytopharmaceuticals, chemotherapeutic agents and amino acids. Examples of suitable active ingredients are acarbose, antigens, beta-receptor blockers, non-steroidal antiinflammatory drugs [NSAIDs], cardiac glycosides, acetylsalicylic acid, alfuzosim, virustatics, aclarubicin, acyclovir, cisplatin, actinomycin, alpha- and beta-sympatomimetics, dmeprazole, allopurinol, alprostadil, prostaglandins, amantadine, ambroxol, amlodipine, methotrexate, S-aminosalicylic acid, amitriptyline, amoxicillin, anastrozole, atenolol, azathioprine, balsalazide, beclomethasone, betahistine, bezafibrate, bicalutamide, diazepam and diazepam derivatives, budesonide, bufexamac, buprenorphine, methadone, calcium salts, potassium salts, magnesium salts, candesartan, carbamazepine, captopril, cefalosporins, cetirizine, chenodeoxycholic acid, ursodeoxycholic acid, theophylline and theophylline derivatives, trypsins, cimetidine, clarithromycin, clavulanic acid, clindamycin, clobutinol, clonidine, cotrimoxazole, codeine, caffeine, vitamin D and derivatives of vitamin D, colestyramine, cromoglicic acid, coumarin and coumarin derivatives, cysteine, cytarabine, cyclophosphamide, ciclosporin, cyproterone, cytabarine, dapiprazole, desogestrel, desonide, dihydralazine, diltiazem, ergot alkaloids, dimenhydrinate, dimethyl sulphoxide, dimeticone, domperidone and domperidan derivatives, dopamine, doxazosin, doxorubizin, doxylamine, benzodiazepines, diclofenac, glycoside antibiotics, desipramine, econazole, ACE inhibitors, enalapril, ephedrine, epinephrine, epoetin and epoetin derivatives, morphinans, calcium antagonists, irinotecan, modafinil, orlistat, peptide antibiotics, phenytoin, riluzoles, risedronate, sildenafil, topiramate, macrolide antibiotics, oestrogen and oestrogen derivatives, progestogen and progestogen derivatives, testosterone and testosterone derivatives, androgen and androgen derivatives, ethenzamide, etofenamate, etofibrate, fenofibrate, etofylline, etoposide, famciclovir, famotidine, felodipine, fenofibrate, fentanyl, fenticonazole, gyrase inhibitors, fluconazole, fludarabine, fluarizine, fluorouracil, fluoxetine, flurbiprofen, ibuprofen, flutamide, fluvastatin, follitropin, formoterol, fosfomicin, furosemide, fusidic acid, gallopamil, ganciclovir, gemfibrozil, gentamicin, ginkgo, Saint John's wort, glibenclamide, urea derivatives as oral antidiabetics, glucagon, glucosamine and glucosamine derivatives, glutathione, glycerol and glycerol derivatives, hypothalamus hormones, goserelin, gyrase inhibitors, guanethidine, halofantrine, haloperidol, heparin and heparin derivatives, hyaluronic acid, hydralazine, hydrochlorothiazide and hydrochlorothiazide derivatives, salicylates, hydroxyzine, idarubicin, ifosfamide, imipramine, indometacin, indoramine, insulin, interferons, iodine and iodine derivatives, isoconazole, isoprenaline, glucitol and glucitol derivatives, itraconazole, ketoconazole, ketoprofen, ketotifen, lacidipine, lansoprazole, levodopa, levomethadone, thyroid hormones, lipoic acid and lipoic acid derivatives, lisinopril, lisuride, lofepramine, lomustine, loperamide, loratadine, maprotiline, mebendazole, meberine, meclozine, mefenamic acid, mefloquine, meloxicam, mepindolol, meprobamate, meropenem, mesalazine, mesuximide, metamizole, metformin, methylphenidate, methylprednisolone, metixene, metoclopramide, metoprolol, metronidazole, mianserin, miconazole, minocycline, minoxidil, misoprostol, mitomycin, mizolastine, moexipril, morphine and morphine derivatives, evening primrose, nalbuphine, naloxone, tilidine, naproxen, narcotine, natamycin, neostigmine, nicergoline, nicethamide, nifedipine, niflumic acid, nimodipine, nimorazole, nimustine, nisoldipine, adrenaline and adrenaline derivatives, norfloxacin, novamine sulfone, noscapine, nystatin, ofloxacin, olanzapine, olsalazine, omeprazole, omoconazole, ondansetron, oxaceprol, oxacillin, oxiconazole, oxymetazoline, pantoprazole, paracetamol, paroxetine, penciclovir, oral penicillins, pentazocine, pentifylline, pentoxifylline, perphenazine, pethidine, plant extracts, phenazone, pheniramine, barbituric acid derivatives, phenylbutazone, pimozide, pindolol, piperazine, piracetam, pirenzepine, piribedil, piroxicam, pramipexole, pravastatin, prazosin, procaine, promazine, propiverine, propranolol, propyphenazone, prostaglandins, protionamide, proxyphylline, quetiapine, quinapril, quinaprilat, ramipril, ranitidine, reproterol, reserpine, ribavirin, rifampicin, risperidone, ritonavir, ropinirole, roxatidine, roxithromycin, ruscogenin, rutoside and rutoside derivatives, sabadilla, salbutamol, salmeterol, scopolamine, selegiline, sertaconazole, sertindole, sertralion, silicates, simvastatin, sitosterol, sotalol, spaglumic acid, sparfloxacin, spectinomycin, spiramycin, spirapril, spironolactone, stavudine, streptomycin, sucralfate, sufentanil, sulbactam, sulphonamides, sulfasalazine, sulpiride, sultamicillin, sultiam, sumatriptan, suxamethonium chloride, tacrine, tacrolimus, taliolol, tamoxifen, taurolidine, tazarotene, temazepam, teniposide, tenoxicam, terazosin, terbinafine, terbutaline, terfenadine, terlipressin, tertatolol, tetracyclins, teryzoline, theobromine, theophylline, butizine, thiamazole, phenothiazines, thiotepa, tiagabine, tiapride, propionic acid derivatives, ticlopidine, timolol, tinidazole, tioconazole, tioguanine, tioxolone, tiropramide, tizanidine, tolazoline, tolbutamide, tolcapone, tolnaftate, tolperisone, topotecan, torasemide, antioestrogens, tramadol, tramazoline, trandolapril, tranylcypromine, trapidil, trazodone, triamcinolone and triamcinolone derivatives, triamterene, trifluperidol, trifluridine, trimethoprim, trimipramine, tripelennamine, triprolidine, trifosfamide, tromantadine, trometamol, tropalpin, troxerutine, tulobuterol, tyramine, tyrothricin, urapidil, ursodeoxycholic acid, chenodeoxycholic acid, valaciclovir, valproic acid, vancomycin, vecuronium chloride, Viagra, venlafaxine, verapamil, vidarabine, vigabatrin, viloazine, vinblastine, vincamine, vincristine, vindesine, vinorelbine, vinpocetine, viquidil, warfarin, xantinol nicotinate, xipamide, zafirlukast, zalcitabine, zidovudine, zolmitriptan, zolpidem, zoplicone, zotipine, clotrimazole, amphotericin B, caspofungin, or voriconazole, resveratrol, PARP-1 inhibitors (including imidazoquinolinone, imidazpyridine, and isoquinolindione, tissue plasminogen activator (tPA), melagatran, lanoteplase, reteplase, staphylokinase, streptokinase, tenecteplase, urokinase, and the like. See, e.g., U.S. Pat. No. 6,897,205; see also U.S. Pat. No. 6,838,528; U.S. Pat. No. 6,497,729.

Examples of pharmaceutical agents employed in conjunction with the invention include, rapamycin, 40-O-(2-Hydroxyethyl)rapamycin (everolimus), 40-O-Benzyl-rapamycin, 40-O-(4'-Hydroxymethyl)benzyl-rapamycin, 40-O-[4'-(1,2-Dihydroxyethyl)]benzyl-rapamycin, 40-O-Allyl-rapamycin, 40-O-[3'-(2,2-Dimethyl-1,3-dioxolan-4(S)-yl)-prop-2'-en-1'-yl]-rapamycin, (2':E,4'S)-40-O-(4',5'-Dihydroxypent-2'-en-1'-yl)-rapamycin 40-O-(2-Hydroxy)ethoxycarbonylmethyl-rapamycin, 40-O-(3-Hydroxy)propyl-rapamycin 4O—O-(6-Hydroxy)hexyl-rapamycin 40-O-[2-(2-Hydroxy)ethoxy]ethyl-rapamycin 4O—O-[(3S)-2,2-Dimethyldioxolan-3-yl]methyl-rapamycin, 40-O-[(2S)-2,3-Dihydroxyprop-1-yl]-rapamycin, 4O—O-(2-Acetoxy)ethyl-rapamycin 4O—O-(2-Nicotinoyloxy)ethyl-rapamycin, 4O—O-[2-(N-Morpholino)acetoxy]ethyl-rapamycin 4O—O-(2-N-Imidazolylacetoxy)ethyl-rapamycin, 40-O-[2-(N-Methyl-N'-piperazinyl)acetoxy]ethyl-rapamycin, 39-O-Desmethyl-39,40-O,O-ethylene-rapamycin, (26R)-26-Dihydro-40-O-(2-hydroxy)ethyl-rapamycin, 28-O-Methyl-rapamycin, 4O—O-(2-Aminoethyl)-rapamycin, 4O—O-(2-Acetaminoethyl)-rapamycin 4O—O-(2-Nicotinamidoethyl)-rapamycin, 4O—O-(2-(N-Methyl-imidazo-2'-ylcarbethoxamido)ethyl)-rapamycin, 4O—O-(2-Ethoxycarbonylaminoethyl)-rapamycin, 40-O-(2-Tolylsulfonamidoethyl)-rapamycin, 40-O-[2-(4',5'-Dicarboethoxy-1',2',3'-triazol-1'-yl)-ethyl]-rapamycin, 42-Epi-(tetrazolyl)rapamycin (tacrolimus), and 42-[3-hydroxy-2-(hydroxymethyl)-2-methylpropanoate]rapamycin (temsirolimus).

In some embodiments, a pharmaceutical agent is at least one of: Acarbose, acetylsalicylic acid, acyclovir, allopurinol, alprostadil, prostaglandins, amantadine, ambroxol, amlodipine, S-aminosalicylic acid, amitriptyline, atenolol, azathioprine, balsalazide, beclomethasone, betahistine, bezafibrate, diazepam and diazepam derivatives, budesonide, bufexamac, buprenorphine, methadone, calcium salts, potassium salts, magnesium salts, candesartan, carbamazepine, captopril, cetirizine, chenodeoxycholic acid, theophylline and theophylline derivatives, trypsins, cimetidine, clobutinol, clonidine, cotrimoxazole, codeine, caffeine, vitamin D and derivatives of vitamin D, colestyramine, cromoglicic acid, coumarin and coumarin derivatives, cysteine, ciclosporin, cyproterone, cytabarine, dapiprazole, desogestrel, desonide, dihydralazine, diltiazem, ergot alkaloids, dimenhydrinate, dimethyl sulphoxide, dimeticone, domperidone and domperidan derivatives, dopamine, doxazosin, doxylamine, benzodiazepines, diclofenac, desipramine, econazole, ACE inhibitors, enalapril, ephedrine, epinephrine, epoetin and epoetin derivatives, morphinans, calcium antagonists, modafinil, orlistat, peptide antibiotics, phenytoin, riluzoles, risedronate, sildenafil, topiramate, estrogen, progestogen and progestogen derivatives, testosterone derivatives, androgen and androgen derivatives, ethenzamide, etofenamate, etofibrate, fenofibrate, etofylline, famciclovir, famotidine, felodipine, fentanyl, fenticonazole, gyrase inhibitors, fluconazole, fluarizine, fluoxetine, flurbiprofen, ibuprofen, fluvastatin, follitropin, formoterol, fosfomicin, furosemide, fusidic acid, gallopamil, ganciclovir, gemfibrozil, ginkgo, Saint John's wort, glibenclamide, urea derivatives as oral antidiabetics, glucagon, glucosamine and glucosamine derivatives, glutathione, glycerol and glycerol derivatives, hypothalamus hormones, guanethidine, halofantrine, haloperidol, heparin (and derivatives), hyaluronic acid, hydralazine, hydrochlorothiazide (and derivatives), salicylates, hydroxyzine, imipramine, indometacin, indoramine, insulin, iodine and iodine derivatives, isoconazole, isoprenaline, glucitol and glucitol derivatives, itraconazole, ketoprofen, ketotifen, lacidipine, lansoprazole, levodopa, levomethadone, thyroid hormones, lipoic acid (and derivatives), lisinopril, lisuride, lofepramine, loperamide, loratadine, maprotiline, mebendazole, mebeverine, meclozine, mefenamic acid, mefloquine, meloxicam, mepindolol, meprobamate, mesalazine, mesuximide, metamizole, metformin, methylphenidate, metixene, metoprolol, metronidazole, mianserin, miconazole, minoxidil, misoprostol, mizolastine, moexipril, morphine and morphine derivatives, evening primrose, nalbuphine, naloxone, tilidine, naproxen, narcotine, natamycin, neostigmine, nicergoline, nicethamide, nifedipine, niflumic acid, nimodipine, nimorazole, nimustine, nisoldipine, adrenaline and adrenaline derivatives, novamine sulfone, noscapine, nystatin, olanzapine, olsalazine, omeprazole, omoconazole, oxaceprol, oxiconazole, oxymetazoline, pantoprazole, paracetamol (acetaminophen), paroxetine, penciclovir, pentazocine, pentifylline, pentoxifylline, perphenazine, pethidine, plant extracts, phenazone, pheniramine, barbituric acid derivatives, phenylbutazone, pimozide, pindolol, piperazine, piracetam, pirenzepine, piribedil, piroxicam, pramipexole, pravastatin, prazosin, procaine, promazine, propiverine, propranolol, propyphenazone, protionamide, proxyphylline, quetiapine, quinapril, quinaprilat, ramipril, ranitidine, reproterol, reserpine, ribavirin, risperidone, ritonavir, ropinirole, roxatidine, ruscogenin, rutoside (and derivatives), sabadilla, salbutamol, salmeterol, scopolamine, selegiline, sertaconazole, sertindole, sertralion, silicates, simvastatin, sitosterol, sotalol, spaglumic acid, spirapril, spironolactone, stavudine, streptomycin, sucralfate, sufentanil, sulfasalazine, sulpiride, sultiam, sumatriptan, suxamethonium chloride, tacrine, tacrolimus, taliolol, taurolidine, temazepam, tenoxicam, terazosin, terbinafine, terbutaline, terfenadine, terlipressin, tertatolol, teryzoline, theobromine, butizine, thiamazole, phenothiazines, tiagabine, tiapride, propionic acid derivatives, ticlopidine, timolol, tinidazole, tioconazole, tioguanine, tioxolone, tiropramide, tizanidine, tolazoline, tolbutamide, tolcapone, tolnaftate, tolperisone, topotecan, torasemide, tramadol, tramazoline, trandolapril, tranylcypromine, trapidil, trazodone, triamcinolone derivatives, triamterene, trifluperidol, trifluridine, trimipramine, tripelennamine, triprolidine, trifosfamide, tromantadine, trometamol, tropalpin, troxerutine, tulobuterol, tyramine, tyrothricin, urapidil, valaciclovir, valproic acid, vancomycin, vecuronium chloride, Viagra, venlafaxine, verapamil, vidarabine, vigabatrin, viloazine, vincamine, vinpocetine, viquidil, warfarin, xantinol nicotinate, xipamide, zafirlukast, zalcitabine, zidovudine, zolmitriptan, zolpidem, zoplicone, zotipine, amphotericin B, caspofungin, voriconazole, resveratrol, PARP-1 inhibitors (including imidazoquinolinone, imidazpyridine, and isoquinolindione, tissue plasminogen activator (tPA), melagatran, lanoteplase, reteplase, staphylokinase, streptokinase, tenecteplase, urokinase, 40-O-(2-Hydroxyethyl)rapamycin (everolimus), 40-O-Benzyl-rapamycin, 40-O-(4'-Hydroxymethyl)benzyl-rapamycin, 40-O-[4'-(1,2-Dihydroxyethyl)]benzyl-rapamycin, 40-O-Allyl-rapamycin, 40-O-[3'-(2,2-Dimethyl-1,3-dioxolan-4 (S)-yl)-prop-2'-en-1'-yl]-rapamycin, (2':E,4'S)-40-O-(4',5'-Dihydroxypent-2'-en-1'-yl)-rapamycin 40-O-(2-Hydroxy) ethoxycar-bonylmethyl-rapamycin, 40-O-(3-Hydroxy) propyl-rapamycin 4O—O-(6-Hydroxy)hexyl-rapamycin 40-O-[2-(2-Hydroxy)ethoxy]ethyl-rapamycin 4O—O-[(3S)-2,2-Dimethyldioxolan-3-yl]methyl-rapamycin, 40-O-[(2S)-2,3-Dihydroxyprop-1-yl]-rapamycin, 4O—O-(2-Acetoxy)ethyl-rapamycin 4O—O-(2-Nicotinoyloxy)ethyl-rapamycin, 4O—O-[2-(N-Morpholino)acetoxy]ethyl-rapamycin 4O—O-(2-N-Imidazolylacetoxy)ethyl-rapamycin, 40-O-[2-(N-Methyl-N'-piperazinyl)acetoxy]ethyl-rapamycin, 39-O-Desmethyl-39,40-O,O-ethylene-rapamycin, (26R)-26-Dihydro-40-O-(2-hydroxy)ethyl-rapamycin, 28-O-Methyl-rapamycin, 4O—O-(2-Aminoethyl)-rapamycin, 4O—O-(2-Acetaminoethyl)-rapamycin 4O—O-(2-Nicotinamidoethyl)-rapamycin, 4O—O-(2-(N-Methyl-imidazo-2'-ylcarbethoxamido)ethyl)-rapamycin, 4O—O-(2-Ethoxycarbonylaminoethyl)-rapamycin, 40-O-(2-Tolylsulfonamidoethyl)-rapamycin, 40-O-[2-(4',5'-Dicarboethoxy-1',2',3'-triazol-1'-yl)-ethyl]-rapamycin, 42-Epi-(tetrazolyl)rapamycin (tacrolimus), and 42-[3-hydroxy-2-(hydroxymethyl)-2-methylpropanoate]rapamycin (temsirolimus), abciximab (ReoPro), eptifibatide, tirofiban, prasugrel, clopidogrel, dipyridamole, cilostazol, VEGF, heparan sulfate, chondroitin sulfate, elongated "RGD" peptide binding domain, CD34 antibodies, cerivastatin, etorvastatin, losartan, valartan, erythropoietin, rosiglitazone, pioglitazone, mutant protein Apo A1 Milano, adiponectin, (NOS) gene therapy, glucagon-like peptide 1, atorvastatin, and atrial natriuretic peptide (ANP), lidocaine, tetracaine, dibucaine, hyssop, ginger, turmeric, Arnica montana, helenalin, cannabichromene, rofecoxib, and hyaluronidase.

The pharmaceutical agents may, if desired, also be used in the form of their pharmaceutically acceptable salts or derivatives (meaning salts which retain the biological effectiveness and properties of the compounds of this invention and which are not biologically or otherwise undesirable), and in the case of chiral active ingredients it is possible to employ both optically active isomers and racemates or mixtures of diastereoisomers. As well, the pharmaceutical agent may include a prodrug, a hydrate, an ester, a derivative or analogs of a compound or molecule.

The pharmaceutical agent may be an antibiotic agent, as described herein.

The pharmaceutical agent may be a chemotherapeutic agent, as described herein.

The phamaceutical agent may be an anti-thrombotic agent, as described herein.

The phamaceutical agent may be a statin, as described herein.

The phamaceutical agent may be an angiogenisis promoter, as described herein.

The phamaceutical agent may be a local anesthetic, as described herein.

The phamaceutical agent may be an anti-inflammatory agent, as described herein.

A "pharmaceutically acceptable salt" may be prepared for any pharmaceutical agent having a functionality capable of forming a salt, for example an acid or base functionality. Pharmaceutically acceptable salts may be derived from organic or inorganic acids and bases. The term "pharmaceutically-acceptable salts" in these instances refers to the relatively non-toxic, inorganic and organic base addition salts of the pharmaceutical agents.

"Prodrugs" are derivative compounds derivatized by the addition of a group that endows greater solubility to the compound desired to be delivered. Once in the body, the prodrug is typically acted upon by an enzyme, e.g., an esterase, amidase, or phosphatase, to generate the active compound.

An "anti-cancer agent", "anti-tumor agent" or "chemotherapeutic agent" refers to any agent useful in the treatment of a neoplastic condition. There are many chemotherapeutic agents available in commercial use, in clinical evaluation and in pre-clinical development that are useful in the devices and methods of the present invention for treatment of cancers.

In some embodiments, a chemotherapeutic agent comprises at least one of an angiostatin, DNA topoisomerase, endostatin, genistein, ornithine decarboxylase inhibitors, chlormethine, melphalan, pipobroman, triethylenemelamine, triethylenethiophosphoramine, busulfan, carmustine (BCNU), streptozocin, 6-mercaptopurine, 6-thioguanine, Deoxyco-formycin, IFN-α, 17α-ethinylestradiol, diethylstilbestrol, testosterone, prednisone, fluoxymesterone, dromostanolone propionate, testolactone, megestrolacetate, methylprednisolone, methyl-testosterone, prednisolone, triamcinolone, chlorotrianisene, hydroxyprogesterone, estramustine, medroxyprogesteroneacetate, flutamide, zoladex, mitotane, hexamethylmelamine, indolyl-3-glyoxylic acid derivatives, (e.g., indibulin), doxorubicin and idarubicin, plicamycin (mithramycin) and mitomycin, mechlorethamine, cyclophosphamide analogs, trazenes-dacarbazinine (DTIC), pentostatin and 2-chlorodeoxyadenosine, letrozole, camptothecin (and derivatives), navelbine, erlotinib, capecitabine, acivicin, acodazole hydrochloride, acronine, adozelesin, aldesleukin, ambomycin, ametantrone acetate, anthramycin, asperlin, azacitidine, azetepa, azotomycin, batimastat, benzodepa, bisnafide, bisnafide dimesylate, bizelesin, bropirimine, cactinomycin, calusterone, carbetimer, carubicin hydrochloride, carzelesin, cedefingol, celecoxib (COX-2 inhibitor), cirolemycin, crisnatol mesylate, decitabine, dexormaplatin, dezaguanine mesylate, diaziquone, duazomycin, edatrexate, eflomithine, elsamitrucin, enloplatin, enpromate, epipropidine, erbulozole, etanidazole, etoprine, flurocitabine, fosquidone, lometrexol, losoxantrone hydrochloride, masoprocol, maytansine, megestrol acetate, melengestrol acetate, metoprine, meturedepa, mitindomide, mitocarcin, mitocromin, mitogillin, mitomalcin, mitosper, mycophenolic acid, nocodazole, nogalamycin, ormaplatin, oxisuran, pegaspargase, peliomycin, pentamustine, perfosfamide, piposulfan, plomestane, porfimer sodium, porfiromycin, puromycin, pyrazofurin, riboprine, safingol, simtrazene, sparfosate sodium, spiromustine, spiroplatin, streptonigrin, sulofenur, tecogalan sodium, taxotere, tegafur, teloxantrone hydrochloride, temoporfin, thiamiprine, tirapazamine, trestolone acetate, triciribine phosphate, trimetrexate glucuronate, tubulozole hydrochloride, uracil mustard, uredepa, verteporfin, vinepidine sulfate, vinglycinate sulfate, vinleurosine sulfate, vinorelbine tartrate, vinrosidine sulfate, zeniplatin, zinostatin, 20-epi-1,25 dihydroxyvitamin D3, 5-ethynyluracil, acylfulvene, adecypenol, ALL-TK antagonists, ambamustine, amidox, amifostine, aminolevulinic acid, amrubicin, anagrelide, andrographolide, antagonist D, antagonist G, antarelix, anti-dorsalizing morphogenetic protein-1, antiandrogen, antiestrogen, estrogen agonist, apurinic acid, ara-CDP-DL-PTBA, arginine deaminase, asulacrine, atamestane, atrimustine, axinastatin 1, axinastatin 2, axinastatin 3, azasetron, azatoxin, azatyrosine, baccatin III derivatives, balanol, BCR/ABL antagonists, benzochlorins, benzoylstaurosporine, beta lactam derivatives, beta-alethine, betaclamycin B, betulinic acid, bFGF inhibitor, bisaziridinylspermine, bistratene A, breflate, buthionine sulfoximine, calcipotriol, calphostin C, carboxamide-amino-triazole, carboxyamidotriazole, CaRest M3, CARN 700, cartilage derived inhibitor, casein kinase inhibitors (ICOS), castanospermine, cecropin B, cetrorelix, chloroquinoxaline sulfonamide, cicaprost, cisporphyrin, clomifene analogues, clotrimazole, collismycin A, collismycin B, combretastatin A4, combretastatin analogue, conagenin, crambescidin 816, cryptophycin 8, cryptophycin A derivatives, curacin A, cyclopentanthraquinones, cycloplatam, cypemycin, cytolytic factor, cytostatin, dacliximab, dehydrodidemnin B, dexamethasone, dexifosfamide, dexrazoxane, dexverapamil, didemnin B, didox, diethylnorspermine, dihydro-5-azacytidine, dihydrotaxol, 9-, dioxamycin, docosanol, dolasetron, dronabinol, duocarmycin SA, ebselen, ecomustine, edelfosine, edrecolomab, elemene, emitefur, estramustine analogue, filgrastim, flavopiridol, flezelastine, fluasterone, fluorodaunorunicin hydrochloride, forfenimex, gadolinium texaphyrin, galocitabine, gelatinase inhibitors, glutathione inhibitors, hepsulfam, heregulin, hexamethylene bisacetamide, hypericin, ibandronic acid, idramantone, ilomastat, imatinib (e.g., Gleevec), imiquimod, immunostimulant peptides, insulin-like growth factor-1 receptor inhibitor, interferon agonists, interferons, interleukins, iobenguane, iododoxorubicin, ipomeanol, 4-, iroplact, irsogladine, isobengazole, isohomohalicondrin B, itasetron, jasplakinolide, kahalalide F, lamellarin-N triacetate, leinamycin, lenograstim, lentinan sulfate, leptolstatin, leukemia inhibiting factor, leukocyte alpha interferon, leuprolide+estrogen+progesterone, linear polyamine analogue, lipophilic disaccharide peptide, lipophilic platinum compounds, lissoclinamide 7, lobaplatin, lombricine, loxoribine, lurtotecan, lutetium texaphyrin, lysofylline, lytic peptides, maitansine, mannostatin A, marimastat, maspin, matrilysin inhibitors, matrix metalloproteinase inhibitors, meterelin, methioninase, metoclopramide, MIF inhibitor, mifepristone, miltefosine, mirimostim, mitoguazone, mitotoxin fibroblast growth factor-saporin, mofarotene, molgramostim, Erbitux, human chorionic gonadotrophin, monophosphoryl lipid A+myobacterium cell wall sk, mustard anticancer agent, mycaperoxide B, mycobacterial cell wall extract, myriaporone, N-acetyldinaline, N-substituted benzamides, nagrestip, naloxone+pentazocine, napavin, naphterpin, nartograstim, nedaplatin, nemorubicin, neridronic acid, nisamycin, nitric oxide modulators, nitroxide antioxidant, nitrullyn, oblimersen (Genasense), $O^6$-benzylguanine, okicenone, onapristone, ondansetron, oracin, oral cytokine inducer, paclitaxel analogues and derivatives, palauamine, palmitoylrhizoxin, pamidronic acid, panaxytriol, panomifene, parabactin, peldesine, pentosan polysulfate sodium, pentrozole, perflubron, perillyl alcohol, phenazinomycin, phenylacetate, phosphatase inhibitors, picibanil, pilocarpine hydrochloride, placetin A, placetin B, plasminogen activator inhibitor, platinum complex, platinum compounds, platinum-triamine complex, propyl bis-acridone, prostaglandin J2, proteasome inhibitors, protein A-based immune modulator, protein kinase C inhibitors, microalgal, pyrazoloacridine, pyridoxylated hemoglobin polyoxyethylene conjugate, raf antagonists, raltitrexed, ramosetron, ras farnesyl protein transferase inhibitors, ras-GAP inhibitor, retelliptine demethylated, rhenium Re 186 etidronate, ribozymes, RII retinamide, rohitukine, romurtide, roquinimex, rubiginone B1, ruboxyl, saintopin, SarCNU, sarcophytol A, sargramostim, Sdi 1 mimetics, senescence derived inhibitor 1, signal transduction inhibitors, sizofiran, sobuzoxane, sodium borocaptate, solverol, somatomedin binding protein, sonermin, sparfosic acid, spicamycin D, splenopentin, spongistatin 1, squalamine, stipiamide, stromelysin inhibitors, sulfinosine, superactive vasoactive intestinal peptide antagonist, suradista, suramin, swainsonine, tallimustine, tazarotene, tellurapyrylium, telomerase inhibitors, tetrachlorodecaoxide, tetrazomine, thiocoraline, thrombopoietin, thrombopoietin mimetic, thymalfasin, thymopoietin receptor agonist, thymotrinan, thyroid stimulating hormone, tin ethyl etiopurpurin, titanocene bichloride, topsentin, translation inhibitors, tretinoin, triacetyluridine, tropisetron, turosteride, ubenimex, urogenital sinus-derived growth inhibitory factor, variolin B, velaresol, veramine, verdins, vinxaltine, vitaxin, zanoterone, zilascorb, zinostatin stimalamer, acanthifolic acid, aminothiadiazole, anastrozole, bicalutamide, brequinar sodium, capecitabine, carmofur, Ciba-Geigy CGP-30694, cladribine, cyclopentyl cytosine, cytarabine phosphate stearate, cytarabine conjugates, cytarabine ocfosfate, Lilly DATHF, Merrel Dow DDFC, dezaguanine, dideoxycytidine, dideoxyguanosine, didox, Yoshitomi DMDC, doxifluridine, Wellcome EHNA, Merck & Co. EX-015, fazarabine, floxuridine, fludarabine, fludarabine phosphate, N-(2'-furanidyl)-5-fluorouracil, Daiichi Seiyaku FO-152, 5-FU-fibrinogen, isopropyl pyrrolizine, Lilly LY-188011, Lilly LY-264618, methobenzaprim, methotrexate, Wellcome MZPES, norspermidine, nolvadex, NCI NSC-127716, NCI NSC-264880, NCI NSC-39661, NCI NSC-612567, Warner-Lambert PALA, pentostatin, piritrexim, plicamycin, Asahi Chemical PL-AC, stearate, Takeda TAC-788, thioguanine, tiazofurin, Erbamont TIF, trimetrexate, tyrosine kinase inhibitors, tyrosine protein kinase inhibitors, Taiho UFT, uricytin, Shionogi 254-S, aldo-phosphamide analogues, altretamine, anaxirone, Boehringer Mannheim BBR-2207, bestrabucil, budotitane, Wakunaga CA-102, carboplatin, carmustine (BiCNU), Chinoin-139, Chinoin-153, chlorambucil, cisplatin, cyclophosphamide, American Cyanamid CL-286558, Sanofi CY-233, cyplatate, dacarbazine, Degussa D-19-384, Sumimoto DACHP(Myr)2, diphenylspiromustine, diplatinum cytostatic, Chugai DWA-2114R, ITI E09, elmustine, Erbamont FCE-24517, estramustine phosphate sodium, etoposide phosphate, fotemustine, Unimed G-6-M, Chinoin GYKI-17230, hepsul-fam, ifosfamide, iproplatin, lomustine, mafosfamide, mitolactol, mycophenolate, Nippon Kayaku NK-121, NCI NSC-264395, NCI NSC-342215, oxaliplatin, Upjohn PCNU, prednimustine, Proter PTT-119, ranimustine, semustine, SmithKline SK&F-101772, thiotepa, Yakult Honsha SN-22, spiromus-tine, Tanabe Seiyaku TA-077, tauromustine, temozolomide, teroxirone, tetraplatin and trimelamol, Taiho 4181-A, aclarubicin, actinomycin D, actinoplanone, Erbamont ADR-456, aeroplysinin derivative, Ajinomoto AN-201-II, Ajinomoto AN-3, Nippon Soda anisomycins, anthracycline, azino-mycin-A, bisucaberin, Bristol-Myers BL-6859, Bristol-Myers BMY-25067, Bristol-Myers BMY-25551, Bristol-Myers BMY-26605, Bristol-Myers BMY-27557, Bristol-Myers BMY-28438, bleomycin sulfate, bryostatin-1, Taiho C-1027, calichemycin, chromoximycin, dactinomycin, daunorubicin, Kyowa Hakko DC-102, Kyowa Hakko DC-79, Kyowa Hakko DC-88A, Kyowa Hakko DC89-A1, Kyowa Hakko DC92-B, ditrisarubicin B, Shionogi DOB-41, doxorubicin, doxorubicin-fibrinogen, elsamicin-A, epirubicin, erbstatin, esorubicin, esperamicin-A1, esperamicin-A1b, Erbamont FCE-21954, Fujisawa FK-973, fostriecin, Fujisawa FR-900482, glidobactin, gregatin-A, grincamycin, herbimycin, idarubicin, illudins, kazusamycin, kesarirhodins, Kyowa Hakko KM-5539, Kirin Brewery KRN-8602, Kyowa Hakko KT-5432, Kyowa Hakko KT-5594, Kyowa Hakko KT-6149, American Cyanamid LL-D49194, Meiji Seika ME 2303, menogaril, mitomycin, mitomycin analogues, mitoxantrone, SmithKline M-TAG, neoenactin, Nippon Kayaku NK-313, Nippon Kayaku NKT-01, SRI International NSC-357704, oxalysine, oxaunomycin, peplomycin, pilatin, pirarubicin, porothramycin, pyrindamycin A, Tobishi RA-I, rapamycin, rhizoxin, rodorubicin, sibanomicin, siwenmycin, Sumitomo SM-5887, Snow Brand SN-706, Snow Brand SN-07, sorangicin-A, sparsomycin, SS Pharmaceutical SS-21020, SS Pharmaceutical SS-7313B, SS Pharmaceutical SS-9816B, steffimycin B, Taiho 4181-2, talisomycin, Takeda TAN-868A, terpentecin, thrazine, tricrozarin A, Upjohn U-73975, Kyowa Hakko UCN-10028A, Fujisawa WF-3405, Yoshitomi Y-25024, zorubicin, 5-fluorouracil (5-FU), the peroxidate oxidation product of inosine, adenosine, or cytidine with methanol or ethanol, cytosine arabinoside (also referred to as Cytarabin, araC, and Cytosar), 5-Azacytidine, 2-Fluoroadenosine-5'-phosphate (Fludara, also referred to as FaraA), 2-Chlorodeoxyadenosine, Abarelix, Abbott A-84861, Abiraterone acetate, Aminoglutethimide, Asta Medica AN-207, Antide, Chugai AG-041R, Avorelin, aseranox, Sensus B2036-PEG, buserelin, BTG CB-7598, BTG CB-7630, Casodex, cetrolix, clastroban, clodronate disodium, Cosudex, Rotta Research CR-1505, cytadren, crinone, deslorelin, droloxifene, dutasteride, Elimina, Laval University EM-800, Laval University EM-652, epitiostanol, episteride, Mediolanum EP-23904, EntreMed 2-ME, exemestane, fadrozole, finasteride, formestane, Pharmacia & Upjohn FCE-24304, ganirelix, goserelin, Shire gonadorelin agonist, Glaxo Wellcome GW-5638, Hoechst Marion Roussel Hoe-766, NCI hCG, idoxifene, isocordoin, Zeneca ICI-182780, Zeneca ICI-118630, Tulane University J015X, Schering Ag J96, ketanserin, lanreotide, Milkhaus LDI-200, letrozol, leuprolide, leuprorelin, liarozole, lisuride hydrogen maleate, loxiglumide, mepitiostane, Ligand Pharmaceuticals LG-1127, LG-1447, LG-2293, LG-2527, LG-2716, Bone Care International LR-103, Lilly LY-326315, Lilly LY-353381-HCl, Lilly LY-326391, Lilly LY-353381, Lilly LY-357489, miproxifene phosphate, Orion Pharma MPV-2213ad, Tulane University MZ-4-71, nafarelin, nilutamide, Snow Brand NKS01, Azko Nobel ORG-31710, Azko Nobel ORG-31806, orimeten, orimetene, orimetine, ormeloxifene, osaterone, Smithkline Beecham SKB-105657, Tokyo University OSW-1, Peptech PTL-03001, Pharmacia & Upjohn PNU-156765, quinagolide, ramorelix, Raloxifene, statin, sandostatin LAR, Shionogi S-10364, Novartis SMT-487, somavert, somatostatin, tamoxifen, tamoxifen methiodide, teverelix, toremifene, triptorelin, TT-232, vapreotide, vorozole, Yamanouchi YM-116, Yamanouchi YM-511, Yamanouchi YM-55208, Yamanouchi YM-53789, Schering AG ZK-1911703, Schering AG ZK-230211, and Zeneca ZD-182780, alpha-carotene, alpha-difluoromethyl-arginine, acitretin, Biotec AD-5, Kyorin AHC-52, alstonine, amonafide, amphethinile, amsacrine, Angiostat, ankinomycin, antineoplaston A10, antineoplaston A2, antineoplaston A3, antineoplaston A5, antineoplaston AS2-1, Henkel APD, aphidicolin glycinate, asparaginase, Avarol, baccharin, batracylin, benfluron, benzotript, Ipsen-Beaufour BIM-23015, bisantrene, Bristo-Myers BMY-40481, Vestar boron-10, bromofosfamide, Wellcome BW-502, Wellcome BW-773, calcium carbonate, Calcet, Calci-Chew, Calci-Mix, Roxane calcium carbonate tablets, caracemide, carmethizole hydrochloride, Ajinomoto CDAF, chlorsulfaquinoxalone, Chemes CHX-2053, Chemex CHX-100, Warner-Lambert CI-921, Warner-Lambert CI-937, Warner-Lambert CI-941, Warner-Lambert CI-958, clanfenur, claviridenone, ICN compound 1259, ICN compound 4711, Contracan, Cell Pathways CP-461, Yakult Honsha CPT-11, crisnatol, curaderm, cytochalasin B, cytarabine, cytocytin, Merz D-609, DABIS maleate, datelliptinium, DFMO, didemnin-B, dihaematoporphyrin ether, dihydrolenperone dinaline, distamycin, Toyo Pharmar DM-341, Toyo Pharmar DM-75, Daiichi Seiyaku DN-9693, docetaxel, Encore Pharmaceuticals E7869, elliprabin, elliptinium acetate, Tsumura EPMTC, ergotamine, etoposide, etretinate, Eulexin, Cell Pathways Exisulind (sulindac sulphone or CP-246), fenretinide, Florical, Fujisawa FR-57704, gallium nitrate, gemcitabine, genkwadaphnin, Gerimed, Chugai GLA-43, Glaxo GR-63178, grifolan NMF-5N, hexadecylphosphocholine, Green Cross HO-221, homoharringtonine, hydroxyurea, BTG ICRF-187, ilmofosine, irinotecan, isoglutamine, isotretinoin, Otsuka JI-36, Ramot K-477, ketoconazole, Otsuak K-76COONa, Kureha Chemical K-AM, MECT Corp KI-8110, American Cyanamid L-623, leucovorin, levamisole, leukoregulin, lonidamine, Lundbeck LU-23-112, Lilly LY-186641, Materna, NCI (US) MAP, marycin, Merrel Dow MDL-27048, Medco MEDR-340, megestrol, merbarone, merocyanine derivatives, methylanilinoacridine, Molecular Genetics MGI-136, minactivin, mitonafide, mitoquidone, Monocal, mopidamol, motretinide, Zenyaku Kogyo MST-16, Mylanta, N-(retinoyl)amino acids, Nilandron, Nisshin Flour Milling N-021, N-acylated-dehydroalanines, nafazatrom, Taisho NCU-190, Nephro-Calci tablets, nocodazole derivative, Normosang, NCI NSC-145813, NCI NSC-361456, NCI NSC-604782, NCI NSC-95580, octreotide, Ono ONO-112, oquizanocine, Akzo Org-10172, paclitaxel, pancratistatin, pazelliptine, Warner-Lambert PD-111707, Warner-Lambert PD-115934, Warner-Lambert PD-131141, Pierre Fabre PE-1001, ICRT peptide D, piroxantrone, polyhaematoporphyrin, polypreic acid, Efamol porphyrin, probimane, procarbazine, proglumide, Invitron protease nexin I, Tobishi RA-700, razoxane, retinoids, R-flurbiprofen (Encore Pharmaceuticals), Sandostatin, Sapporo Breweries RBS, restrictin-P, retelliptine, retinoic acid, Rhone-Poulenc RP-49532, Rhone-Poulenc RP-56976, Scherring-Plough SC-57050, Scherring-Plough SC-57068, selenium (selenite and selenomethionine), SmithKline SK&F-104864, Sumitomo SM-108, Kuraray SMANCS, SeaPharm SP-10094, spatol, spirocyclopropane derivatives, spirogermanium, Unimed, SS Pharmaceutical SS-554, strypoldinone, Stypoldione, Suntory SUN 0237, Suntory SUN 2071, Sugen SU-101, Sugen SU-5416, Sugen SU-6668, sulindac, sulindac sulfone, superoxide dismutase, Toyama T-506, Toyama T-680, taxol, Teijin TEI-0303, teniposide, thaliblastine, Eastman Kodak TJB-29, tocotrienol, Topostin, Teijin TT-82, Kyowa Hakko UCN-01, Kyowa Hakko UCN-1028, ukrain, Eastman Kodak USB-006, vinblastine, vinblastine sulfate, vincristine, vincristine sulfate, vindesine, vindesine sulfate, vinestramide, vinorelbine, vintriptol, vinzolidine, withanolides, Yamanouchi YM-534, Zileuton, ursodeoxycholic acid, Zanosar.

Chemotherapeutic agents and dosing recommendations for treating specific diseases, are described at length in the literature, e.g., in U.S. Pat. No. 6,858,598, "Method of Using a Matrix Metalloproteinase Inhibitor and One or More Antineoplastic Agents as a Combination Therapy in the Treatment of Neoplasia," and U.S. Pat. No. 6,916,800, "Combination Therapy Including a Matrix Metalloproteinase Inhibitor and an Antineoplastic Agent," both incorporated herein by reference in their entirety.

Methods for the safe and effective administration of chemotherapeutic agents are known to those skilled in the art. In addition, their administration is described in the standard literature. For example, the administration of many chemotherapeutic agents is described in the "Physicians' Desk Reference" (PDR), e.g., 1996 edition (Medical Economics Company, Montvale, N.J. 07645-1742, USA), incorporated herein by reference.

Combinations of two or more agents can be used in the devices and methods of the invention. Guidance for selecting drug combinations for given indications is provided in the published literature, e.g., in the "Drug Information Handbook for Oncology: A Complete Guide to Combination Chemotherapy Regimens" (edited by Dominic A. Solimando, Jr., MA BCOP; published by Lexi-Comp, Hudson, Ohio, 2007. ISBN 978-1-59195-175-9), as well as in U.S. Pat. No. 6,858,598. Specific combinations of chemotherapeutic agents having enhanced activity relative to the individual agents, are described in, e.g., WO 02/40702, "Methods for the Treatment of Cancer and Other Diseases and Methods of Developing the Same," incorporated herein by reference in its entirety. WO 02/40702 reports enhanced activity when treating cancer using a combination of a platin-based compound (e.g., cisplatin, oxoplatin), a folate inhibitor (e.g., MTA, ALIMTA, LY231514), and deoxycytidine or an analogue thereof (e.g., cytarabin, gemcitabine).

Chemotherapeutic agents can be classified into various groups, e.g., ACE inhibitors, alkylating agents, angiogenesis inhibitors, anthracyclines/DNA intercalators, anti-cancer antibiotics or antibiotic-type agents, antimetabolites, antimetastatic compounds, asparaginases, bisphosphonates, cGMP phosphodiesterase inhibitors, cyclooxygenase-2 inhibitors DHA derivatives, epipodophylotoxins, hormonal anticancer agents, hydrophilic bile acids (URSO), immunomodulators or immunological agents, integrin antagonists, interferon antagonists or agents, MMP inhibitors, monoclonal antibodies, nitrosoureas, NSAIDs, ornithine decarboxylase inhibitors, radio/chemo sensitizers/protectors, retinoids, selective inhibitors of proliferation and migration of endothelial cells, selenium, stromelysin inhibitors, taxanes, vaccines, and vinca alkaloids.

Alternatively, chemotherapeutic agents can be classified by target, e.g., agents can be selected from a tubulin binding agent, a kinase inhibitor (e.g., a receptor tyrosine kinase inhibitor), an anti-metabolic agent, a DNA synthesis inhibitor, and a DNA damaging agent.

Other classes into which chemotherapeutic agents can be divided include: alkylating agents, antimetabolites, natural products and their derivatives, hormones and steroids (including synthetic analogs), and synthetics. Examples of compounds within these classes are given herein.

Alkylating agents (e.g., nitrogen mustards, ethylenimine derivatives, alkyl sulfonates, nitrosoureas and triazenes) include Uracil mustard, Chlormethine, Cyclophosphamide (Cytoxan), Ifosfamide, Melphalan, Chlorambucil, Pipobroman, Triethylene-melamine, Triethylenethiophosphoramine, Busulfan, Carmustine, Lomustine, Streptozocin, Dacarbazine, and Temozolomide.

Antimetabolites (e.g., folic acid antagonists, pyrimidine analogs, purine analogs and adenosine deaminase inhibitors) include Methotrexate, 5-Fluorouracil, Floxuridine, Cytarabine, 6-Mercaptopurine, 6-Thioguanine, Fludarabine phosphate, Pentostatine, and Gemcitabine.

Natural products and their derivatives (e.g., vinca alkaloids, antitumor antibiotics, enzymes, lymphokines and epipodophyllotoxins) include Vinblastine, Vincristine, Vindesine, Bleomycin, Dactinomycin, Daunorubicin, Doxorubicin, Epirubicin, Idarubicin, paclitaxel (paclitaxel is commercially available as Taxol), Mithramycin, Deoxycoformycin, Mitomycin-C, L-Asparaginase, Interferons (especially IFN-α), Etoposide, and Teniposide.

Hormones and steroids (e.g., synthetic analogs) include 17α-Ethinylestradiol, Diethylstilbestrol, Testosterone, Prednisone, Fluoxymesterone, Dromostanolone propionate, Testolactone, Megestrolacetate, Tamoxifen, Methylprednisolone, Methyl-testosterone, Prednisolone, Triamcinolone, Chlorotrianisene, Hydroxyprogesterone, Aminoglutethimide, Estramustine, Medroxyprogesteroneacetate, Leuprolide, Flutamide, Toremifene, Zoladex.

Synthetics (e.g., inorganic complexes such as platinum coordination complexes) include Cisplatin, Carboplatin, Hydroxyurea, Amsacrine, Procarbazine, Mitotane, Mitoxantrone, Levamisole, and Hexamethylmelamine.

Chemotherapeutic agents can also be classified by chemical family, for example, therapeutic agents selected from vinca alkaloids (e.g., vinblastine, vincristine, and vinorelbine), taxanes (e.g., paclitaxel and docetaxel), indolyl-3-glyoxylic acid derivatives, (e.g., indibulin), epipidophyllotoxins (e.g., etoposide, teniposide), antibiotics (e.g., dactinomycin or actinomycin D, daunorubicin, doxorubicin and idarubicin), anthracyclines, mitoxantrone, bleomycins, plicamycin (mithramycin) and mitomycin, enzymes (L-asparaginase which systemically metabolizes L-asparagine and deprives cells which do not have the capacity to synthesize their own asparagine); antiplatelet agents; antiproliferative/antimitotic alkylating agents such as nitrogen mustards (e.g., mechlorethamine, ifosphamide, cyclophosphamide and analogs, melphalan, chlorambucil), ethylenimines and methylmelamines (e.g., hexamethylmelamine and thiotepa), alkyl sulfonates (busulfan), nitrosoureas (e.g., carmustine (BCNU) and analogs, streptozocin), trazenes-dacarbazinine (DTIC); antiproliferative/antimitotic antimetabolites such as folic acid analogs (e.g., methotrexate), pyrimidine analogs (e.g., fluorouracil, floxuridine, and cytarabine), purine analogs and related inhibitors (e.g., mercaptopurine, thioguanine, pentostatin and 2-chlorodeoxyadenosine); aromatase inhibitors (e.g., anastrozole, exemestane, and letrozole); and platinum coordination complexes (e.g., cisplatin, carboplatin), procarbazine, hydroxyurea, mitotane, aminoglutethimide; hormones (e.g., estrogen) and hormone agonists such as leutinizing hormone releasing hormone (LHRH) agonists (e.g., goserelin, leuprolide and triptorelin).

Antineoplastic agents are often placed into categories, including antimetabolite agents, alkylating agents, antibiotic-type agents, hormonal anticancer agents, immunological agents, interferon-type agents, and a category of miscellaneous antineoplastic agents. Some antineoplastic agents operate through multiple or unknown mechanisms and can thus be classified into more than one category.

A first family of antineoplastic agents which may be used in combination with the present invention consists of anti-metabolite-type antineoplastic agents. Antimetabolites are typically reversible or irreversible enzyme inhibitors, or compounds that otherwise interfere with the replication, translation or transcription of nucleic acids. Suitable antimetabolite antineoplastic agents that may be used in the present invention include, but are not limited to acanthifolic acid, aminothiadiazole, anastrozole, bicalutamide, brequinar sodium, capecitabine, carmofur, Ciba-Geigy CGP-30694, cladribine, cyclopentyl cytosine, cytarabine phosphate stearate, cytarabine conjugates, cytarabine ocfosfate, Lilly DATHF, Merrel Dow DDFC, dezaguanine, dideoxycytidine, dideoxyguanosine, didox, Yoshitomi DMDC, doxifluridine, Wellcome EHNA, Merck & Co. EX-015, fazarabine, finasteride, floxuridine, fludarabine, fludarabine phosphate, N-(2'-furanidyl)-5-fluorouracil, Daiichi Seiyaku FO-152, fluorouracil (5-FU), 5-FU-fibrinogen, isopropyl pyrrolizine, Lilly LY-188011, Lilly LY-264618, methobenzaprim, methotrexate, Wellcome MZPES, nafarelin, norspermidine, nolvadex, NCI NSC-127716, NCI NSC-264880, NCI NSC-39661, NCI NSC-612567, Warner-Lambert PALA, pentostatin, piritrexim, plicamycin, Asahi Chemical PL-AC, stearate; Takeda TAC-788, thioguanine, tiazofurin, Erbamont TIF, trimetrexate, tyrosine kinase inhibitors, tyrosine protein kinase inhibitors, Taiho UFT, toremifene, and uricytin.

Antimetabolite agents that may be used in the present invention include, but are not limited to, those identified in Table No. 5 of U.S. Pat. No. 6,858,598, incorporated herein by reference.

A second family of antineoplastic agents which may be used in combination with the present invention consists of alkylating-type antineoplastic agents. The alkylating agents are believed to act by alkylating and cross-linking guanine and possibly other bases in DNA, arresting cell division. Typical alkylating agents include nitrogen mustards, ethyleneimine compounds, alkyl sulfates, cisplatin, and various nitrosoureas. A disadvantage with these compounds is that they not only attack malignant cells, but also other cells which are naturally dividing, such as those of bone marrow, skin, gastro-intestinal mucosa, and fetal tissue. Suitable alkylating-type antineoplastic agents that may be used in the present invention include, but are not limited to, Shionogi 254-S, aldo-phosphamide analogues, altretamine, anaxirone, Boehringer Mannheim BBR-2207, bestrabucil, budotitane, Wakunaga CA-102, carboplatin, carmustine (BiCNU), Chinoin-139, Chinoin-153, chlorambucil, cisplatin, cyclophosphamide, American Cyanamid CL-286558, Sanofi CY-233, cyplatate, dacarbazine, Degussa D-19-384, Sumimoto DACHP(Myr)2, diphenylspiromustine, diplatinum cytostatic, Erba distamycin derivatives, Chugai DWA-2114R, ITI E09, elmustine, Erbamont FCE-24517, estramustine phosphate sodium, etoposide phosphate, fotemustine, Unimed G-6-M, Chinoin GYKI-17230, hepsulfam, ifosfamide, iproplatin, lomustine, mafosfamide, mitolactol, mycophenolate, Nippon Kayaku NK-121, NCI NSC-264395, NCI NSC-342215, oxaliplatin, Upjohn PCNU, prednimustine, Proter PTT-119, ranimustine, semustine, SmithKline SK&F-101772, thiotepa, Yakult Honsha SN-22, spiromus-tine, Tanabe Seiyaku TA-077, tauromustine, temozolomide, teroxirone, tetraplatin and trimelamol.

Preferred alkylating agents that may be used in the present invention include, but are not limited to, those identified in Table No. 6 of U.S. Pat. No. 6,858,598, incorporated herein by reference.

A third family of antineoplastic agents which may be used in combination with the present invention consists of antibiotic-type antineoplastic agents. Suitable antibiotic-type antineoplastic agents that may be used in the present invention include, but are not limited to Taiho 4181-A, aclarubicin, actinomycin D, actinoplanone, Erbamont ADR-456, aeroplysinin derivative, Ajinomoto AN-201-II, Ajinomoto AN-3, Nippon Soda anisomycins, anthracycline, azino-mycin-A, bisucaberin, Bristol-Myers BL-6859, Bristol-Myers BMY-25067, Bristol-Myers BMY-25551, Bristol-Myers BMY-26605, Bristol-Myers BMY-27557, Bristol-Myers BMY-28438, bleomycin sulfate, bryostatin-1, Taiho C-1027, calichemycin, chromoximycin, dactinomycin, daunorubicin, Kyowa Hakko DC-102, Kyowa Hakko DC-79, Kyowa Hakko DC-88A, Kyowa Hakko DC89-A1, Kyowa Hakko DC92-B, ditrisarubicin B, Shionogi DOB-41, doxorubicin, doxorubicin-fibrinogen, elsamicin-A, epirubicin, erbstatin, esorubicin, esperamicin-A1, esperamicin-A1b, Erbamont FCE-21954, Fujisawa FK-973, fostriecin, Fujisawa FR-900482, glidobactin, gregatin-A, grincamycin, herbimycin, idarubicin, illudins, kazusamycin, kesarirhodins, Kyowa Hakko KM-5539, Kirin Brewery KRN-8602, Kyowa Hakko KT-5432, Kyowa Hakko KT-5594, Kyowa Hakko KT-6149, American Cyanamid LL-D49194, Meiji Seika ME 2303, menogaril, mitomycin, mitoxantrone, SmithKline M-TAG, neoenactin, Nippon Kayaku NK-313, Nippon Kayaku NKT-01, SRI International NSC-357704, oxalysine, oxaunomycin, peplomycin, pilatin, pirarubicin, porothramycin, pyrindamycin A, Tobishi RA-I, rapamycin, rhizoxin, rodorubicin, sibanomicin, siwenmycin, Sumitomo SM-5887, Snow Brand SN-706, Snow Brand SN-07, sorangicin-A, sparsomycin, SS Pharmaceutical SS-21020, SS Pharmaceutical SS-7313B, SS Pharmaceutical SS-9816B, steffimycin B, Taiho 4181-2, talisomycin, Takeda TAN-868A, terpentecin, thrazine, tricrozarin A, Upjohn U-73975, Kyowa Hakko UCN-10028A, Fujisawa WF-3405, Yoshitomi Y-25024 and zorubicin.

Preferred antibiotic anticancer agents that may be used in the present invention include, but are not limited to, those identified in Table No. 7 of U.S. Pat. No. 6,858,598, incorporated herein by reference.

A fourth family of antineoplastic agents which may be used in combination with the present invention consists of synthetic nucleosides. Several synthetic nucleosides have been identified that exhibit anticancer activity. A well known nucleoside derivative with strong anticancer activity is 5-fluorouracil (5-FU). 5-Fluorouracil has been used clinically in the treatment of malignant tumors, including, for example, carcinomas, sarcomas, skin cancer, cancer of the digestive organs, and breast cancer. 5-Fluorouracil, however, causes serious adverse reactions such as nausea, alopecia, diarrhea, stomatitis, leukocytic thrombocytopenia, anorexia, pigmentation, and edema. Derivatives of 5-fluorouracil with anti-cancer activity have been described in U.S. Pat. No. 4,336,381. Further 5-FU derivatives have been described in the following patents identified in Table No. 8 of U.S. Pat. No. 6,858,598, incorporated herein by reference.

U.S. Pat. No. 4,000,137 discloses that the peroxidate oxidation product of inosine, adenosine, or cytidine with methanol or ethanol has activity against lymphocytic leukemia. Cytosine arabinoside (also referred to as Cytarabin, araC, and Cytosar) is a nucleoside analog of deoxycytidine that was first synthesized in 1950 and introduced into clinical medicine in 1963. It is currently an important drug in the treatment of acute myeloid leukemia. It is also active against acute lymphocytic leukemia, and to a lesser extent, is useful in chronic myelocytic leukemia and non-Hodgkin's lymphoma. The primary action of araC is inhibition of nuclear DNA synthesis. Handschumacher, R. and Cheng, Y., "Purine and Pyrimidine Antimetabolites", Cancer Medicine, Chapter XV-1, 3rd Edition, Edited by J. Holland, et al., Lea and Febigol, publishers.

5-Azacytidine is a cytidine analog that is primarily used in the treatment of acute myelocytic leukemia and myelodysplastic syndrome.

2-Fluoroadenosine-5'-phosphate (Fludara, also referred to as FaraA) is one of the most active agents in the treatment of chronic lymphocytic leukemia. The compound acts by inhibiting DNA synthesis. Treatment of cells with F-araA is associated with the accumulation of cells at the G1/S phase boundary and in S phase; thus, it is a cell cycle S phase-specific drug. InCorp of the active metabolite, F-araATP, retards DNA chain elongation. F-araA is also a potent inhibitor of ribonucleotide reductase, the key enzyme responsible for the formation of dATP. 2-Chlorodeoxyadenosine is useful in the treatment of low grade B-cell neoplasms such as chronic lymphocytic leukemia, non-Hodgkins' lymphoma, and hairy-cell leukemia. The spectrum of activity is similar to that of Fludara. The compound inhibits DNA synthesis in growing cells and inhibits DNA repair in resting cells.

A fifth family of antineoplastic agents which may be used in combination with the present invention consists of hormonal agents. Suitable hormonal-type antineoplastic agents that may be used in the present invention include, but are not limited to Abarelix; Abbott A-84861; Abiraterone acetate; Aminoglutethimide; anastrozole; Asta Medica AN-207; Antide; Chugai AG-041R; Avorelin; aseranox; Sensus B2036-PEG; Bicalutamide; buserelin; BTG CB-7598, BTG CB-7630; Casodex; cetrolix; clastroban; clodronate disodium; Cosudex; Rotta Research CR-1505; cytadren; crinone; deslorelin; droloxifene; dutasteride; Elimina; Laval University EM-800; Laval University EM-652; epitiostanol; episteride; Mediolanum EP-23904; EntreMed 2-ME; exemestane; fadrozole; finasteride; flutamide; formestane; Pharmacia & Upjohn FCE-24304; ganirelix; goserelin; Shire gonadorelin agonist; Glaxo Wellcome GW-5638; Hoechst Marion Roussel Hoe-766; NCI hCG; idoxifene; isocordoin; Zeneca ICI-182780; Zeneca ICI-118630; Tulane University J015X; Schering Ag J96; ketanserin; lanreotide; Milkhaus LDI-200; letrozol; leuprolide; leuprorelin; liarozole; lisuride hydrogen maleate; loxiglumide; mepitiostane; Leuprorelin; Ligand Pharmaceuticals LG-1127; LG-1447; LG-2293; LG-2527; LG-2716; Bone Care International LR-103; Lilly LY-326315; Lilly LY-353381-HCl; Lilly LY-326391; Lilly LY-353381; Lilly LY-357489; miproxifene phosphate; Orion Pharma MPV-2213ad; Tulane University MZ-4-71; nafarelin; nilutamide; Snow Brand NKS01; octreotide; Azko Nobel ORG-31710; Azko Nobel ORG-31806; orimeten; orimetene; orimetine; ormeloxifene; osaterone; Smithkline Beecham SKB-105657; Tokyo University OSW-1; Peptech PTL-03001; Pharmacia & Upjohn PNU-156765; quinagolide; ramorelix; Raloxifene; statin; sandostatin LAR; Shionogi S-10364; Novartis SMT-487; somavert; somatostatin; tamoxifen; tamoxifen methiodide; teverelix; toremifene; triptorelin; TT-232; vapreotide; vorozole; Yamanouchi YM-116; Yamanouchi YM-511; Yamanouchi YM-55208; Yamanouchi YM-53789; Schering AG ZK-1911703; Schering AG ZK-230211; and Zeneca ZD-182780.

Preferred hormonal agents that may be used in the present invention include, but are not limited to, those identified in Table No. 9 of U.S. Pat. No. 6,858,598, incorporated herein by reference.

A sixth family of antineoplastic agents which may be used in combination with the present invention consists of a miscellaneous family of antineoplastic agents including, but not limited to alpha-carotene, alpha-difluoromethyl-arginine, acitretin, Biotec AD-5, Kyorin AHC-52, alstonine, amonafide, amphethinile, amsacrine, Angiostat, ankinomycin, anti-neoplaston A10, antineoplaston A2, antineoplaston A3, antineoplaston A5, antineoplaston AS2-1, Henkel APD, aphidicolin glycinate, asparaginase, Avarol, baccharin, batracylin, benfluron, benzotript, Ipsen-Beaufour BIM-23015, bisantrene, Bristo-Myers BMY-40481, Vestar boron-10, bromofosfamide, Wellcome BW-502, Wellcome BW-773, calcium carbonate, Calcet, Calci-Chew, Calci-Mix, Roxane calcium carbonate tablets, caracemide, carmethizole hydrochloride, Ajinomoto CDAF, chlorsulfaquinoxalone, Chemes CHX-2053, Chemex CHX-100, Warner-Lambert CI-921, Warner-Lambert CI-937, Warner-Lambert CI-941, Warner-Lambert CI-958, clanfenur, claviridenone, ICN compound 1259, ICN compound 4711, Contracan, Cell Pathways CP-461, Yakult Honsha CPT-11, crisnatol, curaderm, cytochalasin B, cytarabine, cytocytin, Merz D-609, DABIS maleate, dacarbazine, datelliptinium, DFMO, didemnin-B, dihaematoporphyrin ether, dihydrolenperone dinaline, distamycin, Toyo Pharmar DM-341, Toyo Pharmar DM-75, Daiichi Seiyaku DN-9693, docetaxel, Encore Pharmaceuticals E7869, elliprabin, elliptinium acetate, Tsumura EPMTC, ergotamine, etoposide, etretinate, Eulexin, Cell Pathways Exisulind (sulindac sulphone or CP-246), fenretinide, Merck Research Labs Finasteride, Florical, Fujisawa FR-57704, gallium nitrate, gemcitabine, genkwadaphnin, Gerimed, Chugai GLA-43, Glaxo GR-63178, grifolan NMF-5N, hexadecylphosphocholine, Green Cross HO-221, homoharringtonine, hydroxyurea, BTG ICRF-187, ilmofosine, irinotecan, isoglutamine, isotretinoin, Otsuka JI-36, Ramot K-477, ketoconazole, Otsuak K-76COONa, Kureha Chemical K-AM, MECT Corp KI-8110, American Cyanamid L-623, leucovorin, levamisole, leukoregulin, lonidamine, Lundbeck LU-23-112, Lilly LY-186641, Materna, NCI (US) MAP, marycin, Merrel Dow MDL-27048, Medco MEDR-340, megestrol, merbarone, merocyanine derivatives, methylanilinoacridine, Molecular Genetics MGI-136, minactivin, mitonafide, mitoquidone, Monocal, mopidamol, motretinide, Zenyaku Kogyo MST-16, Mylanta, N-(retinoyl)amino acids, Nilandron; Nisshin Flour Milling N-021, N-acylated-dehydroalanines, nafazatrom, Taisho NCU-190, Nephro-Calci tablets, nocodazole derivative, Normosang, NCI NSC-145813, NCI NSC-361456, NCI NSC-604782, NCI NSC-95580, octreotide, Ono ONO-112, oquizanocine, Akzo Org-10172, paclitaxel, pancratistatin, pazelliptine, Warner-Lambert PD-111707, Warner-Lambert PD-115934, Warner-Lambert PD-131141, Pierre Fabre PE-1001, ICRT peptide D, piroxantrone, polyhaematoporphyrin, polypreic acid, Efamol porphyrin, probimane, procarbazine, proglumide, Invitron protease nexin I, Tobishi RA-700, razoxane, retinoids, R-flurbiprofen (Encore Pharmaceuticals), Sandostatin; Sapporo Breweries RBS, restrictin-P, retelliptine, retinoic acid, Rhone-Poulenc RP-49532, Rhone-Poulenc RP-56976, Scherring-Plough SC-57050, Scherring-Plough SC-57068, selenium(selenite and selenomethionine), SmithKline SK&F-104864, Sumitomo SM-108, Kuraray SMANCS, SeaPharm SP-10094, spatol, spirocyclopropane derivatives, spirogermanium, Unimed, SS Pharmaceutical SS-554, strypoldinone, Stypoldione, Suntory SUN 0237, Suntory SUN 2071, Sugen SU-101, Sugen SU-5416, Sugen SU-6668, sulindac, sulindac sulfone; superoxide dismutase, Toyama T-506, Toyama T-680, taxol, Teijin TEI-0303, teniposide, thaliblastine, Eastman Kodak TJB-29, tocotrienol, Topostin, Teijin TT-82, Kyowa Hakko UCN-01, Kyowa Hakko UCN-1028, ukrain, Eastman Kodak USB-006, vinblastine sulfate, vincristine, vindesine, vinestramide, vinorelbine, vintriptol, vinzolidine, withanolides, Yamanouchi YM-534, Zileuton, ursodeoxycholic acid, and Zanosar.

Preferred miscellaneous agents that may be used in the present invention include, but are not limited to, those identified in (the second) Table No. 6 of U.S. Pat. No. 6,858,598, incorporated herein by reference.

Some additional preferred antineoplastic agents include those described in the individual patents listed in U.S. Pat. No. 6,858,598 in (the second) Table No. 7, and are hereby individually incorporated by reference.

In embodiments, the agent delivered by the balloon is a radiosensitizer, administered prior to radiation therapy. Radiosensitizers increase sensitivity to radiation, thereby allowing reduction of the radiation dosage.

An "antibiotic agent," as used herein, is a substance or compound that kills bacteria (i.e., is bacteriocidal) or inhibits the growth of bacteria (i.e., is bacteriostatic).

Antibiotics that can be used in the devices and methods of the present invention include, but are not limited to, amikacin, amoxicillin, gentamicin, kanamycin, neomycin, netilmicin, paromomycin, tobramycin, geldanamycin, herbimycin, carbacephem (loracarbef), ertapenem, doripenem, imipenem, cefadroxil, cefazolin, cefalotin, cephalexin, cefaclor, cefamandole, cefoxitin, cefprozil, cefuroxime, cefixime, cefdinir, cefditoren, cefoperazone, cefotaxime, cefpodoxime, ceftazidime, ceftibuten, ceftizoxime, ceftriaxone, cefepime, ceftobiprole, clarithromycin, clavulanic acid, clindamycin, teicoplanin, azithromycin, dirithromycin, erythromycin, troleandomycin, telithromycin, aztreonam, ampicillin, azlocillin, bacampicillin, carbenicillin, cloxacillin, dicloxacillin, flucloxacillin, mezlocillin, meticillin, nafcillin, norfloxacin, oxacillin, penicillin G, penicillin V, piperacillin, pvampicillin, pivmecillinam, ticarcillin, bacitracin, colistin, polymyxin B, ciprofloxacin, enoxacin, gatifloxacin, levofloxacin, lomefloxacin, moxifloxacin, ofloxacin, trovafloxacin, grepafloxacin, sparfloxacin, afenide, prontosil, sulfacetamide, sulfamethizole, sulfanilimide, sulfamethoxazole, sulfisoxazole, trimethoprim, trimethoprim-sulfamethoxazole, demeclocycline, doxycycline, oxytetracycline, tetracycline, arsphenamine, chloramphenicol, lincomycin, ethambutol, fosfomycin, furazolidone, isoniazid, linezolid, mupirocin, nitrofurantoin, platensimycin, pyrazinamide, quinupristin/dalfopristin, rifampin, thiamphenicol, rifampicin, minocycline, sultamicillin, sulbactam, sulphonamides, mitomycin, spectinomycin, spiramycin, roxithromycin, and meropenem.

Antibiotics can also be grouped into classes of related drugs, for example, aminoglycosides (e.g., amikacin, gentamicin, kanamycin, neomycin, netilmicin, paromomycin, streptomycin, tobramycin), ansamycins (e.g., geldanamycin, herbimycin), carbacephem (loracarbef) carbapenems (e.g., ertapenem, doripenem, imipenem, meropenem), first generation cephalosporins (e.g., cefadroxil, cefazolin, cefalotin, cefalexin), second generation cephalosporins (e.g., cefaclor, cefamandole, cefoxitin, cefprozil, cefuroxime), third generation cephalosporins (e.g., cefixime, cefdinir, cefditoren, cefoperazone, cefotaxime, cefpodoxime, ceftazidime, ceftibuten, ceftizoxime, ceftriaxone), fourth generation cephalosporins (e.g., cefepime), fifth generation cephalosporins (e.g., ceftobiprole), glycopeptides (e.g., teicoplanin, vancomycin), macrolides (e.g., azithromycin, clarithromycin, dirithromycin, erythromycin, roxithromycin, troleandomycin, telithromycin, spectinomycin), monobactams (e.g., aztreonam), penicillins (e.g., amoxicillin, ampicillin, azlocillin, bacampicillin, carbenicillin, cloxacillin, dicloxacillin, flucloxacillin, mezlocillin, meticillin, nafcillin, oxacillin, penicillins G and V, piperacillin, pvampicillin, pivmecillinam, ticarcillin), polypeptides (e.g., bacitracin, colistin, polymyxin B), quinolones (e.g., ciprofloxacin, enoxacin, gatifloxacin, levofloxacin, lomefloxacin, moxifloxacin, norfloxacin, ofloxacin, trovafloxacin, grepafloxacin, sparfloxacin, trovafloxacin), sulfonamides (e.g., afenide, prontosil, sulfacetamide, sulfamethizole, sulfanilimide, sulfasalazine, sulfamethoxazole, sulfisoxazole, trimethoprim, trimethoprim-sulfamethoxazole), tetracyclines (e.g., demeclocycline, doxycycline, minocycline, oxytetracycline, tetracycline).

For treatment of abcesses, commonly caused by Staphylococcus aureus bacteria, use of an anti-staphylococcus antibiotic such as flucloxacillin or dicloxacillin is contemplated. With the emergence of community-acquired methicillin-resistant staphylococcus aureus MRSA, these traditional antibiotics may be ineffective; alternative antibiotics effective against community-acquired MRSA often include clindamycin, trimethoprim-sulfamethoxazole, and doxycycline. These antibiotics may also be prescribed to patients with a documented allergy to penicillin. If the condition is thought to be cellulitis rather than abscess, consideration should be given to possibility of strep species as cause that are still sensitive to traditional anti-staphylococcus agents such as dicloxacillin or cephalexin in patients able to tolerate penicillin.

Anti-thrombotic agents are contemplated for use in the methods of the invention in adjunctive therapy for treatment of coronary stenosis. The use of anti-platelet drugs, e.g., to prevent platelet binding to exposed collagen, is contemplated for anti-restenotic or anti-thrombotic therapy. Anti-platelet agents include "GpIIb/IIIa inhibitors" (e.g., abciximab, eptifibatide, tirofiban, RheoPro) and "ADP receptor blockers" (prasugrel, clopidogrel, ticlopidine). Particularly useful for local therapy are dipyridamole, which has local vascular effects that improve endothelial function (e.g., by causing local release of t-PA, that will break up clots or prevent clot formation) and reduce the likelihood of platelets and inflammatory cells binding to damaged endothelium, and cAMP phosphodiesterase inhibitors, e.g., cilostazol, that could bind to receptors on either injured endothelial cells or bound and injured platelets to prevent further platelet binding.

The methods of the invention are useful for encouraging migration and proliferation of endothelial cells from adjacent vascular domains to "heal" the damaged endothelium and/or encourage homing and maturation of blood-borne endothelial progenitor cells to the site of injury. There is evidence that both rapamycin and paclitaxel prevent endothelial cell growth and reduce the colonization and maturation of endothelial progenitor cells (EPCs) making both drugs 'anti-healing.' While local delivery of growth factors could accelerate endothelial cell regrowth, virtually all of these agents are equally effective at accelerating the proliferation of vascular smooth muscle cells, which can cause restenosis. VEGF is also not selective for endothelial cells but can cause proliferation of smooth muscle cells. To make VEGF more selective for endothelial cells it can be combined with a proteoglycan like heparan sulfate or chondroitin sulfate or even with an elongated "RGD" peptide binding domain. This may sequester it away from the actual lesion site but still allow it to dissociate and interact with nearby endothelial cells. The use of CD34 antibodies and other specific antibodies, which bind to the surface of blood borne progenitor cells, can be used to attract endothelial progenitor cells to the vessel wall to potential accelerate endothelialization.

Statins (e.g., cerivastatin, etorvastatin), which can have endothelial protective effects and improve progenitor cell function, are contemplated for use in embodiments of methods and/or devices provided herein. Other drugs that have demonstrated some evidence to improve EPC colonization, maturation or function and are contemplated for use in the methods of the invention are angiotensin converting enzyme inhibitors (ACE-I, e.g., Captopril, Enalapril, and Ramipril), Angiotensin II type I receptor blockers (AT-II-blockers, e.g., losartan, valartan), peroxisome proliferator-activated receptor gamma (PPAR-γ) agonists, and erythropoietin. The PPAR-γ agonists like the glitazones (e.g., rosiglitazone, pioglitazone) can provide useful vascular effects, including the ability to inhibit vascular smooth muscle cell proliferation, and have anti-inflammatory functions, local antithrombotic properties, local lipid lowering effects, and can inhibit matrix metalloproteinase (MMP) activity so as to stabilize vulnerable plaque.

Atherosclerosis is viewed as a systemic disease with significant local events. Adjunctive local therapy can be used in addition to systemic therapy to treat particularly vulnerable areas of the vascular anatomy. The mutant protein Apo A1 Milano has been reported to remove unwanted lipid from a blood vessel and can cause regression of atherosclerosis. Either protein therapy, or gene therapy to provide sustained release of a protein therapy, can be delivered using the methods of the invention. Adiponectin, a protein produced by adipocytes, is another protein with anti-atherosclerotic properties. It prevents inflammatory cell binding and promotes generation of nitric oxide (NO). NO has been shown to have antiatherogenic activity in the vessel wall; it promotes antiinflammatory and other beneficial effects. The use of agents including nitric oxide synthase (NOS) gene therapy that act to increase NO levels, are contemplated herein. NOS gene therapy is described, e.g., by Channon, et al., 2000, "Nitric Oxide Synthase in Atherosclerosis and Vascular Injury: Insights from Experimental Gene Therapy," Arteriosclerosis, Thrombosis, and Vascular Biology, 20(8):1873-1881. Compounds for treating NO deficiency are described, e.g., in U.S. Pat. No. 7,537,785, "Composition for treating vascular diseases characterized by nitric oxide insufficiency," incorporated herein by reference in its entirety. "Vulnerable plaque" occurs in blood vessels where a pool of lipid lies below a thin fibrous cap. If the cap ruptures then the highly thrombogenic lipid leaks into the artery often resulting in abrupt closure of the vessel due to rapid clotting. Depending on the location of the vulnerable plaque, rupture can lead to sudden death. Both statins and glitazones have been shown to strengthen the fibrous cap covering the plaque and make it less vulnerable. Other agents, e.g., batimastat or marimastat, target the MMPs that can destroy the fibrin cap.

Angiogenesis promoters can be used for treating reperfusion injury, which can occur when severely stenotic arteries, particular chronic total occlusions, are opened. Angiogenesis promoters are contemplated for use in embodiments of methods and/or devices provided herein. Myocardial cells downstream from a blocked artery will downregulate the pathways normally used to prevent damage from oxygen free radicals and other blood borne toxins. A sudden infusion of oxygen can lead to irreversible cell damage and death. Drugs developed to prevent this phenomenon can be effective if provided by sustained local delivery. Neurovascular interventions can particularly benefit from this treatment strategy. Examples of pharmacological agents potentially useful in preventing reperfusion injury are glucagon-like peptide 1, erythropoietin, atorvastatin, and atrial natriuretic peptide (ANP). Other angiogenesis promoters have been described, e.g., in U.S. Pat. No. 6,284,758, "Angiogenesis promoters and angiogenesis potentiators," U.S. Pat. No. 7,462,593, "Compositions and methods for promoting angiogenesis," and U.S. Pat. No. 7,456,151, "Promoting angiogenesis with netrin1 polypeptides."

"Local anesthetics" are substances which inhibit pain signals in a localized region. Examples of such anesthetics include procaine, lidocaine, tetracaine and dibucaine. Local anesthetics are contemplated for use in embodiments of methods and/or devices provided herein.

"Anti-inflammatory agents" as used herein refer to agents used to reduce inflammation. Anti-inflammatory agents useful in the devices and methods of the invention include, but are not limited to: aspirin, ibuprofen, naproxen, hyssop, ginger, turmeric, helenalin, cannabichromene, rofecoxib, celecoxib, paracetamol (acetaminophen), sirolimus (rapamycin), dexamethasone, dipyridamole, alfuzosin, statins, and glitazones. Antiinflammatory agents are contemplated for use in embodiments of methods and/or devices provided herein.

Antiinflammatory agents can be classified by action. For example, glucocorticoids are steroids that reduce inflammation or swelling by binding to cortisol receptors. Non-steroidal anti-inflammatory drugs (NSAIDs), alleviate pain by acting on the cyclooxygenase (COX) enzyme. COX synthesizes prostaglandins, causing inflammation. A cannabinoid, cannabichromene, present in the cannabis plant, has been reported to reduce inflammation. Newer COX-inhibitors, e.g., rofecoxib and celecoxib, are also antiinflammatory agents. Many antiinflammatory agents are also analgesics (painkillers), including salicylic acid, paracetamol (acetaminophen), COX-2 inhibitors and NSAIDs. Also included among analgesics are, e.g., narcotic drugs such as morphine, and synthetic drugs with narcotic properties such as tramadol.

Other antiinflammatory agents useful in the methods of the present invention include sirolimus (rapamycin) and dexamethasone. Stents coated with dexamethasone were reported to be useful in a particular subset of patients with exaggerated inflammatory disease evidenced by high plasma C-reactive protein levels. Because both restenosis and atherosclerosis have such a large inflammatory component, anti-inflammatories remain of interest with regard to local therapeutic agents. In particular, the use of agents that have anti-inflammatory activity in addition to other useful pharmacologic actions is contemplated. Examples include dipyridamole, statins and glitazones. Despite an increase in cardiovascular risk and systemic adverse events reported with use of cyclooxygenase (COX)-inhibitors (e.g., celocoxib), these drugs can be useful for short term local therapy.

"Stability" as used herein in refers to the stability of the drug in a coating deposited on a substrate in its final product form (e.g., stability of the drug in a coated stent). The term "stability" and/or "stable" in some embodiments is defined by 5% or less degradation of the drug in the final product form. The term stability in some embodiments is defined by 3% or less degradation of the drug in the final product form. The term stability in some embodiments is defined by 2% or less degradation of the drug in the final product form. The term stability in some embodiments is defined by 1% or less degradation of the drug in the final product form.

In some embodiments, the pharmaceutical agent is at least one of: 50% crystalline, 75% crystalline, 80% crystalline, 90% crystalline, 95% crystalline, 97% crystalline, and 99% crystalline following sterilization of the device. In some embodiments, the pharmaceutical agent crystallinity is stable wherein the crystallinity of the pharmaceutical agent following sterilization is compared to the crystallinity of the pharmaceutical agent at least one of: 1 week after sterilization, 2 weeks after sterilization, 4 weeks after sterilization, 1 month after sterilization, 2 months after sterilization, 45 days after sterilization, 60 days after sterilization, 90 days after sterilization, 3 months after sterilization, 4 months after sterilization, 6 months after sterilization, 9 months after sterilization, 12 months after sterilization, 18 months after sterilization, and 2 years after sterilization. In some embodiments, the pharmaceutical agent crystallinity is stable wherein the crystallinity of the pharmaceutical agent prior to sterilization is compared to the crystallinity of the pharmaceutical agent at least one of: 1 week after sterilization, 2 weeks after sterilization, 4 weeks after sterilization, 1 month after sterilization, 2 months after sterilization, 45 days after sterilization, 60 days after sterilization, 90 days after sterilization, 3 months after sterilization, 4 months after sterilization, 6 months after sterilization, 9 months after sterilization, 12 months after sterilization, 18 months after sterilization, and 2 years after sterilization. In such embodiments, different devices may be tested from the same manufacturing lot to determine stability of the pharmaceutical agent at the desired time points.

In some embodiments, the pharmaceutical agent crystallinity is stable at at least one of: 1 week after sterilization, 2 weeks after sterilization, 4 weeks after sterilization, 1 month after sterilization, 2 months after sterilization, 45 days after sterilization, 60 days after sterilization, 90 days after sterilization, 3 months after sterilization, 4 months after sterilization, 6 months after sterilization, 9 months after sterilization, 12 months after sterilization, 18 months after sterilization, and 2 years after sterilization.

In some embodiments, the pharmaceutical agent crystallinity on the device tested at a time point after sterilization does not differ more than 1%, 2%, 3%, 4%, and/or 5% from the crystallinity tested on a second device manufactured from the same lot of devices and the same lot of pharmaceutical agent at testing time point before sterilization (i.e. the crystallinity drops no more than from 99 to 94% crystalline, for example, which is a 5% difference in crystallinity; the crystallinity drops no more than from 99 to 95% crystalline, which is a 4% difference in crystallinity; the crystallinity drops no more than from 99 to 96% crystalline, for example, which is a 3% difference in crystallinity; the crystallinity drops no more than from 99 to 97% crystalline, for example, which is a 2% difference in crystallinity; the crystallinity drops no more than from 99 to 98% crystalline, for example, which is a 1% difference in crystallinity; in other examples, the starting crystallinity percentage is one of 100%, 98%, 96%, 97%, 96%, 95%, 90%, 85%, 80%, 75%, 70%, 60%, 50%, 30%, 25%, and/or anything in between).

In some embodiments, crystallinity of the pharmaceutical agent on the device tested at a time point after sterilization does not differ more than 1%, 2%, 3%, 4%, and/or 5% from the crystallinity of pharmaceutical from the same lot of pharmaceutical agent tested at testing time point before sterilization of the pharmaceutical agent.

In some embodiments, crystallinity of the pharmaceutical agent does not drop more than 1%, 2%, 3%, 4%, and/or 5% between two testing time points after sterilization neither of which time point being greater than 2 years after sterilization. In some embodiments, crystallinity of the pharmaceutical agent does not drop more than 1%, 2%, 3%, 4%, and/or 5% between two testing time points after sterilization neither of which time point being greater than 5 years after sterilization. In some embodiments, two time points comprise two of: 1 week after sterilization, 2 weeks after sterilization, 4 weeks after sterilization, 1 month after sterilization, 2 months after sterilization, 45 days after sterilization, 60 days after sterilization, 90 days after sterilization, 3 months after sterilization, 4 months after sterilization, 6 months after sterilization, 9 months after sterilization, 12 months after sterilization, 18 months after sterilization, 2 years after sterilization, 3 years after sterilization, 4 years after sterilization, and 5 years after sterilization.

"Active biological agent" as used herein refers to a substance, originally produced by living organisms, that can be used to prevent or treat a disease (meaning any treatment of a disease in a mammal, including preventing the disease, i.e. causing the clinical symptoms of the disease not to develop; inhibiting the disease, i.e. arresting the development of clinical symptoms; and/or relieving the disease, i.e. causing the regression of clinical symptoms). It is possible that the active biological agents of the invention may also comprise two or more active biological agents or an active biological agent combined with a pharmaceutical agent, a stabilizing agent or chemical or biological entity. Although the active biological agent may have been originally produced by living organisms, those of the present invention may also have been synthetically prepared, or by methods combining biological isolation and synthetic modification. By way of a non-limiting example, a nucleic acid could be isolated form from a biological source, or prepared by traditional techniques, known to those skilled in the art of nucleic acid synthesis. Furthermore, the nucleic acid may be further modified to contain non-naturally occurring moieties. Non-limiting examples of active biological agents include growth factors, cytokines, peptides, proteins, enzymes, glycoproteins, nucleic acids (including deoxyribonucleotide or ribonucleotide polymers in either single or double stranded form, and unless otherwise limited, encompasses known analogues of natural nucleotides that hybridize to nucleic acids in a manner similar to naturally occurring nucleotides), antisense nucleic acids, fatty acids, antimicrobials, vitamins, hormones, steroids, lipids, polysaccharides, carbohydrates and the like. They further include, but are not limited to, antirestenotic agents, antidiabetics, analgesics, antiinflammatory agents, antirheumatics, antihypotensive agents, antihypertensive agents, psychoactive drugs, tranquillizers, antiemetics, muscle relaxants, glucocorticoids, agents for treating ulcerative colitis or Crohn's disease, antiallergics, antibiotics, antiepileptics, anticoagulants, antimycotics, antitussives, arteriosclerosis remedies, diuretics, proteins, peptides, enzymes, enzyme inhibitors, gout remedies, hormones and inhibitors thereof, cardiac glycosides, immunotherapeutic agents and cytokines, laxatives, lipid-lowering agents, migraine remedies, mineral products, otologicals, anti parkinson agents, thyroid therapeutic agents, spasmolytics, platelet aggregation inhibitors, vitamins, cytostatics and metastasis inhibitors, phytopharmaceuticals and chemotherapeutic agents. Preferably, the active biological agent is a peptide, protein or enzyme, including derivatives and analogs of natural peptides, proteins and enzymes. The active biological agent may also be a hormone, gene therapies, RNA, siRNA, and/or cellular therapies (for non-limiting example, stem cells or T-cells).

It is understood that certain agents will fall into multiple categories of agents, for example, certain antibiotic agents are also chemotherapeutic agents, and biological agents can include antibiotic agents, etc.

Specific pharmaceutical agents useful in certain embodiments of devices and/or methods of the invention are hyaluronidases. Hylenex (Baxter International, Inc.) is a formulation of a human recombinant hyaluronidase, PH-20, that is used to facilitate the absorption and dispersion of other injected drugs or fluids. When injected under the skin or in the muscle, hyaluronidase can digest the hyaluronic acid gel, allowing for temporarily enhanced penetration and dispersion of other injected drugs or fluids.

Hyaluronidase can allow drugs to pass more freely to target tissues. It has been observed on its own to suppress tumor growth, and is thus a chemotherapeutic agent. For example, increased drug antitumor activity has been reported by Halozyme Therapeutics (Carlsbad, Calif.), when hyaluronidase is used in conjunction with another chemotherapeutic agent to treat an HA-producing tumor (reports available at http://www.halozyme.com). A pegylated hyaluronidase product (PEGPH20) is currently being tested as a treatment for prostate cancer, and a product containing both hyaluronidase and mitomycin C (Chemophase) is being tested for treatment of bladder cancer.

In certain embodiments of devices and/or methods provided herein, hyaluronidase is used for treating any HA-producing cancer, either alone or in combination with another chemotherapeutic agent. In particular embodiments, hyaluronidase is used in the methods of the invention for treating bladder cancer, e.g., in combination with mitomycin C. In other embodiments, hyaluronidase is used for treating prostate cancer. Cancers potentially treated with hyaluronidase include, but are not limited to, Kaposi's sarcoma, glioma, melanocyte, head and neck squamous cell carcinoma, breast cancer, gastrointestinal cancer, and other genitourinary cancers, e.g., testicular cancer and ovarian cancer. The correlation of HA with various cancers has been described in the literature, e.g., by Simpson, et al., Front Biosci. 13:5664-5680. In embodiments, hyaluronidase is used in the devices and methods of the invention to enhance penetration and dispersion of any agents described herein, including, e.g., painkillers, antiinflammatory agents, etc., in particular, to tissues that produce HA.

Hyaluronidases are described, e.g., in U.S. Pat. App. No. 2005/0260186 and 2006/0104968, both titled "Soluble glycosaminoglycanases and methods of preparing and using soluble glycosaminoglycanases" and incorporated herein by reference in their entirety. Bookbinder, et al., 2006, "A recombinant human enzyme for enhanced interstitial transport of therapeutics," Journal of Controlled Release 114: 230-241 reported improved pharmacokinetic profile and absolute bioavailability, of peginterferon alpha-2b or the antiinflammatory agent infliximab, when either one is coinjected with rHuPH20 (human recombinant hyaluronidase PH-20). They also reported that an increased volume of drug could be injected subcutaneously when coinjected with hyaluronidase. Methods for providing human plasma hyaluronidases, and assays for hyaluronidases, are described in, e.g., U.S. Pat. No. 7,148,201, "Use of human plasma hyaluronidase in cancer treatment," incorporated herein by reference in its entirety. The use of hyaluronidase in the devices and methods of the invention is expected to increase the rate and amount of drug absorbed, providing an added aspect to control over release rates.

Hyaluronidase co-delivery is also useful when an agent is administered using the devices and methods of the invention within a tissue not having a well-defined preexisting cavity or having a cavity that is smaller than the inflated delivery balloon. In these embodiments, inflation of the delivery balloon creates a cavity where either none existed or greatly enlarges an existing cavity. For example, a solid tumor can be treated with hyaluronidase and a chemotherapeutic agent using a delivery balloon inserted through, e.g., a biopsy needle or the like. Vasoactive agents, e.g., TNF-alpha and histamine, also can be used to improve drug distribution within the tumor tissue. (See, e.g., Brunstein, et al., 2006, "Histamine, a vasoactive agent with vascular disrupting potential improves tumour response by enhancing local drug delivery," British Journal of Cancer 95:1663-1669). As another example of treatment of a location lacking a preexisting cavity, dense muscle tissue can be treated locally with a slow-release painkiller, using a delivery balloon inserted through a hollow needle.

"Active agent" as used herein refers to any pharmaceutical agent or active biological agent as described herein. An active agent, in some embodiments, may comprise a polymer, wherein the polymer provides a desired treatment in the body.

"Activity" as used herein refers to the ability of a pharmaceutical or active biological agent to prevent or treat a disease (meaning any treatment of a disease in a mammal, including preventing the disease, i.e. causing the clinical symptoms of the disease not to develop; inhibiting the disease, i.e. arresting the development of clinical symptoms; and/or relieving the disease, i.e. causing the regression of clinical symptoms). Thus the activity of a pharmaceutical or active biological agent should be of therapeutic or prophylactic value.

"Secondary, tertiary and quaternary structure" as used herein are defined as follows. The active biological agents of the present invention will typically possess some degree of secondary, tertiary and/or quaternary structure, upon which the activity of the agent depends. As an illustrative, non-limiting example, proteins possess secondary, tertiary and quaternary structure. Secondary structure refers to the spatial arrangement of amino acid residues that are near one another in the linear sequence. The α-helix and the β-strand are elements of secondary structure. Tertiary structure refers to the spatial arrangement of amino acid residues that are far apart in the linear sequence and to the pattern of disulfide bonds. Proteins containing more than one polypeptide chain exhibit an additional level of structural organization. Each polypeptide chain in such a protein is called a subunit. Quaternary structure refers to the spatial arrangement of subunits and the nature of their contacts. For example hemoglobin consists of two α and two β chains. It is well known that protein function arises from its conformation or three dimensional arrangement of atoms (a stretched out polypeptide chain is devoid of activity). Thus one aspect of the present invention is to manipulate active biological agents, while being careful to maintain their conformation, so as not to lose their therapeutic activity.

"Polymer" as used herein, refers to a series of repeating monomeric units that have been cross-linked or polymerized. Any suitable polymer can be used to carry out the present invention. It is possible that the polymers of the invention may also comprise two, three, four or more different polymers. In some embodiments of the invention only one polymer is used. In certain embodiments a combination of two polymers is used. Combinations of polymers can be in varying ratios, to provide coatings with differing properties. Polymers useful in the devices and methods of the present invention include, for example, stable or inert polymers, organic polymers, organic-inorganic copolymers, inorganic polymers, bioabsorbable, bioresorbable, resorbable, degradable, and biodegradable polymers. Those of skill in the art of polymer chemistry will be familiar with the different properties of polymeric compounds.

In some embodiments, the coating further comprises a polymer. In some embodiments, the active agent comprises a polymer. In some embodiments, the polymer comprises at least one of polyalkyl methacrylates, polyalkylene-co-vinyl acetates, polyalkylenes, polyurethanes, polyanhydrides, aliphatic polycarbonates, polyhydroxyalkanoates, silicone containing polymers, polyalkyl siloxanes, aliphatic polyesters, polyglycolides, polylactides, polylactide-co-glycolides, poly(e-caprolactone)s, polytetrahalooalkylenes, polystyrenes, poly(phosphasones), copolymers thereof, and combinations thereof.

In embodiments, the polymer is capable of becoming soft after implantation, for example, due to hydration, degradation or by a combination of hydration and degradation. In embodiments, the polymer is adapted to transfer, free, and/or dissociate from the substrate when at the intervention site due to hydrolysis of the polymer. In various embodiments, the device is coated with a bioabsorbable polymer that is capable of resorbtion in at least one of: about 1 day, about 3 days, about 5 days, about 7 days, about 14 days, about 3 weeks, about 4 weeks, about 45 days, about 60 days, about 90 days, about 180 days, about 6 months, about 9 months, about 1 year, about 1 to about 2 days, about 1 to about 5 days, about 1 to about 2 weeks, about 2 to about 4 weeks, about 45 to about 60 days, about 45 to about 90 days, about 30 to about 90 days, about 60 to about 90 days, about 90 to about 180 days, about 60 to about 180 days, about 180 to about 365 days, about 6 months to about 9 months, about 9 months to about 12 months, about 9 months to about 15 months, and about 1 year to about 2 years.

Examples of polymers that may be used in the present invention include, but are not limited to polycarboxylic acids, cellulosic polymers, proteins, polypeptides, polyvinylpyrrolidone, maleic anhydride polymers, polyamides, polyvinyl alcohols, polyethylene oxides, glycosaminoglycans, polysaccharides, polyesters, aliphatic polyesters, polyurethanes, polystyrenes, copolymers, silicones, silicone containing polymers, polyalkyl siloxanes, polyorthoesters, polyanhydrides, copolymers of vinyl monomers, polycarbonates, polyethylenes, polypropytenes, polylactic acids, polylactides, polyglycolic acids, polyglycolides, polylactide-co-glycolides, polycaprolactones, poly(e-caprolactone)s, polyhydroxybutyrate valerates, polyacrylamides, polyethers, polyurethane dispersions, polyacrylates, acrylic latex dispersions, polyacrylic acid, polyalkyl methacrylates, polyalkylene-co-vinyl acetates, polyalkylenes, aliphatic polycarbonates polyhydroxyalkanoates, polytetrahalooalkylenes, poly(phosphasones), polytetrahalooalkylenes, poly (phosphasones), and mixtures, combinations, and copolymers thereof.

The polymers of the present invention may be natural or synthetic in origin, including gelatin, chitosan, dextrin, cyclodextrin, Poly(urethanes), Poly(siloxanes) or silicones, Poly(acrylates) such as [rho]oly(methyl methacrylate), poly (butyl methacrylate), and Poly(2-hydroxy ethyl methacrylate), Poly(vinyl alcohol) Poly(olefins) such as poly(ethylene), [rho]oly(isoprene), halogenated polymers such as Poly (tetrafluoroethylene)—and derivatives and copolymers such as those commonly sold as Teflon® products, Poly(vinylidine fluoride), Poly(vinyl acetate), Poly(vinyl pyrrolidone), Poly(acrylic acid), Polyacrylamide, Poly(ethylene-co-vinyl acetate), Poly(ethylene glycol), Poly(propylene glycol), Poly(methacrylic acid); etc.

Suitable polymers also include absorbable and/or resorbable polymers including the following, combinations, copolymers and derivatives of the following: Polylactides (PLA), Polyglycolides (PGA), PolyLactide-co-glycolides (PLGA), Polyanhydrides, Polyorthoesters, Poly(N-(2-hydroxypropyl) methacrylamide), Poly(1-aspartamide), including the derivatives DLPLA—poly(dl-lactide); LPLA—poly(1-lactide); PDO—poly(dioxanone); PGA-TMC—poly(glycolide-co-trimethylene carbonate); PGA-LPLA—poly(1-lactide-co-glycolide); PGA-DLPLA—poly(dl-lactide-co-glycolide); LPLA-DLPLA—poly(1-lactide-co-dl-lactide); and PDO-PGA-TMC—poly(glycolide-co-trimethylene carbonate-co-dioxanone), and combinations thereof.

"Copolymer" as used herein refers to a polymer being composed of two or more different monomers. A copolymer may also and/or alternatively refer to random, block, graft, copolymers known to those of skill in the art.

The term "image enhanced polymer" or "imaging agent" as used herein refer to an agent that can be used with the devices and methods of the invention to view at least one component of the coating, either while the coating is on the substrate or after it is freed, dissociated and/or transferred. In embodiments, an image enhanced polymer serves as a tracer, allowing the movement or location of the coated device to be identified, e.g., using an imaging system. In other embodiments, an image enhanced polymer allows the practitioner to monitor the delivery and movement of a coating component. In embodiments, use of an image enhanced polymer enables the practitioner to determine the dose of a component of the coating (e.g., the active agent) that is freed, dissociated and/or transferred. Information provided by the image enhanced polymer or imaging agent about the amount of coating transferred to the intervention site can allow the practitioner to determine the rate at which the coating will be released, thereby allowing prediction of dosing over time. Imaging agents may comprise barium compounds such as, for non-limiting example, barium sulfate. Imaging agents may comprise iodine compounds. Imaging agents may comprise any compound that improves radiopacity.

In embodiments, an image enhanced polymer is used with the device and methods of the invention for a purpose including, but not limited to, one or more of the following: monitoring the location of the substrate, e.g., a balloon or other device; assessing physiological parameters, e.g., flow and perfusion; and targeting to a specific molecule. In embodiments, "smart" agents that activate only in the presence of their intended target are used with the device and methods of the invention.

In embodiments, imaging agents useful with the device and methods of the present invention include, for example: EgadMe (in which a galactopyranose ring is synthesized to protect a Gd(III) ion from bulk water); conjugated polymer MEH-PPV nanoparticles; bismuth trioxide; near infrared (NIR) fluorochromes; bioluminescence agents (e.g., green fluorescent protein, red fluorescent protein); SPECT radionuclides, e.g., 99Tcm (6 h), 111In (2.8 days), 123I (13.2 h) and 125I (59.5 days); PET radionuclides, e.g., 15O (2.07 min), 13N (10 min), 11C (20.3 min), 18F (1.83 h), 124I (4.2 days) and 94Tcm (53 min); Gd-DTPA (gadolinium diethylenetriamine pentaacetic acid); Echo-Coat, an ultrasound imaging agent (STS-Biopolymers); and barium sulfate. In embodiments employing nanoparticles, it is important that the particles are small enough to allow renal clearance (e.g. have a hydrodynamic diameter less than 5.5 nm) and contain non-toxic components, and that the material decomposition products can be eliminated from the body. It is understood that an imaging agent can be conjugated or otherwise attached or associated with a compound in the coating according to methods known to those of skill in the art to form an image enhanced polymer.

Biological imaging agents useful in embodiments of the device and methods of the present invention are described in, e.g.: U.S. Pat. No. 6,077,880, "Highly radiopaque polyolefins and method for making the same," which sets forth a highly radiopaque polyolefin; U.S. Pat. No. 7,229,837, "Enhanced photophysics of conjugated polymers," relating to fluorescent ionic conjugated polymers; Dzik-Jurasz, 2003, "Molecular imaging in vivo: an introduction," The British Journal of Radiology, 76: S98-S109, providing an overview of in vivo molecular imaging methods; von zur Muhlen, et al., 2008, Magnetic Resonance Imaging Contrast Agent Targeted Toward Activated Platelets Allows In Vivo Detection of Thrombosis and Monitoring of Thrombolysis Circulation," 118:258-267, reporting imaging of activated platelets using an antibody-containing MRI imaging agent; and Green, et al., "Simple conjugated polymer nanoparticles as biological labels," Proc. Roy. Soc. A, published online 24 Jun. 2009 doi: 10.1098/rspa.2009.0181, describing the use of nanoparticles of conjugated polymers in biological imaging; all incorporated herein by reference in their entirety.

"Biocompatible" as used herein, refers to any material that does not cause injury or death to the animal or induce an adverse reaction in an animal when placed in intimate contact with the animal's tissues. Adverse reactions include for example inflammation, infection, fibrotic tissue formation, cell death, or thrombosis. The terms "biocompatible" and "biocompatibility" when used herein are art-recognized and mean that the referent is neither itself toxic to a host (e.g., an animal or human), nor degrades (if it degrades) at a rate that produces byproducts (e.g., monomeric or oligomeric subunits or other byproducts) at toxic concentrations, causes inflammation or irritation, or induces an immune reaction in the host. It is not necessary that any subject composition have a purity of 100% to be deemed biocompatible. Hence, a subject composition may comprise 99%, 98%, 97%, 96%, 95%, 90% 85%, 80%, 75% or even less of biocompatible agents, e.g., including polymers and other materials and excipients described herein, and still be biocompatible. "Non-biocompatible" as used herein, refers to any material that may cause injury or death to the animal or induce an adverse reaction in the animal when placed in intimate contact with the animal's tissues. Such adverse reactions are as noted above, for example.

To determine whether a polymer or other material is biocompatible, it may be necessary to conduct a toxicity analysis. Such assays are well known in the art. One example of such an assay may be performed with live carcinoma cells, such as GT3TKB tumor cells, in the following manner: the sample is degraded in 1 M NaOH at 37 degrees C. until complete degradation is observed. The solution is then neutralized with 1 M HCl. About 200 microliters of various concentrations of the degraded sample products are placed in 96-well tissue culture plates and seeded with human gastric carcinoma cells (GT3TKB) at 104/well density. The degraded sample products are incubated with the GT3TKB cells for 48 hours. The results of the assay may be plotted as % relative growth vs. concentration of degraded sample in the tissue-culture well. In addition, polymers and formulations of the present invention may also be evaluated by well-known in vivo tests, such as subcutaneous implantations in rats to confirm that they do not cause significant levels of irritation or inflammation at the subcutaneous implantation sites.

The terms "bioabsorbable," "biodegradable," "bioerodible," "bioresorbable," and "resorbable" are art-recognized synonyms. These terms are used herein interchangeably. Bioabsorbable polymers typically differ from non-bioabsorbable polymers in that the former may be absorbed (e.g.; degraded) during use. In certain embodiments, such use involves in vivo use, such as in vivo therapy, and in other certain embodiments, such use involves in vitro use. In general, degradation attributable to biodegradability involves the degradation of a bioabsorbable polymer into its component subunits, or digestion, e.g., by a biochemical process, of the polymer into smaller, non-polymeric subunits. In certain embodiments, biodegradation may occur by enzymatic mediation, degradation in the presence of water (hydrolysis) and/or other chemical species in the body, or both. The bioabsorbability of a polymer may be shown in-vitro as described herein or by methods known to one of skill in the art. An in-vitro test for bioabsorbability of a polymer does not require living cells or other biologic materials to show bioabsorption properties (e.g. degradation, digestion). Thus, resorbtion, resorption, absorption, absorbtion, erosion may also be used synonymously with the terms "bioabsorbable," "biodegradable," "bioerodible," and "bioresorbable." Mechanisms of degradation of a bioabsorbable polymer may include, but are not limited to, bulk degradation, surface erosion, and combinations thereof.

As used herein, the term "biodegradation" encompasses both general types of biodegradation. The degradation rate of a biodegradable polymer often depends in part on a variety of factors, including the chemical identity of the linkage responsible for any degradation, the molecular weight, crystallinity, biostability, and degree of cross-linking of such polymer, the physical characteristics (e.g., shape and size) of the implant, and the mode and location of administration. For example, the greater the molecular weight, the higher the degree of crystallinity, and/or the greater the biostability, the biodegradation of any bioabsorbable polymer is usually slower.

In some embodiments, the coating comprises a biodegradable material that is adhered and/or cohered to the substrate prior to implantation, wherein the biodegradable material is capable of degrading over time to lose its cohesion and/or adhesion to the substrate. In some embodiments, the pharmaceutical agent and/or the active agent is released from the coating within at least one of about 1 day, about 3 days, about 5 days, about 7 days, about 14 days, about 3 weeks, about 4 weeks, about 45 days, about 60 days, about 90 days, about 180 days, about 6 months, about 9 months, about 1 year, about 1 to about 2 days, about 1 to about 5 days, about 1 to about 2 weeks, about 2 about 4 weeks, about 45 to about 60 days, about 45 to about 90 days, about 30 to about 90 days, about 60 to about 90 days, about 90 to about 180 days, about 60 to about 180 days, about 180 to about 365 days, about 6 months to about 9 months, about 9 months to about 12 months, about 9 months to about 15 months, and about 1 year to about 2 years.

"Hydration" as used herein refers to the absorption of water by a substance, or the combination of a substance with water. Hydration of the coating may reduce the coating's cohesive and adhesive binding to the device, thereby facilitating transfer of the coating to the intervention site.

"Hydrolysis" as used herein refers to a chemical reaction in which water reacts with a compound to produce other compounds; involves the splitting of a bond and the addition of the hydrogen cation and the hydroxide anion from the waterImage enhanced polymer, imaging agent.

"Degradation" as used herein refers to the conversion or reduction of a chemical compound to one less complex, e.g., by splitting off one or more groups of atoms. Degradation of the coating may reduce the coating's cohesive and adhesive binding to the device, thereby facilitating transfer of the coating to the intervention site.

"Therapeutically desirable morphology" as used herein refers to the gross form and structure of the pharmaceutical agent, once deposited on the substrate, so as to provide for optimal conditions of ex vivo storage, in vivo preservation and/or in vivo release. Such optimal conditions may include, but are not limited to increased shelf life (i.e., shelf stability), increased in vivo stability, good biocompatibility, good bioavailability or modified release rates. Typically, for the present invention, the desired morphology of a pharmaceutical agent would be crystalline or semi-crystalline or amorphous, although this may vary widely depending on many factors including, but not limited to, the nature of the pharmaceutical agent, the disease to be treated/prevented, the intended storage conditions for the substrate prior to use or the location within the body of any biomedical implant. Preferably at least 10%, 20%, 30%, 40%, 50%, 60%, 70%, 80%, 90%, 95%, 97%, 98%, 99%, 99.5%, and/or 100% of the pharmaceutical agent is in crystalline or semi-crystalline form.

In some embodiments of the methods and/or devices provided herein, the macrolide immunosuppressive drug is at least 50% crystalline. In some embodiments, the macrolide immunosuppressive drug is at least 75% crystalline. In some embodiments, the macrolide immunosuppressive drug is at least 90% crystalline. In some embodiments of the methods and/or devices provided herein the macrolide immunosuppressive drug is at least 95% crystalline. In some embodiments of the methods and/or devices provided herein the macrolide immunosuppressive drug is at least 97% crystalline. In some embodiments of the methods and/or devices provided herein macrolide immunosuppressive drug is at least 98% crystalline. In some embodiments of the methods and/or devices provided herein the macrolide immunosuppressive drug is at least 99% crystalline.

In some embodiments of the methods and/or devices provided herein wherein the pharmaceutical agent is at least 50% crystalline. In some embodiments of the methods and/or devices provided herein the pharmaceutical agent is at least 75% crystalline. In some embodiments of the methods and/or devices provided herein the pharmaceutical agent is at least 90% crystalline. In some embodiments of the methods and/or devices provided herein the pharmaceutical agent is at least 95% crystalline. In some embodiments of the methods and/or devices provided herein the pharmaceutical agent is at least 97% crystalline. In some embodiments of the methods and/or devices provided herein pharmaceutical agent is at least 98% crystalline. In some embodiments of the methods and/or devices provided herein the pharmaceutical agent is at least 99% crystalline.

"Stabilizing agent" as used herein refers to any substance that maintains or enhances the stability of the biological agent. Ideally these stabilizing agents are classified as Generally Regarded As Safe (GRAS) materials by the US Food and Drug Administration (FDA). Examples of stabilizing agents include, but are not limited to carrier proteins, such as albumin, gelatin, metals or inorganic salts. Pharmaceutically acceptable excipient that may be present can further be found in the relevant literature, for example in the Handbook of Pharmaceutical Additives: An International Guide to More Than 6000 Products by Trade Name, Chemical, Function, and Manufacturer; Michael and Irene Ash (Eds.); Gower Publishing Ltd.; Aldershot, Hampshire, England, 1995.

"Intervention site" as used herein refers to the location in the body where the coating is intended to be delivered (by transfer from, freeing from, and/or dissociating from the substrate). The intervention site can be any substance in the medium surrounding the device, e.g., tissue, cartilage, a body fluid, etc. The intervention site can be the same as the treatment site, i.e., the substance to which the coating is delivered is the same tissue that requires treatment. Alternatively, the intervention site can be separate from the treatment site, requiring subsequent diffusion or transport of the pharmaceutical or other agent away from the intervention site.

"Compressed fluid" as used herein refers to a fluid of appreciable density (e.g., >0.2 g/cc) that is a gas at standard temperature and pressure. "Supercritical fluid," "near-critical fluid," "near-supercritical fluid," "critical fluid," "densified fluid," or "densified gas," as used herein refers to a compressed fluid under conditions wherein the temperature is at least 80% of the critical temperature of the fluid and the pressure is at least 50% of the critical pressure of the fluid, and/or a density of +50% of the critical density of the fluid.

Examples of substances that demonstrate supercritical or near critical behavior suitable for the present invention include, but are not limited to carbon dioxide, isobutylene, ammonia, water, methanol, ethanol, ethane, propane, butane, pentane, dimethyl ether, xenon, sulfur hexafluoride, halogenated and partially halogenated materials such as chlorofluorocarbons, hydrochlorofluorocarbons, hydrofluorocarbons, perfluorocarbons (such as perfluoromethane and perfuoropropane, chloroform, trichloro-fluoromethane, dichloro-difluoromethane, dichloro-tetrafluoroethane) and mixtures thereof. Preferably, the supercritical fluid is hexafluoropropane (FC-236EA), or 1,1,1,2,3,3-hexafluoropropane. Preferably, the supercritical fluid is hexafluoropropane (FC-236EA), or 1,1,1,2,3,3-hexafluoropropane for use in PLGA polymer coatings.

"Sintering" as used herein refers to the process by which parts of the polymer or the entire polymer becomes continuous (e.g., formation of a continuous polymer film). As discussed herein, the sintering process is controlled to produce a fully conformal continuous polymer (complete sintering) or to produce regions or domains of continuous coating while producing voids (discontinuities) in the polymer. As well, the sintering process is controlled such that some phase separation is obtained or maintained between polymer different polymers (e.g., polymers A and B) and/or to produce phase separation between discrete polymer particles. Through the sintering process, the adhesions properties of the coating are improved to reduce flaking of detachment of the coating from the substrate during manipulation in use. As described herein, in some embodiments, the sintering process is controlled to provide incomplete sintering of the polymer. In embodiments involving incomplete sintering, a polymer is formed with continuous domains, and voids, gaps, cavities, pores, channels or, interstices that provide space for sequestering a therapeutic agent which is released under controlled conditions. Depending on the nature of the polymer, the size of polymer particles and/or other polymer properties, a compressed gas, a densified gas, a near critical fluid or a super-critical fluid may be employed.

In one example, carbon dioxide is used to treat a substrate that has been coated with a polymer and a drug, using dry powder and RESS electrostatic coating processes. In another example, isobutylene is employed in the sintering process. In other examples a mixture of carbon dioxide and isobutylene is employed. In another example, 1,1,2,3,3-hexafluoropropane is employed in the sintering process.

When an amorphous material is heated to a temperature above its glass transition temperature, or when a crystalline material is heated to a temperature above a phase transition temperature, the molecules comprising the material are more mobile, which in turn means that they are more active and thus more prone to reactions such as oxidation. However, when an amorphous material is maintained at a temperature below its glass transition temperature, its molecules are substantially immobilized and thus less prone to reactions. Likewise, when a crystalline material is maintained at a temperature below its phase transition temperature, its molecules are substantially immobilized and thus less prone to reactions. Accordingly, processing drug components at mild conditions, such as the deposition and sintering conditions described herein, minimizes cross-reactions and degradation of the drug component. One type of reaction that is minimized by the processes of the invention relates to the ability to avoid conventional solvents which in turn minimizes-oxidation of drug, whether in amorphous, semi-crystalline, or crystalline form, by reducing exposure thereof to free radicals, residual solvents, protic materials, polar-protic materials, oxidation initiators, and autoxidation initiators.

"Rapid Expansion of Supercritical Solutions" or "RESS" as used herein involves the dissolution of a polymer into a compressed fluid, typically a supercritical fluid, followed by rapid expansion into a chamber at lower pressure, typically near atmospheric conditions. The rapid expansion of the supercritical fluid solution through a small opening, with its accompanying decrease in density, reduces the dissolution capacity of the fluid and results in the nucleation and growth of polymer particles. The atmosphere of the chamber is maintained in an electrically neutral state by maintaining an isolating "cloud" of gas in the chamber. Carbon dioxide, nitrogen, argon, helium, or other appropriate gas is employed to prevent electrical charge is transferred from the substrate to the surrounding environment.

"Electrostatic Rapid Expansion of Supercritical Solutions" or "e-RESS" or "eRESS" as used herein refers to Electrostatic Capture as described herein combined with Rapid Expansion of Supercritical Solutions as described herein. In some embodiments, Electrostatic Rapid Expansion of Supercritical Solutions refers to Electrostatic capture as described in the art, e.g., in U.S. Pat. No. 6,756,084, "Electrostatic deposition of particles generated from rapid expansion of supercritical fluid solutions," incorporated herein by reference in its entirety.

"Solution Enhanced Dispersion of Supercritical Solutions" or "SEDS" as used herein involves a spray process for the generation of polymer particles, which are formed when a compressed fluid (e.g. supercritical fluid, preferably supercritical $CO_2$) is used as a diluent to a vehicle in which a polymer is dissolved (one that can dissolve both the polymer and the compressed fluid). The mixing of the compressed fluid diluent with the polymer-containing solution may be achieved by encounter of a first stream containing the polymer solution and a second stream containing the diluent compressed fluid, for example, within one spray nozzle or by the use of multiple spray nozzles. The solvent in the polymer solution may be one compound or a mixture of two or more ingredients and may be or comprise an alcohol (including diols, triols, etc.), ether, amine, ketone, carbonate, or alkanes, or hydrocarbon (aliphatic or aromatic) or may be a mixture of compounds, such as mixtures of alkanes, or mixtures of one or more alkanes in combination with additional compounds such as one or more alcohols, (e.g., from 0 or 0.1 to 5% of a $C_i$ to $Ci_5$ alcohol, including diols, triols, etc.). See for example U.S. Pat. No. 6,669,785, incorporated herein by reference in its entirety. The solvent may optionally contain a surfactant, as also described in, e.g., U.S. Pat. No. 6,669,785.

In one embodiment of the SEDS process, a first stream of fluid comprising a polymer dissolved in a common solvent is co-sprayed with a second stream of compressed fluid. Polymer particles are produced as the second stream acts as a diluent that weakens the solvent in the polymer solution of the first stream. The now combined streams of fluid, along with the polymer particles, flow out of the nozzle assembly into a collection vessel. Control of particle size, particle size distribution, and morphology is achieved by tailoring the following process variables: temperature, pressure, solvent composition of the first stream, flow-rate of the first stream, flow-rate of the second stream, composition of the second stream (where soluble additives may be added to the compressed gas), and conditions of the capture vessel. Typically the capture vessel contains a fluid phase that is at least five to ten times (5-10×) atmospheric pressure.

"Electrostatic Dry Powder Coating" or "e-DPC" or "eDPC" as used herein refers to Electrostatic Capture as described herein combined with Dry Powder Coating. e-DPC deposits material (including, for example, polymer or impermeable dispersed solid) on the device or other substrate as dry powder, using electrostatic capture to attract the powder particles to the substrate. Dry powder spraying ("Dry Powder Coating" or "DPC") is well known in the art, and dry powder spraying coupled with electrostatic capture has been described, for example in U.S. Pat. Nos. 5,470,603, 6,319,541, and 6,372,246, all incorporated herein by reference in their entirety. Methods for depositing coatings are described, e.g., in WO 2008/148013, "Polymer Films for Medical Device Coating," incorporated herein by reference in its entirety.

"Dipping Process" and "Spraying Process" as used herein refer to methods of coating substrates that have been described at length in the art. These processes can be used for coating medical devices with pharmaceutical agents. Spray coating, described in, e.g., U.S. Pat. No. 7,419,696, "Medical devices for delivering a therapeutic agent and method of preparation" and elsewhere herein, can involve spraying or airbrushing a thin layer of solubilized coating or dry powder coating onto a substrate. Dip coating involves, e.g., dipping a substrate in a liquid, and then removing and drying it. Dip coating is described in, e.g., U.S. Pat. No. 5,837,313 "Drug release stent coating process," incorporated herein by reference in its entirety.

"Bulk properties" properties of a coating including a pharmaceutical or a biological agent that can be enhanced through the methods of the invention include for example: adhesion, smoothness, conformality, thickness, and compositional mixing.

"Electrostatically charged" or "electrical potential" or "electrostatic capture" as used herein refers to the collection of the spray-produced particles upon a substrate that has a different electrostatic potential than the sprayed particles. Thus, the substrate is at an attractive electronic potential with respect to the particles exiting, which results in the capture of the particles upon the substrate. i.e. the substrate and particles are oppositely charged, and the particles transport through the gaseous medium of the capture vessel onto the surface of the substrate is enhanced via electrostatic attraction. This may be achieved by charging the particles and grounding the substrate or conversely charging the substrate and grounding the particles, by charging the particles at one potential (e.g. negative charge) and charging the substrate at an opposed potential (e.g. positive charge), or by some other process, which would be easily envisaged by one of skill in the art of electrostatic capture.

"Depositing the active agent by an e-RESS, an e-SEDS, or an e-DPC process without electrically charging the substrate" as used herein refers to any of these processes as performed without intentionally electrically charging the substrate. It is understood that the substrate might become electrically charged unintentially during any of these processes.

"Depositing the active agent by an e-RESS, an e-SEDS, or an e-DPC process without creating an electrical potential between the substrate and a coating apparatus" as used herein refers to any of these processes as performed without intentionally generating an electrical potential between the substrate and the coating apparatus. It is understood that electrical potential between the substrate and the coating apparatus might be generated unintentially during any of these processes.

"Intimate mixture" as used herein, refers to two or more materials, compounds, or substances that are uniformly distributed or dispersed together.

"Layer" as used herein refers to a material covering a surface or forming an overlying part or segment. Two different layers may have overlapping portions whereby material from one layer may be in contact with material from another layer. Contact between materials of different layers can be measured by determining a distance between the materials. For example, Raman spectroscopy may be employed in identifying materials from two layers present in close proximity to each other.

While layers defined by uniform thickness and/or regular shape are contemplated herein, several embodiments described herein relate to layers having varying thickness and/or irregular shape. Material of one layer may extend into the space largely occupied by material of another layer. For example, in a coating having three layers formed in sequence as a first polymer layer, a pharmaceutical agent layer and a second polymer layer, material from the second polymer layer which is deposited last in this sequence may extend into the space largely occupied by material of the pharmaceutical agent layer whereby material from the second polymer layer may have contact with material from the pharmaceutical layer. It is also contemplated that material from the second polymer layer may extend through the entire layer largely occupied by pharmaceutical agent and contact material from the first polymer layer.

It should be noted however that contact between material from the second polymer layer (or the first polymer layer) and material from the pharmaceutical agent layer (e.g.; a pharmaceutical agent crystal particle or a portion thereof) does not necessarily imply formation of a mixture between the material from the first or second polymer layers and material from the pharmaceutical agent layer. In some embodiments, a layer may be defined by the physical three-dimensional space occupied by crystalline particles of a pharmaceutical agent (and/or biological agent). It is contemplated that such layer may or may not be continuous as physical space occupied by the crystal particles of pharmaceutical agents may be interrupted, for example, by polymer material from an adjacent polymer layer. An adjacent polymer layer may be a layer that is in physical proximity to be pharmaceutical agent particles in the pharmaceutical agent layer. Similarly, an adjacent layer may be the layer formed in a process step right before or right after the process step in which pharmaceutical agent particles are deposited to form the pharmaceutical agent layer.

As described herein, material deposition and layer formation provided herein are advantageous in that the pharmaceutical agent remains largely in crystalline form during the entire process. While the polymer particles and the pharmaceutical agent particles may be in contact, the layer formation process is controlled to avoid formation of a mixture between the pharmaceutical agent particles the polymer particles during formation of a coated device.

In some embodiments, the coating comprises a plurality of layers deposited on said substrate, wherein at least one of the layers comprises the active agent. In some embodiments, at least one of the layers comprises a polymer. In some embodiments, the polymer is bioabsorbable. In some embodiments, the active agent and the polymer are in the same layer, in separate layers, or form overlapping layers. In some embodiments, the plurality of layers comprise five layers deposited as follows: a first polymer layer, a first active agent layer, a second polymer layer, a second active agent layer and a third polymer layer.

In some embodiments of the methods and/or devices provided herein, the coating comprises a plurality of layers deposited on said substrate, wherein at least one of the layers comprises the active agent. In some embodiments, at least one of the layers comprises a polymer. In some embodiments, the polymer is bioabsorbable. In some embodiments, the active agent and the polymer are in the same layer, in separate layers, or form overlapping layers. In some embodiments, the coating comprises a plurality of layers deposited on said substrate, wherein at least one of the layers comprises the pharmaceutical agent. In some embodiments, the pharmaceutical agent and the polymer are in the same layer, in separate layers, or form overlapping layers. In some embodiments, the plurality of layers comprise five layers deposited as follows: a first polymer layer, a first active agent layer, a second polymer layer, a second active agent layer and a third polymer layer. In some embodiments, the plurality of layers comprise five layers deposited as follows: a first polymer layer, a first pharmaceutical agent layer, a second polymer layer, a second pharmaceutical agent layer and a third polymer layer. In some embodiments, the plurality of layers comprise five layers deposited as follows: a first polymer layer, a first active biological agent layer, a second polymer layer, a second active biological agent layer and a third polymer layer.

In some embodiments, the device provides the coating to the intervention site over an area of delivery greater than the outer surface contact area of the substrate. In some embodiments, the area of delivery is at least 110% greater than the outer surface contact area of the substrate. In some embodiments, the area of delivery is at least 110% to 200% greater than the outer surface contact area of the substrate. In some embodiments, the area of delivery is at least 200% greater than the outer surface contact area of the substrate.

"Laminate coating" as used herein refers to a coating made up of two or more layers of material. Means for creating a laminate coating as described herein (e.g.; a laminate coating comprising bioabsorbable polymer(s) and pharmaceutical agent) may include coating the stent with drug and polymer as described herein (e-RESS, e-DPC, compressed-gas sintering). The process comprises performing multiple and sequential coating steps (with sintering steps for polymer materials) wherein different materials may be deposited in each step, thus creating a laminated structure with a multitude of layers (at least 2 layers) including polymer layers and pharmaceutical agent layers to build the final device (e.g.; laminate coated stent).

"Portion of the coating" and "portion of the active agent" as used herein refer to an amount or percentage of the coating or active agent that is freed, dissociated, and/or transferred from the substrate to the intervention site, either at a designated point in delivery, during a certain period of delivery, or in total throughout the entire delivery process. In embodiments, the device and methods of the invention are adapted to free, dissociate, and/or transfer a certain amount of the coating and/or active agent.

For example, in embodiments, at least about 10%, at least about 20%, at least about 30%, at least about 50%, at least about 75%, at least about 85%, at least about 90%, at least about 95%, and/or at least about 99% of the coating is adapted to be freed, dissociated, and/or to be transferred from the substrate to the intervention site. In embodiments, at least about 10%, at least about 20%, at least about 30%, at least about 50%, at least about 75%, at least about 85%, at least about 90%, at least about 95%, and/or at least about 99% of the active agent is adapted to be freed, dissociated, and/or to be transferred from the substrate to the intervention site.

The portion of the coating and/or that is freed, dissociated, or transferred from the device substrate is influenced by any or a combination of, e.g., the size, shape, and flexibility of the device substrate, the size, shape, surface qualities of and conditions (e.g., blood or lymph circulation, temperature, etc.) at the intervention site, the composition of the coating, including the particular active agent(s) and specific polymer component(s) used in the coating, the relative proportions of these components, the use of any release agent(s), and substrate characteristics. Any one or more of these and other aspects of the device and methods of the invention can be adapted to influence the portion of the coating and/or active agent freed, dissociated, and/or transferred, as desired to produce the desired clinical outcome.

"Substantially all of the coating" as used herein refers to at least about 50%, at least about 75%, at least about 85%, at least about 90%, at least about 95%, at least about 97%, and/or at least about 99% percent of the coating that was present on the device prior to use.

"At least a portion of the substrate" as used herein refers to an amount and/or percentage of the substrate. In embodiments of the device and methods of the invention wherein a coating is on "at least a portion of the substrate," at least about 10%, at least about 20%, at least about 30%, at least about 50%, at least about 75%, at least about 85%, at least about 90%, at least about 95%, and/or at least about 99% of the substrate is coated. In embodiments wherein "at least a portion of the substrate" is bioabsorbable, at least about 10%, at least about 20%, at least about 30%, at least about 50%, at least about 75%, at least about 85%, at least about 90%, at least about 95%, and/or at least about 99% of the substrate is bioabsorbable.

"Transferring at least a portion" as used herein in the context of transferring a coating or active agent from the substrate to an intervention site refers to an amount and/or percentage of the coating or active agent that is transferred from the substrate to an intervention site. In embodiments of the device and methods of the invention wherein at least a portion of a coating or active agent is transferred from the substrate to an intervention site, at least about 10%, at least about 20%, at least about 30%, at least about 50%, at least about 75%, at least about 85%, at least about 90%, at least about 95%, and/or at least about 99% of the coating or active agent is transferred from the substrate to the intervention site. In some embodiments, at least about 10%, at least about 20%, at least about 30%, at least about 50%, at least about 75%, at least about 85%, at least about 90%, at least about 95%, and/or at least about 99% of the coating is adapted to transfer from the substrate to the intervention site. In some embodiments, at least about 10% of the coating is adapted to transfer from the substrate to the intervention site. In some embodiments, at least about 20% of the coating is adapted to transfer from the substrate to the intervention site. In some embodiments, at least about 30% of the coating is adapted to transfer from the substrate to the intervention site. In some embodiments, at least about 50% of the coating is adapted to transfer from the substrate to the intervention site. In some embodiments, at least about 75% of the coating is adapted to transfer from the substrate to the intervention site. In some embodiments, at least about 85% of the coating is adapted to transfer from the substrate to the intervention site. In some embodiments, at least about 90% of the coating is adapted to transfer from the substrate to the intervention site. In some embodiments, at least about 95% of the coating is adapted to transfer from the substrate to the intervention site. In some embodiments, at least about 99% of the coating is adapted to transfer from the substrate to the intervention site. As used herein, "about" when used in reference to a percentage of the coating can mean ranges of 1%-5%, of 5%-10%, of 10%-20%, and/or of 10%-50% (as a percent of the percentage of the coating transferred, or as a variation of the percentage of the coating transferred).

In some embodiments, the coating portion that is adapted to transfer upon stimulation is on at least one of a distal surface of the substrate, a middle surface of the substrate, a proximal surface of the substrate, and an abluminal surface of the substrate. In some embodiments, the stimulation decreases the contact between the coating and the substrate. In some embodiments, device is adapted to transfer less than about 1%, less than about 5%, less than about 10%. less than about 15%, less than about 25%, less than about 50%, less than about 70%, less than about 80%, and/or less than about 90% of the coating absent stimulation of the coating.

In some embodiments, at least about 10%, at least about 20%, at least about 30%, at least about 50%, at least about 75%, at least about 85%, at least about 90%, at least about 95%, and/or at least about 99% of the active agent is adapted to transfer from the substrate to the intervention site. In some embodiments, at least about 10% of the active agent is adapted to transfer from the substrate to the intervention site. In some embodiments, at least about 20% of the active agent is adapted to transfer from the substrate to the intervention site. In some embodiments, at least about 30% of the active agent is adapted to transfer from the substrate to the intervention site. In some embodiments, at least about 50% of the active agent is adapted to transfer from the substrate to the intervention site. In some embodiments, at least about 75% of the active agent is adapted to transfer from the substrate to the intervention site. In some embodiments, at least about 85% of the active agent is adapted to transfer from the substrate to the intervention site. In some embodiments, at least about 90% of the active agent is adapted to transfer from the substrate to the intervention site. In some embodiments, at least about 95% of the active agent is adapted to transfer from the substrate to the intervention site. In some embodiments, at least about 99% of the active agent is adapted to transfer from the substrate to the intervention site. As used herein, "about" when used in reference to a percentage of the active agent can mean ranges of 1%-5%, of 5%-10%, of 10%-20%, and/or of 10%-50% (as a percent of the percentage of the active agent transferred, or as a variation of the percentage of the active agent transferred).

In some embodiments, the active agent portion that is adapted to transfer upon stimulation is on at least one of a distal surface of the substrate, a middle surface of the substrate, a proximal surface of the substrate, and an abluminal surface of the substrate. In some embodiments, the stimulation decreases the contact between the coating and the substrate. In some embodiments, the device is adapted to transfer less than about 1%, less than about 5%, less than about 10%. less than about 15%, less than about 25%, less than about 50%, less than about 70%, less than about 80%, and/or less than about 90% of the active agent absent stimulation of the coating.

In some embodiments, the device is adapted to transfer at least about 10%, at least about 20%, at least about 30%, at least about 50%, at least about 75%, at least about 85%, at least about 90%, at least about 95%, and/or at least about 99% of the coating from the substrate to the intervention site. In some embodiments, the device is adapted to transfer at least about 10% of the coating from the substrate to the intervention site. In some embodiments, the device is adapted to transfer at least about 20% of the coating from the substrate to the intervention site. In some embodiments, the device is adapted to transfer at least about 30% of the coating from the substrate to the intervention site. In some embodiments, the device is adapted to transfer at least about 50% of the coating from the substrate to the intervention site. In some embodiments, the device is adapted to transfer at least about 75% of the coating from the substrate to the intervention site. In some embodiments, the device is adapted to transfer at least about 85% of the coating from the substrate to the intervention site. In some embodiments, the device is adapted to transfer at least about 90% of the coating from the substrate to the intervention site. In some embodiments, the device is adapted to transfer at least about 95% of the coating from the substrate to the intervention site. In some embodiments, the device is adapted to transfer at least about 99% of the coating from the substrate to the intervention site. As used herein, "about" when used in reference to a percentage of the coating can mean ranges of 1%-5%, of 5%-10%, of 10%-20%, and/or of 10%-50% (as a percent of the percentage of the coating transferred, or as a variation of the percentage of the coating transferred).

In some embodiments, the coating portion that transfers upon stimulation is on at least one of a distal surface of the substrate, a middle surface of the substrate, a proximal surface of the substrate, and an abluminal surface of the substrate. In some embodiments, stimulation decreases the contact between the coating and the substrate. In some embodiments, the device is adapted to transfer less than about 1%, less than about 5%, less than about 10%. less than about 15%, less than about 25%, less than about 50%, less than about 70%, less than about 80%, and/or less than about 90% of the coating absent stimulation of the coating.

In some embodiments, the device is adapted to transfer at least about 10%, at least about 20%, at least about 30%, at least about 50%, at least about 75%, at least about 85%, at least about 90%, at least about 95%, and/or at least about 99% of the active agent from the substrate to the intervention site. In some embodiments, the device is adapted to transfer at least about 10% of the active agent from the substrate to the intervention site. In some embodiments, the device is adapted to transfer at least about 20% of the active agent from the substrate to the intervention site. In some embodiments, the device is adapted to transfer at least about 30% of the active agent from the substrate to the intervention site. In some embodiments, the device is adapted to transfer at least about 50% of the active agent from the substrate to the intervention site. In some embodiments, the device is adapted to transfer at least about 75% of the active agent from the substrate to the intervention site. In some embodiments, the device is adapted to transfer at least about 85% of the active agent from the substrate to the intervention site. In some embodiments, the device is adapted to transfer at least about 90% of the active agent from the substrate to the intervention site. In some embodiments, the device is adapted to transfer at least about 95% of the active agent from the substrate to the intervention site. In some embodiments, the device is adapted to transfer at least about 99% of the active agent from the substrate to the intervention site. As used herein, "about" when used in reference to a percentage of the active agent can mean ranges of 1%-5%, of 5%-10%, of 10%-20%, and/or of 10%-50% (as a percent of the percentage of the active agent transferred, or as a variation of the percentage of the active agent transferred).

In some embodiments, the coating portion that transfers upon stimulation is on at least one of a distal surface of the substrate, a middle surface of the substrate, a proximal surface of the substrate, and an abluminal surface of the substrate. In some embodiments, the stimulation decreases the contact between the coating and the substrate. In some embodiments, the device is adapted to transfer less than about 1%, less than about 5%, less than about 10%. less than about 15%, less than about 25%, less than about 50%, less than about 70%, less than about 80%, less than about 90% of the active agent absent stimulation of the coating.

"Freeing at least a portion" as used herein in the context of freeing a coating and/or active agent from the substrate at an intervention site refers to an amount and/or percentage of a coating or active agent that is freed from the substrate at an intervention site. In embodiments of the device and methods of the invention wherein at least a portion of a coating or active agent is freed from the substrate at an intervention site, at least about 10%, at least about 20%, at least about 30%, at least about 50%, at least about 75%, at least about 85%, at least about 90%, at least about 95%, and/or at least about 99% of the coating or active agent is freed from the substrate at the intervention site. In some embodiments, the device is adapted to free at least about 10%, at least about 20%, at least about 30%, at least about 50%, at least about 75%, at least about 85%, at least about 90%, at least about 95%, and/or at least about 99% of the coating from the substrate. In some embodiments, the device is adapted to free at least about 10% of the coating from the substrate to the intervention site. In some embodiments, the device is adapted to free at least about 20% of the coating from the substrate to the intervention site. In some embodiments, the device is adapted to free at least about 30% of the coating from the substrate to the intervention site. In some embodiments, the device is adapted to free at least about 50% of the coating from the substrate to the intervention site. In some embodiments, the device is adapted to free at least about 75% of the coating from the substrate to the intervention site. In some embodiments, the device is adapted to free at least about 85% of the coating from the substrate to the intervention site. In some embodiments, the device is adapted to free at least about 90% of the coating from the substrate to the intervention site. In some embodiments, the device is adapted to free at least about 95% of the coating from the substrate to the intervention site. In some embodiments, the device is adapted to free at least about 99% of the coating from the substrate to the intervention site. As used herein, "about" when used in reference to a percentage of the coating can mean ranges of 1%-5%, of 5%-10%, of 10%-20%, and/or of 10%-50% (as a percent of the percentage of the coating freed, or as a variation of the percentage of the coating freed).

In some embodiments, the coating portion that frees upon stimulation is on at least one of a distal surface of the substrate, a middle surface of the substrate, a proximal surface of the substrate, and an abluminal surface of the substrate.

In some embodiments, the stimulation decreases the contact between the coating and the substrate. In some embodiments, the device is adapted to free less than about 1%, less than about 5%, less than about 10%. less than about 15%, less than about 25%, less than about 50%, less than about 70%, less than about 80%, less than about 90% of the coating absent stimulation of the coating.

"Dissociating at least a portion" as used herein in the context of dissociating a coating and/or active agent from the substrate at an intervention site refers to an amount and/or percentage of a coating and/or active agent that is dissociated from the substrate at an intervention site. In embodiments of the device and methods of the invention wherein at least a portion of a coating and/or active agent is dissociated from the substrate at an intervention site, at least about 10%, at least about 20%, at least about 30%, at least about 50%, at least about 75%, at least about 85%, at least about 90%, at least about 95%, and/or at least about 99% of the coating and/or active agent is dissociated from the substrate at the intervention site.

In some embodiments, the device is adapted to dissociate at least about 10%, at least about 20%, at least about 30%, at least about 50%, at least about 75%, at least about 85%, at least about 90%, at least about 95%, and/or at least about 99% of the coating from the substrate. In some embodiments, the device is adapted to dissociate at least about 10% of the coating from the substrate to the intervention site. In some embodiments, the device is adapted to dissociate at least about 20% of the coating from the substrate to the intervention site. In some embodiments, the device is adapted to dissociate at least about 30% of the coating from the substrate to the intervention site. In some embodiments, the device is adapted to dissociate at least about 50% of the coating from the substrate to the intervention site. In some embodiments, the device is adapted to dissociate at least about 75% of the coating from the substrate to the intervention site. In some embodiments, the device is adapted to dissociate at least about 85% of the coating from the substrate to the intervention site. In some embodiments, the device is adapted to dissociate at least about 90% of the coating from the substrate to the intervention site. In some embodiments, the device is adapted to dissociate at least about 95% of the coating from the substrate to the intervention site. In some embodiments, the device is adapted to dissociate at least about 99% of the coating from the substrate to the intervention site. As used herein, "about" when used in reference to a percentage of the coating can mean ranges of 1%-5%, of 5%-10%, of 10%-20%, and/or of 10%-50% (as a percent of the percentage of the coating dissociated, or as a variation of the percentage of the coating dissociated).

In some embodiments, the coating portion that dissociates upon stimulation is on at least one of a distal surface of the substrate, a middle surface of the substrate, a proximal surface of the substrate, and an abluminal surface of the substrate. In some embodiments, stimulation decreases the contact between the coating and the substrate. In some embodiments, the device is adapted to dissociate less than about 1%, less than about 5%, less than about 10%. less than about 15%, less than about 25%, less than about 50%, less than about 70%, less than about 80%, less than about 90% of the coating absent stimulation of the coating.

"Depositing at least a portion" as used herein in the context of a coating and/or active agent at an intervention site refers to an amount and/or percentage of a coating and/or active agent that is deposited at an intervention site. In embodiments of the device and methods of the invention wherein at least a portion of a coating and/or active agent is deposited at an intervention site, at least about 10%, at least about 20%, at least about 30%, at least about 50%, at least about 75%, at least about 85%, at least about 90%, at least about 95%, and/or at least about 99% of the coating and/or active agent is deposited at the intervention site. In some embodiments, stimulating decreases the contact between the coating and the substrate. In some embodiments, depositing deposits less than about 1%, less than about 5%, less than about 10%. less than about 15%, less than about 25%, less than about 50%, less than about 70%, less than about 80%, and/or less than about 90% of the coating absent stimulating at least one of the coating and the substrate.

"Delivering at least a portion" as used herein in the context of a coating and/or active agent at an intervention site refers to an amount and/or percentage of a coating and/or active agent that is delivered to an intervention site. In embodiments of the device and methods of the invention wherein at least a portion of a coating and/or active agent is delivered to an intervention site, at least about 10%, at least about 20%, at least about 30%, at least about 50%, at least about 75%, at least about 85%, at least about 90%, at least about 95%, and/or at least about 99% of the coating and/or active agent is delivered to the intervention site.

In some embodiments, the device is adapted to deliver at least about 10%, at least about 20%, at least about 30%, at least about 50%, at least about 75%, at least about 85%, at least about 90%, at least about 95%, and/or at least about 99% of the coating to the intervention site. In some embodiments, the device is adapted to deliver at least about 10% of the coating to the intervention site. In some embodiments, the device is adapted to deliver at least about 20% of the coating to the intervention site. In some embodiments, the device is adapted to deliver at least about 30% of the coating to the intervention site. In some embodiments, the device is adapted to deliver at least about 50% of the coating to the intervention site. In some embodiments, the device is adapted to deliver at least about 75% of the coating to the intervention site. In some embodiments, the device is adapted to deliver at least about 85% of the coating to the intervention site. In some embodiments, the device is adapted to deliver at least about 90% of the coating to the intervention site. In some embodiments, the device is adapted to deliver at least about 95% of the coating to the intervention site. In some embodiments, the device is adapted to deliver at least about 99% of the coating to the intervention site. As used herein, "about" when used in reference to a percentage of the coating can mean ranges of 1%-5%, of 5%-10%, of 10%-20%, and/or of 10%-50% (as a percent of the percentage of the coating delivered, or as a variation of the percentage of the coating delivered).

In some embodiments, the coating portion that is delivered upon stimulation is on at least one of a distal surface of the substrate, a middle surface of the substrate, a proximal surface of the substrate, and an abluminal surface of the substrate. In some embodiments, the stimulation decreases the contact between the coating and the substrate. In some embodiments, the device is adapted to deliver less than about 1%, less than about 5%, less than about 10%. less than about 15%, less than about 25%, less than about 50%, less than about 70%, less than about 80%, less than about 90% of the coating absent stimulation of the coating.

In some embodiments, depositing at least a portion of the coating comprises depositing at least about 10%, at least about 20%, at least about 30%, at least about 50%, at least about 75%, at least about 85%, at least about 90%, at least about 95%, and/or at least about 99% of the coating at the intervention site. In some embodiments, stimulating decreases the contact between the coating and the substrate. In some embodiments, depositing deposits less than about 1%, less than about 5%, less than about 10%. less than about 15%, less than about 25%, less than about 50%, less than about 70%, less than about 80%, and/or less than about 90% of the coating absent stimulating at least one of the coating and the substrate.

"Tacking at least a portion" as used herein in the context of tacking at least a portion of the coating to an intervention site refers to an amount and/or percentage of a coating and/or active agent that is tacked at an intervention site. In embodiments of the device and methods of the invention wherein at least a portion of a coating and/or active agent is tacked at an intervention site, at least about 10%, at least about 20%, at least about 30%, at least about 50%, at least about 75%, at least about 85%, at least about 90%, at least about 95%, and/or at least about 99% of the coating and/or active agent is tacked at the intervention site. In some embodiments, stimulating decreases the contact between the coating and the substrate. In some embodiments, tacking tacks less than about 1%, less than about 5%, less than about 10%. less than about 15%, less than about 25%, less than about 50%, less than about 70%, less than about 80%, and/or less than about 90% of the coating absent stimulating at least one of the coating and the substrate. In some embodiments, the device comprises a tacking element that cooperates with the stimulation to tack the coating to the intervention site. In some embodiments, the device comprises a tacking element that tacks the coating to the substrate until stimulating with a stimulation.

"Adhere," "adherence," "adhered," "cohere," "coherence," "cohered," and related terms, as used herein in the context of adherence or coherence of the substrate to the coating refer to an interaction between the substrate and the coating that is sufficiently strong to maintain the association of the coating with the substrate for an amount of time prior to the stimulation, e.g., mechanical, chemical, thermal, electromagnetic, or sonic stimulation, that is intended to cause the coating to be freed, dissociated, and/or transferred. These same terms, as used in the context of an interaction between the coating and the target tissue area and/or intervention site refer to an interaction between the coating and the target tissue area and/or intervention site that is sufficient to keep the coating associated with the target tissue area and/or intervention site for an amount of time as desired for treatment, e.g., at least about 12 hours, about 1 day, about 3 days, about 5 days, about 7 days, about 14 days, about 3 weeks, about 4 weeks, about 45 days, about 60 days, about 90 days, about 180 days, about 6 months, about 9 months, about 1 year, about 1 to about 2 days, about 1 to about 5 days, about 1 to about 2 weeks, about 2 to about 4 weeks, about 45 to about 60 days, about 45 to about 90 days, about 30 to about 90 days, about 60 to about 90 days, about 90 to about 180 days, about 60 to about 180 days, about 180 to about 365 days, about 6 months to about 9 months, about 9 months to about 12 months, about 9 months to about 15 months, and about 1 year to about 2 years.

"Balloon" as used herein refers to a flexible sac that can be inflated within a natural or non-natural body lumen or cavity, or used to create a cavity, or used to enlarge an existing cavity. The balloon can be used transiently to dilate a lumen or cavity and thereafter may be deflated and/or removed from the subject during the medical procedure or thereafter. In embodiments, the balloon can be expanded within the body and has a coating thereon that is freed (at least in part) from the balloon and left behind in the lumen or cavity when the balloon is removed. A coating can be applied to a balloon either after the balloon has been compacted for insertion, resulting in a coating that partially covers the surface of the balloon, or it can be applied prior to or during compaction. In embodiments, a coating is applied to the balloon both prior to and after compaction of the balloon. In embodiments, the balloon is compacted by, e.g., crimping or folding. Methods of compacting balloons have been described, e.g., in U.S. Pat. No. 7,308,748, "Method for compressing an intraluminal device," and U.S. Pat. No. 7,152,452, "Assembly for crimping an intraluminal device and method of use," relating to uniformly crimping a balloon onto a catheter or other intraluminal device, and U.S. Pat. No. 5,350,361 "Tri-fold balloon for dilatation catheter and related method," relating to balloon folding methods and devices, all incorporated herein by reference in their entirety. In some embodiments the balloon is delivered to the intervention site by a delivery device. In some embodiments, the delivery device comprises catheter. In some embodiments, the balloon is an angioplasty balloon. Balloons can be delivered, removed, and visualized during delivery and removal by methods known in the art, e.g., for inserting angioplasty balloons, stents, and other medical devices. Methods for visualizing a treatment area and planning instrument insertion are described, e.g., in U.S. Pat. No. 7,171,255, "Virtual reality 3D visualization for surgical procedures" and U.S. Pat. No. 6,610,013, "3D ultrasound-guided intraoperative prostate brachytherapy," incorporated herein by reference in their entirety.

"Compliant balloon" as used herein refers to a balloon which conforms to the intervention site relatively more than a semi-compliant balloon and still more so than a non-compliant balloon. Compliant balloons expand and stretch with increasing pressure within the balloon, and are made from such materials as polyethylene or polyolefin copolymers. There is in the art a general classification of balloons based on their expandability or "compliance" relative to each other, as described e.g., in U.S. Pat. No. 5,556,383, "Block copolymer elastomer catheter balloons." Generally, "non-compliant" balloons are the least elastic, increasing in diameter about 2-7%, typically about 5%, as the balloon is pressurized from an inflation pressure of about 6 atm to a pressure of about 12 atm, that is, they have a "distension" over that pressure range of about 5%. "Semi-compliant" balloons have somewhat greater distensions, generally 7-16% and typically 10-12% over the same pressurization range. "Compliant" balloons are still more distensible, having distensions generally in the range of 16-40% and typically about 21% over the same pressure range. Maximum distensions, i.e. distension from nominal diameter to burst, of various balloon materials may be significantly higher than the distension percentages discussed above because wall strengths, and thus burst pressures, vary widely between balloon materials. These distension ranges are intended to provide general guidance, as one of skill in the art will be aware that the compliance of a balloon is dependent on the dimensions and/or characteristics of the cavity and/or lumen walls, not only the expandability of the balloon.

A compliant balloon may be used in the vasculature of a subject. A compliant balloon might also be used in any tube or hole outside the vasculature (whether naturally occurring or man-made, or created during an injury). For a non-limiting example, a compliant balloon might be used in a lumpectomy to put a coating at the site where a tumor was removed, to: treat an abscess, treat an infection, prevent an infection, aid healing, promote healing, or for a combination of any of these purposes. The coating in this embodiment may comprise a growth factor.

"Non-Compliant balloon" as used herein refers to a balloon that does not conform to the intervention site, but rather, tends to cause the intervention site to conform to the balloon shape. Non-compliant balloons, commonly made from such materials as polyethylene terephthalate (PET) or polyamides, remain at a preselected diameter as the internal balloon pressure increases beyond that required to fully inflate the balloon. Non-compliant balloons are often used to dilate spaces, e.g., vascular lumens. As noted with respect to a compliant balloon, one of skill in the art will be aware that the compliance of a balloon is dependent on the dimensions and/or characteristics of the cavity and/or lumen walls, not only the expandability of the balloon.

"Cutting balloon" as used herein refers to a balloon commonly used in angioplasty having a special balloon tip with cutting elements, e.g., small blades, wires, etc. The cutting elements can be activated when the balloon is inflated. In angioplasty procedures, small blades can be used score the plaque and the balloon used to compress the fatty matter against the vessel wall. A cutting balloon might have tacks or other wire elements which in some embodiments aid in freeing the coating from the balloon, and in some embodiments, may promote adherence or partial adherence of the coating to the target tissue area, or some combination thereof. In some embodiments, the cutting balloon cutting elements also score the target tissue to promote the coating's introduction into the target tissue. In some embodiments, the cutting elements do not cut tissue at the intervention site. In some embodiments, the cutting balloon comprises tacking elements as the cutting elements.

"Inflation pressure" as used herein refers to the pressure at which a balloon is inflated. As used herein the nominal inflation pressure refers to the pressure at which a balloon is inflated in order to achieve a particular balloon dimension, usually a diameter of the balloon as designed. The "rated burst pressure" or "RBP" as used herein refers to the maximum statistically guaranteed pressure to which a balloon can be inflated without failing. For PTCA and PTA catheters, the rated burst pressure is based on the results of in vitro testing ot the PTCA and/or PTA catheters, and normally means that at least 99.9% of the balloons tested (with 95% confidence) will not burst at or below this pressure.

"Tacking element" as used herein refers to an element on the substrate surface that is used to influence transfer of the coating to the intervention site. For example, the tacking element can comprise a projection, e.g., a bump or a spike, on the surface of the substrate. In embodiments, the tacking element is adapted to secure the coating to the cutting balloon until inflation of the cutting balloon. In some embodiments, tacking element can comprise a wire, and the wire can be shaped in the form of an outward pointing wedge. In certain embodiments, the tacking element does not cut tissue at the intervention site.

As used herein, a "surgical tool" refers to any tool used in a surgical procedure. Examples of surgical tools include, but are not limited to: As used herein, a "surgical tool" refers to any tool used in a surgical procedure. Examples of surgical tools include, but are not limited to: a knife, a scalpel, a guidewire, a guiding catheter, a introduction catheter, a distracter, a needle, a syringe, a biopsy device, an articulator, a Galotti articulator, a bone chisel, a bone crusher, a cottle cartilage crusher, a bone cutter, a bone distractor, an Ilizarov apparatus, an intramedullary kinetic bone distractor, a bone drill, a bone extender, a bone file, a bone lever, a bone mallet, a bone rasp, a bone saw, a bone skid, a bone splint, a bone button, a caliper, a cannula, a catheter, a cautery, a clamp, a coagulator, a curette, a depressor, a dilator, a dissecting knife, a distractor, a dermatome, forceps, dissecting forceps, tissue forceps, sponge forceps, bone forceps, Carmalt forceps, Cushing forceps, Dandy forceps, DeBakey forceps, Doyen intestinal forceps, epilation forceps, Halstead forceps, Kelly forceps, Kocher forceps, mosquito forceps, a hemostat, a hook, a nerve hook, an obstetrical hook, a skin hook, a hypodermic needle, a lancet, a luxator, a lythotome, a lythotript, a mallet, a partsch mallet, a mouth prop, a mouth gag, a mammotome, a needle holder, an occluder, an osteotome, an Epker osteotome, a periosteal elevator, a Joseph elevator, a Molt periosteal elevator, an Obweg periosteal elevator, a septum elevator, a Tessier periosteal elevator, a probe, a retractor, a Senn retractor, a Gelpi retractor, a Weitlaner retractor, a USA-Army/Navy retractor, an O'Connor-O'Sullivan retractor, a Deaver retractor, a Bookwalter retractor, a Sweetheart retractor, a Joseph skin hook, a Lahey retractor, a Blair (Rollet) retractor, a rigid rake retractor, a flexible rake retractor, a Ragnell retractor, a Linde-Ragnell retractor, a Davis retractor, a Volkman retractor, a Mathieu retractor, a Jackson tracheal hook, a Crile retractor, a Meyerding finger retractor, a Little retractor, a Love Nerve retractor, a Green retractor, a Goelet retractor, a Cushing vein retractor, a Langenbeck retractor, a Richardson retractor, a Richardson-Eastmann retractor, a Kelly retractor, a Parker retractor, a Parker-Mott retractor, a Roux retractor, a Mayo-Collins retractor, a Ribbon retractor, an Alm retractor, a self retaining retractor, a Weitlaner retractor, a Beckman-Weitlaner retractor, a Beckman-Eaton retractor, a Beckman retractor, an Adson retractor, a rib spreader, a rongeur, a scalpel, an ultrasonic scalpel, a laser scalpel, scissors, iris scissors, Kiene scissors, Metzenbaum scissors, Mayo scissors, Tenotomy scissors, a spatula, a speculum, a mouth speculum, a rectal speculum, Sim's vaginal speculum, Cusco's vaginal speculum, a sternal saw, a suction tube, a surgical elevator, a surgical hook, a surgical knife, surgical mesh, a surgical needle, a surgical snare, a surgical sponge, a surgical spoon, a surgical stapler, a suture, a syringe, a tongue depressor, a tonsillotome, a tooth extractor, a towel clamp, towel forceps, Backhaus towel forceps, Lorna towel forceps, a tracheotome, a tissue expander, a subcutaneus inflatable balloon expander, a trephine, a trocar, tweezers, and a venous cliping. In some embodiments, a surgical tool may also and/or alternatively be referred to as a tool for performing a medical procedure. In some embodiments, a surgical tool may also and/or alternatively be a tool for delivering to the intervention site a biomedical implant.

"Reproductive care" as used herein refers to care of a subject's reproductive system. Active agents are contemplated for use in embodiments of methods and/or devices provided herein for Reproductive care. Devices and methods provided herein are contemplated for use in Reproductive care. The subject may be male or female, the care may be preventative, or to treat a condition, ailment, or disease. As used herein, the terms "condition" and "ailment" are interchangeable. For example, Reproductive care of a subject's reproductive system may include, in some embodiments, hormone delivery to reproductive organs, whether for birth control or reproductive assistance or for another purpose, fertility treatment, whether to reduce fertility or to increase fertility, infection treatment, such as treatment of yeast infections or other infections, and treatment and/or prevention of sexually transmitted diseases (STDs) such as bacterial vaginosis, chancroid, donovanosis, gonorrhea, lymphogranuloma venereum, chlamydia, non-gonococcal urethritis, staphylococcal infection, syphillis, tinea cruris, adenovirus, viral hepatitus, herpes symplex, HIV/AIDS, HTLV 1,2, genital warts, human papillomavirus HPV, molluscum contagiosum, mononucleosis, kaposi's sarcoma (Herpes 8), and/or trichomoniasis. In embodiments, the devices and methods of the invention are used to treat pelvic inflammatory disease (PID), including, e.g., infection and/or inflammation of the fallopian tube, ovary, endometrium, and other pelvic infections. In embodiments, PID is treated by local delivery to the fallopian tubes and/or ovaries. In other embodiments, STDs such as chlamydia and gonorrhoea are treated via a similar administration route. A dosage of clindamycin for the systemic treatment of pelvic inflammatory disease is, e.g., 900 mg IV q8h (in combination with gentamicin) administered for 14 days. Treatment of PID is described by, e.g., Mollen, et al., 2006, "Prevalence of tubo-ovarian abcess in adolescents diagnosed with pelvic inflammatory disease in a pediatric emergency department," Pediatr Emerg Care 22(9): 621-625; Hartmann, et al., 2009, "Tubo-ovarian abscess in virginal adolescents:exposure of the underlying etiology," J Pediatr Adolesc Gynecol 22(3): e13-16; Lehmann, et al., 2001, "Drug treatment of nonviral sexually transmitted diseases: specific issues in adolescents," Paediatr Drugs 3(7):481-494. Reproductive organs include not only the gonads and/or ovaries, but any tissue in the reproductive system of a male or a female subject.

Intravaginal and transvaginal treatment of infections are also contemplated in certain embodiments of the methods and/or devices of the invention. Formulations of drugs for these indications are described in, e.g., U.S. Pat. No. 6,416,779, "Device and method for intravaginal or transvaginal treatment of fungal, bacterial, viral or parasitic infections," incorporated herein by reference in its entirety. Fungal, bacterial, viral and parasitic infections and conditions, can be treated by methods comprising inserting into the vagina a device of the invention coated with a drug formulated for treatment of these conditions, with, e.g., a mucoadhesive agent to promote adherence of the drug to the vaginal wall. The mucoadhesive agent can be a polymer such as an alginate, pectin, or a cellulose derivative such as hydroxypropyl methylcellulose. Mucoadhesive formulations are described, e.g., by Edsman, et al., 2005, "Pharmaceutical applications of mucoadhesion for the non-oral routes,' J. Pharm. Pharmacol. 57(1):3-22. The drug may be therapeutically active topically by acting directly on vaginal epithelium or mucosa or it may be transported transvaginally into the uterus, cervix and even into the general circulation. U.S. Pat. No. 6,416,779 describes dosages of agents for intravaginal and transvaginal formulations for treating various diseases, e.g., as follows: in general, the dosage comprises from about 10 to about 2000 mg of the antibiotic per daily dose to be delivered transvaginally to the cervix. The transvaginal formulation can comprise a penetration enhancer and/or sorption promoter and/or mucoadhesive agent. The antibiotic dose depends on the antibiotic anti-infective activity. For treatment of chlamydia, the dosage is typically within 100-2000 mg/day dose administered for at least seven days, unless otherwise indicated. For transvaginal treatment of gonorrhea, lumefloxacin (400 mg), norfloxacin (800 mg), afloxam (400 mg), ciproflaxin (500 mg), azitromycin (1000 mg), cefltoxime (400 mg) and doxycycline (100 mg) twice a day/7 days can be administered in doses as needed to alleviate the symptoms and to effectively eliminate gonococcus from the individual organism in daily doses from about 400 mg to about 3000 mg. The formulation may, additionally, contain about 500-1000 mg of probenecid. For local treatment of herpes simplex, antiviral drugs such as acyclovir (200-1200 mg/day) or famciclovir (100-1200 mg/day), are administered for at least 7 days in a combination of transvaginal and intravaginal formulation. When using the devices and methods of the present invention, it is understood that the amount of agent transferred via a coating to an intervention site can be varied depending on the rate of release of the active agent from the coating after transfer, to achieve dosages comparable to those used with other local treatment methods.

Hormones that can be delivered locally using the devices and methods of the invention include, e.g.: delivery of 20 micrograms/day ethinyl estradiol to hypoestrogenic subjects for peak bone mass acquisition during adolescence; 200 micrograms/day of 17β-estradiol to relieve severe postmenopausal symptoms; 400 micrograms/day of the GNRH agonist nafarelin for 4 weeks in the initial treatment of endometriosis, followed by half-dose therapy (200 micrograms/day) for 20 weeks; and estradiol release of 100 mg/day of estradiol, as its 3-acetate ester can maintain a circulating plasma concentration of 300 pmol/L of the drug, to treat vaginal atrophy or for hormone replacement therapy (HRT). In general, estradiol can be administered intravaginally in a dosage amount of 25 about 10 to about 50 ug, preferably about 15 to about 40 g, for example about 25 g, no more than once daily. A suitable dosage amount of methyltestosterone is likely to be found in the range of about 0.5 to about 2.5 mg, no more than once daily, but greater or lesser amounts can be safe and effective in particular cases. Other androgens can be administered in dosage amounts therapeutically equivalent to these dosage amounts of methyltestosterone. One of skill in the art will understand that amount of hormone (or any other active agent) that can be transferred via a coating to an intervention site will vary depending on the rate of release of the active agent from the coating after transfer. Locally administered therapies and dosages have been described in, e.g., U.S. Pat. App. No. 2006/0287611, "Administration of therapeutic or diagnostic agents using interlabial pad," U.S. Pat. No. 6,682,757, "Titratable dosage transdermal delivery system," WO 03/039553, "Compositions for treatment of postmenopausal female sexual dysfunction," all incorporated by reference herein.

Pharmaceutical agents useful in these aspects of the invention are active on the vaginal epithelium, mucosa or on the uterine epithelium or cervix. The pharmaceutical agent is preferably selected from the group consisting of antifungal, antiviral, antibacterial or antiparasitic agents. Examples of anti-fungal drugs suitable for use in this and other uses of the invention include miconazole, terconazole, isoconazole, fenticonazole, fluconazole, ketoconazole, clotrimazole, butoconazole, econazole, metronidazole, clindamycin, and 5-fluoracil. Anti-viral drugs include acyclovir, AZT, famciclovir and valacyclovir. Antibacterial agents suitable for treatment of bacterial vaginosis are metronidazole, clindamycin, ampicillin, amoxicillin, tetracycline, doxycycline and other antibiotics. The anti-trichomonas agent suitable for treatment of trichomoniasis caused by Trichomonas vaginalis is metronidazole.

"Urologic care" as used herein refers to treatment and prevention of any disease or dysfunction of any part of the male and female urinary tract and/or the urinary system, and the male reproductive system. Active agents are contemplated for use in embodiments of methods and/or devices provided herein for urologic care. Devices and methods provided herein are contemplated for use in Urologic care. The urinary tract and/or the urinary system consists of the organs involved in the production and elimination of liquid waste (urine) from the body: the kidneys, ureters, bladder, and urethra. There are also two adrenal glands, one on top of each kidney, that produce important hormones the body needs, which is contemplated to be part of the urinary tract and/or urinary system as used herein. The male reproductive organs include the prostate, penis and testes (testicles).

Urologic conditions and ailments include sexual dysfunction and fertility issues, as well as general urology issues. Conditions include, for example, urinary stones, urinary incontinence, cancers of the urologic tract (e.g., bladder cancer, kidney cancer, and cancer of the urethra), cancers of the male reproductive tracts (e.g., testicular cancer, prostate cancer), Benign Prostate Hyperplasia (BPH), hypogonadism (Decreased Testosterone), erectile dysfunction, premature ejaculation, Peyronie's Disease, prostatitis, seminal vesiculitis, prostatic abscess, bladder neck hypertrophy and adrenal tumors. Urologic care also encompasses vasectomy and reversal of vasectomy.

BPH, including chronic prostatitis and chronic pelvic pain syndrome (CP/CPPS) is a common disorder affecting 50-80% of the aged male population. The cause is attributed to either underlying infection or inflammation and treatment and therefore involves antibiotic therapy such as fluoroquinolones or ciprofloxacin and anti-inflammatory therapy with alpha-adrenergic receptor antagonists such as alfuzosin. These drugs are typically given systemically usually over the course of two to four months. Localized infection and inflammation can be treated much more effectively if therapy is targeted to the infection site thereby allowing increased local concentrations and reduced systemic toxicities.

Using the device and methods of the invention to apply a drug-releasing coating to the wall of the prostate, treatment agents can be delivered for an extended period (at least two months). Local delivery also reduces the risk of development of antibiotic resistance. Using a biodegradable coating matrix, repeat administration can be provided as needed without concerns about build up of polymer.

Treatment of BPH and chonic prostatitis are described in the literature. See, e.g., Murphy, et al., 2009, "Chronic prostatitis: management strategies, Drugs 69(1): 71-84; Pontari, 2003, "Chronic prostatitis/chronic pelvic pain syndrome in elderly men: toward better understanding and treatment," Drugs Aging 20(15): 1111-1115; Mehik, et al., 2003, "Alfuzosin treatment for chronic prostatitis/chronic pelvic pain syndrome: a prospective, randomized, double-blind, placebo-controlled, pilot study," Urology 62(3):425-429; Wagenlehner, et al., Jun. 3, 2009, "A pollen extract (Cernilton) in patients with inflammatory chronic prostatitis chronic pelvic pain syndrome: a multicentre, randomized, prospective, double-blind, placebo-controlled phase 3 study," Eur Urol 9 (Epub); Fibbi, et al., Jun. 8, 2009, "Chronic inflammation in the pathogenesis of benign prostatic hyperplasia," Int. J. Androl. (Epub).

Stress incontinence, urge incontinence, and pyelitis of pregnancy are common urological conditions in the female. The most important factor in the production of urge incontinence is infection. Some pathological conditions which may be associated with urge incontinence are urethritis, cystitis, urethral stricture, bladder-neck obstruction, urethral diverticula, urethral caruncle and the urgency-frequency syndrome. Therapy is directed toward the eradication of infection and treatment of the specific lesion.

In embodiments, antiinflammatory or other agents are delivered, e.g., to the posterior urethra, for treatment of the pain and inflammation associated with prostatitis/chronic pelvic pain syndrome using the devices and methods of the invention. In embodiments, premature ejaculation caused by inflammation is treated in this manner. (See, e.g., A Pontari, M., 2002, "Inflammation and anti-inflammatory therapy in chronic prostatis," Urology 60(6Suppl):29-33, and Boneff, A., 1971, "Topical Treatment of Chronic Prostatitis and Premature Ejaculation," International Urology and Nephrology 4(2): 183-186, describing introduction of a hydrocortisone-antibiotic mixture into the posterior urethra).

In embodiments, the devices and methods of the invention are useful for local delivery of agents including mitomycin C and BCG for treatment of urinary tract transitional cell carcinoma (TCC). Transitional cell carcinoma (TCC, also urothelial cell carcinoma or UCC) is a type of cancer that typically occurs in the urinary system: the kidney, urinary bladder, and accessory organs. It is the most common type of bladder cancer and cancer of the ureter, urethra, and urachus, and it is the second most common type of kidney cancer. TCC arises from the transitional epithelium, a tissue lining the inner surface of these hollow organs. Bacillus Calmette-Guerin (BCG) therapy and CpG-Oligodeoxynucleotides (CpG-ODN), a synthetic agent, have been used to prevent the recurrence of urinary tract transitional cell carcinoma (TCC). Both CpG-ODN and BCG likely work by stimulating a potent immunological response. They are currently infused into the urinary tract through a catheter at weekly intervals under local anesthesia. This procedure is unpleasant, cumbersome and expensive. In embodiments, a single, topical application of the an appropriate agent (e.g., BCG, CpG-ODN, and/or mitomycin C) is applied directly to the wall of the urethra, particularly near the original lesion site, using, e.g., a foley-type catheter.

The use of a bioresorbable polymer with the pharmaceutical agent can increase the concentration of the agent delivered to the target tissue, retaining it locally, thereby increasing effectiveness and reducing overall bladder irritation. It can also reduce the threat of spread of BCG to sexual partners. Use of a polymer that can provide for controlled drug delivery over the course of 6-8 weeks can negate the need for repeat application procedures.

Either alone or in combination with BCG therapy, the application of mitomycin C can also reduce subsequent inflammation and promote healing after endoscopic surgery. Local treatment of TCC using BCG, CpG-ODN, and/or mitomycin C is described in the literature, e.g., by: Thalmann, et al., 2002, "Long-term experience with bacillus Calmette-Guerin therapy of upper urinary tract transitional cell carcinoma in patients not eligible for surgery," J Urol. 168(4 Pt 1): 1381-1385; Olbert, et al., 2009, "In vitro and in vivo effects of CpG-Oligodeoxynucleotides (CpG-ODN) on murine transitional cell carcinoma and on the native murine urinary bladder wall," Anticancer Res. 29(6):2067-2076; Melonakos, et al., "Treatment of low-grade bulbar transitional cell carcinoma with urethral instillation of mitomycin C, Oct. 28, 2008, Adv Urol. 173694 Epub; Di Stasi, et al., 2005, "Percutaneous sequential bacillus Calmette-Guerin and mitomycin C for panurothelial carcinomatosis," Can J Urol 12(6):2895-2898.

In specific embodiments, the devices and methods of the invention are used for intravesical drug therapy of bladder cancer. In bladder cancer, cancer cells invade the wall of the bladder. The wall of the bladder consists of several layers and the treatment modalities used to treat bladder cancer are typically selected on the basis of how far the cancer has penetrated into the layers of the bladder wall.

The majority of superficial tumors (e.g., those that are confined to the mucosa and lamina propria of the bladder) are treated by cystoscopic surgery or in some cases intravesical drug therapy. In cases where the carcinoma has penetrated the muscular wall of the bladder (i.e. where the cancer has progressed to invasive bladder cancer that invades the deeper layers of the bladder wall, and possibly nearby organs, such as the uterus, vagina, or prostate gland) metastatic disease is likely to occur after surgery. Additional chemotherapy, either systemic or local, is thus needed. Response to treatment of bladder transitional cell carcinoma appears to be related to drug concentration and duration of exposure, therefore the capability of the devices and methods of the invention to deliver a concentrated dose of agent directly to the treatment site is advantageous for this indication.

Methods of treatment and agents used in treating bladder and urinary tract cancers are described in, e.g., U.S. Pat. No. 7,326,734, "Treatment of bladder and urinary tract cancers," and U.S. Pat. No. 6,355,691, "Urushiol therapy of transitional cell carcinoma of the bladder," (describing intravesical administration of urushiol) both incorporated herein by reference in their entirety.

A variety of agents have been reported to have significant activity in transitional cell carcinoma of the bladder, including cisplatin-based regimens such as MVAC (methotrexate, vinblastine, doxorubicin, and cisplatin), which has become standard for patients with metastatic urothelial carcinoma. A drawback of MVAC is toxicity and poor patient tolerance. Local administration of MVAC using the devices and methods of the invention could allow lower dosages to be administered, resulting in better tolerance. Other agents useful for treating TCC of the bladder are paclitaxel and docetaxel, gemcitabine, thiotepa, valrubicin, epirubicin, interferon alpha 2b, ifosfamide, and the methotrexate analogues, trimetrexate and piritrexim.

Bladder cancer is frequently treated by an initial instillation of drug, e.g., within 6 hours of tumor resection, followed by a 4-8 week induction treatment, followed by about one year or more of a maintenance regimen. Intravesical combination chemotherapies for administration to patients having bladder cancer are described, e.g., by Witjes, et al., 2008 January, "Intravesical pharmacotherapy for non-muscle-invasive bladder cancer: a critical analysis of currently available drugs, treatment schedules, and long-term results," Eur Urol. 53(1):45-52, and Lamm, et al., Oct. 26, 2005, "Bladder Cancer: Current Optimal Intravesical Treatment: Pharmacologic Treatment," Urologic Nursing 25(5): 323-6, 331-2.

Chemotherapy can be administered at or near the time of tumor resection, to prevent tumor recurrence. Immunotherapy (e.g., BCG), has been shown to reduce recurrence when given as maintenance therapy rather than at the time of resection. In general, immunotherapy is seen as more effective against high-grade carcinoma, and chemotherapy as more effective against low-grade carcinoma.

Chemotherapy agent dosing: The standard intravesicular dosage of thiotepa is 30 mg in 15 cc sterile water. When given as a single instillation at the time of tumor resection, an exposure of 30 minutes is used. When not given in conjunction with tumor resection, doses of 30 mg to 60 mg are used in 15 cc to 30 cc of sterile water and held for 2 hours. Treatment is given weekly for 4 to 8 weeks, depending on volume of residual disease. When repeated treatments are used, blood counts should be obtained, since thiotepa has a molecular weight of 188 and drugs with molecular weight less than 300 are more readily absorbed from the bladder.

The standard dosage of mitomycin C is 40 mg in 20 cc sterile water. Mitomycin C should not be given if bladder perforation is suspected. In a randomized study, recurrence was reportedly nearly cut in half by using an optimized schedule: 40 mg/20 cc (compared with 20 mg/20 cc), overnight dehydration, ultrasound-confirmed complete bladder emptying, alkalinization using 1.3 g of sodium bicarbonate the night before, morning of, and 30 minutes prior to treatment. Mitomycin C is inactivated by acid urine (Au, et al. 2001, "Methods to improve efficacy of intravesical mitomycin C: Results of a randomized phase III trial" Journal of the National Cancer Institute, 93(8), 597-604). It has been reported that that local hyperthermia, which can be obtained with a microwave applicator inserted into the bladder with a special catheter can enhance the efficacy of mitomycin C, albeit with a significant increase in systemic absorption.

The standard dosage of doxorubicin is 50 mg in 25 cc of sterile water. Doxorubicin should not be given if bladder perforation is suspected. Optimal response occurs when given as a single instillation at the time of tumor resection. An exposure of 30 minutes is used when given at the time of surgery. When given to treat existing disease rather than prevent recurrence, treatment is held for 2 hours, and given weekly for 4 to 8 weeks, depending on volume of residual disease.

The standard dosage of epirubicin is 80 mg in 40 cc sterile water. Like doxorubicin, mitomycin C, and valrubicin, epirubicin is a vesicant and will result in necrosis with extravasation. Best results occur with immediate postoperative instillation, but instillation should not be done if bladder perforation or any risk for extravasation is present, since this would put the patient at risk for peritonitis.

Valrubicin was specifically approved for BCG-refractory carcinoma in situ of the bladder. The standard dose is 800 mg in 75 mL normal saline weekly for 6 weeks.

Immunotherapy agent dosing: Immunotherapies (also called adjuvant therapies) include not only bacillus Calmette-Guerin (BCG), as described above, but also Interferon Alpha 2b. The standard intravesicular dose of BCG is 81 mg for TheraCys® and 50 mg for TICE,® both in 50 cc physiologic saline. Treatment should be postponed for at least 1 to 2 weeks following tumor resection or bladder biopsy. Treatments are typically repeated weekly for 6 weeks, with dose reductions to 1/3, 1/10, 1/30, or 1/100 as needed to prevent increasing or severe symptoms of bladder irritation. Additional instillations can be given at 3 months (6 weeks after completion of the initial 6-week course). Maintenance BCG can be provided using up to 3 weekly instillations in disease-free patients given at 3, 6, 12, 18, 24, 30, and 36 months, and at years (counting from the start of treatment) 4, 5, 6, 8, 10, and 12 for patients with CIS or high-grade disease.

Interferon Alpha 2b, which is relatively non-toxic, has been given intravesically in doses as high as 1 billion units without dose-limiting side effects. The standard dose is 50 to 100 million units weekly for 6 weeks. Additional maintenance treatments can be beneficial.

BCG immunotherapy can be combined with chemotherapy, e.g., mitomycin C. Combination chemotherapy can be used in patients with metastatic transitional cell carcinoma. Combination immunotherapy, specifically the use of BCG plus interferon alpha2b, can be effective. According to O'Donnell, et al., 2001, "Salvage intravesical therapy with interferon-alpha 2b plus low dose bacillus Calmette-Guerin is effective in patients with superficial bladder cancer in whom bacillus Calmette-Guerin alone previously failed," Journal of Urology, 166(4):1300-1304), about 60% of patients who fail to respond to BCG can be rescued with BCG plus interferon alpha. The standard dose is 50 mg to 81 mg of BCG plus 50 million units of interferon alpha 2b. Treatments are given weekly for 6 weeks, with maintenance using up to 3 weekly instillations at 3 or 6 months, and then every 6 to 12 months. The dose of BCG is reduced to $\frac{1}{3}$, $\frac{1}{10}$, $\frac{1}{100}$ as needed to prevent increased side effects.

In embodiments, urinary tract cancers are treated with radiolabeled or cytotoxic GRP analogs using the devices and methods of the invention. High levels of vascular gastrin-releasing peptide (GRP) receptors have been reported in urinary tract cancers, making these cancers particularly suitable for therapies that target the tumor vascular bed. (See, e.g., Fleischmann, et al., June 2009, Endocr. Relat. Cancer, 16(2):623-33.)

"Gastrointestinal care" or "GI care" as used herein refers to the treatment and prevention of diseases and/or ailments of gastrointestinal system (GI system) and/or the gastrointestinal tract (GI tract), which can include treatment and prevention of diseases and/or ailments of the esophagus, stomach, first, second and third part of the duodenum, jejunum, ileum, the ileo-cecal complex, large intestine (ascending, transverse and descending colon) sigmoid colon and rectum. Active agents are contemplated for use in embodiments of methods and/or devices provided herein for gastrointestinal care. Devices and methods provided herein are contemplated for use in Gastrointestinal care.

Upper gastrointestinal disease includes disease of the oral cavity, esophagus, and stomach. Intestinal disease includes disease of the small intestine, large intestine, disease that affect both the large and small intestine, and disease of the rectum and anus. Disease of the accessory digestive glands includes liver, pancreas, gall bladder and bile duct disease. Other gastrointestinal diseases include, e.g., hernia, peritoneal disease, and gastrointestinal bleeding.

Diseases of the upper gastrointestinal tract include, e.g., esophagitis, which can be caused by candidiasis, rupture (Boerhaave syndrome, Mallory-Weiss syndrome), UES (Zenker's diverticulum), LES—(Barrett's esophagus), esophageal cancers, bacterial infections, viral infections, esophageal motility disorder (Nutcracker esophagus, Achalasia, Diffuse esophageal spasm, GERD), esophageal stricture, megaesophagus, gastritis (atrophic, Ménétrier's disease, gastroenteritis), peptic (gastric), ulcer (Cushing ulcer, Dieulafoy's lesion), dyspepsia, pyloric stenosis, achlorhydria, gastroparesis, gastroptosis, portal hypertensive gastropathy, gastric antral vascular ectasia, gastric dumping syndrome, and gastric volvulus.

Diseases of the intestine include, e.g., enteritis (duodenitis, jejunitis, ileitis), Peptic (duodenal) ulcer, Curling's ulcer, malabsorption diseases (e.g., coeliac, tropical sprue, blind loop syndrome, Whipple's, short bowel syndrome, steatorrhea), cancers, bacterial infections, viral infections, appendicitis, colitis (pseudomembranous, ulcerative, ischemic, microscopic, collagenous, lymphocytic), functional colonic disease (IBS, intestinal pseudoobstruction/Ogilvie syndrome), megacolon/toxic megacolon, diverticulitis/diverticulosis, enterocolitis, IBD, Crohn's disease, vascular diseases (e.g., abdominal angina, mesenteric ischemia, angiodysplasia), bowel obstruction (due to, e.g., ileus, intussusception, volvulus), fecal impaction, and diarrhea.

Diseases of the rectum and anus include proctitis, e.g., radiation proctitis, proctalgia fugax, rectal prolapse, anal fissure/anal fistula, anal cancer, and anal abscess.

Diseases of the accessory digestive glands include diseases that affect the liver, e.g., hepatitis, cirrhosis, fatty liver disease, liver cancer, vascular disease (e.g., hepatic veno-occlusive disease, portal hypertension, nutmeg liver), alcoholic liver disease, liver failure, liver abscess, hepatorenal syndrome, peliosis hepatis, hemochromatosis, and Wilson's Disease. Additional accessory digestive gland diseases include pancreatitis (Acute, Chronic, Hereditary), pancreatic cancer, pancreatic pseudocyst, exocrine pancreatic insufficiency, and pancreatic fistula. Gall bladder and bile duct diseases include cancers, cholecystitis, gallstones/cholecystolithiasis, cholesterolosis, Rokitansky-Aschoff sinuses, postcholecystectomy syndrome, cholangitis (PSC, Ascending), cholestasis/Mirizzi's syndrome, biliary fistula, haemobilia, gallstones/cholelithiasis, choledocholithiasis, and biliary dyskinesia.

Other diseases affecting the GI system include hernias, peritonitis, hemoperitoneum, and pneumoperitoneum. GI bleeding diseases include, hematemesis, melena, and hematochezia. Treatment of any GI system disease includes administration of drugs in association with surgery or resection, e.g., chemotherapeutic agents, antibiotics, antiinflammatory agents, or combinations thereof.

In certain embodiments, Ankaferd blood stopper, a medicinal plant extract, is locally delivered to prevent uncontrolled bleeding of a passageway such as the rectum using the devices and methods of the invention. Nasal passageways can also be treated in a similar manner. Administration of Ankaferd blood stopper is described by, e.g., Kurt, et al., 2009, "Tandem oral, rectal, and nasal administrations of Ankaferd Blood Stopper to control profuse bleeding leading to hemodynamic instability," Am. J. Emerg. Med. 27(5):631, e1-2.

In other embodiments, tacrolimus is administered using the devices and methods of the invention to treat resistant ulcerative proctitis. The effect of tacrolimus ointment in controlling ulcerative proctitis has been described, e.g., by Lawrance, et al., Nov. 15, 2008, "Rectal tacrolimus in the treatment of resistant ulcerative proctitis," Aliment. Pharmacol. Ther. 28(10): 1214-20.

In embodiments, the devices and methods of the invention are used to protect mucous membranes. For example, the devices and methods of the invention can be used to deliver topical microbicide, rectally or vaginally, for prevention of transmission of HIV or other STDs. (See, e.g., Hladik, et al., 2008, "Can a topical microbicide prevent rectal HIV transmission?" PLoS Med. 5(8):e167.)

"Respiratory care" as used herein refers to the therapy, management, rehabilitation, diagnostic evaluation and care of patients with actual or suspected diseases, including pathogenic infections, or other conditions or ailments that affect the upper and/or lower respiratory system and associated aspects of other system functions. It includes the treatment or management of acute and chronic breathing disorders. Active agents are contemplated for use in embodiments of methods and/or devices provided herein for Respiratory care. Devices and methods provided herein are contemplated for use in Respiratory care. Typically, the disease or condition is a respiratory disease or condition, including, but not limited to, inflammatory airway diseases (e.g., asthma, chronic obstructive pulmonary disease (COPD), bronchiolitis), bronchopulmonary dysplasia, croup, bronchitis, bronchiectasis, emphysema, allergic rhinitis, the pulmonary sequelae of cystic fibrosis, Churg-Strauss syndrome, mycobacterial diseases (caused by, e.g., *M. tuberculosis, M. avium*), severe acute respiratory syndrome (SARS), and pneumonia. Active agents are contemplated for use in embodiments of methods and/or devices provided herein for respiratory care.

In embodiments, the invention is used for administering agents prior to or during endotracheal intubation. Use of an endotracheal tube or laryngeal mask can result in significant postoperative sore throat, coughing and hoarseness. Lidocaine and betamethasone have been applied topically in gels or sprays to reduce discomfort. Extended, controlled, local delivery controlled local delivery can provide significantly greater benefit. For example, the endotracheal tube or laryngeal mask could be coated, fully or partially, with a bioresorbable matrix betamethasone (0.05%) or another appropriate antiinflammatory agent, and/or lidocaine (2.0-4.0%), or another appropriate anesthetic. Alternately, the coating could be delivered to the tissue via a large balloon-type catheter prior to insertion of the endotracheal tube or laryngeal mask.

In related embodiments, compositions can be applied via a drug/polymer delivery device prior to endoscopic procedures, or applied to the endoscope itself. Topical administration of local anesthetic agents can reduce a rise in blood pressure, decrease the time before a patient can drive or operate machinery, as well as increase comfort during conscious endoscopic procedures such as gastroendoscopy. The use of antiinflammatory or anesthetic agents has been described by, e.g.: Sumathi, et al., 2008, "Controlled comparison between betamethasone gel and lidocaine jelly applied over tracheal tube to reduce postoperative sore throat, cough, and hoarseness of voice," Br. J. Anaesth. 100(2): 215-218; Kazemi, et al., 2007, "The effect of betamethasone gel in reducing sore throat, cough, and hoarsness after laryngo-tracheal intubation," Middle East J Anesthesiol. 19(1):197-204; Minoque, et al., 2004, "Laryngotracheal topicalization with lidocaine before intubation decreases the incidence of coughing on emergence from general anesthesia," Anesth Analg. 99(4):1253-1257; Xue, et al., 2009, "Spray-as-you-go airway topical anesthesia in patients with a difficult airway: a randomized, double-blind comparison of 2% and 4% lidocaine," Anesth Analg. 108(2): 536-543; Ristikankare, et al., 2006, "Sedation, topical pharyngeal anesthesia and cardiorespiratory safety during gastroscopy," J Clin Gastroenterol. 40(10):899-905; and Froehlich, et al., 1995, "Conscious sedation for gastroscopy: patient tolerance and cardiorespiratory parameters," Gastroenterology 108(3):697-704.

In embodiments, the devices and methods of the invention can be used to prevention tracheal stenosis in upper airway surgery. Topical application of agents including mitomycin C and heparin have been described to improve healing and reduce scarring following laryngeal/tracheal surgery. The methods described do not necessarily provide sufficient delivery time, or thorough coating of the affected area. The devices and methods of the invention can be used for local delivery of a bioresorbable polymer/drug mixture, wherein the polymer than can deliver active agent over the course of the normal wound healing period, e.g., one to three months. This extended delivery can significantly reduce the need for additional surgery to treat scarring and stenosis of the upper airways. Current topical applications known to be safe and somewhat effective use a concentration of about 0.4-0.5 mg/ml (~0.04-0.05%) of mitomycin C or a concentration of heparin of about 5000 U/ml.

In these embodiments, the delivery device can be similar to an endotracheal catheter having a balloon coated with the polymer/drug combination. In further embodiments, one or more repeat procedures are performed after surgery, as needed, to ensure adequate delivery of active agent over the course of the wound healing process. The use of mitomycin C or heparin for reducing scarring after esophageal or tracheal surgery has been described by, e.g.: Smith, et al., 2009, "Mitomycin C and the endoscopic treatment of laryngotracheal stenosis: are two applications better than one?" Laryngoscope 119(2):272-283; Sen, et al., Feb. 21, 2009, "Topical heparin: A promising agent for the prevention of tracheal stenosis in airway surgery," J Surg Res [Epub ahead of print]; Warner, et al., 2008, "Mitomycin C and airway surgery: how well does it work?" Ontolaryngol Head Neck Surg. 138(6): 700-709.

"Ear-Nose-Throat care" or "ENT care" as used herein refers to diagnosis, treatment and prevention of disorders, including but not limited to cancers, bacterial infections, and viral infections, of the ENT system, which can include the head and neck region, including the ear, nose, throat and paranasal sinuses, as well as disorders of the mouth, salivary glands, vocal cords, larynx, face and neck. ENT disorders include, but are not limited to, sinusitis, head and neck cancer, skin cancers, disorders or enlargement of the tonsils and adenoids, sleep disorders, vocal cord disorders, e.g., paralysis, hearing loss and vertigo, and hoarseness. Active agents are contemplated for use in embodiments of methods and/or devices provided herein for ENT care. Devices and methods provided herein are contemplated for use in ENT care.

In particular embodiments, sinusitis and other sinus disorders are treated using the methods of the invention. The sinus system consists of many different pathways, called ducts or ostia, which allow mucus, air and other substances to drain and flow through the system. Inflammation can occur in the tissues that make up the ducts and ostia, causing them to swell and block the normal flow. Inflammation may be caused by allergies, noxious agents, nasal polyps, and other factors. Over time there can be a pathologic increase in inflamed tissue causing permanent disruption in the flow through the sinus system. Obstruction of the narrow ducts and ostia between the paranasal sinuses and nasal cavity develops, resulting in a vicious cycle of increased secretions, edema and ultimately complete blockage of the sinus pathways. The state of chronic sinus inflammation is called sinusitis. Sinusitis can both be caused by and can cause a narrowing of the sinus ostia. In some embodiments, the intervention site is a sinus cavity wall. In some embodiments, the active agent comprises a corticosteroid to treat sinusitis, either alone or in conjunction with an antibiotic agent. Methods for accessing sinus ostia or sinus cavities using devices including balloon catheters, for dilating the ostia of paranasal sinuses are described, e.g., in U.S. Pat. Appl. No. 2009/0076446, "Adjustable catheter for dilation in the ear, nose or throat," incorporated herein by reference in its entirety. In some embodiments, the active agent comprises a corticosteroid.

In embodiments, agents including but not limited to chemotherapeutic, antibiotic, or antiinflammatory agents or a combination thereof are administered in the treatment of laryngeal cancer using the devices and methods of the invention. In other embodiments, the devices and methods of the invention are used to administer painkillers, antibiotics, botulinum toxin, and/or anti-inflammatory agents in vocal cord medialization.

In embodiments, the devices and methods of the invention are used to administer IGF-1 to protect or repair the neurosensory structures in the inner ear. Cochlear administration of IGF-1, delivered locally via a hydrogel to the round window membrane, has been reported to prevent hearing loss caused by noise trauma or ischemia. (See, e.g., Fujiwara, et al., "Insulin-like growth factor 1 treatment via hydrogels rescues cochlear hair cells from ischemic injury" 29 Oct. 2008, NeuroReport 19(16):1585-1588, and Lee, et al., 2007, "Novel therapy for hearing loss: delivery of insulin-like growth factor 1 to the cochlea using gelatin hydrogel," Otol. Neurotol. 28(7):976-81.)

"Ocular care" as used herein refers to the treatment, prevention, and diagnosis of disorders of the eye and tear duct, including but not limited to injury (e.g., blunt trauma, abrasion, and trauma due to surgery), bacterial infection, viral infection, diabetic retinopathy, artery occlusion, glaucoma, chemical exposure, sun damage, keratitis, edema, uveitis, cancers, AMD, vision defects, etc.

For example, the devices and methods of the invention can be used to administer agents for treatment of infection, e.g., antibiotic or anti-inflammatory agents, between the sclera and the eyelid, between the sclera and the conjunctiva, trancsclerally to the retina, or within the vitreous (intravitreally), using methods known in the art. Glaucoma can be treated using beta blockers (e.g., levobunolol, timolol, betaxolol, and metipranolol), alpha-agonists (e.g., apraclonidine, brimonidine), carbonic anhydrase inhibitors (e.g., dorzolamide, brinzolamide), prostaglandin-like compounds, e.g., latanoprost, bimatoprost, and travoprost, miotic or cholinergic agents (e.g., pilocarpine, carbachol), epinephrine compounds (e.g., dipivefrin), carbonic anhydrase inhibitors (e.g., acetazolamide, methazolamide) or with neuroprotective drugs, e.g., memantine and brimonidine. As is the case in other uses of the invention, agents typically taken orally can be given at much lower doses when administered locally, reducing the occurrence of adverse side effects. Unwanted angiogenesis can be treated using, e.g., angiogenesis inhibitors including antisense agents (e.g., Macugen), thalidomide, and EM-138. U.S. Pat. No. 7,524,865, "Methods and compositions for treating an ocular neovascular disease," incorporated herein by reference in its entirety, describes ocular diseases and their treatment using angiogenesis inhibitors. Accessing the vitreous for drug administration is described, e.g., in U.S. Pat. No. 7,485,113, "Method for drug delivery through the vitreous humor," incorporated herein by reference in its entirety.

"Orthopedic care" as used herein refers to the treatment, prevention, and diagnosis of orthopedic diseases and conditions, including but not limited to developmental diseases, genetic diseases, injuries, infections, and cancers of the bones (including the spine and spinal cord), muscles, tendons, and joints. Such conditions include diseased, injured, or abnormal cartilage, bursitis, osteonecrosis, carpal tunnel syndrome, joint pain, and joint injuries, e.g., knee injury. Joint pain not due to injury can be caused by inflammation, for example in gout, sacroiliitis, and arthritis. Examples of types of arthritis that can be treated using the device and methods of the invention include osteoarthritis, rheumatoid arthritis, and infectious arthritis. Infectious arthritis is commonly caused by Staphylococcus aureus, and also can be caused by gonorrhea or fungi. Developmental orthopedic diseases (DOD) include Osteochondritis dissecans, subchondral cystic lesions, physitis, flexural deformities, angular deformities, cuboidal bone disease, and juvenile osteoarthritis. In embodiments, the device and methods of the invention are used to treat arthritis pain and neuropathic pain. In other embodiments, the device and methods of the invention are used to encourage tissue in-growth following, e.g., injury, surgery, abcess, tumor removal, around orthopedic or cosmetic implants, etc. For example, agents that can be administered include growth hormones, cytokines, e.g., anti-inflammatory agents, stem or regenerative cells, BDNF, fibroblast growth factors, platelet-derived growth factors, growth differentiation factors, bone morphogenetic proteins, transforming growth factors, e.g., TGF-beta1, cartilage-derived morphogenic proteins, vascular endothelial growth factors, epidermal growth factors, hepatocyte growth factors, insulin growth factors, angiogenic factors, etc.

In embodiments, the device and methods of the invention are used to administer therapeutic agents for the treatment of orthopedic diseases and conditions, either alone, in conjunction with, or in place of, other therapies and/or surgery and/or diagnostic procedures, including but not limited to ACL surgery and other knee surgeries, rotator cuff surgery, joint replacement surgery, bone grafts, osteotomy, or core decompression. Active agents are contemplated for use in embodiments of methods and/or devices provided herein for Orthopedic care. Devices and methods provided herein are contemplated for use in Orthopedic care.

In embodiments, drugs or compounds useful in the devices and methods of the invention either alone or in combination for treating orthopedic diseases and conditions include, but are not limited to, steroids, anti-inflammatory drugs, antibiotics, anti-viral agents, cancer-fighting drugs (including antioneoplastic, antiproliferative, antimycotic, and antimetabolite compounds), glucocorticoid anti-inflammatories (such as dexamethasone, fluocinolone, cortisone, prednisolone, flumetholone, and derivatives thereof), non-steroidal anti-inflammatory drugs (NSAIDs), immune suppressants, antibiotics, cartilage protectants, disease modifying anti-rheumatic drugs (e.g., adalimumab, azathioprine, chloroquine, hydroxychloroquine, cyclosporine, D-penicillamine, etanercept, gold salts, including sodium aurothiomalate and auranofin, infliximab, leflunomide, methotrexate, minocycline, and sulfasalazine), chondroitin sulfate, enzyme inhibitors, and/or antisense compounds such as antisense oligonucleotides, and pain relieving agents. Specific agents useful in the devices and methods of the invention include, but are not limited to, corticosteroids such as dexamethasone and triamcinolone acetonide, angiostatic steroids such as anecortave acetate, antibiotics including ciprofloxacin, non-steroidal anti-inflammatory agents such as indomethacin and flurbiprofen, co-drugs including low-solubility co-drugs of salts or conjugates of synergistic pharmacological agents such as suramin/amiloride or 5-FU/THS, Bone Morphogenetic Protein (BMP), cell-based therapies (e.g., stem or regenerative cells), imaging agents, and combinations thereof. Drugs and formulations for treating joint conditions are described, e.g., in U.S. Pat. No. 6,936,270 "Device and method for treating conditions of a joint," incorporated herein by reference in its entirety.

In embodiments of the devices and methods of the invention, joint conditions are treated by providing sustained release of at least one therapeutically effective compound for a duration of about 3 months to about 10 years. In embodiments, sustained release is provided for about 6 months to about 5 years. In certain embodiments, sustained release of a therapeutically effective compound is provided for about 1 year, 2 years, 3 years, or 4 years, or longer. As a result, the need for frequent, repeated administrations, such as with injections, is avoided.

"Spinal care" as used herein refers to the treatment, prevention, and diagnosis of spine and spinal cord diseases and conditions, including but not limited to developmental and genetic diseases, injuries, infections, and cancers of the spine and spinal cord, including, e.g., degenerative conditions (e.g., herniated cervical disc, herniated lumbar disc, spondylolysis, spondylolisthesis, stenosis, and osteoporosis), ankylosing spondylitis, Adolescent Idiopathic Scoliosis, spinal cord injury, spinal infection; spinal tumor, whiplash. Active agents are contemplated for use in embodiments of methods and/or devices provided herein for Spinal care. Devices and methods provided herein are contemplated for use in Spinal care.

In embodiments, the device and methods of the invention are used to administer therapeutic agents for the treatment of spine and spinal cord diseases and conditions, either alone, in conjunction with, or in place of, other therapies, surgery, diagnostic procedures, and combinations thereof, including but not limited to discectomy, fusion, laminectomy or laminotomy, Intradiscal Electrothermal Therapy (IDET), Percutaneous Vertebral Augmentation (PVA), Artificial Disc Replacement (ADR), vertebroplasty, joint injections, epidural injections, laparascopic spine surgery, and MRI of the spine.

In embodiments, the devices and methods of the invention are used to administer agents for sustained release in the treatment of degenerative disc disease. Agents useful for treatment of degenerative disc disease include, e.g., MMP inhibitors.

In embodiments, the devices and methods of the invention are used to provide at least one agent to, e.g., the nucleus pulposus of a degenerating disc, the annulus fibrosus of a degenerating disc, the outer wall of the annulus fibrosus, at a location outside but closely adjacent to an outer wall of the annulus fibrosus and/or at a location outside but closely adjacent to an endplate of an adjacent vertebral body. Agents and dosages for sustained release treatment of degenerative disc disease are described in, e.g., U.S. Pat. No. 7,553,827, "Transdiscal administration of cycline compounds," and U.S. Pat. No. 7,429,378, "Transdiscal administration of high affinity anti-MMP inhibitors," incorporated herein by reference in their entirety.

In embodiments, drugs or compounds useful in the devices and methods of the invention either alone or in combination for treating spine and spinal cord diseases and conditions include, but are not limited to, the agents as described herein with regard to orthopedic care. In addition, antibiotics useful for treatment of spinal tuberculosis include, e.g., combination drug therapy with isoniazid and rifampicin. In embodiments, the devices and methods of the invention are used to administer analgesics, e.g., morphine, fentanyl, and/or bupivacaine in the epidural space of the spinal cord, for treatment of pain resulting from surgery, including but not limited to spinal or other orthopedic surgery, gynecological surgery, abdominal surgery, and other major surgical procedures. Appropriate dosages and administration times for epidurally-administered analgesics have been reported and are known to those of skill in the art. Continuous epidural administration offers a safety advantage over intermittent epidural injections because peak and trough levels of the analgesic agent are avoided. Furthermore, administration using the devices and methods of the invention avoids complications associated with the extended use of an epidural catheter.

"Cosmetic care" as used herein refers to surgical and nonsurgical procedures that alter the appearance of body structures, to improve the patient's appearance and/or for reconstructive or therapeutic purposes. Active agents are contemplated for use in embodiments of methods and/or devices provided herein for Cosmetic care. Devices and methods provided herein are contemplated for use in Cosmetic care. Cosmetic care procedures include, but are not limited to, breast augmentation, breast reduction, breast reshaping, body-contouring (e.g., via liposuction or lipectomy), gastric bypass surgery, stomach stapling, Lap Band surgery, abdominoplasty, use of facial fillers, facial implants, neck lift, blepharoplasty, dacryocystorhynostomy, chemical skin resurfacing, laser skin resurfacing, sclerotherapy, phlebectomy, dermabrasion, face lift, lip augmentation and/or restructuring, rhinoplasty, ear restructuring, hair replacement, hair removal, wound, scar, or lesion treatment (e.g., laser removal of skin cancer tissue), grafting, flap surgery, micropigmentation, tissue expansion, and the use of coatings on tissue expanders, breast implants, and on solid molded products (for rhinoplasty, chin implants, etc.). Reconstructive procedures are intended to repair or alter the appearance of defects or structural abnormalities caused by, e.g., congenital defects, developmental abnormalities, trauma, infection, tumors or disease, and/or meant to improve body function or a patient's health. Many reconstructive care procedures also serve a cosmetic purpose, for example, breast reconstruction after full or partial mastectomy, breast reduction to ease discomfort, repair of congenital cleft lip and palate, and blepharoplasty (e.g., when dropping eyelids are obscuring a patient's vision).

Cosmetic care procedures, particularly reconstructive procedures performed using the devices and/or methods of the invention, may require the use of biomedical implants, which are coated with at least one pharmaceutical agent. For example, the devices and methods of the invention can be used, in conjunction with electrosurgery for tissue ablation, to treat a surgery site with agents including but not limited to antiinflammatory agents, vasoconstrictors (such as epinephrine), antibiotics, painkillers, or combinations thereof in both cosmetic procedures and non-cosmetic therapeutic procedures. Electrosurgery is described in, e.g., U.S. Pat. No. 7,201,750 "System for treating articular cartilage defects," incorporated herein by reference in its entirety.

"Canniluzation" or "Cannulize" or "Cannulizable" as used herein refers to the insertion of a cannula or tube, e.g., at or near an intervention site. "Cannulizable" as used herein refers to a location, e.g., a vessel or other lumen or opening, into which a cannula can be inserted.

"Stimulation" as used herein refers to any mechanical stimulation, chemical stimulation, thermal stimulation, electromagnetic stimulation, and/or sonic stimulation that influences, causes, initiates, and/or results in the freeing, dissociation, and/or the transfer of the coating and/or active agent from the substrate.

"Mechanical Stimulation" as used herein refers to use of a mechanical force that influences the freeing, dissociation, and/or transfer of the coating and/or the active agent from the substrate. For example, mechanical stimulation can comprise a shearing force, a compressive force, a force exerted on the coating from a substrate side of the coating, a force exerted on the coating by the substrate, a force exerted on the coating by an external element, a translation, a rotation, a vibration, or a combination thereof. In embodiments, the mechanical stimulation comprises balloon expansion, stent expansion, etc. In embodiments, the mechanical stimulation is adapted to augment the freeing, dissociation and/or transfer of the coating from the substrate. In embodiments, the mechanical stimulation is adapted to initiate the freeing, dissociation and/or transfer of the coating from the substrate. In embodiments, the mechanical stimulation can be adapted to cause the freeing, dissociation and/or transference of the coating from the substrate. In embodiments, an external element is a part of the subject. In embodiments, the external element is not part of the device. In embodiments the external element comprises a liquid, e.g., saline or water. In certain embodiments the liquid is forced between the coating and the substrate. In embodiments, the mechanical stimulation comprises a geometric configuration of the substrate that maximizes a shear force on the coating.

"Chemical Stimulation" as used herein refers to use of a chemical force to influence the freeing, dissociation, and/or transfer of the coating from the substrate. For example, chemical stimulation can comprise bulk degradation, interaction with a bodily fluid, interaction with a bodily tissue, a chemical interaction with a non-bodily fluid, a chemical interaction with a chemical, an acid-base reaction, an enzymatic reaction, hydrolysis, or a combination thereof. In embodiments, the chemical stimulation is adapted to augment the freeing, dissociation and/or transfer of the coating from the substrate. In embodiments, the chemical stimulation is adapted to initiate the freeing, dissociation and/or transfer of the coating from the substrate. In embodiments, the chemical stimulation is adapted to cause the freeing, dissociation and/or transfer of the coating from the substrate. In embodiments, the chemical stimulation is achieved through the use of a coating that comprises a material that is adapted to transfer, free, and/or dissociate from the substrate when at the intervention site in response to an in-situ enzymatic reaction resulting in a weak bond between the coating and the substrate.

"Thermal Stimulation" as used herein refers to use of a thermal stimulus to influence the freeing, dissociation, and/or transfer of the coating from the substrate. For example, thermal stimulation can comprise at least one of a hot stimulus and a cold stimulus. In embodiments, thermal stimulation comprises at least one of a hot stimulus and a cold stimulus adapted to augment the freeing, dissociation and/or transference of the coating from the substrate. In embodiments, thermal stimulation comprises at least one of a hot stimulus and a cold stimulus adapted to initiate the freeing, dissociation and/or transference of the coating from the substrate. In embodiments, thermal stimulation comprises at least one of a hot stimulus and a cold stimulus adapted to cause the freeing, dissociation and/or transference of the coating from the substrate.

"Electromagnetic Stimulation" as used herein refers to use of an electromagnetic stimulus to influence the freeing, dissociation, and/or transfer of the coating from the substrate. For example, the electromagnetic stimulation is an electromagnetic wave comprising at least one of, e.g., a radio wave, a micro wave, a infrared wave, near infrared wave, a visible light wave, an ultraviolet wave, a X-ray wave, and a gamma wave. In embodiments, the electromagnetic stimulation is adapted to augment the freeing, dissociation and/or transference of the coating from the substrate. In embodiments, the electromagnetic stimulation is adapted to initiate the freeing, dissociation and/or transference of the coating from the substrate. In embodiments, the electromagnetic stimulation is adapted to cause the freeing, dissociation and/or transference of the coating from the substrate.

"Sonic Stimulation" as used herein refers to use of a sonic stimulus to influence the freeing, dissociation, and/or transfer of the coating from the substrate. For example, sonic stimulation can comprise a sound wave, wherein the sound wave is at least one of an ultrasound wave, an acoustic sound wave, and an infrasound wave. In embodiments, the sonic stimulation is adapted to augment the freeing, dissociation and/or transfer of the coating from the substrate. In embodiments, the sonic stimulation is adapted to initiate the freeing, dissociation and/or transfer of the coating from the substrate. In embodiments, the sonic stimulation is adapted to cause the freeing, dissociation and/or transfer of the coating from the substrate.

"Release Agent" as used herein refers to a substance or substrate structure that influences the ease, rate, or extent, of release of the coating from the substrate. In certain embodiments wherein the device is adapted to transfer a portion of the coating and/or active agent from the substrate to the intervention site, the device can be so adapted by, e.g., substrate attributes and/or surface modification of the substrate (for non-limiting example: substrate composition, substrate materials, substrate shape, substrate deployment attributes, substrate delivery attributes, substrate pattern, and/or substrate texture), the delivery system of the substrate and coating (for non-limiting example: control over the substrate, control over the coating using the delivery system, the type of delivery system provided, the materials of the delivery system, and/or combinations thereof), coating attributes and/or physical characteristics of the coating (for non-limiting example: selection of the active agent and/or the polymer and/or the polymer-active agent composition, or by the coating having a particular pattern—e.g. a ribbed pattern, a textured surface, a smooth surface, and/or another pattern, coating thickness, coating layers, and/or another physical and/or compositional attribute), release agent attributes (for non-limiting example: through the selection a particular release agent and/or the manner in which the release agent is employed to transfer the coating and/or the active agent, and/or the amount of the release agent used), and/or a combination thereof. Release agents may include biocompatible release agents, non-biocompatible release agents to aggravate and/or otherwise induce a healing response or induce inflammation, powder release agents, lubricants (e.g. ePTFE, sugars, other known lubricants), micronized drugs as the release agent (to create a burst layer after the coating is freed from the substrate, physical release agents (patterning of the substrate to free the coating, others), and/or agents that change properties upon insertion (e.g. gels, lipid films, vitamin E, oil, mucosal adhesives, adherent hydrogels, etc.). Methods of patterning a substrate are described, e.g., in U.S. Pat. No. 7,537,610, "Method and system for creating a textured surface on an implantable medical device." In embodiments, more than one release agent is used, for example, the substrate can be patterned and also lubricated. In some embodiments, the release agent comprises a viscous fluid.

In some embodiments, the release agent comprises a viscous fluid. In some embodiments, the viscous fluid comprises oil. In some embodiments, the viscous fluid is a fluid that is viscous relative to water. In some embodiments, the viscous fluid is a fluid that is viscous relative to blood. In some embodiments, the viscous fluid is a fluid that is viscous relative to urine. In some embodiments, the viscous fluid is a fluid that is viscous relative to bile. In some embodiments, the viscous fluid is a fluid that is viscous relative to synovial fluid. In some embodiments, the viscous fluid is a fluid that is viscous relative to saline. In some embodiments, the viscous fluid is a fluid that is viscous relative to a bodily fluid at the intervention site.

In some embodiments, the release agent comprises a physical characteristic of the substrate. In some embodiments, the physical characteristic of the substrate comprises at least one of a patterned coating surface and a ribbed coating surface. In some embodiments, the patterned coating surface comprises a stent framework. In some embodiments, the ribbed coating surface comprises an undulating substrate surface. In some embodiments, the ribbed coating surface comprises an substrate surface having bumps thereon.

In some embodiments, the release agent comprises a physical characteristic of the coating. In some embodiments, the physical characteristic of the coating comprises a pattern. In some embodiments, the pattern is a textured surface on the substrate side of the coating, wherein the substrate side of the coating is the part of the coating on the substrate. In some embodiments, the pattern is a textured surface on the intervention site side of the coating, wherein the intervention site side of the coating is the part of the coating that is transferred to, and/or delivered to, and/or deposited at the intervention site.

"Extrusion" and/or "Extruded" and/or to "Extrude" as used herein refers to the movement of a substance away from another substance or object, especially upon stimulation, e.g., by a mechanical force. For example, in embodiments of the invention, the coating is extruded from the substrate.

Provided herein is a medical device comprising a substrate and a coating on at least a portion of said substrate, wherein said coating comprises an active agent, wherein the coating is patterned, and wherein at least a portion of the coating is adapted to free from the substrate upon stimulation of the coating.

Provided herein is a medical device comprising a substrate and a coating on at least a portion of said substrate, wherein said coating comprises an active agent, wherein the coating is patterned, and wherein at least a portion of the coating is adapted to dissociate from the substrate upon stimulation of the coating.

Provided herein is a medical device comprising a substrate and a coating on at least a portion of said substrate, wherein said coating comprises an active agent, wherein the coating is patterned, and wherein at least a portion of the coating is adapted to transfer from the substrate to an intervention site upon stimulation of the coating.

In some embodiments, the patterned coating comprises at least two different shapes.

"Patterned" as used herein in reference to the coating refers to a coating having at least two different shapes. The shapes can be formed by various methods, including for example, etching, masking, electrostatic capture, and/or by the coating methods described herein. For example the coating may have voids that are at least partially through the thickness of the coating. In some embodiments, the voids extend fully through the coating. The voids may be in a regular configuration, or irregular in shape. The voids may form a repeating configuration to form the patterned coating. The voids may have been removed from a smooth or solid coating to form a patterned coating. The coating may in some embodiments be patterned by having a surface that is ribbed, wavy or bumpy. The coating may in some embodiments be patterned by having been cut and/or etched from a coating sheath and/or sheet in a particular design. The sheath and/or sheet in such embodiments may have been formed using the coating methods for manufacture as described herein. The pattern design may be chosen to improve the freeing, transfer, and/or dissociation from the substrate. The pattern design may be chosen to improve the transfer and/or delivery to the intervention site.

Patterned coatings may be created using the methods and processes described herein, for non-limiting example, by providing a substrate having a patterned design thereon comprising, for example, a material that is chosen to selectively capture the coating particles (whether active agent, polymer, or other coating particles) to coat only a desired portion of the substrate. This portion that is coated may be the patterned design of the substrate.

The term "image enhanced polymer" or "imaging agent" as used herein refer to an agent that can be used with the devices and methods of the invention to view at least one component of the coating, either while the coating is on the substrate or after it is freed, dissociated and/or transferred. In embodiments, an image enhanced polymer serves as a tracer, allowing the movement or location of the coated device to be identified, e.g., using an imaging system. In other embodiments, an image enhanced polymer allows the practitioner to monitor the delivery and movement of a coating component. In embodiments, use of an image enhanced polymer enables the practitioner to determine the dose of a component of the coating (e.g., the active agent) that is freed, dissociated and/or transferred. Information provided by the image enhanced polymer or imaging agent about the amount of coating transferred to the intervention site can allow the practitioner to determine the rate at which the coating will be released, thereby allowing prediction of dosing over time. Imaging agents may comprise barium compounds such as, for non-limiting example, barium sulfate. Imaging agents may comprise iodine compounds. Imaging agents may comprise any compound that improves radiopacity.

In embodiments, an image enhanced polymer is used with the device and methods of the invention for a purpose including, but not limited to, one or more of the following: monitoring the location of the substrate, e.g., a balloon or other device; assessing physiological parameters, e.g., flow and perfusion; and targeting to a specific molecule. In embodiments, "smart" agents that activate only in the presence of their intended target are used with the device and methods of the invention.

In embodiments, imaging agents useful with the device and methods of the present invention include, for example: EgadMe (in which a galactopyranose ring is synthesized to protect a Gd(III) ion from bulk water); conjugated polymer MEH-PPV nanoparticles; bismuth trioxide; near infrared (NIR) fluorochromes; bioluminescence agents (e.g., green fluorescent protein, red fluorescent protein); SPECT radionuclides, e.g., $^{99}Tc^m$ (6 h), $^{111}In$ (2.8 days), $^{123}I$ (13.2 h) and $^{125}I$ (59.5 days); PET radionuclides, e.g., $^{15}O$ (2.07 min), $^{13}N$ (10 min), $^{11}C$ (20.3 min), $^{18}F$ (1.83 h), $^{124}I$ (4.2 days) and $^{94}Tc^m$ (53 min); Gd-DTPA (gadolinium diethylenetriamine pentaacetic acid); Echo-Coat, an ultrasound imaging agent (STS-Biopolymers); and barium sulfate. In embodiments employing nanoparticles, it is important that the particles are small enough to allow renal clearance (e.g. have a hydrodynamic diameter less than 5.5 nm) and contain non-toxic components, and that the material decomposition products can be eliminated from the body. It is understood that an imaging agent can be conjugated or otherwise attached or associated with a compound in the coating according to methods known to those of skill in the art to form an image enhanced polymer.

Biological imaging agents useful in embodiments of the device and methods of the present invention are described in, e.g.: U.S. Pat. No. 6,077,880, "Highly radiopaque polyolefins and method for making the same," which sets forth a highly radiopaque polyolefin; U.S. Pat. No. 7,229,837, "Enhanced photophysics of conjugated polymers," relating to fluorescent ionic conjugated polymers; Dzik-Jurasz, 2003, "Molecular imaging in vivo: an introduction," The British Journal of Radiology, 76: S98-S109, providing an overview of in vivo molecular imaging methods; von zur Muhlen, et al., 2008, Magnetic Resonance Imaging Contrast Agent Targeted Toward Activated Platelets Allows In Vivo Detection of Thrombosis and Monitoring of Thrombolysis Circulation," 118:258-267, reporting imaging of activated platelets using an antibody-containing MRI imaging agent; and Green, et al., "Simple conjugated polymer nanoparticles as biological labels," Proc. Roy. Soc. A, published online 24 Jun. 2009 doi: 10.1098/rspa.2009.0181, describing the use of nanoparticles of conjugated polymers in biological imaging; all incorporated herein by reference in their entirety.

Certain Applications of the Technology

Provided herein is a medical device comprising a substrate and a coating on at least a portion of the substrate, wherein the coating comprises a plurality of layers, wherein at least one layer comprises a pharmaceutical agent in a therapeutically desirable morphology, and wherein the device is adapted to free at least a portion of the coating from the substrate upon stimulation of the coating.

Provided herein is a medical device comprising a substrate and a coating on at least a portion of the substrate, wherein the coating comprises a plurality of layers, wherein at least one layer comprises a pharmaceutical agent in a therapeutically desirable morphology, and wherein the device is adapted to dissociate at least a portion of the coating from the substrate upon stimulation of the coating.

Provided herein is a medical device comprising a substrate and a coating on at least a portion of said substrate, wherein the coating comprises a plurality of layers, wherein at least one layer comprises a pharmaceutical agent in a therapeutically desirable morphology, and wherein the device is adapted to transfer at least a portion of the coating from the substrate to an intervention site upon stimulation of the coating.

Provided herein is a medical device comprising a substrate and a coating on at least a portion of said substrate, wherein said coating is at least partially continuous, has at least one portion conformal to the substrate, and comprises a pharmaceutical agent in a therapeutically desirable morphology, and wherein the device is adapted to free at least a portion of the coating from the substrate upon stimulation of the coating.

Provided herein is a medical device comprising: a substrate and a coating on at least a portion of said substrate, wherein said coating is at least partially continuous, has at least one portion conformal to the substrate, and comprises a pharmaceutical agent in a therapeutically desirable morphology, and wherein the device is adapted to dissociate at least a portion of the coating from the substrate upon stimulation of the coating.

Provided herein is a medical device comprising a substrate and a coating on at least a portion of said substrate, wherein said coating is at least partially continuous, has at least one portion conformal to the substrate, and comprises a pharmaceutical agent in a therapeutically desirable morphology, and wherein the device is adapted to transfer at least a portion of the coating from the substrate to an intervention site upon stimulation of the coating.

In some embodiments, the therapeutically desirable morphology comprises a crystalline form of the pharmaceutical agent that is not a microcapsule.

Provided herein is a medical device comprising: a substrate; and a coating on at least a portion of said substrate, wherein said coating comprises an active agent, and wherein at least a portion of the coating is adapted to transfer from the substrate to an intervention site. In some embodiments, the portion of the coating is adapted to transfer from the substrate to the intervention site upon stimulation of the coating. In some embodiments, the device is adapted to transfer the portion of the coating from the substrate to the intervention site upon stimulation of the substrate. In some embodiments, stimulation of the coating is achieved by stimulation of the substrate. In some embodiments, stimulation of the substrate translates into a stimulation of the coating to transfer the coating portion from the substrate to the intervention site.

Provided herein is a medical device comprising: a substrate; and a coating on at least a portion of said substrate, wherein said coating comprises an active agent, and wherein at least a portion of the active agent is adapted to transfer from the substrate to an intervention site. In some embodiments, the portion of the active agent is adapted to transfer from the substrate to the intervention site upon stimulation of the coating.

Provided herein is a medical device comprising: a substrate; and a coating on at least a portion of said substrate, wherein said coating comprises an active agent, and wherein the device is adapted to transfer at least a portion of the coating from the substrate to an intervention site. In some embodiments, the device is adapted to transfer the portion of the coating (coating portion) from the substrate to the intervention site upon stimulation of the coating.

Provided herein is a medical device comprising: a substrate; and a coating on at least a portion of said substrate, wherein said coating comprises an active agent, and wherein the device is adapted to transfer at least a portion of the active agent from the substrate to an intervention site. In some embodiments, the device is adapted to transfer the portion of the active agent from the substrate to the intervention site upon stimulation of the coating.

Provided herein is a medical device comprising: a substrate; and a coating on at least a portion of said substrate, wherein said coating comprises an active agent, wherein the device is adapted to free at least a portion of the coating from the substrate at an intervention site. In some embodiments, the device is adapted to free the portion of the coating from the substrate at the intervention site upon stimulation of the coating.

Provided herein is a medical device comprising: a substrate; and a coating on at least a portion of said substrate, wherein said coating comprises an active agent, wherein the device is adapted to dissociate at least a portion of the coating from the substrate at an intervention site. In some embodiments, the device is adapted to dissociate the portion of the coating from the substrate at the intervention site upon stimulation of the coating.

Provided herein is a medical device comprising: a substrate; and a coating on at least a portion of said substrate, wherein said coating comprises an active agent, wherein the device is adapted to dissociate at least a portion of the coating from the substrate and to deliver said portion of the coating to an intervention site. In some embodiments, the device is adapted to deliver the portion of the coating to the intervention site upon stimulation of the coating.

Provided herein are drug delivery devices and methods that provide (1) a drug or multiple drugs in the form of, for example, films, solid solutions, particle mixtures containing nano, – micro and/or macro particles. The particles may be coated particles, polymerized particles containing one drug or multiple drugs optionally mixed with a polymer or multiple polymers. The polymers may be permanent or bioabsorbable.

One embodiment provides a percutaneous medical device with a coating that, upon deployment in the body, delivers some or all of the coating to a specific therapeutic site in the body. The device can be a permanent implant, for example a stent, or a transient device, such as a balloon catheter. Several other types of devices are contemplated in the present application. Another embodiment provides intraocular drug delivery device. Another embodiment provides a surgical tool. An illustrative but non-exhaustive list of devices contemplated herein is provided herein.

In one embodiment, delivery of the coating to the tissue at a site inside the body of a subject occurs by a coating that dissociates from the substrate via: (1) plastic deformation of the coating by compressive, shear, internally generated and/or externally generated forces, (2) shearing of the coating from the surface of the device, (3) bulk migration of the coating from the device into the tissue, and/or (4) separation from the device due to hydrolysis of the polymer, resulting in a weak bond between the coating and the device. The devices provided herein are for the transfer of some or all of the coating from the device to the local tissue to provide a targeted therapeutic effect. In some embodiments (need more details of dissociation—from the "stimulation" and other ideas in the claims)

The devices and method provided herein allow for intervention at targeted disease-states that in some embodiments are site-specific medical indications, including without limitation lesions, occlusions, infections, tumors, regional sites for tumor therapy such as intraperitoneal delivery, local sites of angiogenesis or inflammation such as sites within the eye or retina, gingival delivery for periodontal disease, within the joints in the synovial fluid, in the ventricle to delivery to the CNS spinal fluid, and embolic devices that also delivery drugs.

The devices and methods provided herein are contemplated to be used in the treatment of any disease that would benefit from targeted local delivery of a pharmaceutical and/or active biological agent. Examples of diseases include without limitation coronary artery disease, peripheral artery disease (e.g. carotid, femorial, etc), urinary tract obstructions and/or infections, biliary tract obstructions and/or infections, tumors/cancer, vascular obstructions (e.g. embolisms, lacunar or embolic stroke, varicose veins, etc.), neurological disorders, post-operative infections, diseases of the GI tract, diseases of the reproductive system (fallopian tubes), diseases of the Ear-Nose-Throat and any disease associated with an impairment of flow through a body tubular structure (e.g., dry eye).

In one embodiment, the coating comprises one or more drugs, optionally one or more adjuncts or excipients and one or more polymer compositions. The polymer compositions may be permanent or bioabsorbable; more preferably bioabsorbable (e.g.; PLGA based w/1-95% glycolic acid content).

One pervasive challenge to alternative technologies to deliver drugs via percutaneous catheter devices is how to insure that the drug-formulation is not shed during positioning of the device to the therapeutic site. In other words: how to insure that the drug is not washed off during insertion. This challenge leads to an advantage of the current invention vs. prior art because of the specific use of a polymeric formulation in the coating and the method of creating the coating and its formulation.

Embodiments provided herein maintain the drug within a mechanically sound polymeric coating (as opposed to coated as particles or formulated in a viscous oil), the coating is much more likely to maintain adhesion to the device during insertion. In these embodiments, there is little or no release of the coating until the device is deployed at the therapeutic site.

For example, and without limitation, the devices and methods provided herein may be advantageously employed in the local treatment of vascular diseases, the local treatment of internal diseases via providing drug 'upstream' in the vasculature from disease sites for: infection, oncology, etc., the local or regional treatment of tumors, the local treatment infections, particularly those that are hard to treat with systemic antibiotics, for example due to poor circulation to the infected site (e.g.; orthopedic, extremities in diabetics, etc), the local treatment of neurological disorders such as pain ailments.

In embodiments involving vascular diseases, the devices and methods provided herein may advantageously employ coating technology to mitigate the formation of free particles that could become entrained in the blood stream and cause negative complications such as emboli. For example, some embodiments are based on the utilization of soft coatings that undergo facile bulk flow under stress. Other embodiments are based on the utilization of biodegradable materials such as PLGA polymers that are mechanically sound at the time of implant, then over time degrade to lose their cohesion and/or adhesion to the surface of the device. Yet other embodiments are based on utilization of layered or laminated coatings (laminated layers) to directly control the transfer mechanisms of plastic deformation, shear and bulk-migration. Yet other embodiments use all three aspects described above.

In some embodiments, the coating comprises laminated layers that allow direct control of the transfer, freeing, and/or dissociation of the coating from the substrate. In some embodiments, the coating comprises laminated layers that allow direct control of the delivering, depositing, and/or tacking of the coating at and/or to the intervention site. In some embodiments, the coating comprises laminated layers that allow direct control of the transferring, freeing, depositing, tacking, and/or dissociating of the coating from the substrate, wherein at least one of the layers comprises the active agent. In some embodiments, the coating comprises laminated layers that allow direct control of the transferring, freeing, depositing, tacking, and/or dissociating of the coating from the substrate, wherein at least one of the layers comprises the pharmaceutical agent. The embodiments incorporating a stent form or framework provide the ability to radiographically monitor the stent in deployment. In an alternative embodiment, the inner-diameter of the stent can be masked (e.g. by a non-conductive mandrel). Such masking would prevent additional layers from being on the interior diameter (abluminal) surface of the stent. The resulting configuration may be desirable to provide preferential elution of the drug toward the vessel wall (luminal surface of the stent) where the therapeutic effect of anti-restenosis is desired, without providing the same antiproliferative drug(s) on the abluminal surface, where they may retard healing, which in turn is suspected to be a cause of late-stage safety problems with current DESs.

One particular advantage provided herein for embodiments wherein the device is a stent (coronary, peripheral, non-vascular etc.) is the ability to deliver the coating to a much greater area/volume of the arterial wall due to the 'spreading' of the drug and polymer formulation. This is in contrast to a traditional DES that delivers drug solely by diffusion of the drug out of the coating that permanently remains on the stent strut. This embodiment may provide clinical advantages, especially as stent struts advance to thinner and smaller diameters, of treating more, and more homogenously, the entire site of arterial injury caused by deployment of the stent.

Provided herein is a method comprising providing a medical device, wherein the medical device comprises a substrate and a coating on at least a portion of said substrate, and wherein the coating comprises a plurality of layers, wherein at least one layer comprises a pharmaceutical agent in a therapeutically desirable morphology, and freeing at least a portion of the coating from the substrate upon stimulating the coating with a stimulation.

Provided herein is a method comprising providing a medical device, wherein the medical device comprises a substrate and a coating on at least a portion of said substrate, and wherein the coating comprises a plurality of layers, wherein at least one layer comprises a pharmaceutical agent in a therapeutically desirable morphology, and dissociating at least a portion of the coating from the substrate upon stimulating the coating with a stimulation.

Provided herein is a method comprising providing a medical device, wherein the medical device comprises a substrate and a coating on at least a portion of said substrate, and wherein the coating comprises a plurality of layers, wherein at least one layer comprises a pharmaceutical agent in a therapeutically desirable morphology, and transferring at least a portion of the coating from the substrate to the intervention site upon stimulating the coating with a stimulation.

Provided herein is a method comprising providing a medical device, wherein the medical device comprises a substrate and a coating on at least a portion of said substrate, wherein said coating is at least partially continuous, has at least one portion conformal to the substrate, and comprises a pharmaceutical agent in a therapeutically desirable morphology, and freeing at least a portion of the coating from the substrate upon stimulating the coating with a stimulation.

Provided herein is a method comprising providing a medical device, wherein the medical device comprises a substrate and a coating on at least a portion of said substrate, wherein said coating is at least partially continuous, has at least one portion conformal to the substrate, and comprises a pharmaceutical agent in a therapeutically desirable morphology, and dissociating at least a portion of the coating from the substrate upon stimulating the coating with a stimulation.

Provided herein is a method comprising providing a medical device, wherein the medical device comprises a substrate and a coating on at least a portion of said substrate, wherein said coating is at least partially continuous, has at least one portion conformal to the substrate, and comprises a pharmaceutical agent in a therapeutically desirable morphology, and transferring at least a portion of the coating from the substrate to the intervention site upon stimulating the coating with a stimulation.

In some embodiments, the therapeutically desirable morphology comprises a crystalline form of the pharmaceutical agent that is not a microcapsule.

Provided herein is a method comprising providing a medical device, wherein the medical device comprises a substrate and a coating on at least a portion of said substrate, and wherein said coating comprises an active agent, and freeing greater than 35% of the coating from the substrate upon stimulating the coating with a stimulation.

Provided herein is a method comprising providing a medical device, wherein the medical device comprises a substrate and a coating on at least a portion of said substrate, and wherein said coating comprises an active agent, and dissociating greater than 35% of the coating from the substrate upon stimulating the coating with a stimulation.

Provided herein is a method comprising providing a medical device, wherein the medical device comprises a substrate and a coating on at least a portion of said substrate, and wherein said coating comprises an active agent, and transferring greater than 35% of the coating from the substrate to the intervention site upon stimulating the coating with a stimulation.

In some embodiments, the single stimulation lasts at most 20 seconds. In some embodiments, the device is adapted to free, dissociate, and/or transfer substantially all of the coating upon the single stimulation of the coating. In some embodiments, substantially all of the coating frees, dissociates, and/or transfers from the substrate instantaneously upon stimulating the coating.

Provided herein is a method comprising providing a medical device, wherein the medical device comprises a substrate and a coating on at least a portion of said substrate, wherein said coating comprises an active agent, and wherein the coating is patterned, and freeing at least a portion of the coating from the substrate upon stimulating the coating with a stimulation.

Provided herein is a method comprising providing a medical device, wherein the medical device comprises a substrate and a coating on at least a portion of said substrate, wherein said coating comprises an active agent, and wherein the coating is patterned, and dissociatng at least a portion of the coating from the substrate upon stimulating the coating with a stimulation.

Provided herein is a method comprising providing a medical device, wherein the medical device comprises a substrate and a coating on at least a portion of said substrate, wherein said coating comprises an active agent, and wherein the coating is patterned, and transferring at least a portion of the coating from the substrate to the intervention site upon stimulating the coating with a stimulation.

In some embodiments, the patterned coating comprises at least two different shapes.

Provided herein is a method comprising: providing a medical device, wherein the medical device comprises a substrate and a coating on at least a portion of the substrate, wherein the coating comprises an active agent; and transferring at least a portion of the coating from the substrate to an intervention site. In some embodiments, the transferring the coating portion (i.e. the portion of the coating) from the substrate to the intervention site is upon stimulating the coating with a stimulation. In some embodiments, the transferring the coating portion from the substrate to the intervention site is upon stimulating the substrate with a stimulation. In some embodiments, stimulating the coating is achieved by stimulating the substrate. In some embodiments, stimulating the substrate translates into stimulating the coating to transfer the coating portion from the substrate to the intervention site.

Provided herein is a method comprising: providing a medical device, wherein the medical device comprises a substrate and a coating on at least a portion of the substrate, wherein the coating comprises an active agent; and transferring at least a portion of the active agent from the substrate to an intervention site. In some embodiments, the transferring the active agent portion (i.e. the portion of the active agent) from the substrate to the intervention site is upon stimulating the coating with a stimulation.

Provided herein is a method comprising: providing a medical device, wherein the medical device comprises a substrate and a coating on at least a portion of the substrate, wherein the coating comprises an active agent; and freeing at least a portion of the coating from the substrate at an intervention site. In some embodiments, the freeing the coating portion (i.e. the portion of the coating) from the substrate is upon stimulating the coating with a stimulation.

Provided herein is a method comprising: providing a medical device, wherein the medical device comprises a substrate and a coating on at least a portion of the substrate, wherein the coating comprises an active agent; and dissociating at least a portion of the coating from the substrate at an intervention site. In some embodiments, the dissociating the coating portion (i.e. the portion of the coating) from the substrate is upon stimulating the coating with a stimulation.

Provided herein is a method comprising: providing a medical device, wherein the medical device comprises a substrate and a coating on at least a portion of the substrate, wherein the coating comprises an active agent; and depositing at least a portion of the coating at an intervention site. In some embodiments, the depositing the coating portion (i.e. the portion of the coating) at the intervention site is upon stimulating the coating with a stimulation.

Provided herein is a method comprising: providing a medical device, wherein the medical device comprises a substrate and a coating on at least a portion of the substrate, wherein the coating comprises an active agent; and tacking at least a portion of the coating to an intervention site. In some embodiments, the tacking the coating portion (i.e. the portion of the coating) to the intervention site is upon stimulating the coating with a stimulation.

In some embodiments, the substrate comprises a balloon. In some embodiments, the portion of the balloon having coating thereon comprises an outer surface of the balloon. In some embodiments, the outer surface is a surface of the balloon exposed to a coating prior to balloon folding. In some embodiments, the outer surface is a surface of the balloon exposed to a coating following balloon folding. In some embodiments, the outer surface is a surface of the balloon exposed to a coating following balloon crimping. In some embodiments, the coating comprises a material that undergoes plastic deformation at pressures provided by inflation of the balloon. In some embodiments, the coating comprises a material that undergoes plastic deformation at a pressure that is less than the rated burst pressure of the balloon.

In some embodiments, the coating comprises a material that undergoes plastic deformation at a pressure that is less than the nominal inflation pressure of the balloon. In some embodiments, the coating comprises a material that undergoes plastic deformation with at least 8 ATM of pressure. In some embodiments, the coating comprises a material that undergoes plastic deformation with at least 6 ATM of pressure. In some embodiments, the coating comprises a material that undergoes plastic deformation with at least 4 ATM of pressure. In some embodiments, the coating comprises a material that undergoes plastic deformation with at least 2 ATM of pressure.

In some embodiments, the balloon is a compliant balloon. In some embodiments, the balloon is a semi-compliant balloon. In some embodiments, the balloon is a non-compliant balloon. In some embodiments, the balloon conforms to a shape of the intervention site.

In some embodiments, the balloon comprises a cylindrical portion. In some embodiments, the balloon comprises a substantially spherical portion. In some embodiments, the balloon comprises a complex shape. In some embodiments, the complex shape comprises at least one of a double noded shape, a triple noded shape, a waisted shape, an hourglass shape, and a ribbed shape.

Some embodiments provide devices that can serve interventional purposes in addition to delivery of therapeutics, such as a cutting balloon. In some embodiments, the substrate comprises a cutting balloon. In some embodiments, the cutting balloon comprises at least one tacking element adapted to tack the coating to the intervention site. In some embodiments, the tacking element is adapted to secure the coating to the cutting balloon until inflation of the cutting balloon. In some embodiments, the tacking element comprises a wire. In some embodiments, the wire is shaped in the form of an outward pointing wedge. In some embodiments, the tacking element does not cut tissue at the intervention site.

One illustration devices provided herein include a cutting balloon for the treatment of vascular disease (e.g.; occluded lesions in the coronary or peripheral vasculature). In this embodiment, the coating may be preferentially located on the 'cutting wire' portion of the device. Upon deployment, the wire pushes into the plaque to provide the desired therapeutic 'cutting' action. During this cutting, the polymer and drug coating is plastically deformed off of the wire by the combination of compressive and shear forces acting on the wire—leaving some or all of the coating embedded in the plaque and/or artery wall. A similar approach may be applied to delivery of oncology drugs (a) directly to tumors and/or, (b) to the arteries delivering blood to the tumors for site-specific chemotherapy, and/or (c) to the voids left after the removal of a tumor (lumpectomy). These oncology (as well as other non-vascular) applications may not require the 'cutting' aspects and could be provided by coatings directly onto the balloon or onto a sheath over the balloon or according to an embodiment wherein the coating forms a sheath over the deflated (pleated) balloon.

A cutting balloon embodiment described herein provides several advantages. Such embodiment allows for concentrating the mechanical force on the coating/wire as the balloon is inflated—the wire may serve to concentrate the point-of-contact-area of the balloon expansion pressure resulting in a much higher force for plastic deformation of the drug and polymer coating vs. the non-cutting plain balloon which may distribute the pressure over a much larger area (therefore lower force proportional to the ratio of the areas). Embodiments involving a cutting balloon provide for the use of polymers that would otherwise be too rigid (higher modulus) to deform from a non-cutting balloon.

Other embodiments provided herein are based on geometric configurations of the device that optimize both the deformation and the bulk-migration of the coating from the device. In one embodiment wherein the device is a cutting balloon, the (coated) wire of the cutting balloon is shaped like a wedge, pointed outward.

Another embodiment provides catheter-based devices where the drug-delivery formulation is delivered to the therapeutic site in the vasculature via inflation of a balloon.

One embodiment provides coated percutaneous devices (e.g.; balloons, whether cutting balloons or other balloon types) that, upon deployment at a specific site in the patient, transfer some or all of the drug-delivery formulation (5-10%, 10-25%, 25-50%, 50-90%, 90-99%, 99-100%) to the site of therapeutic demand. In certain embodiments, the balloon is at least in part cylindrical as expanded or as formed. In certain embodiments, the balloon is at least in part bulbous as expanded or as formed. In certain embodiments, the balloon is at least in part spherical as expanded or as formed. In certain embodiments, the balloon has a complex shape as expanded or as formed (such as a double noded shape, a triple noded shape, has a waist, and/or has an hourglass shape, for non-limiting example).

In some embodiments, the substrate comprises a biomedical implant. In some embodiments, the substrate comprises a surgical tool.

In some embodiments, the substrate comprises at least one of a stent, a joint, a screw, a rod, a pin, a plate, a staple, a shunt, a clamp, a clip, a suture, a suture anchor, an electrode, a catheter, a lead, a graft, a dressing, a pacemaker, a pacemaker housing, a cardioverter, a cardioverter housing, a defibrillator, a defibrillator housing, a prostheses, an ear drainage tube, an ophthalmic implant, an orthopedic device, a vertebral disk, a bone substitute, an anastomotic device, a perivascular wrap, a colostomy bag attachment device, a hemostatic barrier, a vascular implant, a vascular support, a tissue adhesive, a tissue sealant, a tissue scaffold, and an intraluminal device.

In some embodiments, the substrate comprises at least a portion of a tool for delivering to the intervention site a biomedical implant, wherein the substrate is the biomedical implant or wherein the substrate is a portion of the device that is not the biomedical implant. In some embodiments, the substrate comprises at least a portion of a tool for performing a medical procedure. In some embodiments, the tool comprises at least one of: a knife, a scalpel, a guidewire, a guiding catheter, a introduction catheter, a distracter, a needle, a syringe, a biopsy device, an articulator, a Galotti articulator, a bone chisel, a bone crusher, a cottle cartilage crusher, a bone cutter, a bone distractor, an Ilizarov apparatus, an intramedullary kinetic bone distractor, a bone drill, a bone extender, a bone file, a bone lever, a bone mallet, a bone rasp, a bone saw, a bone skid, a bone splint, a bone button, a caliper, a cannula, a catheter, a cautery, a clamp, a coagulator, a curette, a depressor, a dilator, a dissecting knife, a distractor, a dermatome, forceps, dissecting forceps, tissue forceps, sponge forceps, bone forceps, Carmalt forceps, Cushing forceps, Dandy forceps, DeBakey forceps, Doyen intestinal forceps, epilation forceps, Halstead forceps, Kelly forceps, Kocher forceps, mosquito forceps, a hemostat, a hook, a nerve hook, an obstetrical hook, a skin hook, a hypodermic needle, a lancet, a luxator, a lythotome, a lythotript, a mallet, a partsch mallet, a mouth prop, a mouth gag, a mammotome, a needle holder, an occluder, an osteotome, an Epker osteotome, a periosteal elevator, a Joseph elevator, a Molt periosteal elevator, an Obweg periosteal elevator, a septum elevator, a Tessier periosteal elevator, a probe, a retractor, a Senn retractor, a Gelpi retractor, a Weitlaner retractor, a USA-Army/Navy retractor, an O×Connor-O×Sullivan retractor, a Deaver retractor, a Bookwalter retractor, a Sweetheart retractor, a Joseph skin hook, a Lahey retractor, a Blair (Rollet) retractor, a rigid rake retractor, a flexible rake retractor, a Ragnell retractor, a Linde-Ragnell retractor, a Davis retractor, a Volkman retractor, a Mathieu retractor, a Jackson tracheal hook, a Crile retractor, a Meyerding finger retractor, a Little retractor, a Love Nerve retractor, a Green retractor, a Goelet retractor, a Cushing vein retractor, a Langenbeck retractor, a Richardson retractor, a Richardson-Eastmann retractor, a Kelly retractor, a Parker retractor, a Parker-Mott retractor, a Roux retractor, a Mayo-Collins retractor, a Ribbon retractor, an Alm retractor, a self retaining retractor, a Weitlaner retractor, a Beckman-Weitlaner retractor, a Beckman-Eaton retractor, a Beckman retractor, an Adson retractor, a rib spreader, a rongeur, a scalpel, an ultrasonic scalpel, a laser scalpel, scissors, iris scissors, Kiene scissors, Metzenbaum scissors, Mayo scissors, Tenotomy scissors, a spatula, a speculum, a mouth speculum, a rectal speculum, Sim's vaginal speculum, Cusco's vaginal speculum, a sternal saw, a suction tube, a surgical elevator, a surgical hook, a surgical knife, surgical mesh, a surgical needle, a surgical snare, a surgical sponge, a surgical spoon, a surgical stapler, a suture, a syringe, a tongue depressor, a tonsillotome, a tooth extractor, a towel clamp, towel forceps, Backhaus towel forceps, Lorna towel forceps, a tracheotome, a tissue expander, a subcutaneus inflatable balloon expander, a trephine, a trocar, tweezers, and a venous cliping.

One particular advantage provided herein for embodiments wherein the device is a stent (coronary, peripheral, non-vascular etc.) is the ability to deliver the coating to a much greater area/volume of the arterial wall due to the 'spreading' of the drug and polymer formulation. This is in contrast to a traditional DES that delivers drug solely by diffusion of the drug out of the coating that permanently remains on the stent strut. This embodiment may provide clinical advantages, especially as stent struts advance to thinner and smaller diameters, of treating more, and more homogenously, the entire site of arterial injury caused by deployment of the stent.

One embodiment provides coated percutaneous devices (e.g.; balloons, whether cutting balloons or other balloons) that, upon deployment at a specific site in the patient (intervention site), transfer some or all of the drug-delivery formulation (5-10%, 10-25%, 25-50%, 50-90%, 90-99%, 99-100%) to the site of therapeutic demand (intervention site). In certain embodiments, the balloon is at least in part cylindrical as expanded or as formed. In certain embodiments, the balloon is at least in part bulbous as expanded or as formed. In certain embodiments, the balloon is at least in part spherical as expanded or as formed. In certain embodiments, the balloon has a complex shape as expanded or as formed (such as a double noded shape, a triple noded shape, has a waist, and/or has an hourglass shape, for non-limiting example).

Other embodiments provided herein are based on geometric configurations of the device that optimize both the deformation and the bulk-migration of the coating from the device. In one embodiment wherein the device is a cutting balloon, the (coated) wire of the cutting balloon is shaped like a wedge, pointed outward.

In some embodiments, the device comprises a tacking element that cooperates with the stimulation to tack the coating to the intervention site. In some embodiments, the device comprises a tacking element that tacks the coating to the substrate until the stimulating.

In some embodiments, the intervention site is in or on the body of a subject. In some embodiments, the intervention site is a vascular wall. In some embodiments, the intervention site is a non-vascular lumen wall. In some embodiments, the intervention site is a vascular cavity wall.

In some embodiments, the intervention site is a wall of a body cavity. In some embodiments, the body cavity is the result of a lumpectomy. In some embodiments, the intervention site is a cannulized site within a subject.

In some embodiments, the intervention site is a sinus wall. In some embodiments, the intervention site is a sinus cavity wall. In some embodiments, the active agent comprises a corticosteroid.

In some embodiments, the intervention site is located in the reproductive system of a subject. In some embodiments, the device is adapted to aid in fertility. In some embodiments, the device is adapted to treat a sexually transmitted disease. In some embodiments, the device is adapted to substantially prevent pregnancy. In some embodiments, the active agent comprises a hormone. In some embodiments, the device is adapted to substantially prevent transmission of a sexually transmitted disease. In some embodiments, the device is adapted to treat an ailment of the reproductive system.

In some embodiments, the intervention site is located in the urinary system of a subject. In some embodiments, the device is adapted to treat a disease of the urinary system. In some embodiments, the active agent comprises fluoroquinolone. In some embodiments, the pharmaceutical agent comprises fluoroquinolone.

In some embodiments, the intervention site is located at a tumor site. In some embodiments, the tumor site is where a tumor is located. In some embodiments, the tumor site is where a tumor was located prior to removal and/or shrinkage of the tumor. In some embodiments, the active agent comprises mitomycin C. In some embodiments, the pharmaceutical agent comprises mitomycin C.

In some embodiments, the intervention site is located in the ear. In some embodiments, the intervention site is located in the esophagus. In some embodiments, the active agent comprises a lidocaine. In some embodiments, the pharmaceutical agent comprises a lidocaine.

In some embodiments, the intervention site is located in the larynx. In some embodiments, the intervention site is a location of an injury. In some embodiments, the active agent comprises a betamethasone. In some embodiments, the pharmaceutical agent comprises a betamethasone.

In some embodiments, the intervention site is an infection site. In some embodiments, the infection site is a site wherein an infection may occur, and wherein the active agent is capable of substantially preventing the infection. In some embodiments, the infection site is a site wherein an infection has occurred, and wherein the active agent is capable of slowing spread of the infection. In some embodiments, the infection site is a site wherein an infection has occurred, and wherein the active agent is capable of treating the infection. In some embodiments, the active agent comprises an anti-infective agent. In some embodiments, the pharmaceutical agent comprises an anti-infective agent. In some embodiments, the anti-infective agent comprises clindamycin.

In some embodiments, the intervention site is a surgery site. In some embodiments, the intervention site is an ocular site.

In some embodiments, the coating is capable of promoting healing. In some embodiments, the active agent comprises a growth factor. In some embodiments, the growth factor comprises at least one of: an epidermal growth factor (EGF), a transforming growth factor-alpha (TGF-alpha), a hepatocyte growth factor (HGF), a vacscular endothelial growth factor (VEGF), a platelet derived growth factor (PDGF), a fibroblast growth factor 1 (FGF-1), a fibroblast growth factor 2 (FGF-2), a transforming growth factor-beta (TGF-beta), and a keratinocyte growth factor (KGF). In some embodiments, the active agent comprises a stem cell.

In some embodiments, the coating is capable of at least one of: retarding healing, delaying healing, and preventing healing. In some embodiments, the coating is capable of at least one of: retarding, delaying, and preventing the inflammatory phase of healing. In some embodiments, the coating is capable of at least one of: retarding, delaying, and preventing the proliferative phase of healing. In some embodiments, the coating is capable of at least one of: retarding, delaying, and preventing the maturation phase of healing. In some embodiments, the coating is capable of at least one of: retarding, delaying, and preventing the remodeling phase of healing. In some embodiments, the active agent comprises an anti-angiogenic agent. In some embodiments, the coating is capable of releiving pain. In some embodiments, the coating is capable of releiving joint pain. In some embodiments, the coating is capable of blocking pain.

In some embodiments, the coating is a sheath. In some embodiments, the sheath is plastically deformable. In some embodiments, at least a portion of the sheath is capable of being left at the intervention site upon removal of the substrate from the intervention site. In some embodiments, the substrate is capable of mechanically deforming the sheath at the intervention site.

In some embodiments, the device comprises a retractable sheath. In some embodiments, the sheath is adapted to expose the coating to the intervention site upon retraction.

In some embodiments, the coating comprises a bioadhesive. In some embodiments, the active agent comprises a bioadhesive. In some embodiments, the pharmaceutical agent comprises a bioadhesive. In some embodiments, the coating is adapted to close a vascular puncture. In some embodiments, the coating aids in closing a vascular puncture. In some embodiments, the coating is adapated to close a vascular puncture. In some embodiments the active agent comprises a bioadhesive. To close a vascular puncture may include sealing the vascular puncture, and/or providing a seal that closes the vascular puncture. The seal may be the coating of the device. The bioadhesive may comprise an arylates, and/or an cryanoacrylates. Bioadhesives may also and/or alternatively be called tissue adhesives. The bioadhesive may comprise n-butyl cyanoacrylate, n-butyl-2-cyanoacrylate, 2-octylcyanoacrylate, and Dermabond, and/or variations thereof.

Bioadhesives as used herein refer to, in some embodiments, natural polymeric materials that act as adhesives. The term "bioadhesive" may also and/or alternatively be used to describe a glue formed synthetically from biological monomers such as sugars, and/or to mean a synthetic material designed to adhere to biological tissue. Bioadhesives may consist of a variety of substances, for example: proteins and carbohydrates. Proteins such as gelatin and carbohydrates such as starch are contemplated herein, as well as syntehtic alternatives to the same. Bioadhesives secreted by microbes and by marine molluscs and crustaceans are contemplated herein.

In some embodiments, the coating substantially prevents adhesion of body tissue. In some embodiments, the coating promotes prevention of adhesion of body tissue. In some embodiments, the coating comprises hyaluronic acid, hyaluronate, salts, acids, conjugates, and/or derivatives thereof. In some embodiments, the active agent comprises hyaluronic acid, hyaluronate, salts, acids, conjugates, and/or derivatives thereof.

In some embodiments, the device is used to substantially prevent tissue adhesion. In some embodiments, the device is adapted to substantially prevent tissue adhesion. To substantially prevent tissue adhesion, as used herein, refers to the ability for the device to, at least in part, block at least a portion of the biologic process that leads to tissue adhesion. To substantially prevent tissue adhesion, as used herein, amy also and/or alternatively refer to the ability for the device to block at least a portion of fibrin deposition by the body. To substantially prevent tissue adhesion, as used herein, may also and/or alternatively refer to the ability for the device to promote dissolving of fibrin. To substantially prevent tissue adhesion, as used herein, may also and/or alternatively refer to the ability for the device to promote blood contact with injured tissue. In some embodiments, the device comprises a coating comprising hyaluronic to substantially prevent tissue adhesion.

"Tissue adhesion" as used herein refers to internal scars that may form after surgury on or between internal organs and/or body tissue. As used herein, "body tissue" or "tissue" refers to any biologic tissue, which includes any ensemble of cells, not necessarily identical. As used herein, "body tissue" or "tissue" may also or alternatively refer to any one of muscle tissue, connective tissue, nervous tissue, epithelial tissue, and combinations thereof. Tissue between which adhesions may form can be of the same tissue type, and/or of different tissue types.

When tissue is injured, the area becomes inflamed. The body responds by depositing fibrin at the injury site. Fibrin can act like glue between the injury site and nearby tissues, causing them to stick together. Normally, as the body heals, the fibrin dissolves and is replaced with normal tissue. In some cases, however, decreased blood flow to the injured tissue prevents the fibrin from dissolving. The result is an internal scar, also called an adhesion. Adhesions between tissues can twist and/or pull organs out of their normal positions within the body. This scar tissue may form as a result of injury to organs and tissues during surgery. These injuries are typically caused by suturing, cauterization, and abrading tissues and organs during surgery, however, other causes are envisioned herein.

In some embodiments, the device is adapted to close a vascular puncture. In some embodiments, the coating is adapted to close a vascular puncture. In some embodiments the active agent comprises a bioadhesive. To close a vascular puncture may include sealing the vascular puncture, and/or providing a seal that closes the vascular puncture. The seal may be the coating of the device. The bioadhesive may include, but not be limited to: arylates, cryanoacrylates.

Provided herein is a medical device comprising a substrate and a coating on at least a portion of said substrate, wherein said coating comprises an active agent, and wherein the device is adapted to free greater than 35% of the coating from the substrate upon a single stimulation of the coating.

Provided herein is a medical device comprising a substrate and a coating on at least a portion of said substrate, wherein said coating comprises an active agent, and wherein the device is adapted to dissociate greater than 35% of the coating from the substrate upon a single stimulation of the coating.

Provided herein is a medical device comprising a substrate and a coating on at least a portion of said substrate, wherein said coating comprises an active agent, and wherein the device is adapted to transfer greater than 35% of the coating from the substrate to an intervention site upon a single stimulation of the coating.

Provided herein is a method of forming a medical device comprising a substrate and a coating on at least a portion of the substrate, wherein the coating comprises an active agent, the method comprising providing the substrate; and forming the coating on at least a portion of the substrate by depositing the active agent on ths substrate by a dipping and/or a spraying process, wherein forming the coating results in greater than 35% of the coating being adapted to free from the substrate upon stimulating the coating with a single stimulation.

In some embodiments of the methods and/or devices provided herein, the single stimulation lasts at most 20 seconds. In some embodiments of the methods and/or devices provided herein, the device is adapted to free substantially all of the coating upon the single stimulation of the coating. In some embodiments, the single stimulation lasts at most 20 seconds. In some embodiments of the methods and/or devices provided herein, substantially all of the coating frees from the substrate instantaneously upon stimulation of the coating.

"Transfer" or "transference" or "transferring" as used herein in the context of the coating refers to the conveyance of all or any part of the coating from the substrate to an intervention site. The coating can be formulated such that part or all of it is transferred from the substrate, as desired. Some of the embodiments provided herein are based on transfer of the coating from the substrate to the body tissue involving one or more of (1) plastic deformation by compressive and/or shear force induced by deployment and/or induced by the native surrounding tissue and/or induced by the in-growth of new tissue catalyzed by the deployment of the device (2) shear transfer (wiping off) of the coating from the device outward (relative to the device) into the tissue, (3) bulk migration, and (4) separation from the device due to hydrolysis of the polymer, resulting in a week bond to the device. In some embodiments (need more details of dissociation—from the "stimulation" and other ideas in the claims)

Similarly, "transfer" as used herein in the context of the active agent refers to the conveyance of all or any fraction of an active agent from the substrate to an intervention site.

The term "adapted to transfer" a specific portion, e.g., at least about 10%, at least about 20%, at least about 30%, greater than 35%, at least about 50%, at least about 75%, at least about 85%, at least about 90%, at least about 95%, and/or at least about 99%, of a coating and/or active agent from the substrate to the intervention site refers to a device, coating, and/or substrate that is designed to transfer a certain percentage of its coating to the intervention site.

In some embodiments, the device is adapted to transfer a portion of the coating and/or active agent from the substrate to the intervention site. For non-limiting example, the device is so adapted by substrate attributes (for non-limiting example: substrate composition, substrate materials, shape, substrate deployment attributes, substrate delivery attributes, substrate pattern, and/or substrate texture), the delivery system of the substrate and coating (for non-limiting example: control over the substrate, control over the coating using the delivery system, the type of delivery system provided, the materials of the delivery system, and/or combinations thereof), coating attributes (for non-limiting example: selection of the active agent and/or the polymer and/or the polymer-active agent composition, or by the coating having a particular pattern—e.g. a ribbed pattern, a textured surface, a smooth surface, and/or another pattern, coating thickness, coating layers, and/or another physical and/or compositional attribute), release agent attributes (for non-limiting example: through the selection a particular release agent and/or how the release agent is employed to transfer the coating and/or the active agent, and/or how much of the release agent is used), and/or a combination thereof.

In some embodiments, the substrate is adapted to transfer a portion of the coating and/or active agent from the substrate to the intervention site. For non-limiting example, the substrate is so adapted by selection of the substrate composition, substrate materials, shape, substrate deployment attributes, substrate delivery attributes, substrate pattern, and/or substrate texture, and/or combinations thereof. For example, a balloon can be designed to only partially inflate within the confines of the intervention site. Partial inflation can prevent a designated portion of coating from being transferred.

In some embodiments, the coating is adapted to transfer a portion of the coating and/or active agent from the substrate to the intervention site. For non-limiting example the coating may be so adapted by selection of the active agent and/or the polymer and/or the polymer-active agent composition, or by the coating having a particular pattern—e.g. a ribbed pattern, a textured surface, a smooth surface, and/or another pattern, coating thickness, coating layers, and/or another physical and/or compositional attribute.

In some embodiments, the substrate is adapted to transfer a portion of the coating and/or active agent from the substrate to the intervention site. For non-limiting example, the substrate is so adapted by selection of the substrate composition, substrate materials, shape, substrate deployment attributes, substrate delivery attributes, substrate pattern, and/or substrate texture, and/or combinations thereof. For example, a balloon can be designed to only partially inflate within the confines of the intervention site. Partial inflation can prevent a designated portion of coating from being transferred.

In some embodiments, the coating is adapted to transfer a portion of the coating and/or active agent from the substrate to the intervention site. For non-limiting example the coating may be so adapted by selection of the active agent and/or the polymer and/or the polymer-active agent composition, or by the coating having a particular pattern—e.g. a ribbed pattern, a textured surface, a smooth surface, and/or another pattern, coating thickness, coating layers, and/or another physical and/or compositional attribute.

In some embodiments, transferring at least a portion of the coating comprises transferring at least about 10%, at least about 20%, at least about 30%, greater than 35%, at least about 50%, at least about 75%, at least about 85%, at least about 90%, at least about 95%, and/or at least about 99% of the coating from the substrate. In some embodiments, stimulating decreases the contact between the coating and the substrate. In some embodiments, transferring transfers less than about 1%, less than about 5%, less than about 10%. less than about 15%, less than about 25%, at most about 35%, less than about 50%, less than about 70%, less than about 80%, and/or less than about 90% of the coating absent stimulating at least one of the coating and the substrate.

In some embodiments, transferring at least a portion of the active agent comprises transferring at least about 10%, at least about 20%, at least about 30%, greater than 35%, at least about 50%, at least about 75%, at least about 85%, at least about 90%, at least about 95%, and/or at least about 99% of the active agent from the substrate. In some embodiments, stimulating decreases the contact between the coating and the substrate. In some embodiments, transferring transfers less than about 1%, less than about 5%, less than about 10%. less than about 15%, less than about 25%, at most about 35%, less than about 50%, less than about 70%, less than about 80%, and/or less than about 90% of the active agent absent stimulating at least one of the coating and the substrate.

The term "adapted to transfer at least a portion" of the coating or active agent to an intervention site refers to a device that is designed to transfer any portion of the coating or active agent to an intervention site.

The term "adapted to free" a portion of a coating and/or active agent from the substrate refers to a device, coating, and/or substrate that is designed to free a certain percentage of the coating and/or active agent from the substrate. As used herein, a device, coating, and/or substrate that is designed to free a certain percentage of the coating and/or active agent from the substrate is designed to unrestrain the coating and/or active agent from the substrate, and/or to remove any obstruction and/or connection the coating may have to the substrate (whether direct or indirect).

In some embodiments, the device is adapted to free a portion of the coating and/or active agent from the substrate. For non-limiting example, the device is so adapted by substrate attributes (for non-limiting example: substrate composition, substrate materials, shape, substrate deployment attributes, substrate delivery attributes, substrate pattern, and/or substrate texture), the delivery system of the substrate and coating (for non-limiting example: control over the substrate, control over the coating using the delivery system, the type of delivery system provided, the materials of the delivery system, and/or combinations thereof), coating attributes (for non-limiting example: selection of the active agent and/or the polymer and/or the polymer-active agent composition, or by the coating having a particular pattern—e.g. a ribbed pattern, a textured surface, a smooth surface, and/or another pattern, coating thickness, coating layers, and/or another physical and/or compositional attribute), release agent attributes (for non-limiting example: through the selection a particular release agent and/or how the release agent is employed to transfer the coating and/or the active agent, and/or how much of the release agent is used), and/or a combination thereof.

In some embodiments, the substrate is adapted to free a portion of the coating and/or active agent from the substrate. For non-limiting example, the substrate is so adapted by selection of the substrate composition, substrate materials, shape, substrate deployment attributes, substrate delivery attributes, substrate pattern, and/or substrate texture, and/or combinations thereof. For example, a balloon can be designed to only partially inflate within the confines of the intervention site. Partial inflation can prevent a designated portion of coating from being freed.

In some embodiments, the coating is adapted to free a portion of the coating and/or active agent from the substrate. For non-limiting example the coating may be so adapted by selection of the active agent and/or the polymer and/or the polymer-active agent composition, or by the coating having a particular pattern—e.g. a ribbed pattern, a textured surface, a smooth surface, and/or another pattern, coating thickness, coating layers, and/or another physical and/or compositional attribute.

In some embodiments, the substrate is adapted to free a portion of the coating and/or active agent from the substrate to the intervention site. For non-limiting example, the substrate is so adapted by selection of the substrate composition, substrate materials, shape, substrate deployment attributes, substrate delivery attributes, substrate pattern, and/or substrate texture, and/or combinations thereof. For example, a balloon can be designed to only partially inflate within the confines of the intervention site. Partial inflation can prevent a designated portion of coating from being freed.

In some embodiments, the coating is adapted to free a portion of the coating and/or active agent from the substrate to the intervention site. For non-limiting example the coating may be so adapted by selection of the active agent and/or the polymer and/or the polymer-active agent composition, or by the coating having a particular pattern—e.g. a ribbed pattern, a textured surface, a smooth surface, and/or another pattern, coating thickness, coating layers, and/or another physical and/or compositional attribute.

In some embodiments, freeing at least a portion of the coating comprises freeing at least about 10%, at least about 20%, at least about 30%, greater than 35%, at least about 50%, at least about 75%, at least about 85%, at least about 90%, at least about 95%, and/or at least about 99% of the coating from the substrate. In some embodiments, stimulating decreases the contact between the coating and the substrate. In some embodiments, freeing frees less than about 1%, less than about 5%, less than about 10%. less than about 15%, less than about 25%, at most about 35%, less than about 50%, less than about 70%, less than about 80%, and/or less than about 90% of the coating absent stimulating at least one of the coating and the substrate.

The term "adapted to dissociate" a portion of a coating and/or active agent from the substrate refers to a device, coating, and/or substrate that is designed to dissociate a certain percentage of the coating and/or active agent from the substrate. As used herein, a device, coating, and/or substrate that is designed to dissociate a certain percentage of the coating and/or active agent from the substrate is designed to remove from association between the coating (and/or active agent) and the substrate. Also and/or alternatively, as used herein, a device, coating, and/or substrate that is designed to dissociate a certain percentage of the coating and/or active agent from the substrate is designed to separate the coating (and/or active agent) from the substrate. This separation may be reversible in some embodiments. This separation may not be reversible in some embodiments.

In some embodiments, the device is adapted to dissociate a portion of the coating and/or active agent from the substrate. For non-limiting example, the device is so adapted by substrate attributes (for non-limiting example: substrate composition, substrate materials, shape, substrate deployment attributes, substrate delivery attributes, substrate pattern, and/or substrate texture), the delivery system of the substrate and coating (for non-limiting example: control over the substrate, control over the coating using the delivery system, the type of delivery system provided, the materials of the delivery system, and/or combinations thereof), coating attributes (for non-limiting example: selection of the active agent and/or the polymer and/or the polymer-active agent composition, or by the coating having a particular pattern—e.g. a ribbed pattern, a textured surface, a smooth surface, and/or another pattern, coating thickness, coating layers, and/or another physical and/or compositional attribute), release agent attributes (for non-limiting example: through the selection a particular release agent and/or how the release agent is employed to transfer the coating and/or the active agent, and/or how much of the release agent is used), and/or a combination thereof.

In some embodiments, the substrate is adapted to dissociate a portion of the coating and/or active agent from the substrate. For non-limiting example, the substrate is so adapted by selection of the substrate composition, substrate materials, shape, substrate deployment attributes, substrate delivery attributes, substrate pattern, and/or substrate texture, and/or combinations thereof. For example, a balloon can be designed to only partially inflate within the confines of the intervention site. Partial inflation can prevent a designated portion of coating from being freed.

In some embodiments, the coating is adapted to dissociate a portion of the coating and/or active agent from the substrate. For non-limiting example the coating may be so adapted by selection of the active agent and/or the polymer and/or the polymer-active agent composition, or by the coating having a particular pattern—e.g. a ribbed pattern, a textured surface, a smooth surface, and/or another pattern, coating thickness, coating layers, and/or another physical and/or compositional attribute.

In some embodiments, the substrate is adapted to free a portion of the coating and/or active agent from the substrate to the intervention site. For non-limiting example, the substrate is so adapted by selection of the substrate composition, substrate materials, shape, substrate deployment attributes, substrate delivery attributes, substrate pattern, and/or substrate texture, and/or combinations thereof. For example, a balloon can be designed to only partially inflate within the confines of the intervention site. Partial inflation can prevent a designated portion of coating from being freed.

In some embodiments, the coating is adapted to dissociate a portion of the coating and/or active agent from the substrate to the intervention site. For non-limiting example the coating may be so adapted by selection of the active agent and/or the polymer and/or the polymer-active agent composition, or by the coating having a particular pattern—e.g. a ribbed pattern, a textured surface, a smooth surface, and/or another pattern, coating thickness, coating layers, and/or another physical and/or compositional attribute.

In some embodiments, dissociating at least a portion of the coating comprises dissociating at least about 10%, at least about 20%, at least about 30%, greater than 35%, at least about 50%, at least about 75%, at least about 85%, at least about 90%, at least about 95%, and/or at least about 99% of the coating from the substrate. In some embodiments, stimulating decreases the contact between the coating and the substrate. In some embodiments, dissociating dissociates less than about 1%, less than about 5%, less than about 10%. less than about 15%, less than about 25%, at most about 35%, less than about 50%, less than about 70%, less than about 80%, and/or less than about 90% of the coating absent stimulating at least one of the coating and the substrate.

"Plastic deformation" as used herein is the change in the physical shape of the coating by forces induced on the device. Plastic deformation results in increasing the contact area of the coating on the tissue and decreasing the contact area of the coating on the device. This change in contact area results in some or all of the coating being preferentially exposed to the tissue instead of the device. The terms "plastic deformation" and "plastically deform," as used herein in the context of a coating, are intended to include the expansion of the coating material beyond the elastic limit of the material such that the material is permanently deformed. "Elastic deformation" as used herein refers to a reversible alteration of the form or dimensions of the object under stress or strain, e.g., inflation pressure of a balloon substrate. The terms "plastic deformation" and "plastically deform," as used herein in the context of a balloon or other substrate, are intended to include the expansion of the substrate beyond the elastic limit of the substrate material such that the substrate material is permanently deformed. Once plastically deformed, a material becomes substantially inelastic and generally will not, on its own, return to its pre-expansion size and shape. "Residual plastic deformation" refers to a deformation capable of remaining at least partially after removal of the inflation stress, e.g., when the balloon is deflated. "Elastic deformation" as used herein refers to a reversible alteration of the form or dimensions of the object (whether it is the coating or the substrate) under stress or strain, e.g., inflation pressure.

"Shear transfer" as used herein is the force (or component of forces) orthogonal to the device that would drive the coating away from the device substrate. This could be induced on the device by deployment, pressure-response from the surrounding tissue and/or in-growth of tissue around the coating.

"Bulk migration" as used herein is the incorporation of the coating onto/into the tissue provided by the removal of the device and/or provided by degradation of the coating over time and/or provided by hydration of the coating over time. Degradation and hydration of the coating may reduce the coating's cohesive and adhesive binding to the device, thereby facilitating transfer of the coating to the tissue.

One embodiment may described by analogy to contact printing whereby a biochemically active 'ink' (the polymer+ drug coating) from a 'die' (the device) to the 'stock' (the site in the body).

The devices and methods described in conjunction with some of the embodiments provided herein are advantageously based on specific properties provided for in the drug-delivery formulation. One such property, especially well-suited for non-permanent implants such as balloon catheters, cutting balloons, etc. is 'soft' coating that undergoes plastic deformation at pressures provided by the inflation of the balloon (range 2-25 ATM, typically 10-18 ATM). Another such property, especially well-suited to permanent implants such as stents is coatings where the polymer becomes 'soft' at some point after implant either by hydration or by degradation or by combinations of hydration and degradation.

Some embodiments provide devices that can advantageously be used in conjunction with methods that can aid/promote the transfer of the coating. These include introducing stimuli to the coated device once on-site in the body (where the device is delivered either transiently or permanently). Such stimuli can be provided to induce a chemical response (light, heat, radiation, etc.) in the coating or can provide mechanical forces to augment the transfer of the coating into the tissue (ultrasound, translation, rotation, vibration and combinations thereof).

In some embodiments, the coating is freed, dissociated, and/or transferred from the substrate using a mechanical stimulation. In some embodiments, the coating is freed from the substrate using a mechanical stimulation. In some embodiments, the coating is dissociated from the substrate using a mechanical stimulation. In some embodiments, the coating is transferred from the substrate using a mechanical stimulation. In some embodiments, the coating is transferred to the intervention site using a mechanical stimulation. In some embodiments, the coating is delivered to the intervention site using a mechanical stimulation. In some embodiments, the mechanical stimulation is adapted to augment the freeing, dissociation and/or transference of the coating from the substrate. In some embodiments, the mechanical stimulation is adapted to initiate the freeing, dissociation and/or transference of the coating from the substrate. In some embodiments, the mechanical stimulation is adapted to cause the freeing, dissociation and/or transference of the coating from the substrate. In some embodiments, the mechanical stimulation comprises at least one of a compressive force, a shear force, a tensile force, a force exerted on the coating from a substrate side of the coating, a force exerted on the coating by the substrate, a force exerted on the coating from an external element, a translation, a rotation, a vibration, and a combination thereof. In some embodiments, the external element is a part of the subject. In some embodiments, the external element is not part of the device.

In some embodiments, the external element comprises a liquid. In some embodiments, the liquid is forced between the coating and the substrate. In some embodiments, the liquid comprises saline. In some embodiments, the liquid comprises water. In some embodiments, the mechanical stimulation comprises a geometric configuration of the substrate that maximizes a shear force on the coating. In some embodiments, the mechanical stimulation comprises a geometric configuration of the substrate that increases a shear force on the coating. In some embodiments, the mechanical stimulation comprises a geometric configuration of the substrate that enhances a shear force on the coating.

In some embodiments, the coating is freed, dissociated, and/or transferred from the substrate using a chemical stimulation. In some embodiments, the coating is freed from the substrate using a chemical stimulation. In some embodiments, the coating is dissociated from the substrate using a chemical stimulation. In some embodiments, the coating is transferred from the substrate using a chemical stimulation. In some embodiments, the coating is transferred to the intervention site using a chemical stimulation. In some embodiments, the coating is delivered to the intervention site using a chemical stimulation. In some embodiments, the chemical stimulation comprises at least one of bulk degradation, interaction with a bodily fluid, interaction with a bodily tissue, a chemical interaction with a non-bodily fluid, a chemical interaction with a chemical, an acid-base reaction, an enzymatic reaction, hydrolysis, and combinations thereof. In some embodiments, the chemical stimulation comprises bulk degradation of the coating. In some embodiments, the chemical stimulation comprises interaction of the coating or a portion thereof with a bodily fluid. In some embodiments, the chemical stimulation comprises interaction of the coating or a portion thereof with a bodily tissue. In some embodiments, the chemical stimulation comprises a chemical interaction of the coating or a portion thereof with a non-bodily fluid. In some embodiments, the chemical stimulation comprises a chemical interaction of the coating or a portion thereof with a chemical. In some embodiments, the chemical stimulation comprises an acid-base reaction. In some embodiments, the chemical stimulation comprises an enzymatic reaction. In some embodiments, the chemical stimulation comprises hydrolysis.

In some embodiments, the chemical stimulation is adapted to augment the freeing, dissociation and/or transference of the coating from the substrate. In some embodiments, the chemical stimulation is adapted to initiate the freeing, dissociation and/or transference of the coating from the substrate. In some embodiments, the chemical stimulation is adapted to cause the freeing, dissociation and/or transference of the coating from the substrate. In some embodiments, the coating comprises a material that is adapted to transfer, free, and/or dissociate from the substrate when at the intervention site in response to an in-situ enzymatic reaction resulting in a weak bond between the coating and the substrate.

In some embodiments, the coating is freed, dissociated, and/or transferred from the substrate using a thermal stimulation. In some embodiments, the coating is freed from the substrate using a thermal stimulation. In some embodiments, the coating is dissociated from the substrate using a thermal stimulation. In some embodiments, the coating is transferred from the substrate using a thermal stimulation. In some embodiments, the coating is transferred to the intervention site using a thermal stimulation. In some embodiments, the coating is delivered to the intervention site using a thermal stimulation. In some embodiments, the thermal stimulation comprises at least one of a hot stimulus and a cold stimulus adapted to augment the freeing, dissociation and/or transference of the coating from the substrate. In some embodiments, the thermal stimulation is adapted to cause the freeing, dissociation and/or transference of the coating from the substrate. In some embodiments, the thermal stimulation comprises at least one of a hot stimulus and a cold stimulus adapted to initiate the freeing, dissociation and/or transference of the coating from the substrate. In some embodiments, the thermal stimulation comprises at least one of a hot stimulus and a cold stimulus adapted to initiate the freeing, dissociation and/or transference of the coating from the substrate.

In some embodiments, the coating is freed, dissociated, and/or transferred from the device by a electromagnetic stimulation. In some embodiments, the coating is freed from the substrate using a electromagnetic stimulation. In some embodiments, the coating is dissociated from the substrate using a electromagnetic stimulation. In some embodiments, the coating is transferred from the substrate using a electromagnetic stimulation. In some embodiments, the coating is transferred to the intervention site using a electromagnetic stimulation. In some embodiments, the coating is delivered to the intervention site using a electromagnetic stimulation. In some embodiments, the electromagnetic stimulation comprises an electromagnetic wave comprising at least one of a radio wave, a micro wave, a infrared wave, near infrared wave, a visible light wave, an ultraviolet wave, a X-ray wave, and a gamma wave. In some embodiments, the electromagnetic stimulation is adapted to augment the freeing, dissociation and/or transference of the coating from the substrate. In some embodiments, the electromagnetic stimulation is adapted to initiate the freeing, dissociation and/or transference of the coating from the substrate. In some embodiments, the electromagnetic stimulation is adapted to cause the freeing, dissociation and/or transference of the coating from the substrate.

In some embodiments, the coating is freed, dissociated, and/or transferred from the device by a sonic stimulation. In some embodiments, the coating is freed from the substrate using a sonic stimulation. In some embodiments, the coating is dissociated from the substrate using a sonic stimulation. In some embodiments, the coating is transferred from the substrate using a sonic stimulation. In some embodiments, the coating is transferred to the intervention site using a sonic stimulation. In some embodiments, the coating is delivered to the intervention site using a sonic stimulation. In some embodiments, the sonic stimulation comprises a sound wave, wherein the sound wave is at least one of an ultrasound wave, an acoustic sound wave, and an infrasound wave. In some embodiments, the sonic stimulation is adapted to augment the freeing, dissociation and/or transference of the coating from the substrate. In some embodiments, the sonic stimulation is adapted to initiate the freeing, dissociation and/or transference of the coating from the substrate. In some embodiments, the sonic stimulation is adapted to cause the freeing, dissociation and/or transference of the coating from the substrate.

In some embodiments, the coating is freed, dissociated, and/or transferred from the device by a combination of at least two of a mechanical stimulation, a chemical stimulation, an electromagnetic stimulation, and a sonic stimulation.

In some embodiments, the coating is freed, dissociated, and/or transferred from the substrate by extrusion.

Provided herein are device geometries that maximize the shear forces on the coating. Such geometric design of the device provides two advantages: (1) increases (concentrates) the force to plastically deform the drug and polymer coating (2) decreases the force of adhesion of the coating. For example, a wedge-shape aligns the forces of deformation along a shear plan as opposed to direct compression. This embodiment provides for: (1) increased efficiency in terms of % of the coating transferred (2) increased precision in amount transferred on a case-by-case basis (3) utilization of 'harder/stiffer' materials (biopolymers) that would otherwise not deform and/or not bulk-migrate under deployment conditions (4) minimize the chance of particulate shedding via purposefully designing the shape and direction of both the deformation and bulk migration. For example for a wedge, particles would be less likely because the coating would be pre-disposed as a shear from the device in a sheet form—with the use of soft materials, this may be illustrated as a coating of silicone caulk being extruded from the pressure of a rod being pushed into a mattress.

Another embodiment provide a geometric arrangement of the coating whereby layers, e.g. a laminate structure, are provided in the coating to modulate and control the plastic deformation, shearing and bulk-migration of the coating into the tissue.

One embodiment provides coated substrates that, upon deployment at a specific site in the patient, transfer some or all of the coating (5-10%, 10-25%, 25-50%, 50-90%, 90-99%, 99-100%) to the site of therapeutic demand.

In some embodiments, the device further comprises a release agent. In some embodiments, the release agent is biocompatible. In some embodiments, the release agent is non-biocompatible. In some embodiments, the release agent comprises a powder. In some embodiments, the release agent comprises a lubricant. In some embodiments, the release agent comprises a surface modification of the substrate.

In some embodiments, the release agent comprises a physical characteristic of the coating. In some embodiments, the physical characteristic of the coating comprises a pattern. In some embodiments, the pattern is a textured surface on the substrate side of the coating, wherein the substrate side of the coating is the part of the coating on the substrate. In some embodiments, the pattern is a textured surface on the intervention site side of the coating, wherein the intervention site side of the coating is the part of the coating that is transferred to, and/or delivered to, and/or deposited at the intervention site.

In some embodiments, the release agent comprises a viscous fluid. In some embodiments, the viscous fluid comprises oil. In some embodiments, the viscous fluid is a fluid that is viscous relative to water. In some embodiments, the viscous fluid is a fluid that is viscous relative to blood. In some embodiments, the viscous fluid is a fluid that is viscous relative to urine. In some embodiments, the viscous fluid is a fluid that is viscous relative to bile. In some embodiments, the viscous fluid is a fluid that is viscous relative to synovial fluid. In some embodiments, the viscous fluid is a fluid that is viscous relative to saline. In some embodiments, the viscous fluid is a fluid that is viscous relative to a bodily fluid at the intervention site.

In some embodiments, the release agent comprises a gel.

In some embodiments, the release agent comprises at least one of the active agent and another active agent. The active agent may be placed on the substrate prior to the coating in order to act as the release agent. The active agent may be a different active agent than the active agent in the coating. The active agent that is the release agent may provide for a second source of drug to be delivered to the intervention site or another location once the coating is released from (or transferred from, or freed from, or dissociated from) the substrate.

In some embodiments, the release agent comprises a physical characteristic of the substrate. In some embodiments, the physical characteristic of the substrate comprises at least one of a patterned coating surface and a ribbed coating surface. In some embodiments, the patterned coating surface comprises a stent framework. In some embodiments, the ribbed coating surface comprises an undulating substrate surface. In some embodiments, the ribbed coating surface comprises an substrate surface having bumps thereon.

In some embodiments, the release agent comprises a property that is capable of changing at the intervention site. In some embodiments, the property comprises a physical property. In some embodiments, the property comprises a chemical property. In some embodiments, the release agent is capable of changing a property when in contact with at least one of a biologic tissue and a biologic fluid. In some embodiments, the release agent is capable of changing a property when in contact with an aqueous liquid.

In some embodiments, the release agent is between the substrate and the coating.

In some embodiments, substantially all of the coating remains on said substrate until the medical device reaches the intervention site. In some embodiments, at least about 10%, at least about 20%, at least about 30%, at least about 50%, at least about 75%, at least about 85%, at least about 90%, at least about 95%, and/or at least about 99% of the coating is adapted to transfer from the substrate to the intervention site. In some embodiments, at least about 10% of the coating is adapted to transfer from the substrate to the intervention site. In some embodiments, at least about 20% of the coating is adapted to transfer from the substrate to the intervention site. In some embodiments, at least about 30% of the coating is adapted to transfer from the substrate to the intervention site. In some embodiments, at least about 50% of the coating is adapted to transfer from the substrate to the intervention site. In some embodiments, at least about 75% of the coating is adapted to transfer from the substrate to the intervention site. In some embodiments, at least about 85% of the coating is adapted to transfer from the substrate to the intervention site. In some embodiments, at least about 90% of the coating is adapted to transfer from the substrate to the intervention site. In some embodiments, at least about 95% of the coating is adapted to transfer from the substrate to the intervention site. In some embodiments, at least about 99% of the coating is adapted to transfer from the substrate to the intervention site. As used herein, "about" when used in reference to a percentage of the coating can mean ranges of 1%-5%, of 5%-10%, of 10%-20%, and/or of 10%-50% (as a percent of the percentage of the coating transferred, or as a variation of the percentage of the coating transferred).

In some embodiments, the coating portion that is adapted to transfer upon stimulation is on at least one of a distal surface of the substrate, a middle surface of the substrate, a proximal surface of the substrate, and an abluminal surface of the substrate. In some embodiments, the stimulation decreases the contact between the coating and the substrate. In some embodiments, device is adapted to transfer less than about 1%, less than about 5%, less than about 10%. less than about 15%, less than about 25%, less than about 50%, less than about 70%, less than about 80%, and/or less than about 90% of the coating absent stimulation of the coating.

In some embodiments, at least about 10%, at least about 20%, at least about 30%, at least about 50%, at least about 75%, at least about 85%, at least about 90%, at least about 95%, and/or at least about 99% of the active agent is adapted to transfer from the substrate to the intervention site. In some embodiments, at least about 10% of the active agent is adapted to transfer from the substrate to the intervention site. In some embodiments, at least about 20% of the active agent is adapted to transfer from the substrate to the intervention site. In some embodiments, at least about 30% of the active agent is adapted to transfer from the substrate to the intervention site. In some embodiments, at least about 50% of the active agent is adapted to transfer from the substrate to the intervention site. In some embodiments, at least about 75% of the active agent is adapted to transfer from the substrate to the intervention site. In some embodiments, at least about 85% of the active agent is adapted to transfer from the substrate to the intervention site. In some embodiments, at least about 90% of the active agent is adapted to transfer from the substrate to the intervention site. In some embodiments, at least about 95% of the active agent is adapted to transfer from the substrate to the intervention site. In some embodiments, at least about 99% of the active agent is adapted to transfer from the substrate to the intervention site. As used herein, "about" when used in reference to a percentage of the active agent can mean ranges of 1%-5%, of 5%-10%, of 10%-20%, and/or of 10%-50% (as a percent of the percentage of the active agent transferred, or as a variation of the percentage of the active agent transferred).

In some embodiments, the active agent portion that is adapted to transfer upon stimulation is on at least one of a distal surface of the substrate, a middle surface of the substrate, a proximal surface of the substrate, and an abluminal surface of the substrate. In some embodiments, the stimulation decreases the contact between the coating and the substrate. In some embodiments, the device is adapted to transfer less than about 1%, less than about 5%, less than about 10%. less than about 15%, less than about 25%, less than about 50%, less than about 70%, less than about 80%, and/or less than about 90% of the active agent absent stimulation of the coating.

In some embodiments, the device is adapted to transfer at least about 10%, at least about 20%, at least about 30%, at least about 50%, at least about 75%, at least about 85%, at least about 90%, at least about 95%, and/or at least about 99% of the coating from the substrate to the intervention site. In some embodiments, the device is adapted to transfer at least about 10% of the coating from the substrate to the intervention site. In some embodiments, the device is adapted to transfer at least about 20% of the coating from the substrate to the intervention site. In some embodiments, the device is adapted to transfer at least about 30% of the coating from the substrate to the intervention site. In some embodiments, the device is adapted to transfer at least about 50% of the coating from the substrate to the intervention site. In some embodiments, the device is adapted to transfer at least about 75% of the coating from the substrate to the intervention site. In some embodiments, the device is adapted to transfer at least about 85% of the coating from the substrate to the intervention site. In some embodiments, the device is adapted to transfer at least about 90% of the coating from the substrate to the intervention site. In some embodiments, the device is adapted to transfer at least about 95% of the coating from the substrate to the intervention site. In some embodiments, the device is adapted to transfer at least about 99% of the coating from the substrate to the intervention site. As used herein, "about" when used in reference to a percentage of the coating can mean ranges of 1%-5%, of 5%-10%, of 10%-20%, and/or of 10%-50% (as a percent of the percentage of the coating transferred, or as a variation of the percentage of the coating transferred).

In some embodiments, the coating portion that transfers upon stimulation is on at least one of a distal surface of the substrate, a middle surface of the substrate, a proximal surface of the substrate, and an abluminal surface of the substrate. In some embodiments, stimulation decreases the contact between the coating and the substrate. In some embodiments, the device is adapted to transfer less than about 1%, less than about 5%, less than about 10%. less than about 15%, less than about 25%, less than about 50%, less than about 70%, less than about 80%, and/or less than about 90% of the coating absent stimulation of the coating.

In some embodiments, the device is adapted to transfer at least about 10%, at least about 20%, at least about 30%, at least about 50%, at least about 75%, at least about 85%, at least about 90%, at least about 95%, and/or at least about 99% of the active agent from the substrate to the intervention site. In some embodiments, the device is adapted to transfer at least about 10% of the active agent from the substrate to the intervention site. In some embodiments, the device is adapted to transfer at least about 20% of the active agent from the substrate to the intervention site. In some embodiments, the device is adapted to transfer at least about 30% of the active agent from the substrate to the intervention site. In some embodiments, the device is adapted to transfer at least about 50% of the active agent from the substrate to the intervention site. In some embodiments, the device is adapted to transfer at least about 75% of the active agent from the substrate to the intervention site. In some embodiments, the device is adapted to transfer at least about 85% of the active agent from the substrate to the intervention site. In some embodiments, the device is adapted to transfer at least about 90% of the active agent from the substrate to the intervention site. In some embodiments, the device is adapted to transfer at least about 95% of the active agent from the substrate to the intervention site. In some embodiments, the device is adapted to transfer at least about 99% of the active agent from the substrate to the intervention site. As used herein, "about" when used in reference to a percentage of the active agent can mean ranges of 1%-5%, of 5%-10%, of 10%-20%, and/or of 10%-50% (as a percent of the percentage of the active agent transferred, or as a variation of the percentage of the active agent transferred).

In some embodiments, the coating portion that transfers upon stimulation is on at least one of a distal surface of the substrate, a middle surface of the substrate, a proximal surface of the substrate, and an abluminal surface of the substrate. In some embodiments, the stimulation decreases the contact between the coating and the substrate. In some embodiments, the device is adapted to transfer less than about 1%, less than about 5%, less than about 10%. less than about 15%, less than about 25%, less than about 50%, less than about 70%, less than about 80%, less than about 90% of the active agent absent stimulation of the coating.

In some embodiments, the device is adapted to free at least about 10%, at least about 20%, at least about 30%, at least about 50%, at least about 75%, at least about 85%, at least about 90%, at least about 95%, and/or at least about 99% of the coating from the substrate. In some embodiments, the device is adapted to free at least about 10% of the coating from the substrate to the intervention site. In some embodiments, the device is adapted to free at least about 20% of the coating from the substrate to the intervention site. In some embodiments, the device is adapted to free at least about 30% of the coating from the substrate to the intervention site. In some embodiments, the device is adapted to free at least about 50% of the coating from the substrate to the intervention site. In some embodiments, the device is adapted to free at least about 75% of the coating from the substrate to the intervention site. In some embodiments, the device is adapted to free at least about 85% of the coating from the substrate to the intervention site. In some embodiments, the device is adapted to free at least about 90% of the coating from the substrate to the intervention site. In some embodiments, the device is adapted to free at least about 95% of the coating from the substrate to the intervention site. In some embodiments, the device is adapted to free at least about 99% of the coating from the substrate to the intervention site. As used herein, "about" when used in reference to a percentage of the coating can mean ranges of 1%-5%, of 5%-10%, of 10%-20%, and/or of 10%-50% (as a percent of the percentage of the coating freed, or as a variation of the percentage of the coating freed).

In some embodiments, the coating portion that frees upon stimulation is on at least one of a distal surface of the substrate, a middle surface of the substrate, a proximal surface of the substrate, and an abluminal surface of the substrate.

In some embodiments, the stimulation decreases the contact between the coating and the substrate. In some embodiments, the device is adapted to free less than about 1%, less than about 5%, less than about 10%. less than about 15%, less than about 25%, less than about 50%, less than about 70%, less than about 80%, less than about 90% of the coating absent stimulation of the coating.

In some embodiments, the device is adapted to dissociate at least about 10%, at least about 20%, at least about 30%, at least about 50%, at least about 75%, at least about 85%, at least about 90%, at least about 95%, and/or at least about 99% of the coating from the substrate. In some embodiments, the device is adapted to dissociate at least about 10% of the coating from the substrate to the intervention site. In some embodiments, the device is adapted to dissociate at least about 20% of the coating from the substrate to the intervention site. In some embodiments, the device is adapted to dissociate at least about 30% of the coating from the substrate to the intervention site. In some embodiments, the device is adapted to dissociate at least about 50% of the coating from the substrate to the intervention site. In some embodiments, the device is adapted to dissociate at least about 75% of the coating from the substrate to the intervention site. In some embodiments, the device is adapted to dissociate at least about 85% of the coating from the substrate to the intervention site. In some embodiments, the device is adapted to dissociate at least about 90% of the coating from the substrate to the intervention site. In some embodiments, the device is adapted to dissociate at least about 95% of the coating from the substrate to the intervention site. In some embodiments, the device is adapted to dissociate at least about 99% of the coating from the substrate to the intervention site. As used herein, "about" when used in reference to a percentage of the coating can mean ranges of 1%-5%, of 5%-10%, of 10%-20%, and/or of 10%-50% (as a percent of the percentage of the coating dissociated, or as a variation of the percentage of the coating dissociated).

In some embodiments, the coating portion that dissociates upon stimulation is on at least one of a distal surface of the substrate, a middle surface of the substrate, a proximal surface of the substrate, and an abluminal surface of the substrate. In some embodiments, stimulation decreases the contact between the coating and the substrate. In some embodiments, the device is adapted to dissociate less than about 1%, less than about 5%, less than about 10%. less than about 15%, less than about 25%, less than about 50%, less than about 70%, less than about 80%, less than about 90% of the coating absent stimulation of the coating.

In some embodiments, the device is adapted to deliver at least about 10%, at least about 20%, at least about 30%, at least about 50%, at least about 75%, at least about 85%, at least about 90%, at least about 95%, and/or at least about 99% of the coating to the intervention site. In some embodiments, the device is adapted to deliver at least about 10% of the coating to the intervention site. In some embodiments, the device is adapted to deliver at least about 20% of the coating to the intervention site. In some embodiments, the device is adapted to deliver at least about 30% of the coating to the intervention site. In some embodiments, the device is adapted to deliver at least about 50% of the coating to the intervention site. In some embodiments, the device is adapted to deliver at least about 75% of the coating to the intervention site. In some embodiments, the device is adapted to deliver at least about 85% of the coating to the intervention site. In some embodiments, the device is adapted to deliver at least about 90% of the coating to the intervention site. In some embodiments, the device is adapted to deliver at least about 95% of the coating to the intervention site. In some embodiments, the device is adapted to deliver at least about 99% of the coating to the intervention site. As used herein, "about" when used in reference to a percentage of the coating can mean ranges of 1%-5%, of 5%-10%, of 10%-20%, and/or of 10%-50% (as a percent of the percentage of the coating delivered, or as a variation of the percentage of the coating delivered).

In some embodiments, the coating portion that is delivered upon stimulation is on at least one of a distal surface of the substrate, a middle surface of the substrate, a proximal surface of the substrate, and an abluminal surface of the substrate. In some embodiments, the stimulation decreases the contact between the coating and the substrate. In some embodiments, the device is adapted to deliver less than about 1%, less than about 5%, less than about 10%. less than about 15%, less than about 25%, less than about 50%, less than about 70%, less than about 80%, less than about 90% of the coating absent stimulation of the coating.

In some embodiments, the active agent comprises a pharmaceutical agent.

In some embodiments, the pharmaceutical agent comprises a macrolide immunosuppressive drug. In some embodiments the macrolide immunosuppressive drug comprises one or more of rapamycin, 40-O-(2-Hydroxyethyl) rapamycin (everolimus), 40-O-Benzyl-rapamycin, 40-O-(4'-Hydroxymethyl)benzyl-rapamycin, 40-O-[4'-(1,2-Dihydroxyethyl)]benzyl-rapamycin, 40-O-Allyl-rapamycin, 40-O-[3'-(2,2-Dimethyl-1,3-dioxolan-4(S)-yl)-prop-2'-en-1'-yl]-rapamycin, (2':E,4'S)-40-O-(4',5'-Dihydroxypent-2'-en-1'-yl)-rapamycin 40-O-(2-Hydroxy)ethoxycarbonylmethyl-rapamycin, 40-O-(3-Hydroxy)propyl-rapamycin 4O—O-(6-Hydroxy)hexyl-rapamycin 40-O-[2-(2-Hydroxy)ethoxy]ethyl-rapamycin 4O—O-[(3S)-2,2-Dimethyldioxolan-3-yl]methyl-rapamycin, 40-O-[(2S)-2,3-Dihydroxyprop-1-yl]-rapamycin, 4O—O-(2-Acetoxy)ethyl-rapamycin 4O—O-(2-Nicotinoyloxy)ethyl-rapamycin, 4O—O-[2-(N-Morpholino)acetoxy]ethyl-rapamycin 4O—O-(2-N-Imidazolylacetoxy)ethyl-rapamycin, 40-O-[2-(N-Methyl-N'-piperazinyl)acetoxy]ethyl-rapamycin, 39-O-Desmethyl-39,40-O,O-ethylene-rapamycin, (26R)-26-Dihydro-40-O-(2-hydroxy)ethyl-rapamycin, 28-O-Methyl-rapamycin, 4O—O-(2-Aminoethyl)-rapamycin, 4O—O-(2-Acetaminoethyl)-rapamycin 4O—O-(2-Nicotinamidoethyl)-rapamycin, 4O—O-(2-(N-Methyl-imidazo-2'-ylcarbethoxamido) ethyl)-rapamycin, 4O—O-(2-Ethoxycarbonylaminoethyl)-rapamycin, 40-O-(2'-Tolylsulfonamidoethyl)-rapamycin, 40-O-[2-(4',5'-Dicarboethoxy-1',2',3'-triazol-1'-yl)-ethyl]-rapamycin, 42-Epi-(tetrazolyl)rapamycin (tacrolimus), and 42-[3-hydroxy-2-(hydroxymethyl)-2-methylpropanoate]rapamycin (temsirolimus).

In some embodiments of the methods and/or devices provided herein, the macrolide immunosuppressive drug is at least 50% crystalline. In some embodiments, the macrolide immunosuppressive drug is at least 75% crystalline. In some embodiments, the macrolide immunosuppressive drug is at least 90% crystalline. In some embodiments of the methods and/or devices provided herein the macrolide immunosuppressive drug is at least 95% crystalline. In some embodiments of the methods and/or devices provided herein the macrolide immunosuppressive drug is at least 97% crystalline. In some embodiments of the methods and/or devices provided herein macrolide immunosuppressive drug is at least 98% crystalline. In some embodiments of the methods and/or devices provided herein the macrolide immunosuppressive drug is at least 99% crystalline.

In some embodiments of the methods and/or devices provided herein wherein the pharmaceutical agent is at least 50% crystalline. In some embodiments of the methods and/or devices provided herein the pharmaceutical agent is at least 75% crystalline. In some embodiments of the methods and/or devices provided herein the pharmaceutical agent is at least 90% crystalline. In some embodiments of the methods and/or devices provided herein the pharmaceutical agent is at least 95% crystalline. In some embodiments of the methods and/or devices provided herein the pharmaceutical agent is at least 97% crystalline. In some embodiments of the methods and/or devices provided herein pharmaceutical agent is at least 98% crystalline. In some embodiments of the methods and/or devices provided herein the pharmaceutical agent is at least 99% crystalline.

In some embodiments, the pharmaceutical agent is agent is selected form the group consisting of In some embodiments, a pharmaceutical agent is at least one of: Acarbose, acetylsalicylic acid, acyclovir, allopurinol, alprostadil, prostaglandins, amantadine, ambroxol, amlodipine, S-aminosalicylic acid, amitriptyline, atenolol, azathioprine, balsalazide, beclomethasone, betahistine, bezafibrate, diazepam and diazepam derivatives, budesonide, bufexamac, buprenorphine, methadone, calcium salts, potassium salts, magnesium salts, candesartan, carbamazepine, captopril, cetirizine, chenodeoxycholic acid, theophylline and theophylline derivatives, trypsins, cimetidine, clobutinol, clonidine, cotrimoxazole, codeine, caffeine, vitamin D and derivatives of vitamin D, colestyramine, cromoglicic acid, coumarin and coumarin derivatives, cysteine, ciclosporin, cyproterone, cytabarine, dapiprazole, desogestrel, desonide, dihydralazine, diltiazem, ergot alkaloids, dimenhydrinate, dimethyl sulphoxide, dimeticone, domperidone and domperidan derivatives, dopamine, doxazosin, doxylamine, benzodiazepines, diclofenac, desipramine, econazole, ACE inhibitors, enalapril, ephedrine, epinephrine, epoetin and epoetin derivatives, morphinans, calcium antagonists, modafinil, orlistat, peptide antibiotics, phenytoin, riluzoles, risedronate, sildenafil, topiramate, estrogen, progestogen and progestogen derivatives, testosterone derivatives, androgen and androgen derivatives, ethenzamide, etofenamate, etofibrate, fenofibrate, etofylline, famciclovir, famotidine, felodipine, fentanyl, fenticonazole, gyrase inhibitors, fluconazole, fluarizine, fluoxetine, flurbiprofen, ibuprofen, fluvastatin, follitropin, formoterol, fosfomicin, furosemide, fusidic acid, gallopamil, ganciclovir, gemfibrozil, ginkgo, Saint John's wort, glibenclamide, urea derivatives as oral antidiabetics, glucagon, glucosamine and glucosamine derivatives, glutathione, glycerol and glycerol derivatives, hypothalamus hormones, guanethidine, halofantrine, haloperidol, heparin (and derivatives), hyaluronic acid, hydralazine, hydrochlorothiazide (and derivatives), salicylates, hydroxyzine, imipramine, indometacin, indoramine, insulin, iodine and iodine derivatives, isoconazole, isoprenaline, glucitol and glucitol derivatives, itraconazole, ketoprofen, ketotifen, lacidipine, lansoprazole, levodopa, levomethadone, thyroid hormones, lipoic acid (and derivatives), lisinopril, lisuride, lofepramine, loperamide, loratadine, maprotiline, mebendazole, mebeverine, meclozine, mefenamic acid, mefloquine, meloxicam, mepindolol, meprobamate, mesalazine, mesuximide, metamizole, metformin, methylphenidate, metixene, metoprolol, metronidazole, mianserin, miconazole, minoxidil, misoprostol, mizolastine, moexipril, morphine and morphine derivatives, evening primrose, nalbuphine, naloxone, tilidine, naproxen, narcotine, natamycin, neostigmine, nicergoline, nicethamide, nifedipine, niflumic acid, nimodipine, nimorazole, nimustine, nisoldipine, adrenaline and adrenaline derivatives, novamine sulfone, noscapine, nystatin, olanzapine, olsalazine, omeprazole, omoconazole, oxaceprol, oxiconazole, oxymetazoline, pantoprazole, paracetamol (acetaminophen), paroxetine, penciclovir, pentazocine, pentifylline, pentoxifylline, perphenazine, pethidine, plant extracts, phenazone, pheniramine, barbituric acid derivatives, phenylbutazone, pimozide, pindolol, piperazine, piracetam, pirenzepine, piribedil, piroxicam, pramipexole, pravastatin, prazosin, procaine, promazine, propiverine, propranolol, propyphenazone, protionamide, proxyphylline, quetiapine, quinapril, quinaprilat, ramipril, ranitidine, reproterol, reserpine, ribavirin, risperidone, ritonavir, ropinirole, roxatidine, ruscogenin, rutoside (and derivatives), sabadilla, salbutamol, salmeterol, scopolamine, selegiline, sertaconazole, sertindole, sertralion, silicates, simvastatin, sitosterol, sotalol, spaglumic acid, spirapril, spironolactone, stavudine, streptomycin, sucralfate, sufentanil, sulfasalazine, sulpiride, sultiam, sumatriptan, suxamethonium chloride, tacrine, tacrolimus, taliolol, taurolidine, temazepam, tenoxicam, terazosin, terbinafine, terbutaline, terfenadine, terlipressin, tertatolol, teryzoline, theobromine, butizine, thiamazole, phenothiazines, tiagabine, tiapride, propionic acid derivatives, ticlopidine, timolol, tinidazole, tioconazole, tioguanine, tioxolone, tiropramide, tizanidine, tolazoline, tolbutamide, tolcapone, tolnaftate, tolperisone, topotecan, torasemide, tramadol, tramazoline, trandolapril, tranylcypromine, trapidil, trazodone, triamcinolone derivatives, triamterene, trifluperidol, trifluridine, trimipramine, tripelennamine, triprolidine, trifosfamide, tromantadine, trometamol, tropalpin, troxerutine, tulobuterol, tyramine, tyrothricin, urapidil, valaciclovir, valproic acid, vancomycin, vecuronium chloride, Viagra, venlafaxine, verapamil, vidarabine, vigabatrin, viloazine, vincamine, vinpocetine, viquidil, warfarin, xantinol nicotinate, xipamide, zafirlukast, zalcitabine, zidovudine, zolmitriptan, zolpidem, zopiclone, zotipine, amphotericin B, caspofungin, voriconazole, resveratrol, PARP-1 inhibitors (including imidazoquinolinone, imidazpyridine, and isoquinolindione, tissue plasminogen activator (tPA), melagatran, lanoteplase, reteplase, staphylokinase, streptokinase, tenecteplase, urokinase, abciximab (ReoPro), eptifibatide, tirofiban, prasugrel, clopidogrel, dipyridamole, cilostazol, VEGF, heparan sulfate, chondroitin sulfate, elongated "RGD" peptide binding domain, CD34 antibodies, cerivastatin, etorvastatin, losartan, valartan, erythropoietin, rosiglitazone, pioglitazone, mutant protein Apo A1 Milano, adiponectin, (NOS) gene therapy, glucagon-like peptide 1, atorvastatin, and atrial natriuretic peptide (ANP), lidocaine, tetracaine, dibucaine, hyssop, ginger, turmeric, Arnica montana, helenalin, cannabichromene, rofecoxib, hyaluronidase, and salts, derivatives, isomers, racemates, diastereoisomers, prodrugs, hydrate, ester, or analogs thereof.

In some embodiments, the pharmaceutical agent comprises hyaluronidase.

In some embodiments, the pharmaceutical agent comprises cilostazol.

In some embodiments, the pharmaceutical agent comprises dipyridamole.

In some embodiments, the pharmaceutical agent comprises an antibiotic agent.

In some embodiments, the pharmaceutical agent comprises a chemotherapeutic agent.

In some embodiments, the pharmaceutical agent is in a therapeutically desirable morphology.

In certain embodiments, a device of the invention is used for treatment of cancer.

In certain embodiments, devices and methods of the invention are used for intraductal treatment of breast cancer. In these embodiments, the device is introduced into a breast duct using a delivery tool, e.g., a hollow needle such as a cannula, biopsy needle, or the like into the duct to contact target ductal epithelial cells lining the duct. The amount of agent can vary, but optimally will be an amount sufficient to target all atypical or malignant cells in the duct. Estimates of the quantity of target cells can be made upon the initial identification of the target duct, e.g. by cytological evaluation of ductal epithelial cells retrieved from the duct. The amount may vary depending on the agent's potency and other mitigating factors such as the extent of any time delay of delivery of the agent once inside the duct (e.g. with a time release formulation).

In embodiments, a breast cancer is treated using the devices and methods of the invention to deliver a chemotherapeutic or other appropriate agent as known in the art within the tumor resective cavity following lumpectomy. In these embodiments a balloon catheter is inserted into the cavity and inflated using methods similar to those used for delivery of internal radiation therapy using the MammoSite® RTS.

The agent delivered can be a therapeutically active agent, including e.g., any agent suitable for treating the breast condition identified, including e.g., any anti-cancer agents, any prophylactic agents, or any agent for treating any other breast condition or for prophylaxis against a breast condition. Thus, for example, the agent if an anti-cancer agent can include, e.g., an estrogen activity modulator, a cytostatic agent, or a cytotoxic agent. The agent may also include e.g., an antibody, a peptide, a polypeptide, a nucleic acid, a polynucleotide, a small organic molecule, a macromolecule, a polymer, a carbohydrate, or a lipid. The agent can be formulated to be released over time into a breast duct. The agent can be delivered to the lactiferous sinus of the breast duct for release into the rest of the ductal system from there, or the agent may be delivered to any part of the breast duct, e.g., including the ductal lumens of the ductal system and also the terminal ductal lobular unit. Methods and devices for intraductal treatment of breast cancer have been described, e.g., in U.S. Pat. App. No. 2004/0147904, "Methods and devices for delivery of agents to breast milk ducts," and WO 02/078716, "Intraductal Treatment Targeting Methylated Promoters in Breast Cancer," both incorporated herein by reference in their entirety.

In some embodiments, the active agent comprises a chemotherapeutic agent. In some embodiments, the pharmaceutical agent comprises a chemotherapeutic agent. In some embodiments, the chemotherapeutic agent comprises at least one of: an angiostatin, DNA topoisomerase, endostatin, genistein, ornithine decarboxylase inhibitors, chlormethine, melphalan, pipobroman, triethylene-melamine, triethylenethiophosphoramine, busulfan, carmustine (BCNU), streptozocin, 6-mercaptopurine, 6-thioguanine, Deoxycoformycin, IFN-α, 17α-ethinylestradiol, diethylstilbestrol, testosterone, prednisone, fluoxymesterone, dromostanolone propionate, testolactone, megestrolacetate, methylprednisolone, methyl-testosterone, prednisolone, triamcinolone, chlorotrianisene, hydroxyprogesterone, estramustine, medroxyprogesteroneacetate, flutamide, zoladex, mitotane, hexamethylmelamine, indolyl-3-glyoxylic acid derivatives, (e.g., indibulin), doxorubicin and idarubicin, plicamycin (mithramycin) and mitomycin, mechlorethamine, cyclophosphamide analogs, trazenes-dacarbazinine (DTIC), pentostatin and 2-chlorodeoxyadenosine, letrozole, camptothecin (and derivatives), navelbine, erlotinib, capecitabine, acivicin, acodazole hydrochloride, acronine, adozelesin, aldesleukin, ambomycin, ametantrone acetate, anthramycin, asperlin, azacitidine, azetepa, azotomycin, batimastat, benzodepa, bisnafide, bisnafide dimesylate, bizelesin, bropirimine, cactinomycin, calusterone, carbetimer, carubicin hydrochloride, carzelesin, cedefingol, celecoxib (COX-2 inhibitor), cirolemycin, crisnatol mesylate, decitabine, dexormaplatin, dezaguanine mesylate, diaziquone, duazomycin, edatrexate, eflornithine, elsamitrucin, enloplatin, enpromate, epipropidine, erbulozole, etanidazole, etoprine, flurocitabine, fosquidone, lometrexol, losoxantrone hydrochloride, masoprocol, maytansine, megestrol acetate, melengestrol acetate, metoprine, meturedepa, mitindomide, mitocarcin, mitocromin, mitogillin, mitomalcin, mitosper, mycophenolic acid, nocodazole, nogalamycin, ormaplatin, oxisuran, pegaspargase, peliomycin, pentamustine, perfosfamide, piposulfan, plomestane, porfimer sodium, porfiromycin, puromycin, pyrazofurin, riboprine, safingol, simtrazene, sparfosate sodium, spiromustine, spiroplatin, streptonigrin, sulofenur, tecogalan sodium, taxotere, tegafur, teloxantrone hydrochloride, temoporfin, thiamiprine, tirapazamine, trestolone acetate, triciribine phosphate, trimetrexate glucuronate, tubulozole hydrochloride, uracil mustard, uredepa, verteporfin, vinepidine sulfate, vinglycinate sulfate, vinleurosine sulfate, vinorelbine tartrate, vinrosidine sulfate, zeniplatin, zinostatin, 20-epi-1,25 dihydroxyvitamin D3, 5-ethynyluracil, acylfulvene, adecypenol, ALL-TK antagonists, ambamustine, amidox, amifostine, aminolevulinic acid, amrubicin, anagrelide, andrographolide, antagonist D, antagonist G, antarelix, anti-dorsalizing morphogenetic protein-1, antiandrogen, antiestrogen, estrogen agonist, apurinic acid, ara-CDP-DL-PTBA, arginine deaminase, asulacrine, atamestane, atrimustine, axinastatin 1, axinastatin 2, axinastatin 3, azasetron, azatoxin, azatyrosine, baccatin III derivatives, balanol, BCR/ABL antagonists, benzochlorins, benzoylstaurosporine, beta lactam derivatives, beta-alethine, betaclamycin B, betulinic acid, bFGF inhibitor, bisaziridinylspermine, bistratene A, breflate, buthionine sulfoximine, calcipotriol, calphostin C, carboxamide-amino-triazole, carboxyamidotriazole, CaRest M3, CARN 700, cartilage derived inhibitor, casein kinase inhibitors (ICOS), castanospermine, cecropin B, cetrorelix, chloroquinoxaline sulfonamide, cicaprost, cis-porphyrin, clomifene analogues, clotrimazole, collismycin A, collismycin B, combretastatin A4, combretastatin analogue, conagenin, crambescidin 816, cryptophycin 8, cryptophycin A derivatives, curacin A, cyclopentanthraquinones, cycloplatam, cypemycin, cytolytic factor, cytostatin, dacliximab, dehydrodidemnin B, dexamethasone, dexifosfamide, dexrazoxane, dexverapamil, didemnin B, didox, diethylnorspermine, dihydro-5-azacytidine, dihydrotaxol, 9-, dioxamycin, docosanol, dolasetron, dronabinol, duocarmycin SA, ebselen, ecomustine, edelfosine, edrecolomab, elemene, emitefur, estramustine analogue, filgrastim, flavopiridol, flezelastine, fluasterone, fluorodaunorunicin hydrochloride, forfenimex, gadolinium texaphyrin, galocitabine, gelatinase inhibitors, glutathione inhibitors, hepsulfam, heregulin, hexamethylene bisacetamide, hypericin, ibandronic acid, idramantone, ilomastat, imatinib (e.g., Gleevec), imiquimod, immunostimulant peptides, insulin-like growth factor-1 receptor inhibitor, interferon agonists, interferons, interleukins, iobenguane, iododoxorubicin, ipomeanol, 4-, iroplact, irsogladine, isobengazole, isohomohalicondrin B, itasetron, jasplakinolide, kahalalide F, lamellarin-N triacetate, leinamycin, lenograstim, lentinan sulfate, leptolstatin, leukemia inhibiting factor, leukocyte alpha interferon, leuprolide+estrogen+progesterone, linear polyamine analogue, lipophilic disaccharide peptide, lipophilic platinum compounds, lissoclinamide 7, lobaplatin, lombricine, loxoribine, lurtotecan, lutetium texaphyrin, lysofylline, lytic peptides, maitansine, mannostatin A, marimastat, maspin, matrilysin inhibitors, matrix metalloproteinase inhibitors, meterelin, methioninase, metoclopramide, MIF inhibitor, mifepristone, miltefosine, mirimostim, mitoguazone, mitotoxin fibroblast growth factor-saporin, mofarotene, molgramostim, Erbitux, human chorionic gonadotrophin, monophosphoryl lipid A+myobacterium cell wall sk, mustard anticancer agent, mycaperoxide B, mycobacterial cell wall extract, myriaporone, N-acetyldinaline, N-substituted benzamides, nagrestip, naloxone+pentazocine, napavin, naphterpin, nartograstim, nedaplatin, nemorubicin, neridronic acid, nisamycin, nitric oxide modulators, nitroxide antioxidant, nitrullyn, oblimersen (Genasense), $O^6$-benzylguanine, okicenone, onapristone, ondansetron, oracin, oral cytokine inducer, paclitaxel analogues and derivatives, palauamine, palmitoylrhizoxin, pamidronic acid, panaxytriol, panomifene, parabactin, peldesine, pentosan polysulfate sodium, pentrozole, perflubron, perillyl alcohol, phenazinomycin, phenylacetate, phosphatase inhibitors, picibanil, pilocarpine hydrochloride, placetin A, placetin B, plasminogen activator inhibitor, platinum complex, platinum compounds, platinum-triamine complex, propyl bis-acridone, prostaglandin J2, proteasome inhibitors, protein A-based immune modulator, protein kinase C inhibitors, microalgal, pyrazoloacridine, pyridoxylated hemoglobin polyoxyethylene conjugate, raf antagonists, raltitrexed, ramosetron, ras farnesyl protein transferase inhibitors, ras-GAP inhibitor, retelliptine demethylated, rhenium Re 186 etidronate, ribozymes, RII retinamide, rohitukine, romurtide, roquinimex, rubiginone B1, ruboxyl, saintopin, SarCNU, sarcophytol A, sargramostim, Sdi 1 mimetics, senescence derived inhibitor 1, signal transduction inhibitors, sizofiran, sobuzoxane, sodium borocaptate, solverol, somatomedin binding protein, sonermin, sparfosic acid, spicamycin D, splenopentin, spongistatin 1, squalamine, stipiamide, stromelysin inhibitors, sulfinosine, superactive vasoactive intestinal peptide antagonist, suradista, suramin, swainsonine, tallimustine, tazarotene, tellurapyrylium, telomerase inhibitors, tetrachlorodecaoxide, tetrazomine, thiocoraline, thrombopoietin, thrombopoietin mimetic, thymalfasin, thymopoietin receptor agonist, thymotrinan, thyroid stimulating hormone, tin ethyl etiopurpurin, titanocene bichloride, topsentin, translation inhibitors, tretinoin, triacetyluridine, tropisetron, turosteride, ubenimex, urogenital sinus-derived growth inhibitory factor, variolin B, velaresol, veramine, verdins, vinxaltine, vitaxin, zanoterone, zilascorb, zinostatin stimalamer, acanthifolic acid, aminothiadiazole, anastrozole, bicalutamide, brequinar sodium, capecitabine, carmofur, Ciba-Geigy CGP-30694, cladribine, cyclopentyl cytosine, cytarabine phosphate stearate, cytarabine conjugates, cytarabine ocfosfate, Lilly DATHF, Merrel Dow DDFC, dezaguanine, dideoxycytidine, dideoxyguanosine, didox, Yoshitomi DMDC, doxifluridine, Wellcome EHNA, Merck & Co. EX-015, fazarabine, floxuridine, fludarabine, fludarabine phosphate, N-(2'-furanidyl)-5-fluorouracil, Daiichi Seiyaku FO-152, 5-FU-fibrinogen, isopropyl pyrrolizine, Lilly LY-188011, Lilly LY-264618, methobenzaprim, methotrexate, Wellcome MZPES, norspermidine, nolvadex, NCI NSC-127716, NCI NSC-264880, NCI NSC-39661, NCI NSC-612567, Warner-Lambert PALA, pentostatin, piritrexim, plicamycin, Asahi Chemical PL-AC, stearate, Takeda TAC-788, thioguanine, tiazofurin, Erbamont TIF, trimetrexate, tyrosine kinase inhibitors, tyrosine protein kinase inhibitors, Taiho UFT, uricytin, Shionogi 254-S, aldo-phosphamide analogues, altretamine, anaxirone, Boehringer Mannheim BBR-2207, bestrabucil, budotitane, Wakunaga CA-102, carboplatin, carmustine (BiCNU), Chinoin-139, Chinoin-153, chlorambucil, cisplatin, cyclophosphamide, American Cyanamid CL-286558, Sanofi CY-233, cyplatate, dacarbazine, Degussa D-19-384, Sumimoto DACHP(Myr)2, diphenylspiromustine, diplatinum cytostatic, Chugai DWA-2114R, ITI E09, elmustine, Erbamont FCE-24517, estramustine phosphate sodium, etoposide phosphate, fotemustine, Unimed G-6-M, Chinoin GYKI-17230, hepsul-fam, ifosfamide, iproplatin, lomustine, mafosfamide, mitolactol, mycophenolate, Nippon Kayaku NK-121, NCI NSC-264395, NCI NSC-342215, oxaliplatin, Upjohn PCNU, prednimustine, Proter PTT-119, ranimustine, semustine, SmithKline SK&F-101772, thiotepa, Yakult Honsha SN-22, spiromus-tine, Tanabe Seiyaku TA-077, tauromustine, temozolomide, teroxirone, tetraplatin and trimelamol, Taiho 4181-A, aclarubicin, actinomycin D, actinoplanone, Erbamont ADR-456, aeroplysinin derivative, Ajinomoto AN-201-II, Ajinomoto AN-3, Nippon Soda anisomycins, anthracycline, azino-mycin-A, bisucaberin, Bristol-Myers BL-6859, Bristol-Myers BMY-25067, Bristol-Myers BMY-25551, Bristol-Myers BMY-26605, Bristol-Myers BMY-27557, Bristol-Myers BMY-28438, bleomycin sulfate, bryostatin-1, Taiho C-1027, calichemycin, chromoximycin, dactinomycin, daunorubicin, Kyowa Hakko DC-102, Kyowa Hakko DC-79, Kyowa Hakko DC-88A, Kyowa Hakko DC89-A1, Kyowa Hakko DC92-B, ditrisarubicin B, Shionogi DOB-41, doxorubicin, doxorubicin-fibrinogen, elsamicin-A, epirubicin, erbstatin, esorubicin, esperamicin-A1, esperamicin-A1b, Erbamont FCE-21954, Fujisawa FK-973, fostriecin, Fujisawa FR-900482, glidobactin, gregatin-A, grincamycin, herbimycin, idarubicin, illudins, kazusamycin, kesarirhodins, Kyowa Hakko KM-5539, Kirin Brewery KRN-8602, Kyowa Hakko KT-5432, Kyowa Hakko KT-5594, Kyowa Hakko KT-6149, American Cyanamid LL-D49194, Meiji Seika ME 2303, menogaril, mitomycin, mitomycin analogues, mitoxantrone, SmithKline M-TAG, neoenactin, Nippon Kayaku NK-313, Nippon Kayaku NKT-01, SRI International NSC-357704, oxalysine, oxaunomycin, peplomycin, pilatin, pirarubicin, porothramycin, pyrindamycin A, Tobishi RA-I, rapamycin, rhizoxin, rodorubicin, sibanomicin, siwenmycin, Sumitomo SM-5887, Snow Brand SN-706, Snow Brand SN-07, sorangicin-A, sparsomycin, SS Pharmaceutical SS-21020, SS Pharmaceutical SS-7313B, SS Pharmaceutical SS-9816B, steffimycin B, Taiho 4181-2, talisomycin, Takeda TAN-868A, terpentecin, thrazine, tricrozarin A, Upjohn U-73975, Kyowa Hakko UCN-10028A, Fujisawa WF-3405, Yoshitomi Y-25024, zorubicin, 5-fluorouracil (5-FU), the peroxidate oxidation product of inosine, adenosine, or cytidine with methanol or ethanol, cytosine arabinoside (also referred to as Cytarabin, araC, and Cytosar), 5-Azacytidine, 2-Fluoroadenosine-5'-phosphate (Fludara, also referred to as FaraA), 2-Chlorodeoxyadenosine, Abarelix, Abbott A-84861, Abiraterone acetate, Aminoglutethimide, Asta Medica AN-207, Antide, Chugai AG-041R, Avorelin, aseranox, Sensus B2036-PEG, buserelin, BTG CB-7598, BTG CB-7630, Casodex, cetrolix, clastroban, clodronate disodium, Cosudex, Rotta Research CR-1505, cytadren, crinone, deslorelin, droloxifene, dutasteride, Elimina, Laval University EM-800, Laval University EM-652, epitiostanol, epristeride, Mediolanum EP-23904, EntreMed 2-ME, exemestane, fadrozole, finasteride, formestane, Pharmacia & Upjohn FCE-24304, ganirelix, goserelin, Shire gonadorelin agonist, Glaxo Wellcome GW-5638, Hoechst Marion Roussel Hoe-766, NCI hCG, idoxifene, isocordoin, Zeneca ICI-182780, Zeneca ICI-118630, Tulane University J015X, Schering Ag J96, ketanserin, lanreotide, Milkhaus LDI-200, letrozol, leuprolide, leuprorelin, liarozole, lisuride hydrogen maleate, loxiglumide, mepitiostane, Ligand Pharmaceuticals LG-1127, LG-1447, LG-2293, LG-2527, LG-2716, Bone Care International LR-103, Lilly LY-326315, Lilly LY-353381-HCl, Lilly LY-326391, Lilly LY-353381, Lilly LY-357489, miproxifene phosphate, Orion Pharma MPV-2213ad, Tulane University MZ-4-71, nafarelin, nilutamide, Snow Brand NKS01, Azko Nobel ORG-31710, Azko Nobel ORG-31806, orimeten, orimetene, orimetine, ormeloxifene, osaterone, Smithkline Beecham SKB-105657, Tokyo University OSW-1, Peptech PTL-03001, Pharmacia & Upjohn PNU-156765, quinagolide, ramorelix, Raloxifene, statin, sandostatin LAR, Shionogi S-10364, Novartis SMT-487, somavert, somatostatin, tamoxifen, tamoxifen methiodide, teverelix, toremifene, triptorelin, TT-232, vapreotide, vorozole, Yamanouchi YM-116, Yamanouchi YM-511, Yamanouchi YM-55208, Yamanouchi YM-53789, Schering AG ZK-1911703, Schering AG ZK-230211, and Zeneca ZD-182780, alpha-carotene, alpha-difluoromethyl-arginine, acitretin, Biotec AD-5, Kyorin AHC-52, alstonine, amonafide, amphethinile, amsacrine, Angiostat, ankinomycin, antineoplaston A10, antineoplaston A2, antineoplaston A3, antineoplaston A5, antineoplaston AS2-1, Henkel APD, aphidicolin glycinate, asparaginase, Avarol, baccharin, batracylin, benfluron, benzotript, Ipsen-Beaufour BIM-23015, bisantrene, Bristo-Myers BMY-40481, Vestar boron-10, bromofosfamide, Wellcome BW-502, Wellcome BW-773, calcium carbonate, Calcet, Calci-Chew, Calci-Mix, Roxane calcium carbonate tablets, caracemide, carmethizole hydrochloride, Ajinomoto CDAF, chlorsulfaquinoxalone, Chemes CHX-2053, Chemex CHX-100, Warner-Lambert CI-921, Warner-Lambert CI-937, Warner-Lambert CI-941, Warner-Lambert CI-958, clanfenur, claviridenone, ICN compound 1259, ICN compound 4711, Contracan, Cell Pathways CP-461, Yakult Honsha CPT-11, crisnatol, curaderm, cytochalasin B, cytarabine, cytocytin, Merz D-609, DABIS maleate, datelliptinium, DFMO, didemnin-B, dihaematoporphyrin ether, dihydrolenperone dinaline, distamycin, Toyo Pharmar DM-341, Toyo Pharmar DM-75, Daiichi Seiyaku DN-9693, docetaxel, Encore Pharmaceuticals E7869, elliprabin, elliptinium acetate, Tsumura EPMTC, ergotamine, etoposide, etretinate, Eulexin, Cell Pathways Exisulind (sulindac sulphone or CP-246), fenretinide, Florical, Fujisawa FR-57704, gallium nitrate, gemcitabine, genkwadaphnin, Gerimed, Chugai GLA-43, Glaxo GR-63178, grifolan NMF-5N, hexadecylphosphocholine, Green Cross HO-221, homoharringtonine, hydroxyurea, BTG ICRF-187, ilmofosine, irinotecan, isoglutamine, isotretinoin, Otsuka JI-36, Ramot K-477, ketoconazole, Otsuak K-76COONa, Kureha Chemical K-AM, MECT Corp KI-8110, American Cyanamid L-623, leucovorin, levamisole, leukoregulin, lonidamine, Lundbeck LU-23-112, Lilly LY-186641, Materna, NCI (US) MAP, marycin, Merrel Dow MDL-27048, Medco MEDR-340, megestrol, merbarone, merocyanine derivatives, methylanilinoacridine, Molecular Genetics MGI-136, minactivin, mitonafide, mitoquidone, Monocal, mopidamol, motretinide, Zenyaku Kogyo MST-16, Mylanta, N-(retinoyl)amino acids, Nilandron, Nisshin Flour Milling N-021, N-acylated-dehydroalanines, nafazatrom, Taisho NCU-190, Nephro-Calci tablets, nocodazole derivative, Normosang, NCI NSC-145813, NCI NSC-361456, NCI NSC-604782, NCI NSC-95580, octreotide, Ono ONO-112, oquizanocine, Akzo Org-10172, paclitaxel, pancratistatin, pazelliptine, Warner-Lambert PD-111707, Warner-Lambert PD-115934, Warner-Lambert PD-131141, Pierre Fabre PE-1001, ICRT peptide D, piroxantrone, polyhaematoporphyrin, polypreic acid, Efamol porphyrin, probimane, procarbazine, proglumide, Invitron protease nexin I, Tobishi RA-700, razoxane, retinoids, R-flurbiprofen (Encore Pharmaceuticals), Sandostatin, Sapporo Breweries RBS, restrictin-P, retelliptine, retinoic acid, Rhone-Poulenc RP-49532, Rhone-Poulenc RP-56976, Scherring-Plough SC-57050, Scherring-Plough SC-57068, selenium (selenite and selenomethionine), SmithKline SK&F-104864, Sumitomo SM-108, Kuraray SMANCS, SeaPharm SP-10094, spatol, spirocyclopropane derivatives, spirogermanium, Unimed, SS Pharmaceutical SS-554, strypoldinone, Stypoldione, Suntory SUN 0237, Suntory SUN 2071, Sugen SU-101, Sugen SU-5416, Sugen SU-6668, sulindac, sulindac sulfone, superoxide dismutase, Toyama T-506, Toyama T-680, taxol, Teijin TEI-0303, teniposide, thaliblastine, Eastman Kodak TJB-29, tocotrienol, Topostin, Teijin TT-82, Kyowa Hakko UCN-01, Kyowa Hakko UCN-1028, ukrain, Eastman Kodak USB-006, vinblastine, vinblastine sulfate, vincristine, vincristine sulfate, vindesine, vindesine sulfate, vinestramide, vinorelbine, vintriptol, vinzolidine, withanolides, Yamanouchi YM-534, Zileuton, ursodeoxycholic acid, Zanosar.

In some embodiments, the chemotherapeutic agent comprises Bacillus Calmette-Guerin (BCG).

In some embodiments, the active agent comprises an antibiotic agent. In some embodiments, the pharmaceutical agent comprises an antibiotic agent. In some embodiments, the antibiotic agent comprises at least one of: amikacin, amoxicillin, gentamicin, kanamycin, neomycin, netilmicin, paromomycin, tobramycin, geldanamycin, herbimycin, carbacephem (loracarbef), ertapenem, doripenem, imipenem, cefadroxil, cefazolin, cefalotin, cephalexin, cefaclor, cefamandole, cefoxitin, cefprozil, cefuroxime, cefixime, cefdinir, cefditoren, cefoperazone, cefotaxime, cefpodoxime, ceftazidime, ceftibuten, ceftizoxime, ceftriaxone, cefepime, ceftobiprole, clarithromycin, clavulanic acid, clindamycin, teicoplanin, azithromycin, dirithromycin, erythromycin, troleandomycin, telithromycin, aztreonam, ampicillin, azlocillin, bacampicillin, carbenicillin, cloxacillin, dicloxacillin, flucloxacillin, mezlocillin, meticillin, nafcillin, norfloxacin, oxacillin, penicillin G, penicillin V, piperacillin, pvampicillin, pivmecillinam, ticarcillin, bacitracin, colistin, polymyxin B, ciprofloxacin, enoxacin, gatifloxacin, levofloxacin, lomefloxacin, moxifloxacin, ofloxacin, trovafloxacin, grepafloxacin, sparfloxacin, afenide, prontosil, sulfacetamide, sulfamethizole, sulfanilimide, sulfamethoxazole, sulfisoxazole, trimethoprim, trimethoprim-sulfamethoxazole, demeclocycline, doxycycline, oxytetracycline, tetracycline, arsphenamine, chloramphenicol, lincomycin, ethambutol, fosfomycin, furazolidone, isoniazid, linezolid, mupirocin, nitrofurantoin, platensimycin, pyrazinamide, quinupristin/dalfopristin, rifampin, thiamphenicol, rifampicin, minocycline, sultamicillin, sulbactam, sulphonamides, mitomycin, spectinomycin, spiramycin, roxithromycin, and meropenem.

In some embodiments, the antibiotic agent comprises erythromycin.

In some embodiments, the active agent comprises an active biological agent. In some embodiments, the active biological agent comprises an active secondary, tertiary or quaternary structure. In some embodiments, the active biological agent comprises at least one of growth factors, cytokines, peptides, proteins, enzymes, glycoproteins, nucleic acids, antisense nucleic acids, fatty acids, antimicrobials, vitamins, hormones, steroids, lipids, polysaccharides, carbohydrates, a hormone, gene therapies, RNA, siRNA, and/or cellular therapies such as stem cells and/or T-cells.

In some embodiments, the active biological agent comprises siRNA.

In some embodiments of the methods and/or devices provided herein, the device further comprises a stent. In some embodiments, the substrate is not the stent.

Methods of Manufacturing Generally

In some embodiments, a coating is formed on said substrate by a process comprising depositing a polymer and/or the active agent by an e-RESS, an e-SEDS, or an e-DPC process. In some embodiments, the process of forming said coating provides improved adherence of the coating to the substrate prior to deployment of the device at the intervention site and facilitates dissociation of said coating from said substrate at the intervention site. In some embodiments, the coating is formed on said substrate by a process comprising depositing the active agent by an e-RESS, an e-SEDS, or an e-DPC process without electrically charging the substrate. In some embodiments, the coating is formed on said substrate by a process comprising depositing the active agent on the substrate by an e-RESS, an e-SEDS, or an e-DPC process without creating an electrical potential between the substrate and a coating apparatus used to deposit the active agent.

Means for creating the bioabsorbable polymer(s)+drug(s) coating of the device with or without a substrate:

Spray coat the coating-form with drug and polymer as is done in Micell process (e-RESS, e-DPC, compressed-gas sintering).

Perform multiple and sequential coating-sintering steps where different materials may be deposited in each step, thus creating a laminated structure with a multitude of thin layers of drug(s), polymer(s) or drug+polymer that build the final device.

Perform the deposition of polymer(s)+drug(s) laminates with the inclusion of a mask on the inner (luminal) surface of the device. Such a mask could be as simple as a non-conductive mandrel inserted through the internal diameter of the coating form. This masking could take place prior to any layers being added, or be purposefully inserted after several layers are deposited continuously around the entire coating-form.

In some embodiments, the coating comprises a microstructure. In some embodiments, particles of the active agent are sequestered or encapsulated within said microstructure.

In some embodiments, the microstructure comprises microchannels, micropores and/or microcavities. In some embodiments, the microstructure is selected to allow sustained release of the active agent. In some embodiments, the microstructure is selected to allow controlled release of the active agent.

Other methods for preparing the coating include solvent based coating methods and plasma based coating methods. In some embodiments, the coating is prepared by a solvent based coating method. In some embodiments, the coating is prepared by a solvent plasma based coating method.

Another advantage of the present invention is the ability to create a delivery device with a controlled (dialed-in) drug-elution profile. Via the ability to have different materials in each layer of the laminate structure and the ability to control the location of drug(s) independently in these layers, the method enables a device that could release drugs at very specific elution profiles, programmed sequential and/or parallel elution profiles. Also, the present invention allows controlled elution of one drug without affecting the elution of a second drug (or different doses of the same drug).

Provided herein is a method of forming a medical device comprising a substrate and a coating on at least a portion of the substrate, wherein the coating comprises an active agent, the method comprising: providing the substrate; and forming the coating on at least a portion of the substrate by depositing the active agent by on the substrate by at least one of an e-RESS, an e-SEDS, and an e-DPC process, wherein forming the coating results in at least a portion of the coating being adapted to transfer from the substrate to an intervention site upon stimulating the coating with a stimulation.

Provided herein is a method of forming a medical device comprising a substrate and a coating on at least a portion of the substrate, wherein the coating comprises an active agent, the method comprising: providing the substrate; and forming the coating on at least a portion of the substrate by depositing the active agent by on the substrate by at least one of an e-RESS, an e-SEDS, and an e-DPC process without electrically charging the substrate, wherein forming the coating results in at least a portion of the coating being adapted to transfer from the substrate to an intervention site upon stimulating the coating with a stimulation.

Provided herein is a method of forming a medical device comprising a substrate and a coating on at least a portion of the substrate, wherein the coating comprises an active agent, the method comprising: providing the substrate; and forming the coating on at least a portion of the substrate by depositing the active agent by on the substrate by at least one of an e-RESS, an e-SEDS, and an e-DPC process without creating an electrical potential between the substrate and a coating apparatus used in the at least one e-RESS, an e-SEDS, and an e-DPC process, wherein forming the coating results in at least a portion of the coating being adapted to transfer from the substrate to an intervention site upon stimulating the coating with a stimulation.

Provided herein is a method of forming a medical device comprising a substrate and a coating on at least a portion of the substrate, wherein the coating comprises an active agent, the method comprising: providing the substrate; and forming the coating on at least a portion of the substrate by depositing the active agent by on the substrate by at least one of a dipping and/or a spraying process, wherein forming the coating results in at least a portion of the coating being adapted to transfer from the substrate to an intervention site upon stimulating the coating with a stimulation.

Provided herein is a method of forming a medical device comprising a substrate and a coating on at least a portion of the substrate, wherein the coating comprises an active agent, the method comprising: providing the substrate; and forming the coating on at least a portion of the substrate by depositing the active agent by on the substrate by at least one of an e-RESS, an e-SEDS, and an e-DPC process, wherein forming the coating results in at least a portion of the coating being adapted to free from the substrate upon stimulating the coating with a stimulation.

Provided herein is a method of forming a medical device comprising a substrate and a coating on at least a portion of the substrate, wherein the coating comprises an active agent, the method comprising: providing the substrate; and forming the coating on at least a portion of the substrate by depositing the active agent by on the substrate by at least one of a dipping and/or a spraying process, wherein forming the coating results in at least a portion of the coating being adapted to free from the substrate upon stimulating the coating with a stimulation.

Provided herein is a method of forming a medical device comprising a substrate and a coating on at least a portion of the substrate, wherein the coating comprises an active agent, the method comprising: providing the substrate; and forming the coating on at least a portion of the substrate by depositing the active agent by on the substrate by at least one of an e-RESS, an e-SEDS, and an e-DPC process, wherein forming the coating results in at least a portion of the coating being adapted to dissociate from the substrate upon stimulating the coating with a stimulation.

Provided herein is a method of forming a medical device comprising a substrate and a coating on at least a portion of the substrate, wherein the coating comprises an active agent, the method comprising: providing the substrate; and forming the coating on at least a portion of the substrate by depositing the active agent by on the substrate by at least one of a dipping and/or a spraying process, wherein forming the coating results in at least a portion of the coating being adapted to dissociate from the substrate upon stimulating the coating with a stimulation.

Provided herein is a method of forming a medical device comprising a substrate and a coating on at least a portion of the substrate, wherein the coating comprises an active agent, the method comprising: providing the substrate; and forming the coating on at least a portion of the substrate by depositing the active agent by on the substrate by at least one of an e-RESS, an e-SEDS, and an e-DPC process, wherein forming the coating results in at least a portion of the coating being adapted to deliver to the intervention site upon stimulating the coating with a stimulation.

Provided herein is a method of forming a medical device comprising a substrate and a coating on at least a portion of the substrate, wherein the coating comprises an active agent, the method comprising: providing the substrate; and forming the coating on at least a portion of the substrate by depositing the active agent by on the substrate by at least one of a dipping and/or a spraying process, wherein forming the coating results in at least a portion of the coating being adapted to deliver to the intervention site upon stimulating the coating with a stimulation.

In some embodiments, the e-RESS, the e-SEDS, and/or the e-DPC process used in forming the coating is performed without electrically charging the substrate. In some embodiments, the e-RESS, the e-SEDS, and/or the e-DPC process used in forming the coating is performed without creating an electrical potential between the substrate and the coating apparatus used in the e-RESS, the e-SEDS, and/or the e-DPC process.

In some embodiments, forming the coating results in the coating adhering to the substrate prior to the substrate reaching the intervention site.

Some embodiments further comprise providing a release agent on said substrate. In some embodiments, providing the release agent step is performed prior to the forming the coating step. In some embodiments, the release agent comprises at least one of: a biocompatible release agent, a non-biocompatible release agent, a powder, a lubricant, a surface modification of the substrate, a viscous fluid, a gel, the active agent, a second active agent, a physical characteristic of the substrate. In some embodiments, the physical characteristic of the substrate comprises at least one of: a patterned coating surface of the substrate, and a ribbed surface of the substrate. In some embodiments, the release agent comprises a property that is capable of changing at the intervention site. In some embodiments, the property comprises a physical property. In some embodiments, the property comprises a chemical property. In some embodiments, the release agent is capable of changing a property when in contact with at least one of a biologic tissue and a biologic fluid. In some embodiments, the release agent is capable of changing a property when in contact with an aqueous liquid. In some embodiments, the coating results in a coating property that facilitates transfer of the coating to the intervention site. In some embodiments, the coating property comprises a physical characteristic of the coating. In some embodiments, the physical characteristic comprises a pattern.

In some embodiments, forming the coating facilitates transfer of the coating to the intervention site.

In some embodiments, transferring, freeing, dissociating, depositing, and/or tacking step comprises softening the polymer by hydration, degradation or by a combination of hydration and degradation. In some embodiments, the transferring, freeing, dissociating, depositing, and/or tacking step comprises softening the polymer by hydrolysis of the polymer.

In some embodiments, the providing step comprises forming the coating by a solvent based coating method. In some embodiments, the providing step comprises forming the coating by a solvent plasma based method.

In some embodiments, providing the device comprises depositing a plurality of layers on said substrate to form the coating, wherein at least one of the layers comprises the active agent. In some embodiments, at least one of the layers comprises a polymer. In some embodiments, the polymer is bioabsorbable. In some embodiments, the active agent and the polymer are in the same layer, in separate layers, or form overlapping layers. In some embodiments, the plurality of layers comprise five layers deposited as follows: a first polymer layer, a first active agent layer, a second polymer layer, a second active agent layer and a third polymer layer.

EXAMPLES

The following examples are provided to illustrate selected embodiments. They should not be considered as limiting the scope of the invention, but merely as being illustrative and representative thereof. For each example listed herein, multiple analytical techniques may be provided. Any single technique of the multiple techniques listed may be sufficient to show the parameter and/or characteristic being tested, or any combination of techniques may be used to show such parameter and/or characteristic. Those skilled in the art will be familiar with a wide range of analytical techniques for the characterization of drug/polymer coatings. Techniques presented here, but not limited to, may be used to additionally and/or alternatively characterize specific properties of the coatings with variations and adjustments employed which would be obvious to those skilled in the art.

Sample Preparation

Generally speaking, coatings on stents, on balloons, on coupons, on other substrates, or on samples prepared for in-vivo models are prepared as herein. Nevertheless, modifications for a given analytical method are presented within the examples shown, and/or would be obvious to one having skill in the art. Thus, numerous variations, changes, and substitutions will now occur to those skilled in the art without departing from the invention. It should be understood that various alternatives to the embodiments of the invention described herein and examples provided may be employed in practicing the invention and showing the parameters and/or characteristics described.

Coatings on Balloons

Coated balloons as described herein and/or made by a method disclosed herein are prepared. In some examples, the coated balloons have a targeted coating thickness of ~15 microns (~5 microns of active agent). In some examples, the coating process is PDPDP (Polymer, sinter, Drug, Polymer, sinter, Drug, Polymer, sinter) using deposition of drug in dry powder form and deposition of polymer particles by RESS methods and equipment described herein. In the illustrations herein, resulting coated balloons may have a 3-layer coating comprising polymer (for example, PLGA) in the first layer, drug (for example, rapamycin) in a second layer and polymer in the third layer, where a portion of the third layer is substantially drug free (e.g. a sub-layer within the third layer having a thickness equal to a fraction of the thickness of the third layer). As described layer, the middle layer (or drug layer) may be overlapping with one or both first (polymer) and third (polymer) layer. The overlap between the drug layer and the polymer layers is defined by extension of polymer material into physical space largely occupied by the drug. The overlap between the drug and polymer layers may relate to partial packing of the drug particles during the formation of the drug layer. When crystal drug particles are deposited on top of the first polymer layer, voids and or gaps may remain between dry crystal particles. The voids and gaps are available to be occupied by particles deposited during the formation of the third (polymer) layer. Some of the particles from the third (polymer) layer may rest in the vicinity of drug particles in the second (drug) layer. When the sintering step is completed for the third (polymer) layer, the third polymer layer particles fuse to form a continuous film that forms the third (polymer) layer. In some embodiments, the third (polymer) layer however will have a portion along the longitudinal axis of the stent whereby the portion is free of contacts between polymer material and drug particles. The portion of the third layer that is substantially of contact with drug particles can be as thin as 1 nanometer.

Polymer-coated balloons having coatings comprising polymer but no drug are made by a method disclosed herein and are prepared having a targeted coating thickness of, for example, about, about 0.5, 1, 2, 3, 4, 5, 10, 15, 20, 25, 30, 35, 40, 45, or 50 microns, depending in part on whether the coating expands upon hydration and if so whether it is hydrated. In embodiments, the coating thickness is 1-5 microns. In other embodiments, it is 1-10 microns.

An example coating process is PPP (PLGA, sinter, PLGA, sinter, PLGA, sinter) using RESS methods and equipment described herein. These polymer-coated balloons may be used as control samples in some of the examples, infra.

In some examples, the balloons are made of a compliant polymer. In some examples, the balloons are made of a non-compliant polymer. The balloons may be, in some examples, 5 to 50 mm in length, preferably 10-20 mm in length.

Balloons can be coated while inflated, and later compacted, or they can be coated while uninflated. If a balloon is coated while inflated and later folded or otherwise compacted, then a portion of the coating can be protected during insertion by virtue of being disposed within the portion of the balloon that is not exposed until inflation. The coating can also be protected by using a sheath or other covering, as described in the art for facilitating insertion of an angioplasty balloon. The coating released from a balloon may be analyzed (for example, for analysis of a coating band and/or coating a portion of the balloon). Alternatively, in some examples, the coating is analyzed directly on the balloon. This coating, and/or coating and balloon, may be sliced into sections which may be turned 90 degrees and visualized using the surface composition techniques presented herein or other techniques known in the art for surface composition analysis (or other characteristics, such as crystallinity, for example). In this way, what could be an analysis of coating composition through a depth when the coating is on the balloon or as removed from the balloon (i.e. a depth from the abluminal surface of the coating to the surface of the removed coating that once contacted the balloon or a portion thereof), becomes a surface analysis of the coating which can, for example, show the layers in the slice of coating, at much higher resolution. Residual coating on an extracted balloon also can be analyzed and compared to the amount of coating on an unused balloon, using, e.g., HPLC, as noted herein. Coating removed from the balloon, or analyzed without removal and/or release from the balloon, may be treated the same way, and assayed, visualized, and/or characterized as presented herein using the techniques described and/or other techniques known to a person of skill in the art.

Coatings on Stents

Coated stents as described herein and/or made by a method disclosed herein are prepared. In some examples, the coated stents have a targeted thickness of ~15 microns (~5 microns of active agent). In some examples, the coating process is PDPDP (Polymer, sinter, Drug, Polymer, sinter, Drug, Polymer, sinter) using deposition of drug in dry powder form and deposition of polymer particles by RESS methods and equipment described herein. In the illustrations herein, resulting coated stents may have a 3-layer coating comprising polymer (for example, PLGA) in the first layer, drug (for example, rapamycin) in a second layer and polymer in the third layer, where a portion of the third layer is substantially drug free (e.g. a sub-layer within the third layer having a thickness equal to a fraction of the thickness of the third layer). As described, the middle layer (or drug layer) may be overlapping with one or both first (polymer) and third (polymer) layer. The overlap between the drug layer and the polymer layers is defined by extension of polymer material into physical space largely occupied by the drug. The overlap between the drug and polymer layers may relate to partial packing of the drug particles during the formation of the drug layer. When crystal drug particles are deposited on top of the first polymer layer, voids and or gaps may remain between dry crystal particles. The voids and gaps are available to be occupied by particles deposited during the formation of the third (polymer) layer. Some of the particles from the third (polymer) layer may rest in the vicinity of drug particles in the second (drug) layer. When the sintering step is completed for the third (polymer) layer, the third polymer layer particles fuse to form a continuous film that forms the third (polymer) layer. In some embodiments, the third (polymer) layer however will have a portion along the longitudinal axis of the stent whereby the portion is free of contacts between polymer material and drug particles. The portion of the third layer that is substantially of contact with drug particles can be as thin as 1 nanometer.

Polymer-coated stents having coatings comprising polymer but no drug are made by a method disclosed herein and are prepared having a targeted thickness of, for example, ~5 microns. An example coating process is PPP (PLGA, sinter, PLGA, sinter, PLGA, sinter) using RESS methods and equipment described herein. These polymer-coated stents may be used as control samples in some of the examples, infra.

In some examples, the stents are made of a cobalt-chromium alloy and are 5 to 50 mm in length, preferably 10-20 mm in length, with struts of thickness between 20 and 100 microns, preferably 50-70 microns, measuring from an abluminal surface to a luminal surface, or measuring from a side wall to a side wall. In some examples, the stent may be cut lengthwise and opened to lay flat be visualized and/or assayed using the particular analytical technique provided.

The coating may be removed (for example, for analysis of a coating band and/or coating on a strut, and/or coating on the abluminal surface of a flattened stent) by scraping the coating off using a scalpel, knife or other sharp tool. This coating may be sliced into sections which may be turned 90 degrees and visualized using the surface composition techniques presented herein or other techniques known in the art for surface composition analysis (or other characteristics, such as crystallinity, for example). In this way, what was an analysis of coating composition through a depth when the coating was on the stent or as removed from the stent (i.e. a depth from the abluminal surface of the coating to the surface of the removed coating that once contacted the strut or a portion thereof), becomes a surface analysis of the coating which can, for example, show the layers in the slice of coating, at much higher resolution. Coating removed from the stent may be treated the same way, and assayed, visualized, and/or characterized as presented herein using the techniques described and/or other techniques known to a person of skill in the art.

Coatings on Coupons

In some examples, samples comprise coupons of glass, metal, e.g. cobalt-chromium, or another substance that are prepared with coatings as described herein, with a plurality of layers as described herein, and/or made by a method disclosed herein. In some examples, the coatings comprise polymer. In some examples, the coatings comprise polymer and active agent. In some examples, the coated coupons are prepared having a targeted thickness of ~10 microns (with ~5 microns of active agent), and have coating layers as described for the coated stent samples, infra.

Sample Preparation for In-Vivo Models

Devices comprising ballons having coatings disclosed herein are deployed in the porcine coronary arteries of pigs (domestic swine, juvenile farm pigs, or Yucatan miniature swine). Porcine coronary angioplasty is exploited herein since such model yields results that are comparable to other investigations assaying neointimal hyperplasia in human subjects. The balloons are expanded to a 1:1.1 balloon:artery ratio. At multiple time points, animals are euthanized (e.g. t=1 day, 7 days, 14 days, 21 days, and 28 days), the tissue surrounding the intervention site is extracted, and assayed.

Devices comprising balloons having coatings disclosed herein alternatively are implanted in the common iliac arteries of New Zealand white rabbits. The balloons are expanded to a 1:1.1 balloon:artery ratio. At multiple time points, animals are euthanized (e.g., t=1 day, 7 days, 14 days, 21 days, and 28 days), the tissue surrounding the intervention site is extracted, and assayed.

Example 1

General eDPC and eRESS Deposition Methods and Coating of Stent

This example employs equipment and processes described in PCT/US2006/027321, "Polymer coatings containing drug powder of controlled morphology," (WO 2007/011707), the contents of which are herein incorporated by reference in its entirety.

A coated coronary stent is prepared as follows:

3.0×18 mm stainless steel (316 L) metal stent (Burpee Materials Technology, LLC: http://www.burpeetech.com/) is cleaned prior to coating via ultrasonic washing followed by solvent rinse with dichloromethane and hexane.

A drug-containing polymer coating is deposited on the stent as follows:

The metal stent serving as a target substrate for rapamycin coating is placed in a vessel and attached to a high voltage electrode. The vessel (V), of approximately 1500 cm3 volume, is equipped with two separate nozzles through which rapamycin or polymers could be selectively introduced into the vessel. Both nozzles are grounded. Additionally, the vessel (V) is equipped with a separate port is available for purging the vessel. Upstream of one nozzle (D) is a small pressure vessel (PV) approximately 5 cm3 in volume with three ports to be used as inlets and outlets. Each port is equipped with a valve which could be actuated opened or closed. One port, port (1) used as an inlet, is an addition port for the dry powdered rapamycin. Port (2), also an inlet is used to feed pressurized gas, liquid, or supercritical fluid into PV. Port (3), used as an outlet, is used to connect the pressure vessel (PV) with nozzle (D) contained in the primary vessel (V) with the target coupon.

170 micrograms of rapamycin (from Chemwerth www.chemwerth.com) that is jet-milled to an average (crystalline) particle size of ~2 microns; PLGA polymer with 50% glycolic acid content, 0.63 dL/g inherent viscosity (Durect Corp. http://www.absorbables.com/) is employed. Rapamycin is loaded into (PV) through port (1) then port (1) is actuated to the closed position. Gaseous carbon dioxide is then added to (PV) to a pressure of 400 to 600 psig at 20° C. through port (2), then port (2) is closed to the source gas.

The second nozzle, nozzle (P), is used to feed precipitated PLGA polymer particles into vessel (V) to coat the stainless steel stent. Nozzle (P) is equipped with a heater and controller to minimize heat loss due to the expansion of liquefied gases. Upstream of nozzle (P) is a pressure vessel, (PV2), with approximately 25-cm3 internal volume. The pressure vessel (PV2) is equipped with multiple ports to be used for inlets, outlets, thermocouples, and pressure transducers. Additionally, (PV2) is equipped with a heater and a temperature controller. Each port is connected to the appropriate valves, metering valves, pressure regulators, or plugs to ensure adequate control of material into and out of the pressure vessel (PV2). One outlet from (PV2) is connected to a metering valve through pressure rated tubing which is then connected to nozzle (P) located in vessel (V). The metal stent is then charged to 40 kV using a Glassman Series EL high-voltage power source. The following coatings and sintering steps are completed:

e-RESS polymer (approx 200 micrograms),
sinter w/compressed gas,
e-DPC drug (~85 micrograms,
e-RESS polymer (~200-250 micrograms),
sinter w/compressed gas,
e-DPC drug (~85 micrograms),
e-RESS polymer (~200-300 micrograms), and
sinter w/compressed gas.

The process produces a three layer microlaminate construction w/170 micrograms of drug, 600-750 micrograms of polymer and a total coating thickness ~15 microns.

Example 2

General eDPC and eRESS Deposition Methods and Coating of Stent Using a Release Agent A coated coronary stent is prepared as described in Example 1, except that prior to coating with the drug-containing polymer, a layer of PTFE release agent is electrostatically deposited on the stent.

Example 3

Example of Coating a Substrate with No Electrocharging of the Substrate

A coated coronary stent is prepared as described in Example 1, except that the stent is not electrically charged during the coating process.

Example 4

This example illustrates embodiments that provide a coated coronary stent that frees a coating thereon by a stimulation. The stimulation in this embodiment is expansion of the stent, which frees the coating from the stent, at least in part.

The embodiment comprises a nitinol stent framework over an angioplasty balloon, wherein the nitinol stent memory is set to a collapsed diameter, and the stent is expanded to a deployed diameter by inflation of the angioplasty balloon, which thereafter, upon deflation of the balloon allows the stent to return to its collapsed diameter and leave the coating (or a portion thereof), at the intervention site. The coating comprises a rapamycin-polymer coating wherein at least part of rapamycin is in crystalline form and the rapamycin-polymer coating comprises one or more resorbable polymers.

In these experiments two different polymers are employed:

Polymer A: ~50:50 PLGA-Ester End Group, MW~19 kD, degradation rate ~1-2 months

Polymer B: ~50:50 PLGA-Carboxylate End Group, MW~10 kD, degradation rate ~28 days In certain embodiments, stents are coated as follows:

AS1: Polymer A/Rapamycin/Polymer A/Rapamycin/Polymer A

AS2: Polymer A/Rapamycin/Polymer A/Rapamycin/Polymer B

AS1 (B) or AS1(213): Polymer B/Rapamycin/Polymer B/Rapamycin/Polymer B

AS1b: Polymer A/Rapamycin/Polymer A/Rapamycin/Polymer A

AS2b: Polymer A/Rapamycin/Polymer A/Rapamycin/Polymer B

The coated stents stent prepared as described are loaded onto a balloon catheter. A segment of optically clear TYGON® B-44-3 Beverage Tubing with O.D.=0.125", I.D.=0.0625" (available from McMaster-Carr, Part Number: 5114K11 (www.mcmaster.com) is filled with phosphate-buffered saline solution and immersed in a water bath at 37° C. to mimic physiological conditions of deployment into a coronary artery. The coated stents are inserted into the tubing and the catheter-balloon is inflated to 13 ATM for less than 20 seconds to deploy the stent against the tubing wall. Optical microscopy of the stents and of the tubing is performed immediately after retraction of the stent delivery system to show that some of the coating was released from the strut. Calculations of the amount of coating left on the stent and/or freed from the stent, by means of area measurements, can determine the amount of coating that was freed from, transferred from, and or dissociated from the stent, and the amount of coating that was deposited at, and/or delivered to the tubing (i.e., the intervention site).

In an alternative embodiment, the stent framework is not comprised of a memory metal, rather is plastically deformable and connected to the balloon, such that the stent shape (e.g. diameter) is defined by and/or controlled by the shape (e.g., diameter) of the balloon, and the stent expands and collapses with the balloon.

Example 5

This example illustrates embodiments that provide a coated coronary stent that frees a coating thereon by a stimulation. The stimulation in this embodiment is a combination of a mechanical stimulation and a chemical stimulation.

Example 6

This example illustrates embodiments that provide a coated coronary stent that frees a coating thereon by a stimulation. The stimulation in this embodiment is a chemical stimulation. The balloon of the stent delivery system is constructed of a semipermeable polymer. The pressurization medium is pH 8 phosphate buffer. The stent (having the balloon thereunder) is positioned at the intervention site. The balloon is pressurized to at least to at least 25% below its nominal inflation pressure. Upon pressurization of the balloon in the diseased artery, at least about 10% to at least about 30% of the coating is released into the intervention site and upon depressurization and removal of the device, this material is deposited at the intervention site.

Example 7

This example illustrates embodiments that provide a coated coronary stent that frees a coating thereon by a stimulation. The stimulation in this embodiment is a thermal stimulation.

Example 8

In-Vitro Study of Coating Freed From a Stent

One sample of the coated stent prepared as described in Example 1 was loaded onto a balloon catheter. A segment of optically clear TYGON® B-44-3 Beverage Tubing with O.D.=0.125", I.D.=0.0625" (available from McMaster-Carr, Part Number: 5114K11 (www.mcmaster.com) was filled with phosphate-buffered saline solution and immersed in a water bath at 37° C. to mimic physiological conditions of deployment into a coronary artery. The coated stent was inserted into the tubing and the catheter-balloon was inflated to 13 ATM to deploy the stent against the tubing wall. Optical microscopy was performed immediately after deployment, where it was clear that some of the coating was released from the strut.

Example 9

In-Vitro Study of Coating Freed from a Stent Using a Release Agent

One sample of the coated stent was prepared as described in Example 2, using about 700 micrograms polymer and 160 micrograms API, an AS1 formulation (PsDPsDPs), and sintered at 25 psig and 75° C. for 10 minutes, was loaded onto a balloon catheter. The stent was pre-wetted by immersion in an isotonic saline bath at 37° C. for 3 minutes. A segment of optically clear TYGON® B-44-3 Beverage Tubing with O.D.=0.125", I.D.=0.0625" (available from McMaster-Carr Part Number 5114K11; www.mcmaster.com) was filled with phosphate-buffered saline solution and immersed in a water bath at 37° C. to mimic physiological conditions of deployment into a coronary artery. The coated stent was inserted into the tubing and the catheter-balloon was inflated to 13 ATM to deploy the stent against the tubing wall. Optical microscopy was performed immediately after deployment and showed that some of the coating has been released from the strut.

Example 10

In Vivo Studies of Coating Transfer from a Stent

Another sample of the coated stent was prepared for in vivo evaluation in a porcine coronary artery model using the Yucatan pig. Subjects were initially given 650 mg acetylsalicylic acid and 300 mg Plavix. Maintenance doses of 81 mg acetylsalicylic acid and 75 mg Plavix were administered. The target ACT (activated clotting time) for the procedure was about 250 seconds. Stent oversizing in relation to the artery was about 10-20%. The preparation of the sirolimus-coated stent was the same as described in Example 1 and used for the in vitro deployment into tubing, except that the device was sterilized using ETO prior to implantation into the animal. The histology of the stented artery after 28 days showed evidence of the extrusion and bulk-migration of the coating into the surrounding arterial tissue. This extrusion provides treatment of ~2.5× greater arterial tissue (area) vs. the abluminal area of the strut itself.

The bulk concentration of drug was measured in the arterial tissue surrounding the implanted stent at 1, 3, 7, 14, and 28 days after implant, and provided a quantitative measure of the high efficiency of transfer of drug into the therapeutic site using devices and methods of the invention. The amount of drug that was detected in the arterial tissue was as follows: 1 day after implant, ~6 µg; 3 days after implant, ~16 µg; 7 days after implant, ~30 µg; 14 days after implant, ~30 µg; 28 days after implant, ~13 µg. Peak tissue concentration of sirolimus of ~30 µg at 14 days after implant was representative of approximately $\frac{1}{6}^{th}$ of the total drug that had been loaded on the stent. Note that some drug likely metabolized or diffused out of the arterial tissue into other areas of the body. These results demonstrate the effectiveness of the devices and methods of the invention relative to other systems, wherein transfer of the coating via bulk migration is inhibited by permanent and/or hard polymers, typically showing 1 to 5% the level of efficiency of drug transfer shown here.

Example 11

Stent Examples

In one experiment, a coated coronary stent is prepared as follows. 3.0×16 mm Co—Cr alloy metal stent (Skylor stent from Invatec (www.invatec.com)) is coated with a drug-containing coating (170 micrograms of rapamycin from Chemwerth www.chemwerth.com that is jet-milled to an average (crystalline) particle size of ~2 microns; PLGA polymer with 50% glycolic acid content, 0.63 dL/g inherent viscosity (Durect Corp. http://www.absorbables.com/).

Equipment and process similar to those employed in Example 1 are used.

The following coating and sintering steps are carried out:
e-RESS polymer (approx 100 micrograms),
sinter w/compressed gas,
e-DPC drug (~35 micrograms,
e-RESS polymer (~100-150 micrograms),
sinter w/compressed gas,
e-DPC drug (~35 micrograms),
e-RESS polymer (~100-200 micrograms), and
sinter w/compressed gas The process produces a coated stent with a 'three layer microlaminate construction w/~70 micrograms of drug, 300-375 micrograms of polymer and a total coating thickness of 6-8 microns. Upon deployment, 1/10th of the coating is freed from the stent and delivered to the arterial tissue.

In another experiment, a coated coronary stent is prepared as follows. 3.0×16 mm Co—Cr alloy metal stent (Skylor stent from Invatec (www.invatec.com)) is coated with a drug-containing coating by spray coating from a solution of PLGA polymer (Mw~30 kg/mol from Durect Corp) and sirolimus (from Chemwerth www.chemwerth.com).

Equipment and process similar to those employed in Example 4 are used.

Resulting in a coating of ~8 μm thickness, containing 70 μg of sirolimus.

Upon deployment, 1/5th of the coating is extruded from the stent at the intervention site (e.g., the arterial tissue.)

Example 12

Cutting Balloons

Cutting Balloon (1)—Mechanical Stimulation to Free the Coating

A cutting balloon is coated comprising a polymer and an active agent. The coated cutting balloon is positioned at the intervention site. The balloon is inflated to at least 25% below its nominal inflation pressure. Upon deflation and removal of the cutting balloon from the intervention site, at least about 5% to at least about 30% of the coating is freed from the surface of the cutting balloon and is deposited at the intervention site.

In some examples, the balloon unfolds during inflation, causing mechanical shearing forces to at least augment transfer and/or freeing and/or deposition of the coating from the balloon to the intervention site.

In some examples, the balloon twists during inflation, causing mechanical shearing forces to at least augment transfer and/or freeing and/or deposition of the coating from the balloon.

In one example, the polymer of the coating is 50:50 PLGA-Ester End Group, MW~19 kD, degradation rate ~1-2 months or 50:50 PLGA-Carboxylate End Group, MW~10 kD, degradation rate ~28 days. The active agent is a pharmaceutical agent such as a macrolide immunosuppressive drug. Equipment and coating process similar to Example 1 is employed. The intervention site is a vascular lumen wall. Upon inflation of the cutting balloon, at least about 50% of the coating is freed from the device at the intervention site.

In another example, a cutting balloon is coated with a formulation of PLGA+sirolimus with total loading of sirolimus ~20 μg with the coating preferentially on the wire of the cutting balloon. Equipment and process similar to Example 1 is employed. The intervention site is a coronary artery. Upon inflation of the cutting balloon, about 5% to about 15% of the coating is freed from the device resulting in delivery of ~2.0 μg of drug delivered to the artery.

In another example, the polymer of the coating is 50:50 PLGA-Ester End Group, MW~19 kD, degradation rate ~1-2 months or 50:50 PLGA-Carboxylate End Group, MW~10 kD, degradation rate ~28 days. The active agent is a chemotherapeutic agent. Equipment and coating process similar to Example 1 is employed. The intervention site is a cavity resulting from removal of a tumor. Upon inflation of the cutting balloon, at least about 75% of the coating is transferred from the device to the intervention site.

In-Vivo Testing:

A group of 27 New Zealand white rabbits is prepared for a Seldinger procedure using a cutting balloon coated with a formulation of 50:50 PLGA-Ester End Group (MW~19 kD, degradation rate ~1-2 months) and sirolimus with total loading of sirolimus ~20 μg with the coating preferentially on the wire of the cutting balloon. The device is placed at a coronary artery intervention site with the assistance of fluoroscopy to aid in positioning the device at the same location in each subject. Six animals are subjected to the procedure using a coated balloon that does not have sirolimus in the coating. After deployment and removal of the device, 3 control animals are sacrificed at 1 hour post deployment and serum and tissue samples are collected. The 3 remaining control animals are sacrificed at 56 days post deployment. During the course of the study, serum samples are collected from control and drug-treated animals every five days. The drug treated animals, 3 each, are sacrificed at 1 hour, 24 hours, 7 days, 14 days, 28 days, 42 days and 56 days post deployment. A serum sample as well as a tissue sample from the deployment site is collected.

The tissue and serum samples may be subjected to analysis for sirolimus concentration. In order to determine the amount of coating freed from the device and/or delivered to the intervention site as a percent of the total amount of coating on the substrate, the tissue concentration of sirolimus at the one hour time point (or any time point within the first day following of the procedure) may be used along with the total content expected for the coating (based on the total content for the manufacturing lot) or along with the content of coating remaining on the device once removed and the percentage calculated. This percentage is correlative of the percent of coating freed, dissociated, and/or transferred from the device and delivered to the intervention site. Alternatively, the tissue may be analyzed by various means (noted herein, including but not limited to SEM, TEM, and, where image enhanced polymers are used, various imaging means capable of detecting these enhanced polymers) to detect the percent of the coating freed, dissociated and/or transferred from the substrate and delivered to the intervention site. Again, the amount of coating known to be on the substrate based on manufacturing lot characteristics, and/or an assessment of the coating remaining on the device following removal of the device from the subject (for example, wherein the device is an angioplasty catheter and the substrate is the balloon of the catheter) may be used to determine the percent of coating freed, dissociated, and/or transferred from the device. In some instances, an assessment of the device following the procedure alone is sufficient to assess the amount freed or dissociated from the substrate, without determination of the amount delivered to the intervention site. Additionally, where a determination of improvement and/or disease treatment is desired, levels of proinflammatory markers could be tested to show improvement and/or treatment of a disease and/or ailment, for example, by testing high sensitive C-reactive protein (hsCRP), interleukin-6 (IL-6), interleukin-1β (IL-1β), and/or monocyte chemoattractant protein-1 (MCP-1). The release kinetics of the drug may be shown by plotting the sirolimus concentrations at the timepoints noted above.

For embodiments using different drugs other than sirolimus, the biomarkers are selected based on the disease to be treated and the drugs administered during the course of therapy as determined by one of skill in the art. These biomarkers may be used to show the treatment results for each subject.

Other in-vivo tests described herein may be used instead of this test and/or in addition to this test, adjusted for the particularities of this device, as would be known to one of ordinary skill in the art.

In-Vitro Testing:

One sample of the coated cutting balloon prepared in Example 1 is secured to a balloon catheter. A segment of optically clear TYGON® B-44-3 tubing with O.D.=0.125", I.D.=0.0625" (Available from McMaster-Carr Part Number: 5114K11 (www.mcmaster.com)) is filled with phosphate-buffered saline solution and immersed in a water bath at 37° C. to mimic physiological conditions of deployment into a subject. The coated balloon is inserted into the tubing and the balloon is inflated to at least 25% below the balloon's nominal pressure to mechanically transfer the coating from the balloon to the tubing wall. The balloon is deflated and removed from the tubing. Optical microscopy is performed on the tubing and/or the balloon (which is inflated to at least 25% below the balloon's nominal pressure, at least) to determine the presence and amount of coating transferred to the tubing and/or the amount of coating freed, dissociated, and/or transferred from the balloon. Other in-vitro tests described herein may be used instead of this test and/or in addition to this test, adjusted for the particularities of this device, as would be known to one of ordinary skill in the art.

Cutting Balloon (2)

Mechanical Stimulation to Free the Coating

A cutting balloon is coated using a solution-based system (spray or dip coating) comprising a polymer and an active agent. The coated cutting balloon is positioned at the intervention site. The balloon is inflated to at least 25% below its nominal inflation pressure. At least about 5% to at least about 30% of the coating is freed from the surface of the cutting balloon and is deposited at the intervention site.

In some examples, the balloon unfolds during inflation, causing mechanical shearing forces to at least augment transfer and/or freeing and/or deposition of the coating from the balloon to the intervention site.

In some examples, the balloon twists during inflation, causing mechanical shearing forces to at least augment transfer and/or freeing and/or deposition of the coating from the balloon.

In one example, the polymer of the coating is 50:50 PLGA-Ester End Group, MW~19 kD, degradation rate ~1-2 months or 50:50 PLGA-Carboxylate End Group, MW~10 kD, degradation rate ~28 days. The active agent is a pharmaceutical agent such as a macrolide immunosuppressive drug. Equipment and coating process using a spray and/or dip coating process is employed. The intervention site is a vascular lumen wall. Upon inflation of the cutting balloon, at least about 50% of the coating is freed from the device at the intervention site.

In another example, a cutting balloon is coated with a formulation of PLGA+sirolimus with total loading of sirolimus ~20 μg with the coating preferentially on the wire of the cutting balloon. Equipment and coating process using a spray and/or dip coating process is employed. The intervention site is a coronary artery. Upon inflation of the cutting balloon, about 5% to about 15% of the coating is freed from the device resulting in delivery of ~2.0 μg of drug delivered to the artery.

In another example, the polymer of the coating is 50:50 PLGA-Ester End Group, MW~19 kD, degradation rate ~1-2 months or 50:50 PLGA-Carboxylate End Group, MW~10 kD, degradation rate ~28 days. The active agent is a chemotherapeutic agent. Equipment and coating process using a spray and/or dip coating process is employed. The intervention site is a cavity resulting from removal of a tumor. Upon inflation of the cutting balloon, at least about 75% of the coating is transferred from the device to the intervention site.

In-Vivo Testing:

A group of 27 New Zealand white rabbits is prepared for a Seldinger procedure using a cutting balloon coated with a formulation of 50:50 PLGA-Ester End Group (MW~19 kD, degradation rate ~1-2 months) and sirolimus with total loading of sirolimus ~20 μg with the coating preferentially on the wire of the cutting balloon. The device is placed at a coronary artery intervention site with the assistance of fluoroscopy to aid in positioning the device at the same location in each subject. Six animals are subjected to the procedure using a coated balloon that does not have sirolimus in the coating. After deployment and removal of the device, 3 control animals are sacrificed at 1 hour post deployment and serum and tissue samples are collected. The 3 remaining control animals are sacrificed at 56 days post deployment. During the course of the study, serum samples are collected from control and drug-treated animals every five days. The drug treated animals, 3 each, are sacrificed at 1 hour, 24 hours, 7 days, 14 days, 28 days, 42 days and 56 days post deployment.

The tissue and serum samples may be subjected to analysis for sirolimus concentration. In order to determine the amount of coating freed from the device and/or delivered to the intervention site as a percent of the total amount of coating on the substrate, the tissue concentration of sirolimus at the one hour time point (or any time point within the first day following of the procedure) may be used along with the total content expected for the coating (based on the total content for the manufacturing lot) or along with the content of coating remaining on the device once removed and the percentage calculated. This percentage is correlative of the percent of coating freed, dissociated, and/or transferred from the device and delivered to the intervention site. Alternatively, the tissue may be analyzed by various means (noted herein, including but not limited to SEM, TEM, and, where image enhanced polymers are used, various imaging means capable of detecting these enhanced polymers) to detect the percent of the coating freed, dissociated and/or transferred from the substrate and delivered to the intervention site. Again, the amount of coating known to be on the substrate based on manufacturing lot characteristics, and/or an assessment of the coating remaining on the device following removal of the device from the subject (for example, wherein the device is an angioplasty catheter and the substrate is the balloon of the catheter) may be used to determine the percent of coating freed, dissociated, and/or transferred from the device. In some instances, an assessment of the device following the procedure alone is sufficient to assess the amount freed or dissociated from the substrate, without determination of the amount delivered to the intervention site. Additionally, where a determination of improvement and/or disease treatment is desired, levels of proinflammatory markers could be tested to show improvement and/or treatment of a disease and/or ailment, for example, by testing high sensitive C-reactive protein (hsCRP), interleukin-6 (IL-6), interleukin-1β (IL-1β), and/or monocyte chemoattractant protein-1 (MCP-1). The release kinetics of the drug may be shown by plotting the sirolimus concentrations at the timepoints noted above.

For embodiments using different drugs other than sirolimus, the biomarkers are selected based on the disease to be treated and the drugs administered during the course of therapy as determined by one of skill in the art. These biomarkers may be used to show the treatment results for each subject.

Other in-vivo tests described herein may be used instead of this test and/or in addition to this test, adjusted for the particularities of this device, as would be known to one of ordinary skill in the art.

In-Vitro Testing:

One sample of the coated cutting balloon prepared in using spray and/or dip coating process is secured to a balloon catheter. A segment of optically clear TYGON® B-44-3 tubing with O.D.=0.125", I.D.=0.0625" (Available from McMaster-Carr Part Number: 5114K11 (www.mcmaster.com)) is filled with phosphate-buffered saline solution and immersed in a water bath at 37° C. to mimic physiological conditions of deployment into a subject. The coated balloon is inserted into the tubing and the balloon is inflated to at least 25% below the balloon's nominal pressure to mechanically transfer the coating from the balloon to the tubing wall. The balloon is deflated and removed from the tubing. Optical microscopy is performed on the tubing and/or the balloon (which is inflated to at least 25% below the balloon's nominal pressure, at least) to determine the presence and amount of coating transferred to the tubing and/or the amount of coating freed, dissociated, and/or transferred from the balloon. Other in-vitro tests described herein may be used instead of this test and/or in addition to this test, adjusted for the particularities of this device, as would be known to one of ordinary skill in the art.

Cutting Balloon (3)

Mechanical Stimulation to Free the Coating

A cutting balloon is coated comprising a release agent, a polymer and an active agent. The coated cutting balloon is positioned at the intervention site. The balloon is inflated to at least 25% below its nominal inflation pressure. At least about 5% to at least about 50% of the coating is freed from the surface of the cutting balloon and is deposited at the intervention site.

In some examples, the balloon unfolds during inflation, causing mechanical shearing forces to at least augment transfer and/or freeing and/or deposition of the coating from the balloon to the intervention site.

In some examples, the balloon twists during inflation, causing mechanical shearing forces to at least augment transfer and/or freeing and/or deposition of the coating from the balloon.

In one example, the polymer of the coating is 50:50 PLGA-Ester End Group, MW~19 kD, degradation rate ~1-2 months or 50:50 PLGA-Carboxylate End Group, MW~10 kD, degradation rate ~28 days. The active agent is a pharmaceutical agent such as a macrolide immunosuppressive drug. Equipment and coating process similar to Example 2 is employed. The intervention site is a vascular lumen wall. Upon inflation of the cutting balloon, at least about 50% of the coating is freed from the device at the intervention site.

In another example, a cutting balloon is coated with a formulation of PLGA+sirolimus with total loading of sirolimus ~20 μg with the coating preferentially on the wire of the cutting balloon. Equipment and process similar to Example 2 is employed. The intervention site is a coronary artery. The release agent is ePTFE powder. Upon inflation of the cutting balloon, about 5% to about 15% of the coating is freed from the device resulting in delivery of ~2.0 μg of drug delivered to the artery.

In another example, the polymer of the coating is 50:50 PLGA-Ester End Group, MW~19 kD, degradation rate ~1-2 months or 50:50 PLGA-Carboxylate End Group, MW~10 kD, degradation rate ~28 days. The active agent is a chemotherapeutic agent. Equipment and coating process similar to Example 2 is employed. The release agent a micronized active agent or another active agent in a micronized form. The intervention site is a cavity resulting from removal of a tumor. Upon inflation of the cutting balloon, at least about 75% of the coating is transferred from from the device to the intervention site.

In-Vivo Testing:

A group of 27 New Zealand white rabbits is prepared for a Seldinger procedure using a cutting balloon coated with a formulation of 50:50 PLGA-Ester End Group (MW~19 kD, degradation rate ~1-2 months) and sirolimus with total loading of sirolimus ~20 μg with the coating preferentially on the wire of the cutting balloon. The device is placed at a coronary artery intervention site with the assistance of fluoroscopy to aid in positioning the device at the same location in each subject. Six animals are subjected to the procedure using a coated balloon that does not have sirolimus in the coating. After deployment and removal of the device, 3 control animals are sacrificed at 1 hour post deployment and serum and tissue samples are collected. The 3 remaining control animals are sacrificed at 56 days post deployment. During the course of the study, serum samples are collected from control and drug-treated animals every five days. The drug treated animals, 3 each, are sacrificed at 1 hour, 24 hours, 7 days, 14 days, 28 days, 42 days and 56 days post deployment. The tissue and serum samples may be subjected to analysis for sirolimus concentration.

In order to determine the amount of coating freed from the device and/or delivered to the intervention site as a percent of the total amount of coating on the substrate, the tissue concentration of sirolimus at the one hour time point (or any time point within the first day following of the procedure) may be used along with the total content expected for the coating (based on the total content for the manufacturing lot) or along with the content of coating remaining on the device once removed and the percentage calculated. This percentage is correlative of the percent of coating freed, dissociated, and/or transferred from the device and delivered to the intervention site. Alternatively, the tissue may be analyzed by various means (noted herein, including but not limited to SEM, TEM, and, where image enhanced polymers are used, various imaging means capable of detecting these enhanced polymers) to detect the percent of the coating freed, dissociated and/or transferred from the substrate and delivered to the intervention site. Again, the amount of coating known to be on the substrate based on manufacturing lot characteristics, and/or an assessment of the coating remaining on the device following removal of the device from the subject (for example, wherein the device is an angioplasty catheter and the substrate is the balloon of the catheter) may be used to determine the percent of coating freed, dissociated, and/or transferred from the device. In some instances, an assessment of the device following the procedure alone is sufficient to assess the amount freed or dissociated from the substrate, without determination of the amount delivered to the intervention site. Additionally, where a determination of improvement and/or disease treatment is desired, levels of proinflammatory markers could be tested to show improvement and/or treatment of a disease and/or ailment, for example, by testing high sensitive C-reactive protein (hsCRP), interleukin-6 (IL-6), interleukin-1β (IL-1β), and/or monocyte chemoattractant protein-1 (MCP-1). The release kinetics of the drug may be shown by plotting the sirolimus concentrations at the timepoints noted above.

For embodiments using different drugs other than sirolimus, the biomarkers are selected based on the disease to be treated and the drugs administered during the course of therapy as determined by one of skill in the art. These biomarkers may be used to show the treatment results for each subject.

Other in-vivo tests described herein may be used instead of this test and/or in addition to this test, adjusted for the particularities of this device, as would be known to one of ordinary skill in the art.

In-Vitro Testing:

One sample of the coated cutting balloon prepared in Example 2 is secured to a balloon catheter. A segment of optically clear TYGON® B-44-3 tubing with O.D.=0.125", I.D.=0.0625" (Available from McMaster-Carr Part Number: 5114K11 (www.mcmaster.com)) is filled with phosphate-buffered saline solution and immersed in a water bath at 37° C. to mimic physiological conditions of deployment into a subject. The coated balloon is inserted into the tubing and the balloon is inflated to at least 25% below the balloon's nominal pressure to mechanically transfer the coating from the balloon to the tubing wall. The balloon is deflated and removed from the tubing. Optical microscopy is performed on the tubing and/or the balloon (which is inflated to at least 25% below the balloon's nominal pressure, at least) to determine the presence and amount of coating transferred to the tubing and/or the amount of coating transferred from the balloon. Other in-vitro tests described herein may be used instead of this test and/or in addition to this test, adjusted for the particularities of this device, as would be known to one of ordinary skill in the art.

Cutting Balloon (4)

Mechanical Stimulation to Free the Coating

A cutting balloon is coated comprising a polymer and an active agent. The coated cutting balloon is positioned at the intervention site. The balloon is inflated to at least 25% below its nominal inflation pressure. At least about 10% to at least about 50% of the coating is freed from the surface of the cutting balloon and is deposited at the intervention site.

In some examples, the balloon unfolds during inflation, causing mechanical shearing forces to at least augment transfer and/or freeing and/or deposition of the coating from the balloon to the intervention site.

In some examples, the balloon twists during inflation, causing mechanical shearing forces to at least augment transfer and/or freeing and/or deposition of the coating from the balloon.

In one example, the polymer of the coating is 50:50 PLGA-Ester End Group, MW~19 kD, degradation rate ~1-2 months or 50:50 PLGA-Carboxylate End Group, MW~10 kD, degradation rate ~28 days. The active agent is a pharmaceutical agent such as a macrolide immunosuppressive drug. Equipment and coating process similar to Example 3 is employed. The intervention site is a vascular lumen wall. Upon inflation of the cutting balloon, at least about 50% of the coating is freed from the device at the intervention site.

In another example, a cutting balloon is coated with a formulation of PLGA+sirolimus with total loading of sirolimus ~20 µg with the coating preferentially on the wire of the cutting balloon. Equipment and process similar to Example 3 is employed. The intervention site is a coronary artery. Upon inflation of the cutting balloon, about 5% to about 15% of the coating is freed from the device resulting in delivery of ~2.0 µg of drug delivered to the artery.

In another example, the polymer of the coating is 50:50 PLGA-Ester End Group, MW~19 kD, degradation rate ~1-2 months or 50:50 PLGA-Carboxylate End Group, MW~10 kD, degradation rate ~28 days. The active agent is a chemotherapeutic agent. Equipment and coating process similar to Example 3 is employed. The intervention site is a cavity resulting from removal of a tumor. Upon inflation of the cutting balloon, at least about 75% of the coating is transferred from the device to the intervention site.

In-Vivo Testing:

A group of 27 New Zealand white rabbits is prepared for a Seldinger procedure using a cutting balloon coated with a formulation of 50:50 PLGA-Ester End Group (MW~19 kD, degradation rate ~1-2 months) and sirolimus with total loading of sirolimus ~20 µg with the coating preferentially on the wire of the cutting balloon. The device is placed at a coronary artery intervention site with the assistance of fluoroscopy to aid in positioning the device at the same location in each subject. Six animals are subjected to the procedure using a coated balloon that does not have sirolimus in the coating. After deployment and removal of the device, 3 control animals are sacrificed at 1 hour post deployment and serum and tissue samples are collected. The 3 remaining control animals are sacrificed at 56 days post deployment. During the course of the study, serum samples are collected from control and drug-treated animals every five days. The drug treated animals, 3 each, are sacrificed at 1 hour, 24 hours, 7 days, 14 days, 28 days, 42 days and 56 days post deployment.

The tissue and serum samples may be subjected to analysis for sirolimus concentration. In order to determine the amount of coating freed from the device and/or delivered to the intervention site as a percent of the total amount of coating on the substrate, the tissue concentration of sirolimus at the one hour time point (or any time point within the first day following of the procedure) may be used along with the total content expected for the coating (based on the total content for the manufacturing lot) or along with the content of coating remaining on the device once removed and the percentage calculated. This percentage is correlative of the percent of coating freed, dissociated, and/or transferred from the device and delivered to the intervention site. Alternatively, the tissue may be analyzed by various means (noted herein, including but not limited to SEM, TEM, and, where image enhanced polymers are used, various imaging means capable of detecting these enhanced polymers) to detect the percent of the coating freed, dissociated and/or transferred from the substrate and delivered to the intervention site. Again, the amount of coating known to be on the substrate based on manufacturing lot characteristics, and/or an assessment of the coating remaining on the device following removal of the device from the subject (for example, wherein the device is a cutting angioplasty catheter and the substrate is the cutting balloon of the catheter) may be used to determine the percent of coating freed, dissociated, and/or transferred from the device. In some instances, an assessment of the device following the procedure alone is sufficient to assess the amount freed or dissociated from the substrate, without determination of the amount delivered to the intervention site. Additionally, where a determination of improvement and/or disease treatment is desired, levels of proinflammatory markers could be tested to show improvement and/or treatment of a disease and/or ailment, for example, by testing high sensitive C-reactive protein (hsCRP), interleukin-6 (IL-6), interleukin-1β (IL-1β), and/or monocyte chemoattractant protein-1 (MCP-1). The release kinetics of the drug may be shown by plotting the sirolimus concentrations at the timepoints noted above.

For embodiments using different drugs other than sirolimus, the biomarkers are selected based on the disease to be treated and the drugs administered during the course of therapy as determined by one of skill in the art. These biomarkers may be used to show the treatment results for each subject.

Other in-vivo tests described herein may be used instead of this test and/or in addition to this test, adjusted for the particularities of this device, as would be known to one of ordinary skill in the art.

In-Vitro Testing:

One sample of the coated cutting balloon prepared in Example 3 is secured to a balloon catheter. A segment of optically clear TYGON® B-44-3 tubing with O.D.=0.125", I.D.=0.0625" (Available from McMaster-Carr Part Number: 5114K11 (www.mcmaster.com)) is filled with phosphate-buffered saline solution and immersed in a water bath at 37° C. to mimic physiological conditions of deployment into a subject. The coated balloon is inserted into the tubing and the balloon is inflated to at least 25% below the balloon's nominal pressure to mechanically transfer the coating from the balloon to the tubing wall. The balloon is deflated and removed from the tubing. Optical microscopy is performed on the tubing and/or the balloon (which is inflated to at least 25% below the balloon's nominal pressure, at least) to determine the presence and amount of coating transferred to the tubing and/or the amount of coating freed, dissociated, and/or transferred from the balloon. Other in-vitro tests described herein may be used instead of this test and/or in addition to this test, adjusted for the particularities of this device, as would be known to one of ordinary skill in the art.

Cutting Balloon (5)

Mechanical and Chemical Stimulation to Free the Coating

A cutting balloon is coated with a formulation comprising a base layer of methyl acrylate-methacrylic acid copolymer and additional layers of PLGA+paclitaxel with total dose of paclitaxel approx. 0.5 μg/mm2 of the wire. The coating and sintering process is similar to that as described in Example 1. The balloon is constructed of a semipermable polymer. The pressurization medium is pH 8 phosphate buffer. The coated cutting balloon is positioned at the intervention site. The balloon is pressurized to at least to at least 25% below its nominal inflation pressure. Upon pressurization of the cutting balloon in the diseased artery, at least about 10% to at least about 30% of the coating is released into the intervention site and upon depressurization and removal of the device, this material is deposited at the intervention site.

In some examples, the balloon unfolds during inflation, causing mechanical shearing forces to at least augment the pH mediated release of the coating from the balloon to the intervention site.

In some examples, the balloon twists during inflation, causing mechanical shearing forces to at least augment the pH mediated release of the coating from the balloon.

In one example, a base layer of methyl acrylate-methacrylic acid copolymer is formed and additional layers of the coating is 50:50 PLGA-Ester End Group, MW~19 kD, degradation rate ~1-2 months or 50:50 PLGA-Carboxylate End Group, MW~10 kD, degradation rate ~28 days. The active agent is a pharmaceutical agent such as a macrolide immunosuppressive drug. Equipment and coating process similar to Example 1 is employed. The balloon is constructed of a semipermable polymer. The pressurization medium is pH 8 phosphate buffer. The intervention site is a vascular lumen wall. Upon inflation of the cutting balloon, at least about 50% of the coating is freed from the device at the intervention site.

In another example, a cutting balloon is coated with a base layer of methyl acrylate-methacrylic acid copolymer and additional layers of PLGA+sirolimus with total loading of sirolimus ~20μ. Equipment and process similar to Example 1 is employed. The intervention site is a coronary artery. The balloon is constructed of a semipermable polymer. The pressurization medium is pH 8 phosphate buffer. Upon inflation of the cutting balloon, about 5% to about 15% of the coating is freed from the device resulting in delivery of ~2.0 μg of drug delivered to the artery.

In another example, the polymer of the coating is 50:50 PLGA-Ester End Group, MW~19 kD, degradation rate ~1-2 months or 50:50 PLGA-Carboxylate End Group, MW~10 kD, degradation rate ~28 days. The active agent is a chemotherapeutic agent. Equipment and coating process similar to Example 1 is employed. The intervention site is a cavity resulting from removal of a tumor. Upon inflation of the cutting balloon, at least about 75% of the coating is transferred from the device to the intervention site.

In-Vivo Testing:

A group of 27 New Zealand white rabbits is prepared for a Seldinger procedure using a cutting balloon coated with a formulation of 50:50 PLGA-Ester End Group (MW~19 kD, degradation rate ~1-2 months) and sirolimus with total loading of sirolimus ~20 μg with the coating preferentially on the wire of the cutting balloon. The device is placed at a coronary artery intervention site with the assistance of fluoroscopy to aid in positioning the device at the same location in each subject. Six animals are subjected to the procedure using a coated balloon that does not have sirolimus in the coating. After deployment and removal of the device, 3 control animals are sacrificed at 1 hour post deployment and serum and tissue samples are collected. The 3 remaining control animals are sacrificed at 56 days post deployment. During the course of the study, serum samples are collected from control and drug-treated animals every five days. The drug treated animals, 3 each, are sacrificed at 1 hour, 24 hours, 7 days, 14 days, 28 days, 42 days and 56 days post deployment.

The tissue and serum samples may be subjected to analysis for sirolimus concentration. In order to determine the amount of coating freed from the device and/or delivered to the intervention site as a percent of the total amount of coating on the substrate, the tissue concentration of sirolimus at the one hour time point (or any time point within the first day following of the procedure) may be used along with the total content expected for the coating (based on the total content for the manufacturing lot) or along with the content of coating remaining on the device once removed and the percentage calculated. This percentage is correlative of the percent of coating freed, dissociated, and/or transferred from the device and delivered to the intervention site. Alternatively, the tissue may be analyzed by various means (noted herein, including but not limited to SEM, TEM, and, where image enhanced polymers are used, various imaging means capable of detecting these enhanced polymers) to detect the percent of the coating freed, dissociated and/or transferred from the substrate and delivered to the intervention site. Again, the amount of coating known to be on the substrate based on manufacturing lot characteristics, and/or an assessment of the coating remaining on the device following removal of the device from the subject (for example, wherein the device is an cutting angioplasty catheter and the substrate is the cutting balloon of the catheter) may be used to determine the percent of coating freed, dissociated, and/or transferred from the device. In some instances, an assessment of the device following the procedure alone is sufficient to assess the amount freed or dissociated from the substrate, without determination of the amount delivered to the intervention site. Additionally, where a determination of improvement and/or disease treatment is desired, levels of proinflammatory markers could be tested to show improvement and/or treatment of a disease and/or ailment, for example, by testing high sensitive C-reactive protein (hsCRP), interleukin-6 (IL-6), interleukin-1β (IL-1β), and/or monocyte chemoattractant protein-1 (MCP-1). The release kinetics of the drug may be shown by plotting the sirolimus concentrations at the timepoints noted above.

For embodiments using different drugs other than sirolimus, the biomarkers are selected based on the disease to be treated and the drugs administered during the course of therapy as determined by one of skill in the art. These biomarkers may be used to show the treatment results for each subject.

Other in-vivo tests described herein may be used instead of this test and/or in addition to this test, adjusted for the particularities of this device, as would be known to one of ordinary skill in the art.

In-Vitro Testing:

One sample of the coated cutting balloon prepared in Example 1 is secured to a balloon catheter. A segment of optically clear TYGON® B-44-3 tubing with O.D.=0.125", I.D.=0.0625" (Available from McMaster-Carr Part Number: 5114K11 (www.mcmaster.com)) is filled with phosphate-buffered saline solution and immersed in a water bath at 37° C. to mimic physiological conditions of deployment into a subject. The coated balloon is inserted into the tubing and the balloon is inflated to at least 25% below the balloon's nominal pressure to mechanically transfer the coating from the balloon to the tubing wall. The balloon is deflated and removed from the tubing. Optical microscopy is performed on the tubing and/or the balloon (which is inflated to at least 25% below the balloon's nominal pressure, at least) to determine the presence and amount of coating transferred to the tubing and/or the amount of coating freed, dissociated, and/or transferred from the balloon. Other in-vitro tests described herein may be used instead of this test and/or in addition to this test, adjusted for the particularities of this device, as would be known to one of ordinary skill in the art.

Cutting Balloon (6)

Chemical Stimulation to Free the Coating

A cutting balloon is coated with a formulation comprising a base layer of methyl acrylate-methacrylic acid copolymer and additional layers of PLGA+paclitaxel with total dose of paclitaxel approx. 0.5 µg/mm2 of the wire. The coating and sintering process is similar to that as described in Example 1. The balloon is constructed of a semipermable polymer. The pressurization medium is pH 8 phosphate buffer. The coated cutting balloon is positioned at the intervention site. The balloon is pressurized to at least to at least 25% below its nominal inflation pressure. Upon pressurization of the cutting balloon in the diseased artery, at least about 10% to at least about 30% of the coating is released into the intervention site and upon depressurization and removal of the device, this material is deposited at the intervention site. In-vivo and/or in-vitro testing as described herein may be used to analyze the coating, the drug, the device, the intervention site and/or properties thereof.

Cutting Balloon (7)

Thermal Stimulation to Free the Coating

A cutting balloon is coated according to a method described herein and the balloon comprises a thermoreversible polymer Pluronic F127 and an active agent. The coated cutting balloon is positioned at the intervention site. The balloon is inflated to at least 25% below its nominal inflation pressure. Upon deflation and removal of the cutting balloon from the intervention site, at least about 5% to at least about 30% of the coating is freed from the surface of the cutting balloon and is deposited at the intervention site.

In some examples, the balloon unfolds during inflation, causing mechanical shearing forces to at least augment transfer and/or freeing and/or deposition of the coating from the balloon to the intervention site.

In some examples, the balloon twists during inflation, causing mechanical shearing forces to at least augment transfer and/or freeing and/or deposition of the coating from the balloon.

In one example, the active agent is a pharmaceutical agent such as a macrolide immunosuppressive drug. Equipment and coating process similar to Example 1 is employed. The intervention site is a vascular lumen wall. Upon inflation of the cutting balloon, at least about 50% of the coating is freed from the device at the intervention site.

In-Vivo Testing:

A group of 27 New Zealand white rabbits is prepared for a Seldinger procedure using a cutting balloon coated with a formulation of Pluronic F127 and sirolimus with total loading of sirolimus ~20 µg. The device is placed at a coronary artery intervention site with the assistance of fluoroscopy to aid in positioning the device at the same location in each subject. Six animals are subjected to the procedure using a coated balloon that does not have sirolimus in the coating. After deployment and removal of the device, 3 control animals are sacrificed at 1 hour post deployment and serum and tissue samples are collected. The 3 remaining control animals are sacrificed at 56 days post deployment. During the course of the study, serum samples are collected from control and drug-treated animals every five days. The drug treated animals, 3 each, are sacrificed at 1 hour, 24 hours, 7 days, 14 days, 28 days, 42 days and 56 days post deployment.

The tissue and serum samples may be subjected to analysis for sirolimus concentration. In order to determine the amount of coating freed from the device and/or delivered to the intervention site as a percent of the total amount of coating on the substrate, the tissue concentration of sirolimus at the one hour time point (or any time point within the first day following of the procedure) may be used along with the total content expected for the coating (based on the total content for the manufacturing lot) or along with the content of coating remaining on the device once removed and the percentage calculated. This percentage is correlative of the percent of coating freed, dissociated, and/or transferred from the device and delivered to the intervention site. Alternatively, the tissue may be analyzed by various means (noted herein, including but not limited to SEM, TEM, and, where image enhanced polymers are used, various imaging means capable of detecting these enhanced polymers) to detect the percent of the coating freed, dissociated and/or transferred from the substrate and delivered to the intervention site. Again, the amount of coating known to be on the substrate based on manufacturing lot characteristics, and/or an assessment of the coating remaining on the device following removal of the device from the subject (for example, wherein the device is a cutting angioplasty catheter and the substrate is the balloon of the catheter) may be used to determine the percent of coating freed, dissociated, and/or transferred from the device. In some instances, an assessment of the device following the procedure alone is sufficient to assess the amount freed or dissociated from the substrate, without determination of the amount delivered to the intervention site. Additionally, where a determination of improvement and/or disease treatment is desired, levels of proinflammatory markers could be tested to show improvement and/or treatment of a disease and/or ailment, for example, by testing high sensitive C-reactive protein (hsCRP), interleukin-6 (IL-6), interleukin-1β (IL-1β), and/or monocyte chemoattractant protein-1 (MCP-1). The release kinetics of the drug may be shown by plotting the sirolimus concentrations at the timepoints noted above.

For embodiments using different drugs other than sirolimus, the biomarkers are selected based on the disease to be treated and the drugs administered during the course of therapy as determined by one of skill in the art. These biomarkers may be used to show the treatment results for each subject.

Other in-vivo tests described herein may be used instead of this test and/or in addition to this test, adjusted for the particularities of this device, as would be known to one of ordinary skill in the art.

In-Vitro Testing:

One sample of the coated cutting balloon prepared as in Example 1 is secured to a balloon catheter. A segment of optically clear TYGON® B-44-3 tubing with O.D.=0.125", I.D.=0.0625" (Available from McMaster-Carr Part Number: 5114K11 (www.mcmaster.com)) is filled with phosphate-buffered saline solution and immersed in a water bath at 37° C. to mimic physiological conditions of deployment into a subject. The coated balloon is inserted into the tubing and the balloon is inflated to at least 25% below the balloon's nominal pressure to mechanically transfer the coating from the balloon to the tubing wall. The balloon is deflated and removed from the tubing. Optical microscopy is performed on the tubing and/or the balloon (which is inflated to at least 25% below the balloon's nominal pressure, at least) to determine the presence and amount of coating transferred to the tubing and/or the amount of coating transferred from the balloon. Other in-vitro tests described herein may be used instead of this test and/or in addition to this test, adjusted for the particularities of this device, as would be known to one of ordinary skill in the art.

Cutting Balloon (8)

Sonic Stimulation to Free the Coating

A cutting balloon is coated according to a method as described herein and the device comprises a polymer and an active agent. The coated cutting balloon is positioned at the intervention site. The balloon is inflated to at least 25% below its nominal inflation pressure and subjected to ultrasonic stimulation. Upon deflation and removal of the cutting balloon from the intervention site, at least about 5% to at least about 30% of the coating is freed from the surface of the cutting balloon and is deposited at the intervention site.

In some examples, the balloon unfolds during inflation, causing mechanical shearing forces to at least augment transfer and/or freeing and/or deposition of the coating from the balloon effected by ultrasonic stimulation to the intervention site.

In some examples, the balloon twists during inflation, causing mechanical shearing forces to at least augment transfer and/or freeing and/or deposition of the coating from the balloon effected by ultrasonic stimulation.

In one example, the polymer of the coating is 50:50 PLGA-Ester End Group, MW~19 kD, degradation rate ~1-2 months or 50:50 PLGA-Carboxylate End Group, MW~10 kD, degradation rate ~28 days. The active agent is a pharmaceutical agent such as a macrolide immunosuppressive drug. Equipment and coating process similar to Example 1 is employed. The intervention site is a vascular lumen wall. Upon inflation of the cutting balloon and initiation of ultrasonic stimulation, at least about 50% of the coating is freed from the device at the intervention site.

In another example, a cutting balloon is coated with a formulation of PLGA+sirolimus with total loading of sirolimus ~20 μg with the coating preferentially on the wire of the cutting balloon. Equipment and process similar to Example 1 is employed. The intervention site is a coronary artery. Upon inflation of the cutting balloon and initiation of ultrasonic stimulation, about 5% to about 15% of the coating is freed from the device resulting in delivery of ~2.0 μg of drug delivered to the artery.

In another example, the polymer of the coating is 50:50 PLGA-Ester End Group, MW~19 kD, degradation rate ~1-2 months or 50:50 PLGA-Carboxylate End Group, MW~10 kD, degradation rate ~28 days. The active agent is a chemotherapeutic agent. Equipment and coating process similar to Example 1 is employed. The intervention site is a cavity resulting from removal of a tumor. Upon inflation of the cutting balloon and initiation of ultrasonic stimulation, at least about 75% of the coating is transferred from the device to the intervention site.

In-Vivo Testing:

A group of 27 New Zealand white rabbits is prepared for a Seldinger procedure using a cutting balloon coated with a formulation of 50:50 PLGA-Ester End Group (MW~19 kD, degradation rate ~1-2 months) and sirolimus with total loading of sirolimus ~20 µg. The device is placed at a coronary artery intervention site with the assistance of fluoroscopy to aid in positioning the device at the same location in each subject. Six animals are subjected to the procedure using a coated balloon that does not have sirolimus in the coating. After deployment and removal of the device, 3 control animals are sacrificed at 1 hour post deployment and serum and tissue samples are collected. The 3 remaining control animals are sacrificed at 56 days post deployment. During the course of the study, serum samples are collected from control and drug-treated animals every five days. The drug treated animals, 3 each, are sacrificed at 1 hour, 24 hours, 7 days, 14 days, ~28 days, 42 days and 56 days post deployment. The tissue and serum samples may be subjected to analysis for sirolimus concentration.

In order to determine the amount of coating freed from the device and/or delivered to the intervention site as a percent of the total amount of coating on the substrate, the tissue concentration of sirolimus at the one hour time point (or any time point within the first day following of the procedure) may be used along with the total content expected for the coating (based on the total content for the manufacturing lot) or along with the content of coating remaining on the device once removed and the percentage calculated. This percentage is correlative of the percent of coating freed, dissociated, and/or transferred from the device and delivered to the intervention site. Alternatively, the tissue may be analyzed by various means (noted herein, including but not limited to SEM, TEM, and, where image enhanced polymers are used, various imaging means capable of detecting these enhanced polymers) to detect the percent of the coating freed, dissociated and/or transferred from the substrate and delivered to the intervention site. Again, the amount of coating known to be on the substrate based on manufacturing lot characteristics, and/or an assessment of the coating remaining on the device following removal of the device from the subject (for example, wherein the device is a cutting angioplasty catheter and the substrate is the balloon of the catheter) may be used to determine the percent of coating freed, dissociated, and/or transferred from the device. In some instances, an assessment of the device following the procedure alone is sufficient to assess the amount freed or dissociated from the substrate, without determination of the amount delivered to the intervention site. Additionally, where a determination of improvement and/or disease treatment is desired, levels of proinflammatory markers could be tested to show improvement and/or treatment of a disease and/or ailment, for example, by testing high sensitive C-reactive protein (hsCRP), interleukin-6 (IL-6), interleukin-1β (IL-1β), and/or monocyte chemoattractant protein-1 (MCP-1). The release kinetics of the drug may be shown by plotting the sirolimus concentrations at the timepoints noted above.

For embodiments using different drugs other than sirolimus, the biomarkers are selected based on the disease to be treated and the drugs administered during the course of therapy as determined by one of skill in the art. These biomarkers may be used to show the treatment results for each subject.

Other in-vivo tests described herein may be used instead of this test and/or in addition to this test, adjusted for the particularities of this device, as would be known to one of ordinary skill in the art.

In-Vitro Testing:

One sample of the coated cutting balloon prepared in Example 1 is secured to a balloon catheter. A segment of optically clear TYGON® B-44-3 tubing with O.D.=0.125", I.D.=0.0625" (Available from McMaster-Carr Part Number: 5114K11 (www.mcmaster.com)) is filled with phosphate-buffered saline solution and immersed in a ultrasonic water bath at 37° C. to mimic physiological conditions of deployment into a subject. The coated balloon is inserted into the tubing and the balloon is inflated to at least 25% below the balloon's nominal pressure and ultrasonic stimulation is iniatiated to mechanically transfer the coating from the balloon to the tubing wall. The balloon is deflated and removed from the tubing. Optical microscopy is performed on the tubing and/or the balloon (which is inflated to at least 25% below the balloon's nominal pressure, at least) to determine the presence and amount of coating transferred to the tubing and/or the amount of coating freed, dissociated, and/or transferred from the balloon. Other in-vitro tests described herein may be used instead of this test and/or in addition to this test, adjusted for the particularities of this device, as would be known to one of ordinary skill in the art.

Cutting Balloon (9)

Electromagnetic Stimulation to Free the Coating

A cutting balloon is coated according to a method as described herein and the device comprises a polymer and an active agent. The coated cutting balloon is positioned at the intervention site. The balloon is inflated to at least 25% below its nominal inflation pressure and subjected to electromagnetic stimulation. Upon deflation and removal of the cutting balloon from the intervention site, at least about 5% to at least about 30% of the coating is freed from the surface of the cutting balloon and is deposited at the intervention site.

In some examples, the balloon unfolds during inflation, causing mechanical shearing forces to at least augment transfer and/or freeing and/or deposition of the coating from the balloon effected by electromagnetic stimulation to the intervention site.

In some examples, the balloon twists during inflation, causing mechanical shearing forces to at least augment transfer and/or freeing and/or deposition of the coating from the balloon effected by electromagnetic stimulation.

In one example, the polymer of the coating is 50:50 PLGA-Ester End Group, MW~19 kD, degradation rate ~1-2 months or 50:50 PLGA-Carboxylate End Group, MW~10 kD, degradation rate ~28 days. The active agent is a pharmaceutical agent such as a macrolide immunosuppressive drug. Equipment and coating process similar to Example 1 is employed. The intervention site is a vascular lumen wall. Upon inflation of the cutting balloon and initiation of electromagnetic stimulation, at least about 50% of the coating is freed from the device at the intervention site.

In another example, a cutting balloon is coated with a formulation of PLGA+sirolimus with total loading of sirolimus ~20 µg with the coating preferentially on the wire of the cutting balloon. Equipment and process similar to Example 1 is employed. The intervention site is a coronary artery. Upon inflation of the cutting balloon and initiation of electromagnetic stimulation, about 5% to about 15% of the coating is freed from the device resulting in delivery of ~2.0 µg of drug delivered to the artery.

In another example, the polymer of the coating is 50:50 PLGA-Ester End Group, MW~19 kD, degradation rate ~1-2 months or 50:50 PLGA-Carboxylate End Group, MW~10 kD, degradation rate ~28 days. The active agent is a chemotherapeutic agent. Equipment and coating process similar to Example 1 is employed. The intervention site is a cavity resulting from removal of a tumor. Upon inflation of the cutting balloon and initiation of electromagnetic stimulation, at least about 75% of the coating is transferred from the device to the intervention site.

In-Vivo Testing:

A group of 27 New Zealand white rabbits is prepared for a Seldinger procedure using a cutting balloon coated with a formulation of 50:50 PLGA-Ester End Group (MW~19 kD, degradation rate ~1-2 months) and sirolimus with total loading of sirolimus ~20 µg. The device is placed at a coronary artery intervention site with the assistance of fluoroscopy to aid in positioning the device at the same location in each subject. Six animals are subjected to the procedure using a coated balloon that does not have sirolimus in the coating. After deployment and removal of the device, 3 control animals are sacrificed at 1 hour post deployment and serum and tissue samples are collected. The 3 remaining control animals are sacrificed at 56 days post deployment. During the course of the study, serum samples are collected from control and drug-treated animals every five days. The drug treated animals, 3 each, are sacrificed at 1 hour, 24 hours, 7 days, 14 days, ~28 days, 42 days and 56 days post deployment. The tissue and serum samples may be subjected to analysis for sirolimus concentration.

In order to determine the amount of coating freed from the device and/or delivered to the intervention site as a percent of the total amount of coating on the substrate, the tissue concentration of sirolimus at the one hour time point (or any time point within the first day following of the procedure) may be used along with the total content expected for the coating (based on the total content for the manufacturing lot) or along with the content of coating remaining on the device once removed and the percentage calculated. This percentage is correlative of the percent of coating freed, dissociated, and/or transferred from the device and delivered to the intervention site. Alternatively, the tissue may be analyzed by various means (noted herein, including but not limited to SEM, TEM, and, where image enhanced polymers are used, various imaging means capable of detecting these enhanced polymers) to detect the percent of the coating freed, dissociated and/or transferred from the substrate and delivered to the intervention site. Again, the amount of coating known to be on the substrate based on manufacturing lot characteristics, and/or an assessment of the coating remaining on the device following removal of the device from the subject (for example, wherein the device is a cutting angioplasty catheter and the substrate is the balloon of the catheter) may be used to determine the percent of coating freed, dissociated, and/or transferred from the device. In some instances, an assessment of the device following the procedure alone is sufficient to assess the amount freed or dissociated from the substrate, without determination of the amount delivered to the intervention site. Additionally, where a determination of improvement and/or disease treatment is desired, levels of proinflammatory markers could be tested to show improvement and/or treatment of a disease and/or ailment, for example, by testing high sensitive C-reactive protein (hsCRP), interleukin-6 (IL-6), interleukin-1β (IL-1β), and/or monocyte chemoattractant protein-1 (MCP-1). The release kinetics of the drug may be shown by plotting the sirolimus concentrations at the timepoints noted above.

For embodiments using different drugs other than sirolimus, the biomarkers are selected based on the disease to be treated and the drugs administered during the course of therapy as determined by one of skill in the art. These biomarkers may be used to show the treatment results for each subject.

Other in-vivo tests described herein may be used instead of this test and/or in addition to this test, adjusted for the particularities of this device, as would be known to one of ordinary skill in the art.

In-Vitro Testing:

One sample of the coated cutting balloon prepared in Example 1 is secured to a balloon catheter. A segment of optically clear TYGON® B-44-3 tubing with O.D.=0.125", I.D.=0.0625" (Available from McMaster-Carr Part Number: 5114K11 (www.mcmaster.com)) is filled with phosphate-buffered saline solution and immersed in a water bath at 37° C. to mimic physiological conditions of deployment into a subject. The coated balloon is inserted into the tubing and the balloon is inflated to at least 25% below the balloon's nominal pressure and electromagnetic stimulation is initiated to mechanically transfer the coating from the balloon to the tubing wall. The balloon is deflated and removed from the tubing. Optical microscopy is performed on the tubing and/or the balloon (which is inflated to at least 25% below the balloon's nominal pressure, at least) to determine the presence and amount of coating transferred to the tubing and/or the amount of coating transferred from the balloon. Other in-vitro tests described herein may be used instead of this test and/or in addition to this test, adjusted for the particularities of this device, as would be known to one of ordinary skill in the art.

Example 13

Drug-Delivery Balloon Catheters

Drug-Delivery Balloon (1)—Compliant Balloon

A compliant balloon is coated with a material comprising a polymer and an active agent. The coated compliant balloon is positioned at the intervention site. The balloon is inflated to at least 25% below its nominal inflation pressure. Upon deflation and removal of the compliant balloon from the intervention site, at least about 5% to at least about 30% of the coating is freed from the surface of the compliant balloon and is deposited at the intervention site.

In some examples, the balloon unfolds during inflation, causing mechanical shearing forces to at least augment transfer and/or freeing and/or deposition of the coating from the balloon to the intervention site.

In some examples, the balloon twists during inflation, causing mechanical shearing forces to at least augment transfer and/or freeing and/or deposition of the coating from the balloon.

In one example, the polymer of the coating is 50:50 PLGA-Ester End Group, MW~19 kD, degradation rate ~1-2 months or 50:50 PLGA-Carboxylate End Group, MW~10 kD, degradation rate ~28 days. The active agent is a pharmaceutical agent such as a macrolide immunosuppressive drug. Equipment and coating process similar to Example 1 is employed. The intervention site is a vascular lumen wall. Upon inflation of the compliant balloon, at least about 50% of the coating is freed from the device at the intervention site.

In another example, a compliant balloon is coated with a formulation of PLGA+sirolimus with total loading of sirolimus ~20 µg. Equipment and process similar to Example 1 is employed. The intervention site is a coronary artery. Upon inflation of the compliant balloon, about 5% to about 15% of the coating is freed from the device resulting in delivery of ~2.0 µg of drug delivered to the artery.

In another example, the polymer of the coating is 50:50 PLGA-Ester End Group, MW~19 kD, degradation rate ~1-2 months or 50:50 PLGA-Carboxylate End Group, MW~10 kD, degradation rate ~28 days. The active agent is a chemotherapeutic agent. Equipment and coating process similar to Example 1 is employed. The intervention site is a cavity resulting from removal of a tumor. Upon inflation of the compliant balloon, at least about 75% of the coating is transferred from the device to the intervention site.

In-Vivo Testing:

A group of 27 New Zealand white rabbits is prepared for a Seldinger procedure using a compliant balloon coated with a formulation of 50:50 PLGA-Ester End Group (MW~19 kD, degradation rate ~1-2 months) and sirolimus with total loading of sirolimus ~20 μg. The device is placed at a coronary artery intervention site with the assistance of fluoroscopy to aid in positioning the device at the same location in each subject. Six animals are subjected to the procedure using a coated balloon that does not have sirolimus in the coating. After deployment and removal of the device, 3 control animals are sacrificed at 1 hour post deployment and serum and tissue samples are collected. The 3 remaining control animals are sacrificed at 56 days post deployment. During the course of the study, serum samples are collected from control and drug-treated animals every five days. The drug treated animals, 3 each, are sacrificed at 1 hour, 24 hours, 7 days, 14 days, ~28 days, 42 days and 56 days post deployment. The tissue and serum samples may be subjected to analysis for sirolimus concentration.

In order to determine the amount of coating freed from the device and/or delivered to the intervention site as a percent of the total amount of coating on the substrate, the tissue concentration of sirolimus at the one hour time point (or any time point within the first day following of the procedure) may be used along with the total content expected for the coating (based on the total content for the manufacturing lot) or along with the content of coating remaining on the device once removed and the percentage calculated. This percentage is correlative of the percent of coating freed, dissociated, and/or transferred from the device and delivered to the intervention site. Alternatively, the tissue may be analyzed by various means (noted herein, including but not limited to SEM, TEM, and, where image enhanced polymers are used, various imaging means capable of detecting these enhanced polymers) to detect the percent of the coating freed, dissociated and/or transferred from the substrate and delivered to the intervention site. Again, the amount of coating known to be on the substrate based on manufacturing lot characteristics, and/or an assessment of the coating remaining on the device following removal of the device from the subject (for example, wherein the device is a cutting angioplasty catheter and the substrate is the balloon of the catheter) may be used to determine the percent of coating freed, dissociated, and/or transferred from the device. In some instances, an assessment of the device following the procedure alone is sufficient to assess the amount freed or dissociated from the substrate, without determination of the amount delivered to the intervention site. Additionally, where a determination of improvement and/or disease treatment is desired, levels of proinflammatory markers could be tested to show improvement and/or treatment of a disease and/or ailment, for example, by testing high sensitive C-reactive protein (hsCRP), interleukin-6 (IL-6), interleukin-1β (IL-1β), and/or monocyte chemoattractant protein-1 (MCP-1). The release kinetics of the drug may be shown by plotting the sirolimus concentrations at the timepoints noted above.

For embodiments using different drugs other than sirolimus, the biomarkers are selected based on the disease to be treated and the drugs administered during the course of therapy as determined by one of skill in the art. These biomarkers may be used to show the treatment results for each subject.

In-Vitro Testing:

One sample of the coated compliant balloon prepared in Example 1 is secured to a balloon catheter. A segment of optically clear TYGON® B-44-3 tubing with O.D.=0.125", I.D.=0.0625" (Available from McMaster-Carr Part Number: 5114K11 (www.mcmaster.com)) is filled with phosphate-buffered saline solution and immersed in a water bath at 37° C. to mimic physiological conditions of deployment into a subject. The coated balloon is inserted into the tubing and the balloon is inflated to at least 25% below the balloon's nominal pressure to mechanically transfer the coating from the balloon to the tubing wall. The balloon is deflated and removed from the tubing. Optical microscopy is performed on the tubing and/or the balloon (which is inflated to at least 25% below the balloon's nominal pressure, at least) to determine the presence and amount of coating transferred to the tubing and/or the amount of coating freed, dissociated, and/or transferred from the balloon.

Method for the Determination of Sirolimus Levels:

Media may be assayed for sirolimus content using HPLC. Calibration standards containing known amounts of drug are to determine the amount of drug eluted. The multiple peaks present for the sirolimus (also present in the calibration standards) are added to give the amount of drug eluted at that time period (in absolute amount and as a cumulative amount eluted). HPLC analysis is performed using Waters HPLC system, set up and run on each sample as provided in the Table 1 below using an injection volume of 100 L.

TABLE 1

| Time point (minutes) | % Acetonitrile | % Ammonium Acetate (0.5%), pH 7.4 | Flow Rate (mL/min) |
| --- | --- | --- | --- |
| 0.00 | 10 | 90 | 1.2 |
| 1.00 | 10 | 90 | 1.2 |
| 12.5 | 95 | 5 | 1.2 |
| 13.5 | 100 | 0 | 1.2 |
| 14.0 | 100 | 0 | 3 |
| 16.0 | 100 | 0 | 3 |
| 17.0 | 10 | 90 | 2 |
| 20.0 | 10 | 90 | 0 |

In-Vitro Mass Loss Test:

One sample of the coated compliant balloon prepared in Example 1 is weighed on a microbalance and then secured to a balloon catheter. A segment of optically clear TYGON® B-44-3 tubing with O.D.=0.125", I.D.=0.0625" (Available from McMaster-Carr Part Number: 5114K11 (www.mcmaster.com)) is filled with phosphate-buffered saline solution and immersed in a water bath at 37° C. to mimic physiological conditions of deployment into a subject. The coated balloon is inserted into the tubing and the balloon is inflated to at least 25% below the balloon's nominal pressure to mechanically transfer the coating from the balloon to the tubing wall. The balloon is deflated and removed from the tubing. After drying, the balloon is removed from the guidewire, further dried and weighed on a microbalance. Comparison of the pre- and post-deployment weights indicates how much coating is freed, dissociated, and/or transferred from the balloon. This analysis may instead and/or alternatively include testing of the tubing to determine the amount of coating freed, dissociated, and/or transferred from the device during this in-vitro test.

In-Vitro Coating Test:

One sample of the coated compliant balloon prepared in Example 1 is secured to a balloon catheter. A segment of optically clear TYGON® B-44-3 tubing with O.D.=0.125", I.D.=0.0625" (Available from McMaster-Carr Part Number: 5114K11 (www.mcmaster.com)) is filled with phosphate-buffered saline solution and immersed in a water bath at 37° C. to mimic physiological conditions of deployment into a subject. The coated balloon is inserted into the tubing and the balloon is inflated to at least 25% below the balloon's nominal pressure to mechanically transfer the coating from the balloon to the tubing wall. The balloon is deflated and removed from the tubing. The section of tubing exposed to the deployed balloon is cut away from the remainder of the tubing and the interior of the excised tubing rinsed with a small amount of ethanol and an amount of methylene chloride to make up 25 mL total volume of rinsings which are collected in a flask for analysis. Analysis by HPLC as described above is performed to determine the amount of material freed, dissociated, and/or transferred from the balloon. This analysis may instead and/or alternatively include testing of the substrate itself to determine the amount of coating freed, dissociated, and/or transferred from the device during this in-vitro test.

In-Vitro Testing:

One sample of the coated compliant balloon prepared in Example 1 is secured to a balloon catheter. A segment of resected coronary artery from Yucatan miniature swine is positionally fixed and filled with phosphate-buffered saline solution and immersed in a water bath at 37° C. to mimic physiological conditions of deployment into a subject. The coated balloon is inserted into the artery and the balloon is inflated to at least 25% below the balloon's nominal pressure to mechanically transfer the coating from the balloon to the arterial wall. The balloon is deflated and removed from the artery. The section of artery exposed to the deployed balloon is cut away from the remainder of the artery section, placed into a tissue homogonizer and the homogenized material is extracted with methylene chloride to make up 25 mL total volume of rinsings which are collected in a flask for analysis. Analysis by HPLC as described above is performed to determine the amount of material freed, dissociated, and/or transferred from the balloon. This analysis may instead and/or alternatively include testing of the substrate itself to determine the amount of coating freed, dissociated, and/or transferred from the device during this in-vitro test.

For embodiments related to non-vascular or non-lumenal applications, e.g. a tumor site or other cavity or a cannulized site, the same technique is employed with the modification that the tissue to be assayed is resected from the tissue adjoining cavity receiving drug treatment.

In-Vitro Testing:

One sample of the coated compliant balloon prepared in Example 1 is secured to a balloon catheter. A segment of resected coronary artery from Yucatan miniature swine is positionally fixed and filled with phosphate-buffered saline solution and immersed in a water bath at 37° C. to mimic physiological conditions of deployment into a subject. The coated balloon is inserted into the artery and the balloon is inflated to at least 25% below the balloon's nominal pressure to mechanically transfer the coating from the balloon to the arterial wall. The balloon is deflated and removed from the artery. The section of artery exposed to the deployed balloon is cut away from the remainder of the artery section and incised lengthwise to lay open the artery. Optical microscopy is performed on the interior of artery to determine the presence and amount of coating transferred to the artery and/or the amount of coating transferred from the balloon. The tissue sample is also subjected to TEM-SEM analysis.

In-Vitro Testing of Release Kinetics:

One sample of the coated compliant balloon with total loading of sirolimus ~20 µg prepared in Example 1 is secured to a balloon catheter. A flask containing exactly 25 mL of pH 7.4 aqueous phosphate buffer equilibrated to 37° C. equipped for magnetic stirring is prepared. Into this flask is placed the coated balloon and the catheter portion of the apparatus is secured such that the balloon does not touch the sides of the flask. The balloon is inflated to 120 psi with sterile water. Aliquots of 100 L are removed prior to addition of the balloon, after placement of the balloon but prior to inflation of the balloon, and at regular time intervals of 2, 4, 6, 8, 10, 12, and 14 minutes. Upon removal of each aliquot an equivalent volume of aqueous buffer is added to maintain the volume at 25 mL. The aliquots are analyzed by HPLC as described above for the concentration of sirolimus.

In-Vitro Testing for Distal Flow Particulates:

One sample of the coated compliant balloon prepared in Example 1 is secured to a guidewire incorporating a porous filter of 100 m pore size, such as the Cordis AngioGuard emboli capture guidewire. A segment of optically clear TYGON® B-44-3 tubing with O.D.=0.125", I.D.=0.0625" (Available from McMaster-Carr Part Number: 5114K11 (www.mcmaster.com)) is filled with phosphate-buffered saline solution and immersed in a water bath at 37° C. to mimic physiological conditions of deployment into a subject. The coated balloon is inserted into the tubing, the proximal end of the tubing surrounding the guidewire sealed with epoxy, and a hypodermic needle which is attached to an infusion pump and reservoir of 37° C. phosphate-buffered saline solution is inserted into the tubing proximal to the balloon assembly. The flow of saline is commenced, the distal filter is deployed and the balloon is inflated to at least 25% below the balloon's nominal pressure to mechanically transfer the coating from the balloon to the tubing wall. The balloon is deflated and removed from the tubing. The filter is deployed for 5 minutes after removal of the balloon, the flow of saline is halted, the tubing cut adjacent to the epoxy seal, the filter retracted and removed from the tubing. The content of the filter is analyzed.

In-Vitro Testing for Distal Flow Particulates:

One sample of the coated compliant balloon prepared in Example 1 is secured to a guidewire. A segment of optically clear TYGON® B-44-3 tubing with O.D.=0.125", I.D.=0.0625" (Available from McMaster-Carr Part Number: 5114K11 (www.mcmaster.com)) is filled with phosphate-buffered saline solution and immersed in a water bath at 37° C. to mimic physiological conditions of deployment into a subject and the distal end of the tubing is connected to a turbidity light scattering detector as described in Analytical Ultracentrifugation of Polymers and Nanoparticles, W. Machtle and L. Borger, (Springer) 2006, p. 41. The coated balloon is inserted into the proximal end of the tubing, the proximal end of the tubing surrounding the guidewire sealed with epoxy, and a hypodermic needle which is attached to an infusion pump and reservoir of 37° C. phosphate-buffered saline solution is inserted into the tubing proximal to the balloon assembly. The flow of saline is commenced, a baseline for light transmission through the detector is established and the balloon is inflated to at least 25% below the balloon's nominal pressure to mechanically transfer the coating from the balloon to the tubing wall. The balloon is deflated and removed from the tubing. The flow is maintained for 10 minutes after removal of the balloon, and the flow is analyzed for the presence of particles based on detector response.

Drug-Delivery Balloon (2)—Non-Compliant Balloon

A non-compliant balloon is coated with a material comprising a polymer and an active agent. The coated non-compliant balloon is positioned at the intervention site. The balloon is inflated to at least 25% below its nominal inflation pressure. Upon deflation and removal of the non-compliant balloon from the intervention site, at least about 5% to at least about 30% of the coating is freed from the surface of the non-compliant balloon and is deposited at the intervention site.

In some examples, the balloon unfolds during inflation, causing mechanical shearing forces to at least augment transfer and/or freeing and/or deposition of the coating from the balloon to the intervention site.

In some examples, the balloon twists during inflation, causing mechanical shearing forces to at least augment transfer and/or freeing and/or deposition of the coating from the balloon.

In one example, the polymer of the coating is 50:50 PLGA-Ester End Group, MW~19 kD, degradation rate ~1-2 months or 50:50 PLGA-Carboxylate End Group, MW~10 kD, degradation rate ~28 days. The active agent is a pharmaceutical agent such as a macrolide immunosuppressive drug. Equipment and coating process similar to Example 1 is employed. The intervention site is a vascular lumen wall. Upon inflation of the non-compliant balloon, at least about 50% of the coating is freed from the device at the intervention site.

In another example, a non-compliant balloon is coated with a formulation of PLGA+sirolimus with total loading of sirolimus ~20 µg. Equipment and process similar to Example 1 is employed. The intervention site is a coronary artery. Upon inflation of the non-compliant balloon, about 5% to about 15% of the coating is freed from the device resulting in delivery of ~2.0 µg of drug delivered to the artery.

In another example, the polymer of the coating is 50:50 PLGA-Ester End Group, MW~19 kD, degradation rate ~1-2 months or 50:50 PLGA-Carboxylate End Group, MW~10 kD, degradation rate ~28 days. The active agent is a chemotherapeutic agent. Equipment and coating process similar to Example 1 is employed. The intervention site is a cavity resulting from removal of a tumor. Upon inflation of the non-compliant balloon, at least about 75% of the coating is transferred from the device to the intervention site.

In-vivo and/or in-vitro testing may be performed according to the methods described herein.

Drug-Delivery Balloon (3)—Mechanical and Chemical Stimulus

A balloon is coated with a formulation comprising a base layer of methyl acrylate-methacrylic acid copolymer and additional layers of PLGA+paclitaxel with total dose of paclitaxel approx. 0.5 µg/mm2 of the wire. The coating and sintering process is similar to that as described in Example 1. The balloon is constructed of a semipermable polymer. The pressurization medium is pH 8 phosphate buffer. The coated balloon is positioned at the intervention site. The balloon is pressurized to at least to at least 25% below its nominal inflation pressure. Upon pressurization of the balloon in the diseased artery, at least about 10% to at least about 30% of the coating is released into the intervention site and upon depressurization and removal of the device, this material is deposited at the intervention site.

In some examples, the balloon unfolds during inflation, causing mechanical shearing forces to at least augment the pH mediated release of the coating from the balloon to the intervention site.

In some examples, the balloon twists during inflation, causing mechanical shearing forces to at least augment the pH mediated release of the coating from the balloon.

In one example, a base layer of methyl acrylate-methacrylic acid copolymer is formed and additional layers of the coating is 50:50 PLGA-Ester End Group, MW~19 kD, degradation rate ~1-2 months or 50:50 PLGA-Carboxylate End Group, MW~10 kD, degradation rate ~28 days. The active agent is a pharmaceutical agent such as a macrolide immunosuppressive drug. Equipment and coating process similar to Example 1 is employed. The balloon is constructed of a semipermeable polymer. The pressurization medium is pH 8 phosphate buffer. The intervention site is a vascular lumen wall. Upon inflation of the balloon, at least about 50% of the coating is freed from the device at the intervention site.

In another example, a balloon is coated with a base layer of methyl acrylate-methacrylic acid copolymer and additional layers of PLGA+sirolimus with total loading of sirolimus ~20 µg. Equipment and process similar to Example 1 is employed. The intervention site is a coronary artery. The balloon is constructed of a semipermeable polymer. The pressurization medium is pH 8 phosphate buffer. Upon inflation of the balloon, about 5% to about 15% of the coating is freed from the device resulting in delivery of ~2.0 µg of drug delivered to the artery.

In another example, the polymer of the coating is 50:50 PLGA-Ester End Group, MW~19 kD, degradation rate ~1-2 months or 50:50 PLGA-Carboxylate End Group, MW~10 kD, degradation rate ~28 days. The active agent is a chemotherapeutic agent. Equipment and coating process similar to Example 1 is employed. The intervention site is a cavity resulting from removal of a tumor. Upon inflation of the balloon, at least about 75% of the coating is transferred from the device to the intervention site.

In-vivo and/or in-vitro testing may be performed according to the methods described herein.

Drug-Delivery Balloon (4)—Chemical Stimulus

A balloon is coated with a formulation comprising a base layer of methyl acrylate-methacrylic acid copolymer and additional layers of PLGA+paclitaxel with total dose of paclitaxel approx. 0.5 µg/mm2 of the wire. The coating and sintering process is similar to that as described in Example 1. The balloon is constructed of a semipermable polymer. The pressurization medium is pH 8 phosphate buffer. The coated balloon is positioned at the intervention site. The balloon is pressurized to at least to at least 25% below its nominal inflation pressure. Upon pressurization of the balloon in the diseased artery, at least about 10% to at least about 30% of the coating is released into the intervention site and upon depressurization and removal of the device, this material is deposited at the intervention site. In-vivo and/or in-vitro testing may be performed according to the methods described herein.

Drug-Delivery Balloon (5)—Thermal Stimulus

A balloon is coated comprising a thermoreversible polymer Pluronic F127 and an active agent. The coated balloon is positioned at the intervention site. The balloon is inflated to at least 25% below its nominal inflation pressure. Upon deflation and removal of the balloon from the intervention site, at least about 5% to at least about 30% of the coating is freed from the surface of the balloon and is deposited at the intervention site.

In some examples, the balloon unfolds during inflation, causing mechanical shearing forces to at least augment transfer and/or freeing and/or deposition of the coating from the balloon to the intervention site.

In some examples, the balloon twists during inflation, causing mechanical shearing forces to at least augment transfer and/or freeing and/or deposition of the coating from the balloon.

In one example, the active agent is a pharmaceutical agent such as a macrolide immunosuppressive drug. Equipment and coating process similar to Example 1 is employed. The intervention site is a vascular lumen wall. Upon inflation of the balloon, at least about 50% of the coating is freed from the device at the intervention site.

In-vivo and/or in-vitro testing may be performed according to the methods described herein.

Drug-Delivery Balloon (6)—Sonic Stimulus

A balloon is coated with a material comprising a polymer and an active agent. The coated balloon is positioned at the intervention site. The balloon is inflated to at least 25% below its nominal inflation pressure and subjected to ultrasonic stimulation. Upon deflation and removal of the balloon from the intervention site, at least about 5% to at least about 30% of the coating is freed from the surface of the balloon and is deposited at the intervention site.

In some examples, the balloon unfolds during inflation, causing mechanical shearing forces to at least augment transfer and/or freeing and/or deposition of the coating from the balloon effected by ultrasonic stimulation to the intervention site.

In some examples, the balloon twists during inflation, causing mechanical shearing forces to at least augment transfer and/or freeing and/or deposition of the coating from the balloon effected by ultrasonic stimulation.

In one example, the polymer of the coating is 50:50 PLGA-Ester End Group, MW~19 kD, degradation rate ~1-2 months or 50:50 PLGA-Carboxylate End Group, MW~10 kD, degradation rate ~28 days. The active agent is a pharmaceutical agent such as a macrolide immunosuppressive drug. Equipment and coating process similar to Example 1 is employed. The intervention site is a vascular lumen wall. Upon inflation of the balloon and initiation of ultrasonic stimulation, at least about 50% of the coating is freed from the device at the intervention site.

In another example, a balloon is coated with a formulation of PLGA+sirolimus with total loading of sirolimus ~20 µg with the coating preferentially on the wire of the balloon. Equipment and process similar to Example 1 is employed. The intervention site is a coronary artery. Upon inflation of the balloon and initiation of ultrasonic stimulation, about 5% to about 15% of the coating is freed from the device resulting in delivery of ~2.0 µg of drug delivered to the artery.

In another example, the polymer of the coating is 50:50 PLGA-Ester End Group, MW~19 kD, degradation rate ~1-2 months or 50:50 PLGA-Carboxylate End Group, MW~10 kD, degradation rate ~28 days. The active agent is a chemotherapeutic agent. Equipment and coating process similar to Example 1 is employed. The intervention site is a cavity resulting from removal of a tumor. Upon inflation of the balloon and initiation of ultrasonic stimulation, at least about 75% of the coating is transferred from the device to the intervention site.

In-vivo and/or in-vitro testing may be performed according to the methods described herein.

Drug-Delivery Balloon (7)—Electromagnetic Stimulus

A balloon is coated comprising a polymer and an active agent. The coated balloon is positioned at the intervention site. The balloon is inflated to at least 25% below its nominal inflation pressure and subjected to electromagnetic stimulation. Upon deflation and removal of the balloon from the intervention site, at least about 5% to at least about 30% of the coating is freed from the surface of the balloon and is deposited at the intervention site.

In some examples, the balloon unfolds during inflation, causing mechanical shearing forces to at least augment transfer and/or freeing and/or deposition of the coating from the balloon effected by electromagnetic stimulation to the intervention site.

In some examples, the balloon twists during inflation, causing mechanical shearing forces to at least augment transfer and/or freeing and/or deposition of the coating from the balloon effected by electromagnetic stimulation.

In one example, the polymer of the coating is 50:50 PLGA-Ester End Group, MW~19 kD, degradation rate ~1-2 months or 50:50 PLGA-Carboxylate End Group, MW~10 kD, degradation rate ~28 days. The active agent is a pharmaceutical agent such as a macrolide immunosuppressive drug. Equipment and coating process similar to Example 1 is employed. The intervention site is a vascular lumen wall. Upon inflation of the balloon and initiation of electromagnetic stimulation, at least about 50% of the coating is freed from the device at the intervention site.

In another example, a balloon is coated with a formulation of PLGA+sirolimus with total loading of sirolimus ~20 µg with the coating preferentially on the wire of the balloon. Equipment and process similar to Example 1 is employed. The intervention site is a coronary artery. Upon inflation of the balloon and initiation of electromagnetic stimulation, about 5% to about 15% of the coating is freed from the device resulting in delivery of ~2.0 µg of drug delivered to the artery.

In another example, the polymer of the coating is 50:50 PLGA-Ester End Group, MW~19 kD, degradation rate ~1-2 months or 50:50 PLGA-Carboxylate End Group, MW~10 kD, degradation rate ~28 days. The active agent is a chemotherapeutic agent. Equipment and coating process similar to Example 1 is employed. The intervention site is a cavity resulting from removal of a tumor. Upon inflation of the balloon and initiation of electromagnetic stimulation, at least about 75% of the coating is transferred from the device to the intervention site.

In-vivo and/or in-vitro testing may be performed according to the methods described herein.

Drug-Delivery Balloon (8)—Electrostatically Applied Drug Release Layer

A 5×40 mm polyethylene terephthalate (PET) balloon was airbrushed with rapamycin (~5.8 mg from rapamycin/acetone solution) as a release agent, then airbrushed with PLGA (~1 mg) and sintered at 67° C. under vacuum for 1 hour. The balloon was deflated, inserted in the lumen of 3/16" Tygon tubing, and pressurized to ~245 psig at 37° C. (2 minutes equilibration time; 1 minute pressurization). Substantial transfer of the coating (a thick layer) to the tubing was observed. A thin layer of coating remained on the balloon.

In a related experiment, a 5×40 mm polyethylene terephthalate (PET) balloon was electrostatically coated with 240 micrograms of rapamycin as a release agent, then coated with PLGA (1.24 mg) by eRESS and sintered at 68° C. for 1 hour. The balloon was deflated, inserted in the lumen of 3/16" Tygon tubing, and pressurized to 250 psig at 37° C.

(2 minutes equilibration time; 1 minute pressurization). Under these conditions, no transfer of the PLGA coating to the tubing was observed.

Example 14

Balloon Delivery of Weakly Binding Drugs

A compliant balloon was electrostatically coated with a weakly binding drug, cyrstalline sirolimus with a nominal particle size of 2.4 microns, as part of a bioabsorbable polymer matrix in dry powder form, and the coating sintered at low temperature. Upon introduction of the coated balloon into a model lumen (made from Tygon tubing, as described herein) and subsequent inflation, the drug coating was shown by cross-sectional analysis to have transferred to the interior of the lumen. This result shows that dry processing that isolates a weakly binding drug as particles within a bioabsorbable polymer matrix can provide the ability to control the delivery of weakly binding drugs.

Example 15

Drug-Delivery Balloons for Treatment of the Vasculature

Drug-Delivery Balloon (1)—Treatment of Restenosis with Paclitaxel or Sirolimus

A balloon is used to prevent and/or treat restenosis in an artery. A balloon is coated as described herein with 50:50 PLGA-Ester End Group (MW~19 kD, degradation rate ~1-2 months) and paclitaxel or at a loading of 1 g/mm$^2$ or sirolimus at a loading of 5 g/mm$^2$. The coated balloon is positioned at the arterial intervention site. The balloon is inflated to at least 25% below its nominal inflation pressure. The balloon is deflated and removed from the intervention site, allowing the coating to be freed from the surface of the balloon and deposited at the intervention site. The amount of coating transferred upon deployment can be determined using, e.g., test methods as described herein.

Drug-Delivery Balloon (2)—Treatment of Restenosis with Cilostazol

A balloon is used to prevent and/or treat restenosis in an artery. A balloon is coated as described herein with 50:50 PLGA-Ester End Group (MW~19 kD, degradation rate ~1-2 months) and cilostazol. The coated balloon is positioned at the arterial intervention site. The balloon is inflated to at least 25% below its nominal inflation pressure. The balloon is deflated and removed from the intervention site, allowing the coating to be freed from the surface of the balloon and deposited at the intervention site where it can act to prevent further platelet binding. The amount of coating transferred upon deployment can be determined using, e.g., test methods as described herein.

Drug-Delivery Balloon (3)—Promotion of Healing Using CD34 Antibodies

A coated balloon is used to promote healing in a damaged artery. A balloon is coated as described herein with 50:50 PLGA-Ester End Group (MW~19 kD, degradation rate ~1-2 months) and CD34 antibodies. The coated balloon is positioned at the arterial intervention site. The balloon is inflated to at least 25% below its nominal inflation pressure. The balloon is deflated and removed from the intervention site, allowing the coating to be freed from the surface of the balloon and deposited at the intervention site where it can act to attract progenitor cells to the vessel wall. This can result in an acceleration of endothlialization. The amount of coating transferred upon deployment can be determined using, e.g., test methods as described herein.

Drug-Delivery Balloon (4)—Promotion of Healing Using an Agent that Protects Endothelium or Improves EPC Function A coated balloon is used to promote healing in a damaged artery. A balloon is coated as described herein with 50:50 PLGA-Ester End Group (MW~19 kD, degradation rate ~1-2 months) and a statin (e.g., cerivastatin), an ACE inhibitor, an angiotensin II type I receptor blocker, a PPAR-gamma agonist, a glitazone, or erythropoietin. The coated balloon is positioned at the arterial intervention site. The balloon is inflated to at least 25% below its nominal inflation pressure. The balloon is deflated and removed from the intervention site, allowing the coating to be freed from the surface of the balloon and deposited at the intervention site where it can act to protect the endothelium and/or improve EPC colonization, maturation, or function. The amount of coating transferred upon deployment can be determined using, e.g., test methods as described herein.

Drug-Delivery Balloon (5)—Treatment of Atherosclerosis Using Adiponectin

A coated balloon is used to prevent and/or treat atherosclerosis in an artery. A balloon is coated as described herein with 50:50 PLGA-Ester End Group (MW~19 kD, degradation rate ~1-2 months) and adiponectin. The coated balloon is positioned at the arterial intervention site. The balloon is inflated to at least 25% below its nominal inflation pressure. The balloon is deflated and removed from the intervention site, allowing the coating to be freed from the surface of the balloon and deposited at the intervention site where it can prevent inflammatory cell binding and promote generation of nitric oxide. The amount of coating transferred upon deployment can be determined using, e.g., test methods as described herein.

Drug-Delivery Balloon (6)—Treatment of Atherosclerosis Using Batimastat

A coated balloon is used to prevent and/or treat atherosclerosis in an artery. A balloon is coated as described herein with 50:50 PLGA-Ester End Group (MW~19 kD, degradation rate ~1-2 months) and batimastat. The coated balloon is positioned at the arterial intervention site. The balloon is inflated to at least 25% below its nominal inflation pressure. The balloon is deflated and removed from the intervention site, allowing the coating to be freed from the surface of the balloon and deposited at the intervention site where it can prevent vulnerable plaque rupture. The amount of coating transferred upon deployment can be determined using, e.g., test methods as described herein.

Drug-Delivery Balloon (7) Treatment of Reperfusion Injury

A coated balloon is used to prevent and/or treat reperfusion injury in an artery. A balloon is coated as described herein with 50:50 PLGA-Ester End Group (MW~19 kD, degradation rate ~1-2 months) and glucagon-like peptide-1, erythropoietin, atorvastatin, or atrial natriuretic peptide. The coated balloon is positioned at the arterial intervention site. The balloon is inflated to at least 25% below its nominal inflation pressure. The balloon is deflated and removed from the intervention site, allowing the coating to be freed from the surface of the balloon and deposited at the intervention site. The amount of coating transferred upon deployment can be determined using, e.g., test methods as described herein.

Drug-Delivery Balloon (8)—Promotion of Angiogenesis

A coated balloon is used to promote angiogenesis. A balloon is coated as described herein with 50:50 PLGA-Ester End Group (MW~19 kD, degradation rate ~1-2 months) and a fibroblast growth factor gene therapy agent (e.g., Generx, Cardium Therapeutics), or angiopoietin-1.

The coated balloon is positioned in a vessel in a tissue bed in need of better perfusion. The balloon is inflated to at least 25% below its nominal inflation pressure. The balloon is deflated and removed from the intervention site, allowing the coating to be freed from the surface of the balloon and deposited at the intervention site where it can promote angiogenesis. The amount of coating transferred upon deployment can be determined using, e.g., test methods as described herein.

Coated Cutting Balloon (9)—Treatment of Thrombosis Using Dipyridamole

A cutting balloon is used to prevent and/or treat thrombosis in an artery. A cutting balloon is coated with 50:50 PLGA-Ester End Group (MW~19 kD, degradation rate ~1-2 months) and dipyridamole. The coated cutting balloon is positioned at the arterial intervention site. The balloon is inflated to at least 25% below its nominal inflation pressure. The balloon is deflated and removed from the intervention site, allowing the coating to be freed from the surface of the balloon and deposited at the intervention site to cause local release of t-PA to break up clots and/or prevent clot formation. The amount of coating transferred upon deployment can be determined using, e.g., test methods as described herein.

Example 16

Drug-Delivery Balloon Catheter for Treatment of the Trachea

Drug-Delivery Balloon (1)—Prevention of Discomfort from the Use of an Endotracheal Tube Using Betamethasone or Lidocaine A coated balloon catheter is used to prevent discomfort resulting from the use of an endotracheal tube. Prior to insertion of the endotracheal tube, procedure, a compliant balloon is coated with 50:50 PLGA-Ester End Group (MW~19 kD, degradation rate ~1-2 months) and betamethasone (0.05%) or lidocaine (2.0-4.0%), positioned in the endotracheal intervention site and inflated to at least 25% below its nominal inflation pressure. The balloon is deflated and removed from the intervention site, allowing the coating to be freed from the surface of the balloon and deposited at the intervention site. The amount of coating transferred upon deployment can be determined using, e.g., test methods as described herein.

Drug-Delivery Balloon (2)—Reduction of Discomfort from the Use of an Endotracheal Tube Using Betamethasone or Lidocaine A coated balloon catheter is used to reduce discomfort resulting from the use of an endotracheal tube. After the endotracheal procedure, a compliant balloon is coated with 50:50 PLGA-Ester End Group (MW~19 kD, degradation rate ~1-2 months) and betamethasone (0.05%) or lidocaine (2.0-4.0%), positioned in the endotracheal intervention site and inflated to at least 25% below its nominal inflation pressure. The balloon is deflated and removed from the intervention site, allowing the coating to be freed from the surface of the balloon and deposited at the intervention site. The amount of coating transferred upon deployment can be determined using, e.g., test methods as described herein.

Drug-Delivery Balloon (3)—Improved Healing and Reduction of Scarring Following Laryngeal/Tracheal Surgery A coated balloon catheter is used to improve healing and reduce scarring following laryngeal/tracheal surgery. After the endotracheal procedure, a compliant balloon is coated with 50:50 PLGA-Ester End Group (MW~19 kD, degradation rate ~1-2 months) and mitomycin C (0.4-0.5 mg/ml or ~0.04-0.05%) or heparin (5000 U/ml) positioned in the endotracheal intervention site and inflated to at least 25% below its nominal inflation pressure. The balloon is deflated and removed from the intervention site, allowing the coating to be freed from the surface of the balloon and deposited at the intervention site. The amount of coating transferred upon deployment can be determined using, e.g., test methods as described herein. The procedure is repeated as necessary to ensure adequate delivery of active agent over the course of the wound healing process.

Example 17

Drug-Delivery Balloon Catheter for Treatment of the Esophagus

Drug-Delivery Balloon (1)—Prevention of Discomfort Resulting from an Endoscopic Procedure Using Betamethasone or Lidocaine A coated balloon catheter is used to prevent discomfort resulting from an endoscopic procedure. Prior to the endoscopic procedure, a compliant balloon is coated with 50:50 PLGA-Ester End Group (MW~19 kD, degradation rate ~1-2 months) and betamethasone (0.05%) or lidocaine (2.0-4.0%), positioned in the endoscopic intervention site and inflated to at least 25% below its nominal inflation pressure. The balloon is deflated and removed from the intervention site, allowing the coating to be freed from the surface of the balloon and deposited at the intervention site. The amount of coating transferred upon deployment can be determined using, e.g., test methods as described herein.

Drug-Delivery Balloon (2)—Reduction of Discomfort Resulting from an Endoscopic Procedure Using Betamethasone or Lidocaine A coated balloon catheter is used to reduce discomfort resulting from an endoscopic procedure. After the endoscopic procedure, a compliant balloon is coated with 50:50 PLGA-Ester End Group (MW~19 kD, degradation rate ~1-2 months) and betamethasone (0.05%) or lidocaine (2.0-4.0%), positioned in the endoscopic intervention site and inflated to at least 25% below its nominal inflation pressure. The balloon is deflated and removed from the intervention site, allowing the coating to be freed from the surface of the balloon and deposited at the intervention site. The amount of coating transferred upon deployment can be determined using, e.g., test methods as described herein.

Drug-Delivery Balloon (3)—Reduction of Inflammation and Promotion of Healing Following Endoscopic Surgery A coated balloon catheter is used to reduce inflammation and promote healing following endoscopic surgery. After the endoscopic surgery, a compliant balloon is coated with 50:50 PLGA-Ester End Group (MW~19 kD, degradation rate ~1-2 months) and mitomycin C and/or Bacillus Calmette-Guerin is positioned in the endoscopic intervention site and inflated to at least 25% below its nominal inflation pressure. The balloon is deflated and removed from the intervention site, allowing the coating to be freed from the surface of the balloon and deposited at the intervention site. The amount of coating transferred upon deployment can be determined using, e.g., test methods as described herein.

Example 18

Drug-Delivery Balloon Catheter for Treatment of a Cancer

Drug-Delivery Balloon (1)—Treatment of a Bladder Transitional Cell Carcinoma

A coated balloon is used to treat a bladder transitional cell carcinoma. The balloon, which is large enough to contact the bladder walls when inflated, is coated with a polymer combined with active agent sufficient to deliver the equivalent of either: 1) for administration immediately following surgical resection, a combination intravesical treatment of 1000 mg gemcitabine, or 75 mg docetaxel, or 30 mg thiotepa, followed (sequentially) by 40 mg mitomycin C, then the same combination treatment every week for 6 weeks, and followed by a maintenance regimen providing the same combination treatment once a month for 12 months; or 2) for administration starting 2 weeks after surgery, 50 million units Interferon Alpha 2b and 81 mg BCG once a week for 6 weeks, with maintenance of up to 3 weekly instillations at 3 or 6 months, and then once every 6 to 12 months; or 3) for administration as a single instillation at the time of tumor resection, 50 mg doxorubicin, then the same dose weekly for 4-8 weeks, then once a month to provide maintenance as desired; or 4) for administration to treat existing disease, 30 mg thiotepa, then the same dose weekly for 4 to 8 weeks, depending on volume of residual disease, then once a month to provide maintenance as desired. In embodiments, the treatment is delivered in more than one procedure, e.g., a second balloon is used to deliver the maintenance regimen. In treatment 2) the dose of BCG is reduced to ⅓, ⅒, 1/100 as needed to prevent increased side effects. Treatments 1) through 4) are made to include or not include hyaluronidase (rHuPH20, total dose 50-100 U).

The balloon is inflated to at least 25% below its nominal inflation pressure and left in place for a period of time sufficient for transfer of the coating to the bladder walls to take place, e.g., at least about 2 to 30 minutes. The balloon is deflated and removed from the intervention site, allowing the coating to be freed from the surface of the balloon and deposited at the intervention site. The amount of coating transferred upon deployment can be determined using, e.g., test methods as described herein. For example, the residual coating on the balloon or the coating within the bladder can be quantitated. The procedure can be repeated as deemed necessary.

In embodiments of the devices and methods of the invention, the amount of an active agent to be delivered is equal to at least about 35% of that used to coat the balloon. In these embodiments, with regard to intravesical therapy, to deliver a standard dosage of a drug, e.g., 50 mg doxorubicin, the coating could comprise 50 mg×(35%)−1, or about 143 mg doxorubicin. In related embodiments, layers comprising about 143 mg doxorubicin are alternated with layers of a polymer, such that each doxorubicin layer delivers the appropriate weekly dose of doxorubicin as dictated by the treatment protocol. Combination treatments are administered, e.g., by including in the coating layers of additional active agents in the appropriate treatment sequence.

Drug-Delivery Balloon (2)—Treatment of a Urinary Tract Transitional Cell Carcinoma A coated balloon is used to treat a urinary tract transitional cell carcinoma. A balloon is coated with alternating layers of 50:50 PLGA-Ester End Group (MW~19 kD, degradation rate ~1-2 months) and sufficient active agent to deliver either about 10-40 mg mitomycin C with or without hyaluronic acid (rHuPH20, total dose 50-100 U), and/or 10-81 mg bacillus Calmette-Guerin. The coated balloon is loaded into a Foley-type catheter and the balloon is positioned at a urethral lesion site. The balloon is inflated to at least 25% below its nominal inflation pressure. The balloon is deflated and removed from the intervention site, allowing the coating to be freed from the surface of the balloon and deposited at the intervention site. The amount of coating transferred upon deployment can be determined using, e.g., test methods as described herein.

Example 19

Drug-Delivery Balloon Catheter for Treatment of Neurovascular Indications

Drug-Delivery Balloon (1)—Treatment of Post-Stroke Thrombolysis

A coated balloon is used to treat post-stroke thrombolysis. Local delivery of a sustained treatment can circumvent the risk associated with infusion of agents in the local vicinity of a vascular occlusion, which can result in severe bleeding. A balloon is coated with alternating layers of 50:50 PLGA-Ester End Group (MW~19 kD, degradation rate ~1-2 months) and a thrombolytic drug, e.g., tissue plasminogen activator (tPA), melagatran, lanoteplase, reteplase, staphylokinase, streptokinase, tenecteplase, urokinase, or any combination thereof. The coated balloon is positioned within the vessel near the site of thrombolysis as desired and inflated to at least 25% below its nominal inflation pressure. The balloon is deflated and removed from the intervention site, allowing the coating to be freed from the surface of the balloon and deposited at the intervention site. The amount of coating transferred upon deployment can be determined using, e.g., test methods as described herein.

Drug-Delivery Balloon (2)—Treatment with a Neuroprotective Agent After Stroke

A coated balloon is used to administer a neuroprotective agent after stroke. A balloon is coated with alternating layers of 50:50 PLGA-Ester End Group (MW~19 kD, degradation rate ~1-2 months) and a neuroprotective drug, e.g., resveratrol, a PARP-1 inhibitor (including imidazoquinolinone, imidazpyridine, and isoquinolindione). Resveratrol is an antioxidant that has been shown to preserve mitochondrial function and improve neurological deficits after cerebral ischemia that could prove more effective when delivered locally in a controlled fashion than when delivered intravenously. The coated balloon is positioned within the vessel near the ischemic site as desired and inflated to at least 25% below its nominal inflation pressure. The balloon is deflated and removed from the intervention site, allowing the coating to be freed from the surface of the balloon and deposited at the intervention site. The amount of coating transferred upon deployment can be determined using, e.g., test methods as described herein.

Drug-Delivery Balloon (3)—Treatment of Malignant Glioma

A coated balloon is used to treat a glioma. Solid paclitaxel, is mixed with poly[bis(p-carboxyphenoxy) propane-sebacic acid] copolymer (PCPP-SA) (20:80), synthesized, e.g., according to the method of Domb, A. J., and R. Langer (J. Polym. Sci. 25:3373-3386 (1987)), the teachings of which are incorporated herein by reference, to give a mixture containing 0, 20, 30, or 40% paclitaxel by weight. The paclitaxel-polymer mixture is dissolved in methylene chloride (Fluka, Switzerland) to give a 10% solution (w:v). The solvent is evaporated with a nitrogen stream to yield a dry powder. A compliant or semi-compliant balloon is coated with the powder. The coated balloon is inserted into the glioma using methods known in the art for inserting implants, e.g., it is inserted following surgery and resection before the incision is closed. The balloon is inflated in the space previously occupied by the tumor, to at least 25% below its nominal inflation pressure. The balloon is deflated and removed from the intervention site, allowing the coating to be freed from the surface of the balloon and deposited within the tumor cavity. The amount of coating transferred upon deployment can be determined using, e.g., test methods as described herein.

Alternatively, a coated balloon can be inflated within a tumor without first performing surgery. In this case, a non-compliant or semi-compliant could be used.

Local delivery of chemotherapeutic agents, and polymer selection, are described, e.g., in U.S. Pat. No. 5,626,862, "Controlled local delivery of chemotherapeutic agents for treating solid tumors," incorporated herein by reference in its entirety.

The amount of coating transferred upon deployment can be determined using, e.g., test methods as described herein.

Drug-Delivery Balloon (4)—Treatment with a Stabilizing or Healing Agent After Cerebral Aneurysm A coated balloon is used to administer a stabilizing or healing agent after cerebral aneurysm, e.g., to prevent the vessel from rupturing. A balloon is coated with alternating layers of 50:50 PLGA-Ester End Group (MW~19 kD, degradation rate ~1-2 months) and a stabilizing or healing agent, e.g., a polymer matrix (to prevent rupture), doxycyclin (to accelerate the healing response), or a combination thereof. The coated balloon is positioned at the intervention site and inflated to at least 25% below its nominal inflation pressure The balloon is deflated and removed from the intervention site, allowing the coating to be freed from the surface of the balloon and deposited at the intervention site. The amount of coating transferred upon deployment can be determined using, e.g., test methods as described herein.

Related information is available in the literature, e.g., in Mocco, et al., March 2009, "Pharos neurovascular intracranial stent: Elective use for a symptomatic stenosis refractory to medical therapy," Catheter Cardiovasc Interv (Epub); Wang, et al., 2008, "Treatment with melagatran alone or in combination with thrombolytic therapy reduced ischemic brain injury," Exp Neurol 213(1):171-175; Yepes, et al., 2009, "Tissue-type plasminogen activator in the ischemic brain: more than a thrombolytic," Trends Neurosci 32(1): 48-55; Yousuf, et al., 2009, "Resveratrol exerts its neuroprotective effect by modulating mitochondrial dysfunction and associated cell death during cerebral ischemia," Brain Res. 1250:242-253; Moroni, et a., 2009, "Post-ischemic brain damage:targeting PARP-1 within the ischemic neurovascular units as a realistic avenue to stroke treatment," FEBS J 276(1):36-45; Eltze, et al., 2008, "Imidazoquinolinone, imidazopyridine, and isoquinolindione derivatives as novel and potent inhibitors of the poly(ADP-ribose) polymerase (PARP): a comparison with standard PARP inhibitors," Mol Pharmacol. 74(6):1587-1598; Raganath, et al., Jun. 20, 2009, "Hydrogel matrix entrapping PLGA-paclitaxel microspheres: drug delivery with near zero-order release and implantability advantages for malignant brain tumour," Pharm Res (Epub); Kelly, et al., 2008, "Double-balloon trapping technique for embolization of a large wide-necked superior cerebellar artery aneurysm: case report," Neurosurgery 63(4 Suppl 2):291-292.

Example 20

Drug-Delivery Device for Urologic and Reproductive Care

Drug-Delivery Balloon (1)—Treatment of a Urinary Tract Infection

A coated balloon is used to prevent and/or treat a urinary tract infection. Sustained local release of an antibiotic agent eliminates the need for systemic treatment that can raise concerns about the development of antibiotic resistance. Furthermore, systemic administration of antibiotic agents is associated with adverse side effects including gastrointestinal upset, and oral and vaginal candidiasis. A drug-releasing matrix adhered to the urethral wall could provide high local concentrations of drugs without producing negative side effects. In a representative example, a balloon is coated with alternating layers of 50:50 PLGA-Ester End Group (MW~19 kD, degradation rate ~1-2 months) and an antibiotic, e.g., erythromycin, TMP-SMX, cephalexin, ciprofloxacin, or nitrofurantoin. The coated balloon is positioned within the urethra and inflated to at least 25% below its nominal inflation pressure. Upon deflation and removal of the balloon from the intervention site, at least about 20% to at least about 40% of the coating is freed from the surface of the balloon and is deposited at the intervention site. The amount of coating transferred upon deployment can be determined using, e.g., test methods as described herein. In particular examples, the agent is delivered for at least 3-6 months.

For a patient having an indwelling J ureteral stent (e.g., triclosan-eluting ureteral stents), a triclosan-eluting polymer matrix can be transferred to the stented area, e.g., to supplement administration of the triclosan from the stent.

Treatment and prevention of urinary tract infections has been described in the literature, e.g., by Albert, et al., 2004, "Antibiotics for preventing recurrent urinary tract infection in non-pregnant women," Cochrane Database Syst. Rev. 3, CD001209; Borchert, et al., 2008, "Prevention and treatment of urinary tract infection with probiotics: Review and research perspective," Indian J. Urol. 24(2):139-144; Salo, et al., 2009, "Biofilm formation by *Escherichia coli* isolated from patients with urinary tract infections," Clin Nephrol. 71(5): 501-507; Kehinde, et al., 2004, "Bacteriology of urinary tract infection associated with indwelling J ureteral stents," J. Endourol. 18(9):891-896; Cadieux, et al., Jun. 19, 2009, "Use of triclosan-eluting ureteral stents in patients with long-term stents," J. Endourol. (Epub).

Drug-Delivery Balloon (2)—Treatment of a Tubo-Ovarian Abcess

A coated balloon is used to treat a tubo-ovarian abcess. A balloon is coated as described herein with alternating layers of 50:50 PLGA-Ester End Group (MW~19 kD, degradation rate ~1-2 months) and an antibiotic agent, e.g., clindamycin in combination with gentamycin. The coated balloon is positioned at the intervention site, e.g., within the fallopian tube, and inflated to at least 25% below its nominal inflation pressure. The balloon is deflated and removed from the intervention site, allowing the coating to be freed from the surface of the balloon and deposited at the intervention site. The amount of coating transferred upon deployment can be determined using, e.g., test methods as described herein. The procedure is repeated as necessary, e.g., to extend treatment or to administer a different antibiotic. In an example, the coating is designed to release the agents over a period of at least about two weeks.

Drug-Delivery Balloon (3)—Treatment of Benign Prostatic Hyperplasia

A coated balloon is used to treat benign prostatic hyperplasia (BPH). A balloon is coated as described herein with alternating layers of 50:50 PLGA-Ester End Group (MW~19 kD, degradation rate ~1-2 months) and an antibiotic agent combined with an antiinflammatory therapy, e.g., ciprofloxacin and alfuzosin. The coated balloon is inserted into the prostate tissue through the rectum using a needle and ultrasound guidance and inflated to at least 25% below its nominal inflation pressure. The balloon is deflated and removed from the intervention site, allowing the coating to be freed from the surface of the balloon and deposited at the intervention site. The amount of coating transferred upon deployment can be determined using, e.g., test methods as described herein. Methods for inserting implants into the prostate are known in the art and have been described in, e.g., U.S. Pat. No. 7,442,162, "Method and apparatus for treatment planning using implanted radioactive seeds," U.S. Pat. No. 7,282,020, "Deflectable implantation device and method of use," incorporated herein by reference in their entirety. Methods for visualizing a treatment area and planning instrument insertion are described, e.g., in U.S. Pat. No. 7,171,255, "Virtual reality 3D visualization for surgical procedures" and U.S. Pat. No. 6,610,013, "3D ultrasound-guided intraoperative prostate brachytherapy," incorporated herein by reference in their entirety.

Drug-Delivery Balloon (4)—Hormone Delivery

A coated balloon is used to administer a hormone vaginally to alleviate the symptoms of menopause. A balloon is coated as described herein with alternating layers of 50:50 PLGA-Ester End Group (MW~19 kD, degradation rate ~1-2 months), and either estrogen (17β-estradiol can be administered at about 200 micrograms/day) for administration to a patient not having a uterus, or a combination of estrogen and progesterone to a patient having an intact uterus. The coated balloon is positioned at the vaginal intervention site and inflated to at least 25% below its nominal inflation pressure. The balloon is deflated and removed from the intervention site, allowing the coating to be freed from the surface of the balloon and deposited at the intervention site. The amount of coating transferred upon deployment can be determined using, e.g., test methods as described herein.

Drug-Delivery Balloon (5)—Contraceptive

A coated balloon is used to administer a hormone contraceptive. A balloon is coated as described herein with alternating layers of 50:50 PLGA-Ester End Group (MW~19 kD, degradation rate ~1-2 months), and etonogestrel at a total dosage sufficient to provide a concentration of about 150 to 900 pg/ml for a period of about 3 years, accounting for the portion of coating predicted to transfer to the intervention site.

The coated balloon is positioned at the intervention site, e.g., at a location near or within the reproductive organs, at an intramuscular location, or at a subcutaneous location, inflated to at least 25% below its nominal inflation pressure, then deflated and removed. In women the drug is administered, e.g., at anytime starting on Day 1 of menstrual bleeding and ending on Day 5 or as determined by a physician based on parameters including release rate. The amount of coating transferred upon deployment can be determined using, e.g., test methods as described herein. Etonogestrel and its use as a contraceptive via administration to either a male or female subject is described, e.g., in U.S. Pat. No. 7,323,454, "Etonogestrel esters," and in the labeling for Implanon™ etonogestrel implant (Organon USA Inc.).

Drug-Delivery Balloon (6)—Fertility Drug

A coated balloon is used to administer a hormone contraceptive. A balloon is coated as described herein with alternating layers of 50:50 PLGA-Ester End Group (MW~19 kD, degradation rate ~1-2 months), and clomiphene citrate (Seraphene or Clomid) in an amount sufficient to deliver the equivalent of an oral dosage of 25 milligrams to 150 milligrams once a day for five days.

The coated balloon is positioned at the intervention site, e.g., at a location near or within the reproductive organs, at an intramuscular location, or at a subcutaneous location, inflated to at least 25% below its nominal inflation pressure, then deflated and removed. The drug is administered, e.g., early in a woman's menstrual cycle, e.g., days 2 through 6 or as determined by a physician based on parameters including release rate. The amount of coating transferred upon deployment can be determined using, e.g., test methods as described herein.

Response is monitored by methods known to those of skill in the art, e.g., blood estrogen measurement, ultrasound of the ovaries, and measurement of luteinizing hormone levels.

Example 21

Drug-Delivery Balloon Catheter for Treatment of Infection

Drug-Delivery Device—(1)—Orthopedic Implant

A coated balloon is used to treat or prevent staphylococcal infection of an orthopedic implant, either alone or in conjunction with debridement. A balloon is coated as described herein with alternating layers of 50:50 PLGA-Ester End Group (MW~19 kD, degradation rate ~1-2 months), an imaging agent, and a combination of the antibiotics ciprofloxacin and rifampicin. The coated balloon is positioned at the intervention site, e.g., adjacent to the implant, with or without the aid of imaging guidance, inflated to at least 25% below its nominal inflation pressure, then deflated and removed. The amount of coating transferred upon deployment can be determined using, e.g., test methods as described herein.

The procedure is repeated as necessary, e.g., to administer multiple treatments around the implant. In an example, the coating is designed to release the agents over a period of at least about two weeks. For prophylaxis, the coating is designed to release the agents over a longer period of time, e.g., at least about 1 year and/or longer. When using the devices and methods of the invention, antibiotic and other agents are generally administered to achieve local concentrations comparable to those achieved locally when systemic dosages, including IV, SC, or typical oral dosages (e.g., rifampicin, 1 coated 450-mg tablet every 12 hours, and ciprofloxacin, 750 mg every 12 hours by mouth) are given. The locally-administered dosages are much lower overall than the oral dosages, and better tolerated by patients.

Drug-Delivery Balloon (2)—Infection at a Cannulized or Cannulizable Site

A coated balloon is used to treat or prevent infection at a cannulized or cannulizable site. A balloon is coated as described herein with alternating layers of 50:50 PLGA-Ester End Group (MW~19 kD, degradation rate ~1-2 months), an imaging agent, and an antibiotic, e.g., vancomycin or ciprofloxacin. The coated balloon is deployed through the catheter and positioned within the catheter, with or without the aid of imaging guidance, inflated to at least 25% below its nominal inflation pressure, then deflated and removed. The amount of coating transferred upon deployment can be determined using, e.g., test methods as described herein.

In an example, the coating is designed to release the agents over a period of at least about one week, and/or for as long as the site is to remain cannulized. In cases where cannulization time is indefinite, the process can be repeated as necessary for prevention of new infections, or as new infections occur.

In a related example, the devices and methods of the invention are used to percutaneously administer antibiotics at an intervention site within tissue in the vicinity of the infection.

Treatment and prevention of hemodialysis cather infections is described, e.g., by Saxena, et al., 2005, "Haemodialysis catheter-related bloodstream infections: current treatment options and strategies for prevention," Swiss Med Wkly 135:127-138.

Example 22

Crystallinity of Drug on a Device

The presence and or quantification of the Active agent crystallinity can be determined from a number of characterization methods known in the art, but not limited to, XRPD, vibrational spectroscopy (FTIR, NIR, Raman), polarized optical microscopy, calorimetry, thermal analysis and solid-state NMR.

X-Ray Diffraction to Determine the Presence and/or Quantification of Active Agent Crystallinity Active agent and polymer coated proxy substrates are prepared using 316L stainless steel coupons for X-ray powder diffraction (XRPD) measurements to determine the presence of crystallinity of the active agent. The coating on the coupons is equivalent to the coating on the stents described herein. Coupons of other materials described herein, such as cobalt-chromium alloys, may be similarly prepared and tested. Likewise, substrates such as stents, or other medical devices described herein may be prepared and tested. Where a coated stent is tested, the stent may be cut lengthwise and opened to lay flat in a sample holder.

For example XRPD analyses are performed using an X-ray powder diffractometer (for example, a Bruker D8 Advance X-ray diffractometer) using Cu Kα radiation. Diffractograms are typically collected between 2 and 40 degrees 2 theta. Where required low background XRPD sample holders are employed to minimize background noise.

The diffractograms of the deposited active agent are compared with diffractograms of known crystallized active agents, for example micronized crystalline sirolimus in powder form. XRPD patterns of crystalline forms show strong diffraction peaks whereas amorphous show diffuse and non-distinct patterns. Crystallinity is shown in arbitrary Intensity units.

A related analytical technique which may also be used to provide crystallinity detection is wide angle scattering of radiation (e.g.; Wide Anle X-ray Scattering or WAXS), for example, as described in F. Unger, et al., "Poly(ethylene carbonate): A thermoelastic and biodegradable biomaterial for drug eluting stent coatings?" Journal of Controlled Release, Volume 117, Issue 3, 312-321 (2007) for which the technique and variations of the technique specific to a particular sample would be obvious to one of skill in the art.

Raman Spectroscopy

Raman spectroscopy, a vibrational spectroscopy technique, can be useful, for example, in chemical identification, characterization of molecular structures, effects of bonding, identification of solid state form, environment and stress on a sample. Raman spectra can be collected from a very small volume (<1 μm3); these spectra allow the identification of species present in that volume. Spatially resolved chemical information, by mapping or imaging, terms often used interchangeably, can be achieved by Raman microscopy.

Raman spectroscopy and other analytical techniques such as described in Balss, et al., "Quantitative spatial distribution of sirolimus and polymers in drug-eluting stents using confocal Raman microscopy" J. of Biomedical Materials Research Part A, 258-270 (2007), incorporated in its entirety herein by reference, and/or described in Belu et al., "Three-Dimensional Compositional Analysis of Drug Eluting Stent Coatings Using Cluster Secondary Ion Mass Spectroscopy" Anal. Chem. 80: 624-632 (2008) incorporated herein in its entirety by reference may be used.

For example, to test a sample using Raman microscopy and in particular confocal Raman microscopy, it is understood that to get appropriate Raman high resolution spectra sufficient acquisition time, laser power, laser wavelength, sample step size and microscope objective need to be optimized. For example a sample (a coated stent) is prepared as described herein. Alternatively, a coated coupon could be tested in this method. Maps are taken on the coating using Raman microscopy. A WITec CRM 200 scanning confocal Raman microscope using a Nd:YAG laser at 532 nm is applied in the Raman imaging mode. The laser light is focused upon the sample using a 10× dry objective (numerical aperture 0.90), and the finely focused laser spot is scanned into the sample. As the laser scans the sample, over each 0.33 micron interval a Raman spectrum with high signal to noise is collected using 0.3 seconds of integration time. Each confocal cross-sectional image of the coatings displays a region 70 μm wide by 10 μm deep, and results from the gathering of 6300 spectra with a total imaging time of 32 min.

Multivariate analysis using reference spectra from samples of rapamycin (amorphous and crystalline) and polymer are used to deconvolve the spectral data sets, to provide chemical maps of the distribution.

Infrared (IR) Spectroscopy for In-Vitro Testing

Infrared (IR) Spectroscopy such as FTIR and ATR-IR are well utilized techniques that can be applied to show, for example, the quantitative drug content, the distribution of the drug in the sample coating, the quantitative polymer content in the coating, and the distribution of polymer in the coating. Infrared (IR) Spectroscopy such as FTIR and ATR-IR can similarly be used to show, for example, drug crystallinity. The following table (Table 2) lists the typical IR materials for various applications. These IR materials are used for IR windows, diluents or ATR crystals.

TABLE 2

| | MATERIAL | | | | | | |
|---|---|---|---|---|---|---|---|
| | NACL | KBR | CSI | AGCL | GE | ZNSE | DIAMOND |
| Transmission range (cm−1) | 40,000~625 | 40,000~400 | 40,000~200 | 25,000~360 | 5,500~625 | 20,000~454 | 40,000~2,500 & 1667-33 |
| Water sol (g/100 g, 25 C.) | 35.7 | 53.5 | 44.4 | Insol. | Insol. | Insol. | Insol. |

TABLE 2-continued

| | MATERIAL | | | | | | |
|---|---|---|---|---|---|---|---|
| | NACL | KBR | CSI | AGCL | GE | ZNSE | DIAMOND |
| Attacking materials | Wet Solvents | Wet Solvents | Wet Solvents | Ammonium Salts | H2SO4, aqua regin | Acids, strong alkalies, chlorinated solvents | K2Cr2Os, conc. H2SO4 |

In one test, a coupon of crystalline ZnSe is coated by the processes described herein, creating a PDPDP (Polymer, Drug, Polymer, Drug, Polymer) layered coating that is about 10 microns thick. The coated coupon is analyzed using FTIR. The resulting spectrum shows crystalline drug as determined by comparison to the spectrum obtained for the crystalline form of a drug standard (i.e. a reference spectrum).

Differential Scanning Calorimetry (DSC)

DSC can provide qualitative evidence of the crystallinity of the drug (e.g. rapamycin) using standard DSC techniques obvious to one of skilled in the art. Crystalline melt can be shown using this analytical method (e.g. rapamycin crystalline melting—at about 185 decrees C. to 200 degrees C., and having a heat of fusion at or about 46.8 J/g). The heat of fusion decreases with the percent crystallinity. Thus, the degree of crystallinity could be determined relative to a pure sample, or versus a calibration curve created from a sample of amorphous drug spiked and tested by DSC with known amounts of crystalline drug. Presence (at least) of crystalline drug on a stent could be measured by removing (scraping or stripping) some drug from the stent and testing the coating using the DSC equipment for determining the melting temperature and the heat of fusion of the sample as compared to a known standard and/or standard curve.

Confocal Raman Microscopy

Confocal Raman Microscopy can provide nondestructive depth analysis and allows coating specific Raman spectral features to be obtained (Bugay et al., "Raman Analysis of Pharmaceuticals," in "*Applications of Vibrational Spectroscopy in Pharmaceutical Research and Development*," Ed. Pivonka, D. E., Chalmers, J. M., Griffiths, P. R. (2007) Wiley and Sons). In confocal Raman microscopy an aperture is place in a focal place of the collected beam. This limitation defines a shallow portion of the depth of field and thereby provides definition of the z-axis spatial resolution for data collection. By adjusting the aperture and moving the focus within the sample, the sampling position within the sample moves. Moving the sample focus from the top surface, deeper into the specimen facilitates nondestructive depth analysis.

Example 23

Detection of Coating Remaining on a Device Following Use

The ability to uniformly coat a device with controlled composition and thickness using electrostatic capture in a rapid expansion of supercritical solution (RESS) experimental series has been demonstrated.

The coating remaining on a device following use of the device may be examined by any of the following test methods. For example, the coating remaining on a device following use is an indication of the maximum amount of coating freed from the device. In an in-vivo or in-vitro method, an embodiment of the device that is removed from the subject once used is tested for remaining coating (for example, a balloon).

Scanning Electron Microscopy (SEM)

Stents are observed by SEM using a Hitachi S-4800 with an accelerating voltage of 800V. Various magnifications are used to evaluate the integrity, especially at high strain regions. SEM can provide top-down and cross-section images at various magnifications. Coating uniformity and thickness can also be assessed using this analytical technique.

Pre- and post-expansions stents are observed by SEM using a Hitachi S-4800 with an accelerating voltage of 800V. Various magnifications are used to evaluate the integrity of the layers, especially at high strain regions.

Scanning Electron Microscopy (SEM) with Focused Ion Beam (FIB)

Stents as described herein, and or produced by methods described herein are visualized using SEM-FIB analysis. Alternatively, a coated coupon could be tested in this method. Focused ion beam FIB is a tool that allows precise site-specific sectioning, milling and depositing of materials. FIB can be used in conjunction with SEM, at ambient or cryo conditions, to produce in-situ sectioning followed by high-resolution imaging. Cross-sectional FIB images may be acquired, for example, at 7000× and/or at 20000× magnification. An even coating of consistent thickness is visible.

Optical Microscopy

An Optical micrscope may be used to create and inspect the stents and to empirically survey the coating of the substrate (e.g. coating uniformity). Nanoparticles of the drug and/or the polymer can be seen on the surfaces of the substrate using this analytical method. Following sintering, the coatings can be see using this method to view the coating conformaliy and for evidence of crystallinity of the drug.

In-vitro test: One sample of the coated compliant balloon prepared in Example 1 is secured to a balloon catheter. A segment of optically clear TYGON® B-44-3 tubing with O.D.=0.125", I.D.=0.0625" (Available from McMaster-Carr Part Number: 5114K11 (www.mcmaster.com)) is filled with phosphate-buffered saline solution and immersed in a water bath at 37° C. to mimic physiological conditions of deployment into a subject. The coated balloon is inserted into the tubing and the balloon is inflated to at least 25% below the balloon's nominal pressure to mechanically transfer the coating from the balloon to the tubing wall. The balloon is deflated and removed from the tubing. Scanning Electron Microscopy is performed on the tubing and the balloon (which is inflated to at least 25% below the balloon's nominal pressure, at least) to determine the presence and amount of coating transferred to the tubing and/or the amount of coating freed, dissociated, and/or transferred from the balloon.

Example 24

Detection of Coating Freed from a Device Following Use

The ability to uniformly coat a device with controlled composition and thickness using electrostatic capture in a rapid expansion of supercritical solution (RESS) experimental series has been demonstrated.

The amount of coating freed from the device may be determined by testing for the amount of coating deposited to the target site. In an in-vivo or in-vitro method, the target site is tested for coating that is freed from the device, extruded from the device, dissociated from the device, transferred from the device, or sheared from the device.

Scanning Electron Microscopy (SEM)

Stents are observed by SEM using a Hitachi S-4800 with an accelerating voltage of 800V. Various magnifications are used to evaluate the integrity, especially at high strain regions. SEM can provide top-down and cross-section images at various magnifications. Coating uniformity and thickness can also be assessed using this analytical technique.

Pre- and post-expansions stents are observed by SEM using a Hitachi S-4800 with an accelerating voltage of 800V. Various magnifications are used to evaluate the integrity of the layers, especially at high strain regions.

Scanning Electron Microscopy (SEM) with Focused Ion Beam (FIB)

Stents as described herein, and or produced by methods described herein are visualized using SEM-FIB analysis. Alternatively, a coated coupon could be tested in this method. Focused ion beam FIB is a tool that allows precise site-specific sectioning, milling and depositing of materials. FIB can be used in conjunction with SEM, at ambient or cryo conditions, to produce in-situ sectioning followed by high-resolution imaging. Cross-sectional FIB images may be acquired, for example, at 7000× and/or at 20000× magnification. An even coating of consistent thickness is visible.

Optical Microscopy

An Optical micrscope may be used to create and inspect the stents and to empirically survey the coating of the substrate (e.g. coating uniformity). Nanoparticles of the drug and/or the polymer can be seen on the surfaces of the substrate using this analytical method. Following sintering, the coatings can be see using this method to view the coating conformaliy and for evidence of crystallinity of the drug.

Scintigraphy

Use of a radiolabeled drug and/or polymer and/or coating generally can be employed to monitor amount of material freed, dissociated, and/or transferred from the substrate, and/or the amount of material transferred to, delivered to and/or deposited at the intervention site. It may also and/or alternatively be used to determine degradation rate of the polymer and/or release rate of the drug from the delivered coating.

In-Vivo Test: One sample of the coated compliant balloon prepared in Example 1 is prepared using a coating comprising a radiolabelled drug. The balloon is secured to a balloon catheter. A segment of optically clear TYGON® B-44-3 tubing with O.D.=0.125", I.D.=0.0625" (Available from McMaster-Carr Part Number: 5114K11 (www.mcmaster.com)) is filled with phosphate-buffered saline solution and immersed in a water bath at 37° C. to mimic physiological conditions of deployment into a subject. The coated balloon is inserted into the tubing and the balloon is inflated to at least 25% below the balloon's nominal pressure to mechanically transfer the coating from the balloon to the tubing wall. The balloon is deflated and removed from the tubing. The deflated balloon is placed into a vial containing scintillation cocktail, inflated to the deployment presure and the amount of radiation emitted is determined in a liquid scintillation counter. The section of tubing exposed to the balloon is cut away and splayed open to expose the interior. The section of tubing is placed into a vial containing scintillation cocktail, and the amount of radiation emitted is determined in a liquid scintillation counter.

Imaging Techniques

Use of an imaging agent and/or polymer and/or coating generally can be employed to monitor amount of material freed, dissociated, and/or transferred from the substrate, and/or the amount of material transferred to, delivered to and/or deposited at the intervention site. It may also and/or alternatively be used to determine degradation rate of the polymer and/or release rate of the drug from the delivered coating.

In-Vivo Test: One sample of the coated compliant balloon prepared in Example 1 is prepared using a coating comprising a imaging agent such as barium sulfate. The balloon is secured to a balloon catheter. A segment of optically clear TYGON® B-44-3 tubing with O.D.=0.125", I.D.=0.0625" (Available from McMaster-Carr Part Number: 5114K11 (www.mcmaster.com)) is filled with phosphate-buffered saline solution and immersed in a water bath at 37° C. to mimic physiological conditions of deployment into a subject. The coated balloon is inserted into the tubing and the balloon is inflated to at least 25% below the balloon's nominal pressure to mechanically transfer the coating from the balloon to the tubing wall. The balloon is deflated and removed from the tubing. The section of tubing exposed to the balloon is cut away and splayed open to expose the interior. The section of tubing is placed into a x-ray fluoroscope, and the amount of coating deposited is determined.

Example 25

Determination and Detection of Coating Confromality

The ability to uniformly coat devices, e.g., pre- and post-expansion stents, and balloons, with controlled composition and thickness using electrostatic capture in a rapid expansion of supercritical solution (RESS) experimental series has been demonstrated.

Scanning Electron Microscopy (SEM)

Devices are observed by SEM using a Hitachi S-4800 with an accelerating voltage of 800V. Various magnifications are used to evaluate the integrity, especially at high strain regions. SEM can provide top-down and cross-section images at various magnifications. Coating uniformity and thickness can also be assessed using this analytical technique.

Pre- and post-inflation balloons, for example, may be observed by SEM using a Hitachi S-4800 with an accelerating voltage of 800V. Various magnifications may be used to evaluate the integrity of the layers, and or of the coating.

Scanning Electron Microscopy (SEM) with Focused Ion Beam (FIB)

Devices as described herein, and or produced by methods described herein are visualized using SEM-FIB analysis. Alternatively, a coated coupon could be tested in this method. Focused ion beam FIB is a tool that allows precise site-specific sectioning, milling and depositing of materials. FIB can be used in conjunction with SEM, at ambient or cryo conditions, to produce in-situ sectioning followed by high-resolution imaging. Cross-sectional FIB images may be acquired, for example, at 7000× and/or at 20000× magnification. An even coating of consistent thickness is visible.
Optical Microscopy An optical microscope may be used to create and inspect the devices and to empirically survey the coating of the substrate (e.g. coating uniformity). Nanoparticles of the drug and/or the polymer can be seen on the surfaces of the substrate using this analytical method. Following sintering, the coatings can be see using this method to view the coating conformality and for evidence of crystallinity of the drug.

Example 26

Visualization of Polymer/Active Agent Layers Coating a Device Raman Spectroscopy As discussed herein, Raman spectroscopy can be applied to characterize the chemical structure and relative concentrations of drug and polymer coatings. For example, confocal Raman Spectroscopy/microscopy can be used to characterize the relative drug to polymer ratio at the outer ~1 μm of the coated surface. In addition confocal Raman x-z or z (maps or line scans) microscopy can be applied to characterize the relative drug to polymer ratio as a function of depth. Additionally cross-sectioned samples can be analysed. Raman spectroscopy and other analytical techniques such as described in Balss, et al., "Quantitative spatial distribution of sirolimus and polymers in drug-eluting stents using confocal Raman microscopy" *J. of Biomedical Materials Research Part A,* 258-270 (2007), incorporated in its entirety herein by reference, and/or described in Belu et al, "Three-Dimensional Compositional Analysis of Drug Eluting Stent Coatings Using Cluster Secondary Ion Mass Spectroscopy" *Anal. Chem.* 80: 624-632 (2008) incorporated herein in its entirety by reference may be used.

A sample (a coated substrate) is prepared as described herein. Images are taken on the coating using Raman Spectroscopy. Alternatively, a coated coupon could be tested in this method. To test a sample using Raman microscopy and in particular confocal Raman microscopy, it is understood that to get appropriate Raman high resolution spectra sufficient acquisition time, laser power, laser wavelength, sample step size and microscope objective need to be optimized.

For example a WITec CRM 200 scanning confocal Raman microscope using a Nd:YAG laser at 532 nm is applied in the Raman imaging mode to give x-z maps. The sample is placed upon a piezoelectrically driven table, the laser light is focused upon the sample using a 100× dry objective (numerical aperture 0.90), and the finely focused laser spot is scanned into the sample. As the laser scans the sample, over each 0.33 micron interval a Raman spectrum with high signal to noise is collected using 0.3 Seconds of integration time. Each confocal cross-sectional image of the coatings displays a region 70 μm wide by 10 μm deep, and results from the gathering of 6300 spectra with a total imaging time of 32 min. Multivariate analysis using reference spectra from samples of rapamycin and polymer are used to deconvolve the spectral data sets, to provide chemical maps of the distribution.

In another test, spectral depth profiles (x-z maps) of samples are performed with a CRM200 microscope system from WITec Instruments Corporation (Savoy, Ill.). The instrument is equipped with a Nd:YAG frequency doubled laser (532 excitation), a single monochromator (Acton) employing a 600 groove/mm grating and a thermoelectrically cooled 1024 by 128 pixel array CCD camera (Andor Technology). The microscope is equipped with appropriate collection optics that include a holographic laser bandpass rejection filter (Kaiser Optical Systems Inc.) to minimize Rayleigh scatter into the monochromator. The Raman scattered light are collected with a 50 micron optical fiber. Using the "Raman Spectral Imaging" mode of the instrument, spectral images are obtained by scanning the sample in the x, z direction with a piezo driven xyz scan stage and collecting a spectrum at every pixel. Typical integration times are 0.3 s per pixel. The spectral images are 4800 total spectra corresponding to a physical scan dimension of 40 by 20 microns. For presentation of the confocal Raman data, images are generated based on unique properties of the spectra (i.e. integration of a Raman band, band height intensity, or band width). The microscope stage is modified with a custom-built sample holder that positioned and rotated the stents around their primary axis. The x direction is defined as the direction running parallel to the length of the stent and the z direction refers to the direction penetrating through the coating from the air-coating to the coating-metal interface. Typical laser power is <10 mW on the sample stage. All experiments can be conducted with a plan achromat objective, 100×NA=0.9 (Nikon).

Samples (n=5) comprising metal substrates made of L605 (0.05-0.15% C, 1.00-2.00% Mn, maximum 0.040% Si, maximum 0.030% P, maximum 0.3% S, 19.00-21.00% Cr, 9.00-11.00% Ni, 14.00-16.00% W, 3.00% Fe, and Bal. Co) and having coatings as described herein and/or produced by methods described herein can be analyzed. For each sample, three locations are selected along the substrate length. The three locations are located within one-third portions of the substrates so that the entire length of the substrate are represented in the data. The stent is then rotated 180 degrees around the circumference and an additional three locations are sampled along the length. In each case, the data is collected from the strut portion of the substrate. Six random spatial locations are also profiled on coated coupon samples made of L605 and having coatings as described herein and/or produced by methods described herein. The Raman spectra of each individual component present in the coatings are also collected for comparison and reference. Using the instrument software, the average spectra from the spectral image data are calculated by selecting the spectral image pixels that are exclusive to each layer. The average spectra are then exported into GRAMS/AI v. 7.02 software (Thermo Galactic) and the appropriate Raman bands are fit to a Voigt function. The band areas and shift positions are recorded.

The pure component spectrum for each component of the coating (e.g. drug, polymer) are also collected at 532 and 785 nm excitation. The 785 nm excitation spectra are collected with a confocal Raman microscope (WITec Instruments Corp. Savoy, Ill.) equipped with a 785 nm diode laser, appropriate collection optics, and a back-illuminated thermoelectriaclly cooled 1024×128 pixel array CCD camera optimized for visible and infrared wavelengths (Andor Technology).

X-ray Photoelectron Spectroscopy (XPS)

XPS can be used to quantitatively determine elemental species and chemical bonding environments at the outer 5-10 nm of sample surface. The technique can be operated in spectroscopy or imaging mode. When combined with a sputtering source XPS can be utilized to give depth profiling chemical characterization. XPS (ESCA) and other analytical techniques such as described in Belu et al., "Three-Dimensional Compositional Analysis of Drug Eluting Stent Coatings Using Cluster Secondary Ion Mass Spectroscopy" *Anal. Chem.* 80: 624-632 (2008) incorporated herein in its entirety by reference may be used.

For example, in one test, a sample comprising a stent coated by methods described herein and/or a device as described herein is obtained. XPS analysis is performed on a sample using a Physical Electronics Quantum 2000 Scanning ESCA. The monochromatic Al Kα source is operated at 15 kV with a power of 4.5 W. The analysis is done at a 45° take off angle. Three measurements are taken along the length of each sample with the analysis area ~20 microns in diameter. Low energy electron and $Ar^+$ ion floods are used for charge compensation.

Time of Flight Secondary Ion Mass Spectrometery (TOF-SIMS)

TOF-SIMS can be used to determine molecular species (drug and polymer) at the outer 1-2 nm of sample surface when operated under static conditions. The technique can be operated in spectroscopy or imaging mode at high spatial resolution. Additionally cross-sectioned samples can be analysed. When operated under dynamic experimental conditions, known in the art, depth profiling chemical characterization can be achieved.

For example, to analyze the uppermost surface only, static conditions (for example a ToF-SIMS IV (IonToF, Munster)) using a 25 Kv Bi++ primary ion source maintained below 1012 ions per cm2 is used. Where necessary a low energy electron flood gun (0.6 nA DC) is used to charge compensate insulating samples.

Cluster Secondary Ion Mass Spectrometry, may be employed for depth profiling as described Belu et al., "Three-Dimensional Compositional Analysis of Drug Eluting Stent Coatings Using Cluster Secondary Ion Mass Spectroscopy" Anal. Chem. 80: 624-632 (2008) incorporated herein in its entirety by reference.

For example, a ballon coated as described herein is obtained. The balloon is prepared for SIMS analysis by cutting it longitudinally and opening it up with tweezers. The balloon is then pressed into multiple layers of indium foil with the outer diameter facing outward.

TOF-SIMS depth profiling experiments are performed using an Ion-TOF IV instrument equipped with both Bi and SF5+ primary ion beam cluster sources. Sputter depth profiling is performed in the dual-beam mode, whilst preserving the chemical integrity of the sample. The analysis source is a pulsed, 25-keV bismuth cluster ion source, which bombarded the surface at an incident angle of 45° to the surface normal. The target current is maintained at ~0.3 pÅ (+10%) pulsed current with a raster size of 200 um×200 um for all experiments. Both positive and negative secondary ions are extracted from the sample into a reflectron-type time-of-flight mass spectrometer. The secondary ions are then detected by a microchannel plate detector with a post-acceleration energy of 10 kV. A low-energy electron flood gun is utilized for charge neutralization in the analysis mode.

The sputter source used is a 5-keV SF5+ cluster source also operated at an incident angle of 45° to the surface normal. For thin model samples on Si, the SF5+ current is maintained at ~2.7 nÅ with a 750 um×750 um raster. For the thick samples on coupons and for the samples on stents, the current is maintained at 6 nA with a 500 um×500 um raster. All primary beam currents are measured with a Faraday cup both prior to and after depth profiling.

All depth profiles are acquired in the noninterlaced mode with a 5-ms pause between sputtering and analysis. Each spectrum is averaged over a 7.37 second time period. The analysis is immediately followed by 15 seconds of SF5+ sputtering. For depth profiles of the surface and subsurface regions only, the sputtering time was decreased to 1 second for the 5% active agent sample and 2 seconds for both the 25% and 50% active agent samples.

Temperature-controlled depth profiles are obtained using a variable-temperature stage with Eurotherm Controls temperature controller and IPSG V3.08 software. samples are first placed into the analysis chamber at room temperature. The samples are brought to the desired temperature under ultra high-vacuum conditions and are allowed to stabilize for 1 minute prior to analysis. All depth profiling experiments are performed at −100 C and 25 C.

Atomic Force Microscopy (AFM)

AFM is a high resolution surface characterization technique. AFM is used in the art to provide topographical imaging, in addition when employed in Tapping Mode™ can image material and or chemical properties of the surface. Additionally cross-sectioned samples can be analyzed. The technique can be used under ambient, solution, humidified or temperature controlled conditions. Other modes of operation are well known and can be readily employed here by those skilled in the art.

A substrate having a coating as described herein is obtained. AFM is used to determine the structure of the drug polymer layers. AFM may be employed as described in Ranade et al., "Physical characterization of controlled release of paclitaxel from the TAXUS Express2 drug-eluting stent" J. Biomed. Mater. Res. 71(4):625-634 (2004) incorporated herein in its entirety by reference.

Polymer and drug morphologies, coating composition, at least may be determined using atomic force microscopy (AFM) analysis. A multi-mode AFM (Digital Instruments/Veeco Metrology, Santa Barbara, Calif.) controlled with Nanoscope IIIa and NanoScope Extender electronics is used. Samples are examined in the dry state using AFM before elution of the drug (e.g. rapamycin). Samples are also examined at select time points through a elution period (e.g. 48 hours) by using an AFM probe-tip and flow-through stage built to permit analysis of wet samples. The wet samples are examined in the presence of the same elution medium used for in-vitro kinetic drug release analysis (e.g. PBS-Tween20, or 10 mM Tris, 0.4 wt. % SDS, pH 7.4). Saturation of the solution is prevented by frequent exchanges of the release medium with several volumes of fresh medium. Tapping-Mode™ AFM imaging may be used to show topography (a real-space projection of the coating surface microstructure) and phase-angle changes of the AFM over the sample area to contrast differences in the materials properties. The AFM topography images can be three-dimensionally rendered to show the surface of a coated stent, which can show holes or voids of the coating which may occur as the polymer is absorbed and the drug is eluted over time, for example.

Scanning Electron Microscopy (SEM) with Focused Ion Beam (FIB) Milling

Coatings on substrates as described herein, and or produced by methods described herein are visualized using SEM-FIB. Alternatively, a coated coupon could be tested in this method. Focused ion beam FIB is a tool that allows precise site-specific sectioning, milling and depositing of materials. FIB can be used in conjunction with SEM, at ambient or cryo conditions, to produce in-situ sectioning followed by high-resolution imaging. FIB-SEM can produce a cross-sectional image of the polymer and drug layers on the substrate. The image can be used to quantitate the thickness of the layers and uniformity of the layer thickness at manufacture and at time points after stenting (or after in-vitro elution at various time points).

A FEI Dual Beam Strata 235 FIB/SEM system is a combination of a finely focused Ga ion beam (FIB) accelerated by 30 kV with a field emission electron beam in a scanning electron microscope instrument and is used for imaging and sectioning the stents. Both beams focus at the same point of the sample with a probe diameter less than 10 nm. The FIB can also produce thinned down sections for TEM analysis.

To prevent damaging the surface of the substrate with incident ions, a Pt coating is first deposited via electron beam assisted deposition and ion beam deposition prior to FIB sectioning. For FIB sectioning, the Ga ion beam is accelerated to 30 kV and the sectioning process is about 2 h in duration. Completion of the FIB sectioning allows one to observe and quantify by SEM the thickness of the polymer layers that are, for example, left on the substrate as they are absorbed.

Example 27

Determination of Secondary Structures Presence of a Biological Agent

Raman Spectroscopy

FT-Raman or confocal raman microscopy can be employed to determine secondary structure of a biological Agent. For example fitting of the Amide I, II, or III regions of the Raman spectrum can elucidate secondary structures (e.g. alpha-helices, beta-sheets). See, for example, Iconomidou, et al., "Secondary Structure of Chorion Proteins of the Teleosetan Fish Dentex dentex by ATR FR-IR and FT-Raman Spectroscopy" *J. of Structural Biology*, 132, 112-122 (2000); Griebenow, et al., "On Protein Denaturation in Aqueous-Organic Mixtures but Not in Pure Organic Solvents" *J. Am Chem. Soc.*, Vol 118, No. 47, 11695-11700 (1996).

Infrared (IR) Spectroscopy for In-Vitro Testing

Infrared spectroscopy, for example FTIR, ATR-IR and micro ATR-IR can be employed to determine secondary structure of a biological Agent. For example fitting of the Amide I, II, of III regions of the infrared spectrum can elucidate secondary structures (e.g. alpha-helices, beta-sheets).

Example 28

Determination of the Microstructure of a Coating on a Medical Device

Atomic Force Microscopy (AFM)

AFM is a high resolution surface characterization technique. AFM is used in the art to provide topographical imaging, in addition when employed in Tapping Mode™ can image material and or chemical properties of the surface. Additionally cross-sectioned samples can be analyzed. The technique can be used under ambient, solution, humidified or temperature controlled conditions. Other modes of operation are well known and can be readily employed here by those skilled in the art.

A device as described herein is obtained. AFM is used to determine the microstructure of the coating. A stent as described herein is obtained. AFM may be employed as described in Ranade et al., "Physical characterization of controlled release of paclitaxel from the TAXUS Express2 drug-eluting stent" *J. Biomed. Mater. Res.* 71(4):625-634 (2004) incorporated herein in its entirety by reference.

For example, polymer and drug morphologies, coating composition, and physical structure may be determined using atomic force microscopy (AFM) analysis. A multimode AFM (Digital Instruments/Veeco Metrology, Santa Barbara, Calif.) controlled with Nanoscope IIIa and Nano-Scope Extender electronics is used. Samples are examined in the dry state using AFM before elution of the drug (e.g. rapamycin). Samples are also examined at select time points through a elution period (e.g. 48 hours) by using an AFM probe-tip and flow-through stage built to permit analysis of wet samples. The wet samples are examined in the presence of the same elution medium used for in-vitro kinetic drug release analysis (e.g. PBS-Tween20, or 10 mM Tris, 0.4 wt. % SDS, pH 7.4). Saturation of the solution is prevented by frequent exchanges of the release medium with severl volumes of fresh medium. TappingMode™ AFM imaging may be used to show topography (a real-space projection of the coating surface microstructure) and phase-angle changes of the AFM over the sample area to contrast differences in the materials properties. The AFM topography images can be three-dimensionally rendered to show the surface of a coated stent, which can show holes or voids of the coating which may occur as the polymer is absorbed and the drug is released from the polymer over time, for example.

Nano X-Ray Computer Tomography

Another technique that may be used to view the physical structure of a device in 3-D is Nano X-Ray Computer Tomography (e.g. such as made by SkyScan), which could be used in an elution test and/or bioabsorbability test, as described herein to show the physical structure of the coating remaining on substrates at each time point, as compared to a scan prior to elution/bioabsorbtion.

Example 29

Determination of the Total Content of the Active Agent (and/or the Content of Active Agent Remaining on a Device Following an Intervention)

Determination of the total content of the active agent in a coated substrate may be tested using techniques described herein as well as other techniques obvious to one of skill in the art, for example using GPC and HPLC techniques to extract the drug from the coated substrate and determine the total content of drug in the sample.

UV-VIS can be used to quantitatively determine the mass of rapamycin (or another active agent) coated onto the substrates. A UV-Vis spectrum of Rapamycin can be shown and a Rapamycin calibration curve can be obtained, (e.g. $\lambda$@277 nm in ethanol). Rapamycin is then dissolved from the coated substrate in ethanol, and the drug concentration and mass calculated.

In one test, the total amount of rapamycin (or another active agent) present in units of micrograms per substrate is determined by reverse phase high performance liquid chromatography with UV detection (RP-HPLC-UV). The analysis is performed with modifications of literature-based HPLC methods for rapamycin (or the other active agent) that would be obvious to a person of skill in the art. The average drug content of samples (n=10) from devices comprising stents and coatings as described herein, and/or methods described herein are tested.

The foregoing is illustrative of the present invention, and is not to be construed as limiting thereof. While embodiments of the present invention have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the invention described herein may be employed in practicing the invention. It is intended that the following claims define the scope of the invention and that methods and structures within the scope of these claims and their equivalents be covered thereby.

The invention claimed is:

1. A medical device comprising:
a substrate; and
a coating on at least a portion of said substrate,
wherein the coating comprises a plurality of layers, wherein at least one layer comprises a pharmaceutical agent that is crystalline,
wherein the device is adapted to free at least a portion of the coating from the substrate upon stimulation of the coating,
wherein the coating comprises at least one of a non-absorbable polymer and a bioabsorbable polymer, and wherein the portion of the coating freed from the device comprises the at least one of the non-absorbable polymer and the bioabsorbable polymer, and
wherein at least about 35% of the coating is adapted to be freed from the substrate upon stimulation that lasts at most 20 seconds.

2. The device of claim 1, wherein the crystalline pharmaceutical agent is not a microcapsule.

3. The device of claim 1, wherein the substrate comprises a balloon.

4. The device of claim 1, wherein the pharmaceutical agent and a polymer are in the same layer, in separate layers, or form overlapping layers.

5. The device of claim 1, wherein the plurality of layers comprise five layers deposited as follows: a first polymer layer, a first pharmaceutical agent layer, a second polymer layer, a second pharmaceutical agent layer and a third polymer layer.

6. The device of claim 1, wherein the pharmaceutical agent comprises a macrolide immunosuppressive drug.

7. The device of claim 6, wherein the macrolide immunosuppressive drug comprises one or more of rapamycin, 40-O-(2-Hydroxyethyl)rapamycin (everolimus), 40-O-Benzyl-rapamycin, 40-O-(4'-Hydroxymethyl)benzyl-rapamycin, 40-O-[4'-(1,2-Dihydroxyethyl)]benzyl-rapamycin, 40-O-Allyl-rapamycin, 40-O-[3'-(2,2-Dimethyl-1,3-dioxolan-4(S)-yl)-prop-2'-en-1'-yl]-rapamycin, (2':E,4'S)-40-O-(4',5'-Dihydroxypent-2'-en-1'-yl)-rapamycin 40-O-(2-Hydroxy)ethoxycar-bonylmethyl-rapamycin, 40-O-(3-Hydroxy)propyl-rapamycin, 40-O-(6-Hydroxy)hexyl-rapamycin, 40-O-[2-(2-Hydroxy)ethoxy]ethyl-rapamycin, 40-O-[(3S)-2,2-Dimethyldioxolan-3-yl]methyl-rapamycin, 40-O-[(2S)-2,3-Dihydroxyprop-1-yl]-rapamycin, 40-O-(2-Acetoxy)ethyl-rapamycin, 40-O-(2-Nicotinoyloxy)ethyl-rapamycin, 40-O-[2-(N-Morpholino)acetoxy]ethyl-rapamycin, 40-O-(2-N-Imidazolylacetoxy)ethyl-rapamycin, 40-O-[2-(N-Methyl-N'-piperazinyl)acetoxy]ethyl-rapamycin, 39-O-Desmethyl-39, 40-O,O-ethylene-rapamycin, (26R)-26-Dihydro-40-O-(2-hydroxy)ethyl-rapamycin, 28-O-Methyl-rapamycin, 40-O-(2-Aminoethyl)-rapamycin, 40-O-(2-Acetaminoethyl)-rapamycin, 40-O-(2-Nicotinamidoethyl)-rapamycin, 40-O-(2-(N-Methyl-imidazo-2'-ylcarbethoxamido)ethyl)-rapamycin, 40-O-(2-Ethoxycarbonylaminoethyl)-rapamycin, 40-O-(2-Tolylsulfonamidoethyl)-rapamycin, 40-O-[2-(4',5'-Dicarboethoxy-1',2',3'-triazol-1'-yl)-ethyl]-rapamycin, 42-Epi-(tetrazolyl)rapamycin (tacrolimus), and 42-[3-hydroxy-2-(hydroxymethyl)-2-methylpropanoate]rapamycin (temsirolimus).

8. The device of claim 1, wherein the pharmaceutical agent is rapamycin.

9. The device of claim 1, wherein the pharmaceutical agent is at least 50% crystalline.

10. The device of claim 1, wherein the pharmaceutical agent is at least 75% crystalline.

11. The device of claim 1, wherein the pharmaceutical agent is at least 90% crystalline.

12. The device of claim 1, wherein the coating is formed on said substrate by a process comprising at least one of: depositing a polymer by an e-RESS, an e-SEDS, or an e-DPC process, and depositing the pharmaceutical agent by an e-RESS, an e-SEDS, or an e-DPC process.

13. The device of claim 12, wherein the process of forming the coating provides improves adherence of the coating to the substrate prior to deployment of the device and facilitates dissociation of said coating from said substrate upon stimulation.

14. The device of claim 1, wherein the device is adapted to transfer less than about 10% of the coating absent stimulation of the coating.

15. The device of claim 1, wherein the coating comprises a bioabsorbable polymer.

16. The device of claim 15, wherein the bioabsorbable polymer comprises at least one of: Polylactides (PLA); PLGA (poly(lactide-co-glycolide); Polyanhydrides; Polyorthoesters; Poly(N-(2-hydroxypropyl) methacrylamide); DLPLA-poly(dl-lactide); LPLA-poly(l-lactide); PGA-polyglycolide; PDQ-poly(dioxanone); PGA-TMC-poly(glycolide-co-trimethylene carbonate); PGA-LPLA-poly(l-lactide-co-glycolide); PGA-DLPLA-poly(dl-lactide-co-glycolide); LPLA-DLPLA-poly(l-lactide-co-dl-lactide); and PDO-PGA-TMC-poly(glycolide-co-trimethylene carbonate-co-dioxanone), and combinations, copolymers, and derivatives thereof.

17. The device of claim 15, wherein the bioabsorbable polymer comprises between 1% and 95% glycolic acid content PLGA-based polymer.

18. The device of claim 1, wherein at least about 50% of the coating is adapted to be freed from the substrate upon stimulation.

19. The device of claim 1, wherein the device is adapted to free all of the coating upon a single stimulation of the coating.

* * * * *